(12) United States Patent
Shetty

(10) Patent No.: US 12,173,061 B2
(45) Date of Patent: Dec. 24, 2024

(54) COMPOSITIONS AND METHODS FOR TREATMENT OF CHRONIC LUNG DISEASES

(71) Applicant: Board of Regents, The University of Texas System, Austin, TX (US)

(72) Inventor: Sreerama Shetty, Tyler, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 18/481,529

(22) Filed: Oct. 5, 2023

(65) Prior Publication Data

US 2024/0067713 A1 Feb. 29, 2024

Related U.S. Application Data

(63) Continuation of application No. PCT/US2022/023992, filed on Apr. 8, 2022.

(60) Provisional application No. 63/172,980, filed on Apr. 9, 2021.

(51) Int. Cl.
| | |
|---|---|
| C07K 16/22 | (2006.01) |
| A61K 9/00 | (2006.01) |
| A61P 11/00 | (2006.01) |
| C07K 14/47 | (2006.01) |
| C07K 16/28 | (2006.01) |
| C07K 16/40 | (2006.01) |
| A61K 39/00 | (2006.01) |

(52) U.S. Cl.
CPC ............ *C07K 16/22* (2013.01); *A61K 9/0019* (2013.01); *A61P 11/00* (2018.01); *C07K 14/47* (2013.01); *C07K 16/28* (2013.01); *C07K 16/40* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 7,655,628 B2 | 2/2010 | Plater-Zyberk et al. | |
| 8,697,840 B2 | 4/2014 | Shetty et al. | |
| 9,630,990 B2 | 4/2017 | Shetty et al. | |
| 9,833,497 B2 * | 12/2017 | Song | C07K 14/485 |
| 2009/0227515 A1 | 9/2009 | Shetty et al. | |
| 2010/0215588 A1 | 8/2010 | Skaliter | |
| 2014/0010861 A1 * | 1/2014 | Bancel | C07K 14/47 |
| | | | 536/23.4 |
| 2016/0272678 A1 | 9/2016 | Shetty et al. | |
| 2020/0165298 A1 | 5/2020 | Shetty et al. | |

FOREIGN PATENT DOCUMENTS

| | | |
|---|---|---|
| WO | 2000/043512 A1 | 7/2000 |
| WO | 2014145389 A1 | 9/2014 |

OTHER PUBLICATIONS

Attwood (Science 290: 471-473, 2000).*
Skolnick et al. (Trends in Biotech. 18: 34-39, 2000).*
Robert G. Spiro, Protein glycosylation: nature, distribution, enzymatic formation, and disease implications of glycopeptide bonds, Glycobiology, vol. 12, Issue 4, Apr. 1, 2002, pp. 43R-56R.*
International Preliminary Report on Patentability and Written Opinion issued on Oct. 10, 2023 in PCT/US2022/023992 (11 pgs.).
International Search Report issued in PCT/US2022/23992 dated Sep. 8, 2022, 4 pgs.
Brandt-Bohne, et al., MEGF9: a novel transmembrane protein with a strong and developmentally regulated expression in the nervous system. The Biochemical Journal. Jan. 15, 2007, vol. 401, No. 2; pp. 447-452.

* cited by examiner

*Primary Examiner* — Sharon X Wen
(74) *Attorney, Agent, or Firm* — ROTHWELL, FIGG, ERNST & MANBECK, P.C.

(57) ABSTRACT

Methods for treating, reducing, ameliorating or inhibiting symptoms idiopathic pulmonary fibrosis (IPF) or interstitial pneumonia, comprising administering to a subject in need of an effective amount of a) multiple EGF-like-domains-9 (MEGF9) or a biologically active fragment thereof; b) uncoordinated receptor 5A (UNC5A) or a biologically active fragment thereof; c) dolichyl-phosphate beta-glucosyltransferase (ALG5) or a biologically active fragment thereof; d) a combination of two or three of a)-c); e) an antibody specifically binding to a); f) an antibody specifically binding to b); g) an antibody specifically binding to c); h) a combination of two or three of e)-g); or i) a combination of at least one of a)-c) and at least one of e)-g). Pharmaceutical compositions and processes for making and using the compositions are also disclosed.

8 Claims, 56 Drawing Sheets

Specification includes a Sequence Listing.

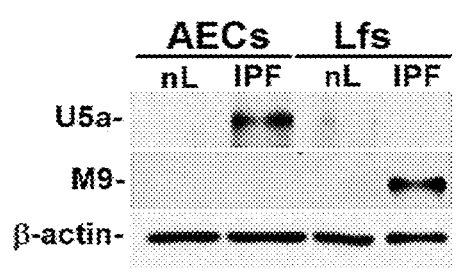
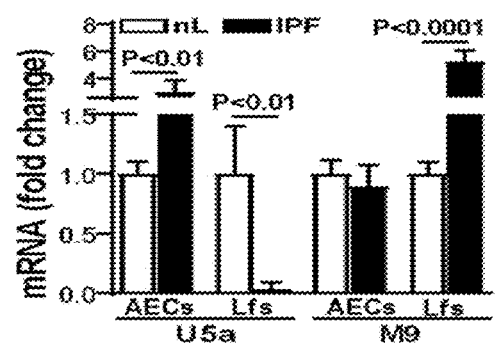
FIG. 1B
FIG. 1A

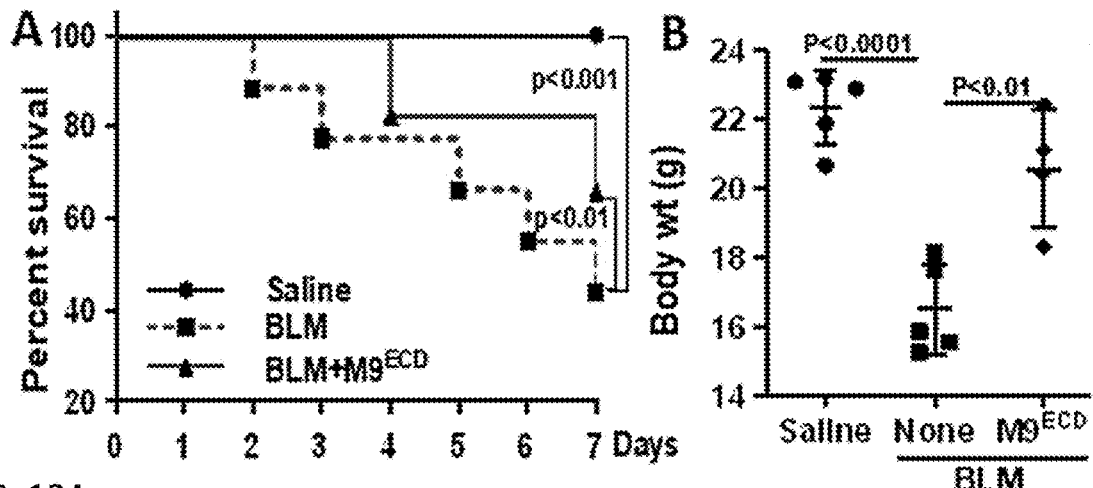
FIG. 12A
FIG. 12B
FIG. 12C
FIG. 12D
FIG. 12E
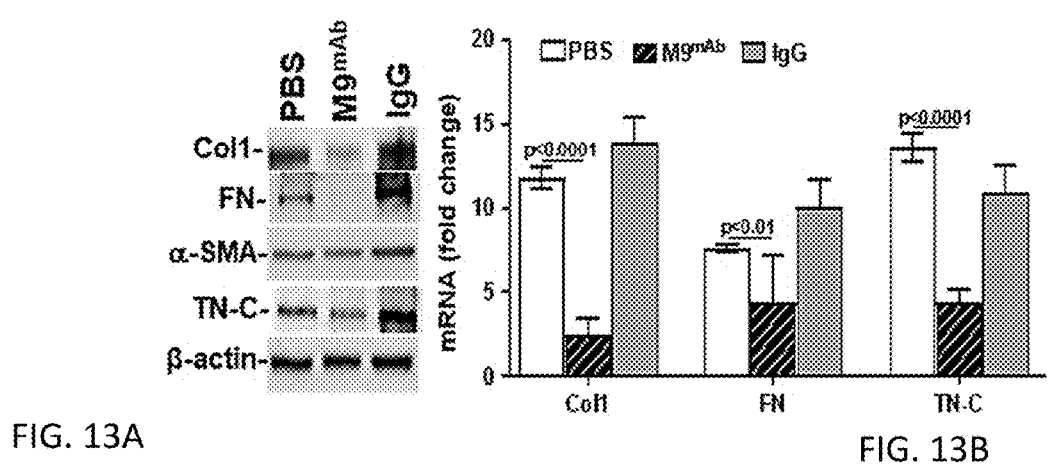
FIG. 13A
FIG. 13B

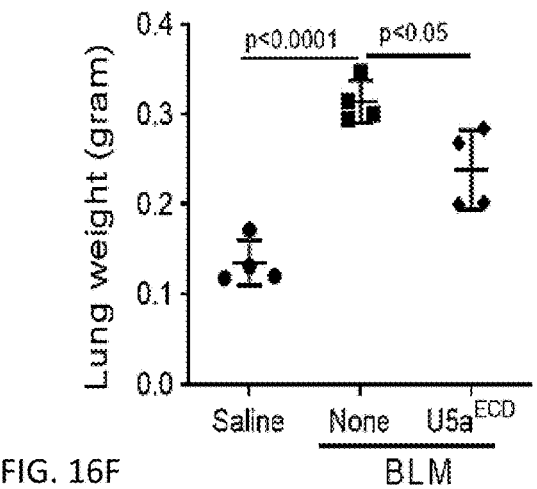
FIG. 16F
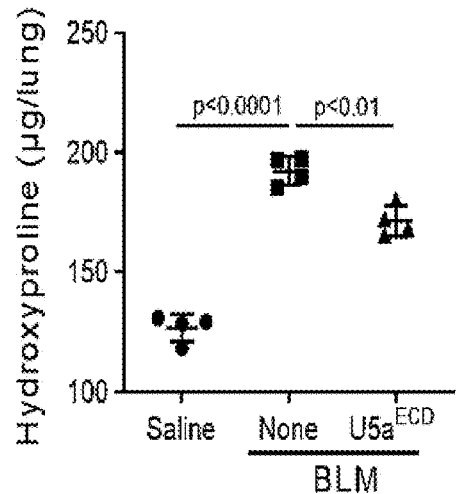
FIG. 16G
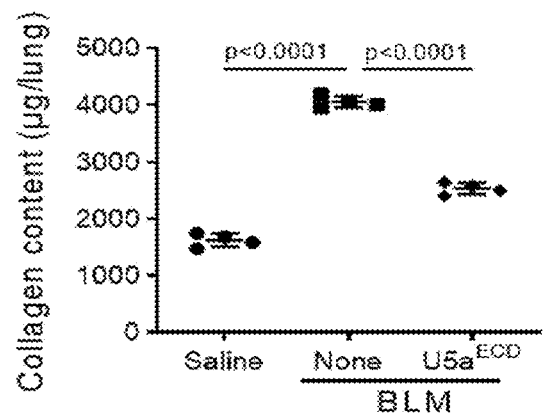
FIG. 16H
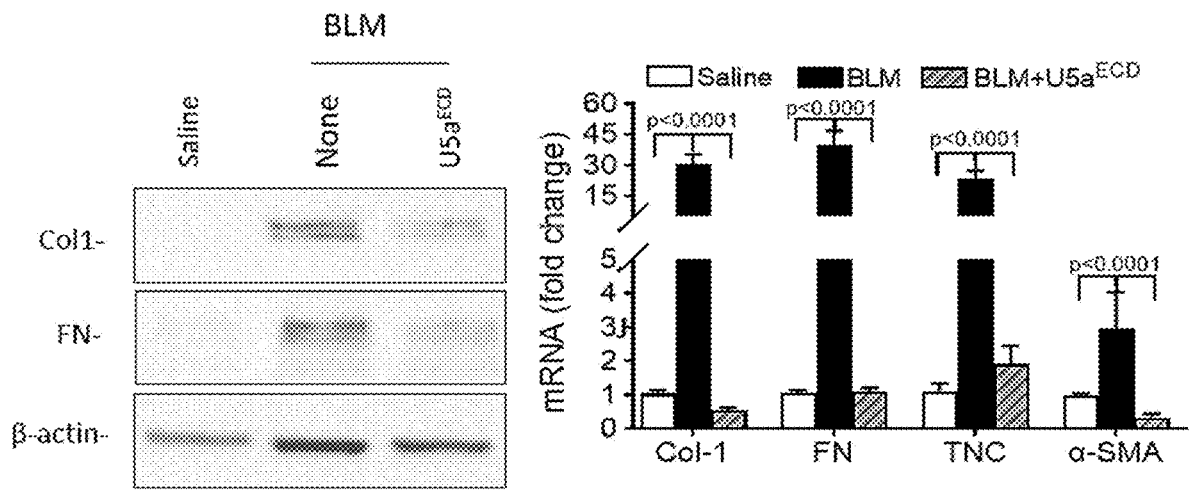
FIG. 16I
FIG. 16J

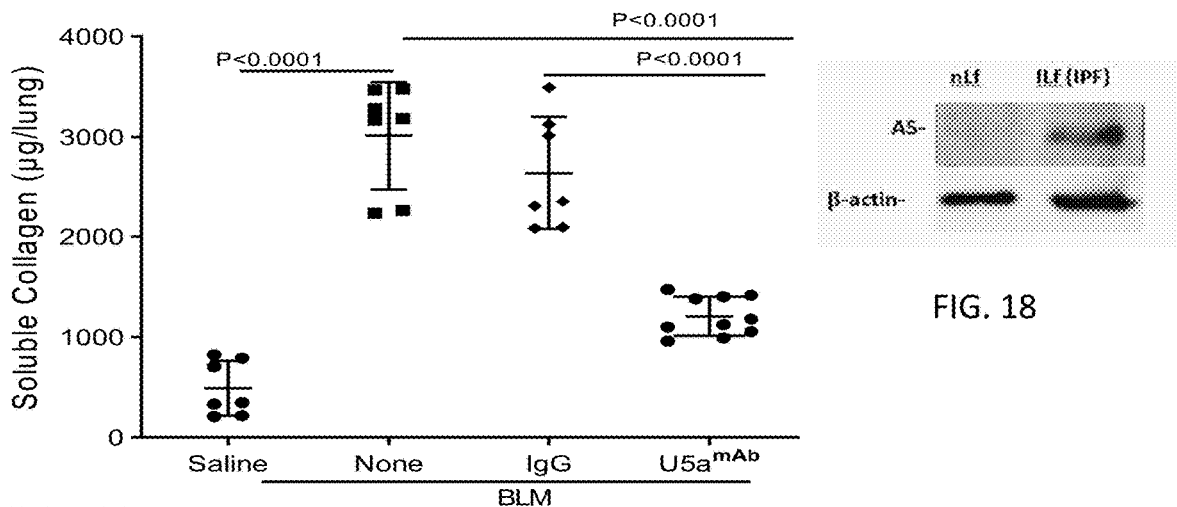
FIG. 17C
FIG. 18
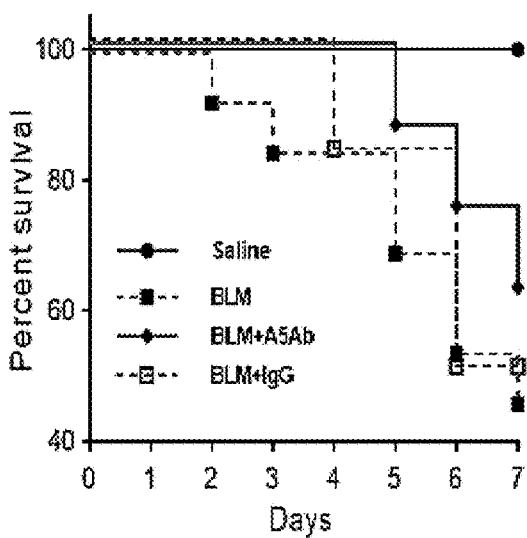
FIG. 19A
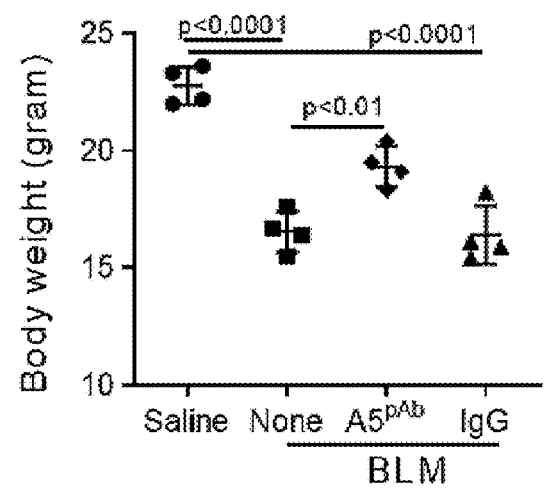
FIG. 19B
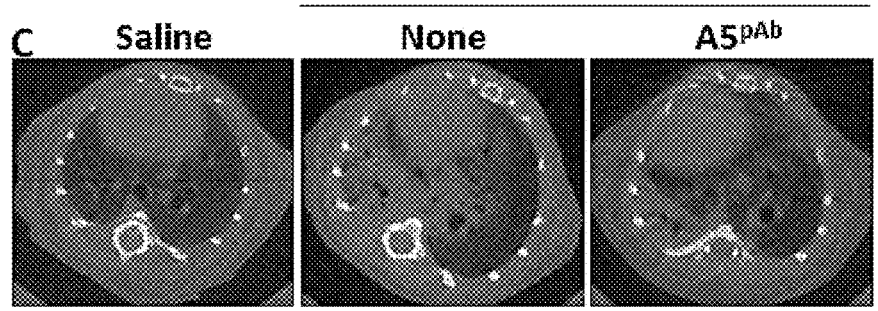
FIG. 19C

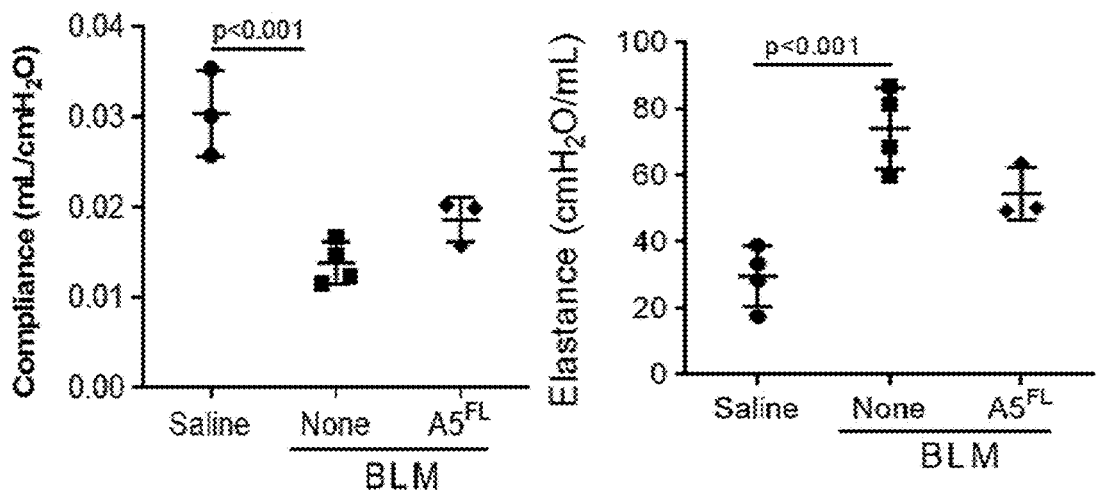
FIG. 20D  FIG. 20E
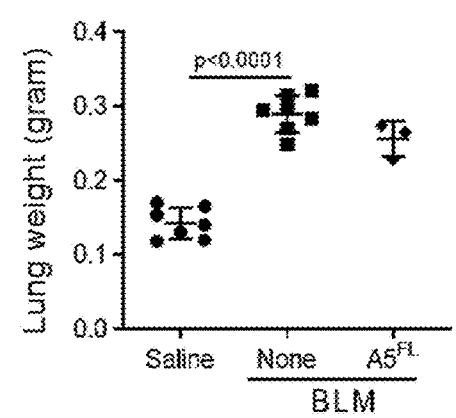 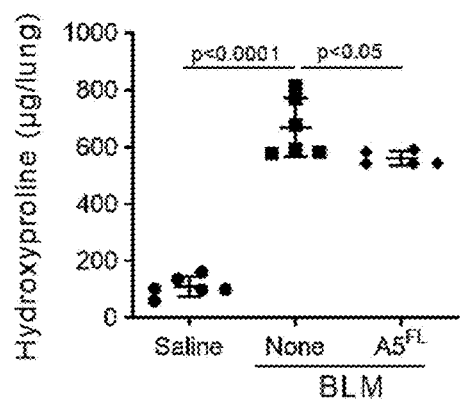
FIG. 20F  FIG. 20G
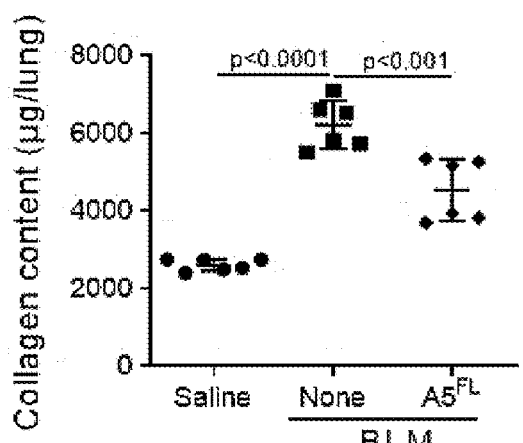 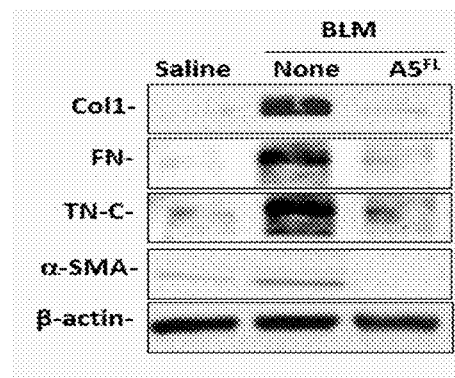
FIG. 20H  FIG. 20I

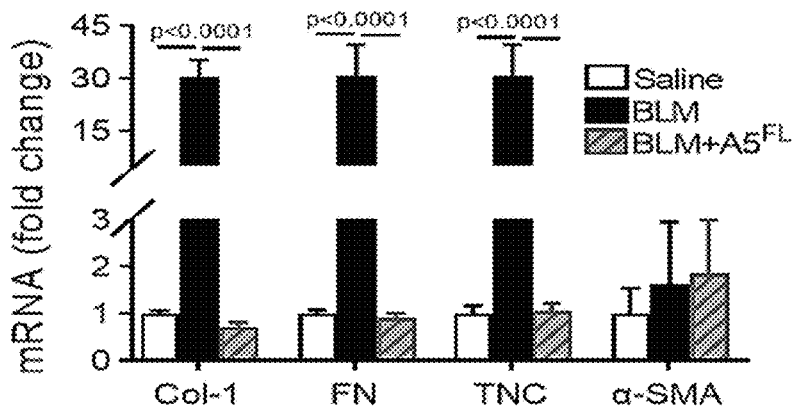
FIG. 20J
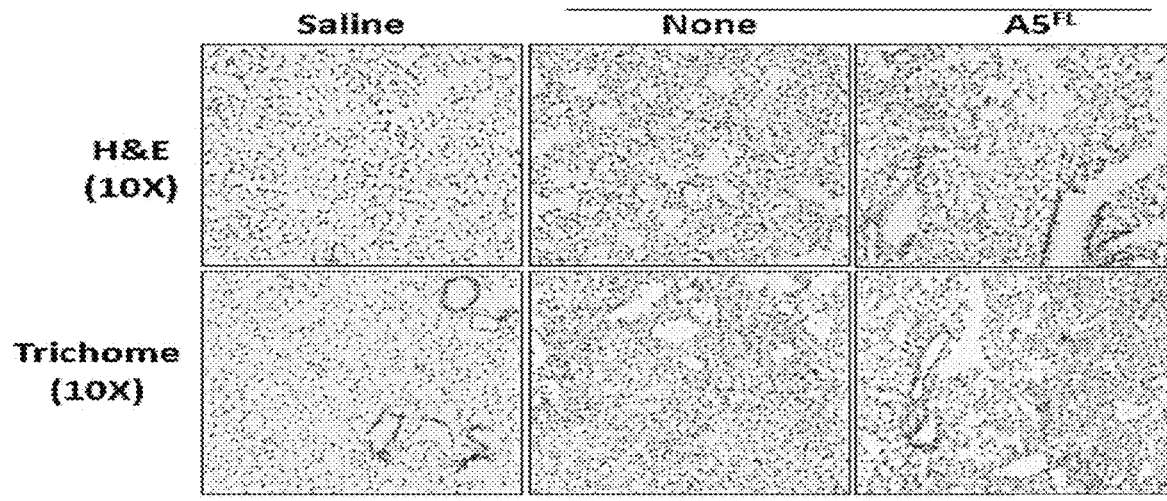
FIG. 20K
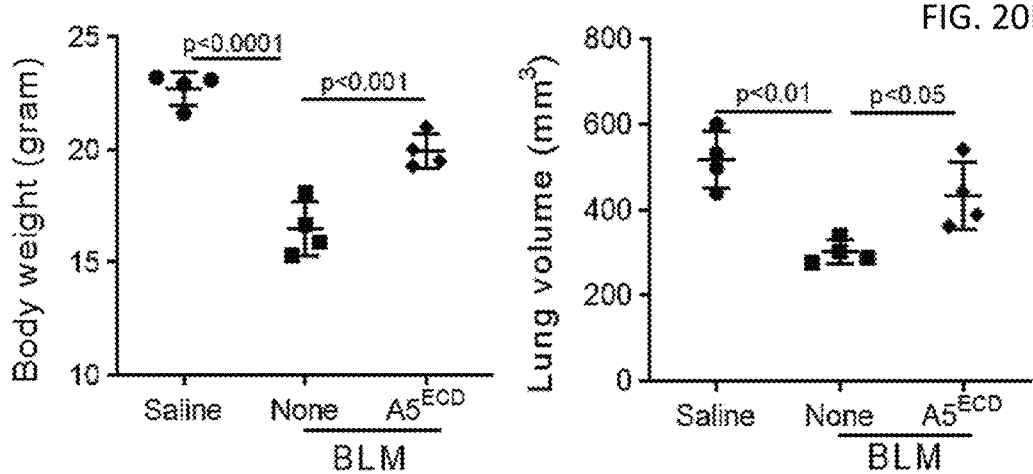
FIG. 21A
FIG. 21C

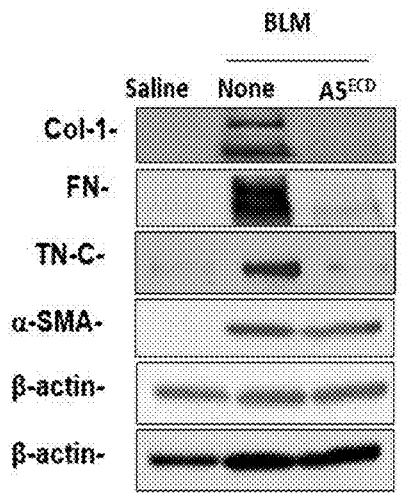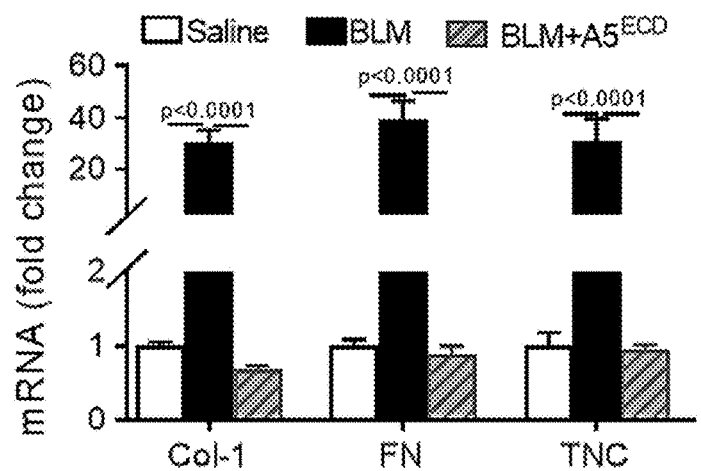
FIG. 21H
FIG. 21I
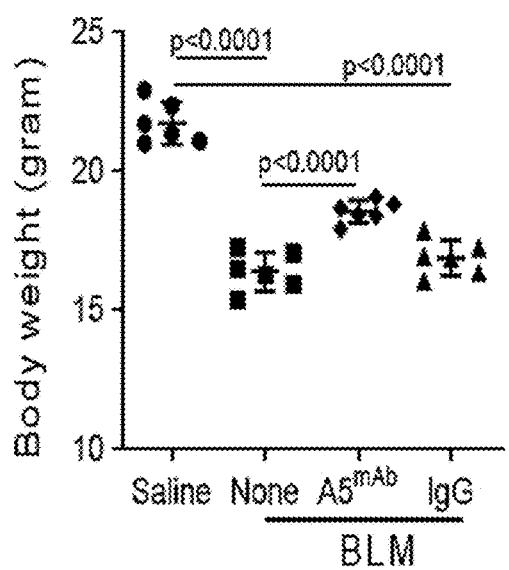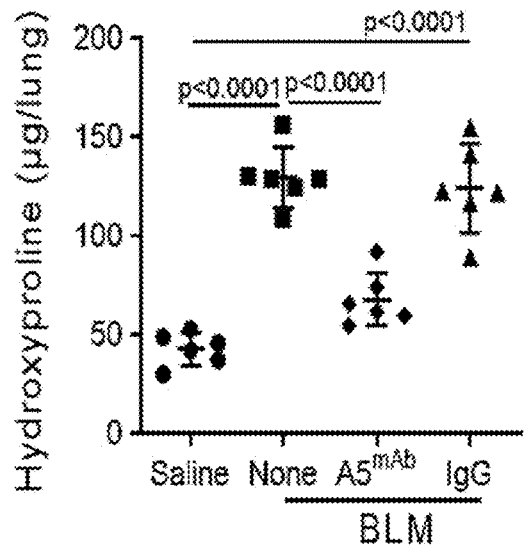
FIG. 22A
FIG. 22B

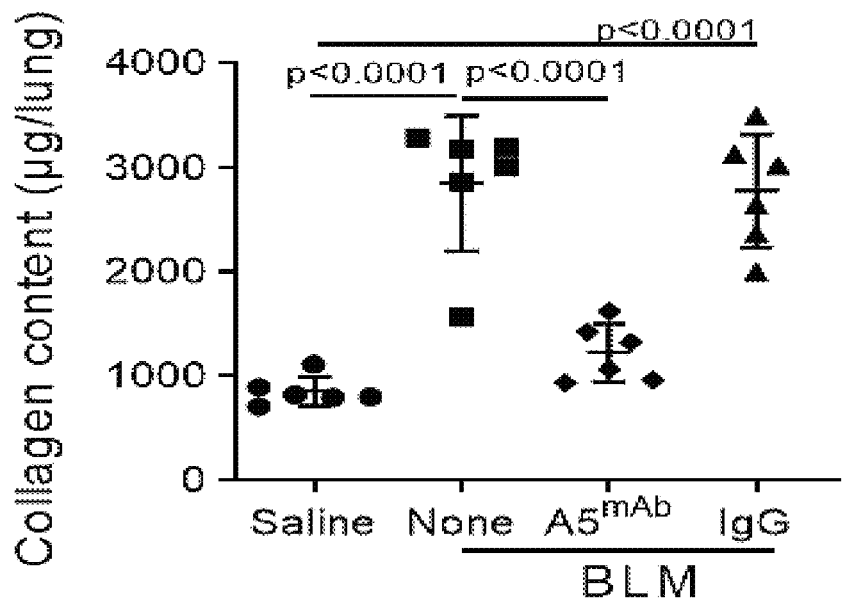
FIG. 22C
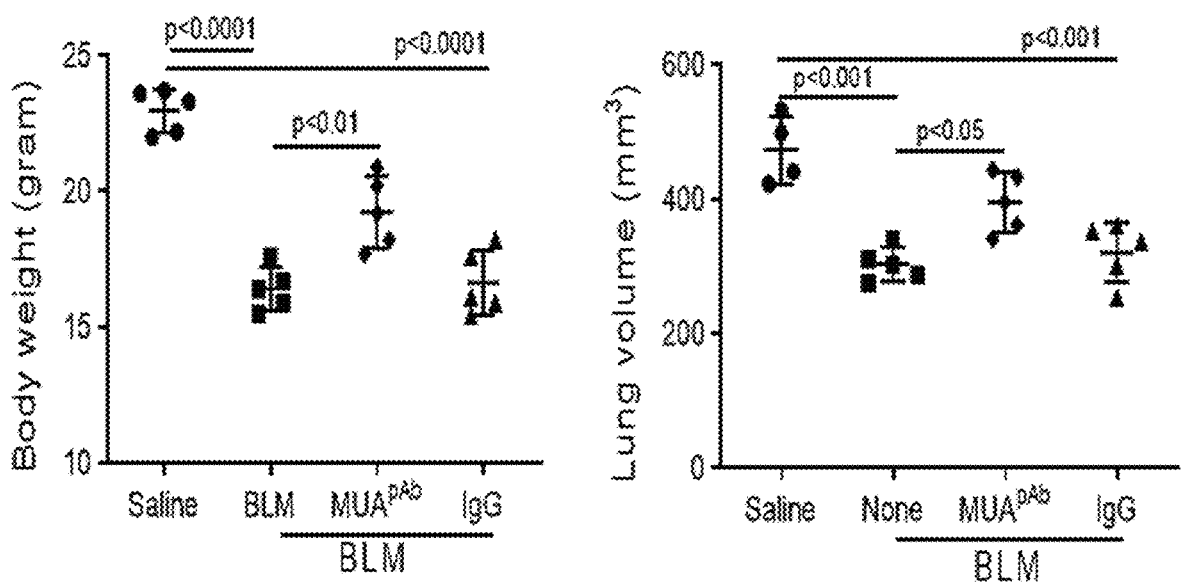
FIG. 23A
FIG. 23C

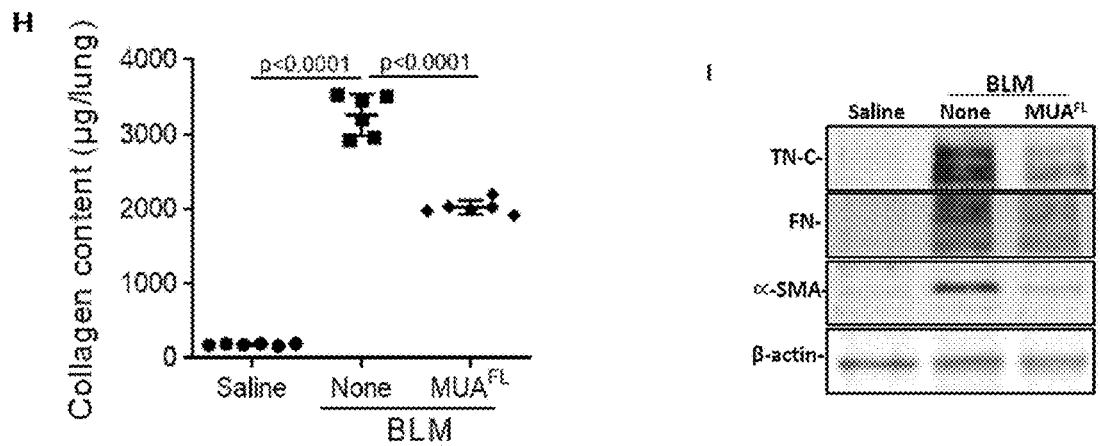
FIG. 24H
FIG. 24I
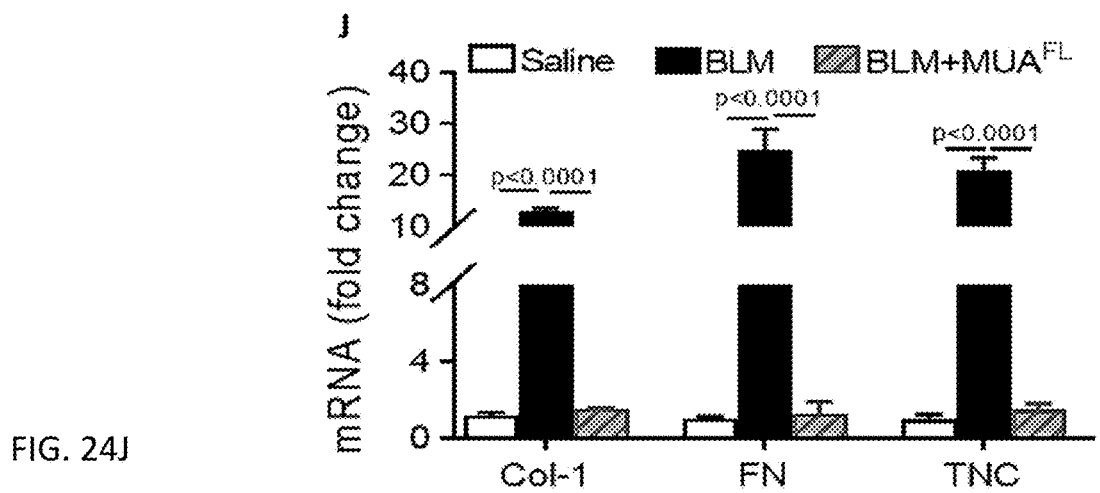
FIG. 24J
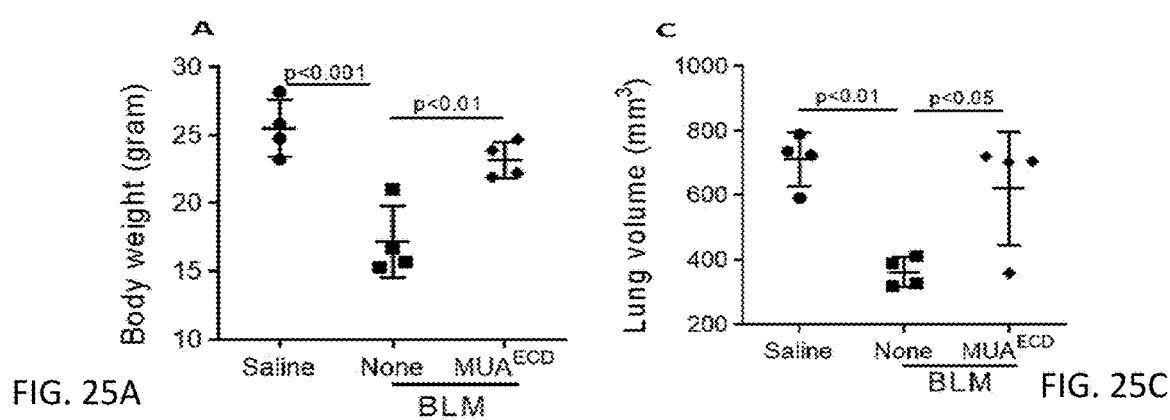
FIG. 25A
FIG. 25C

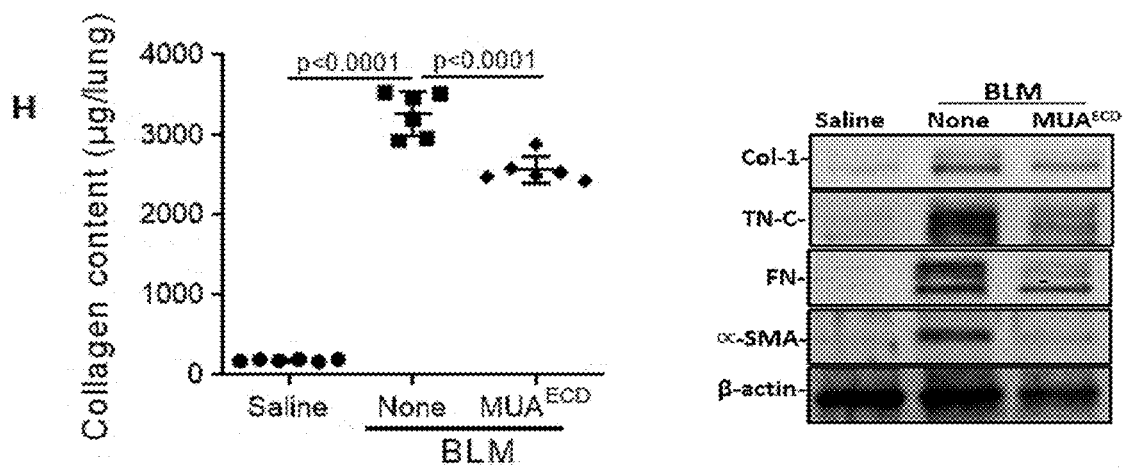
FIG. 25H
FIG. 25I
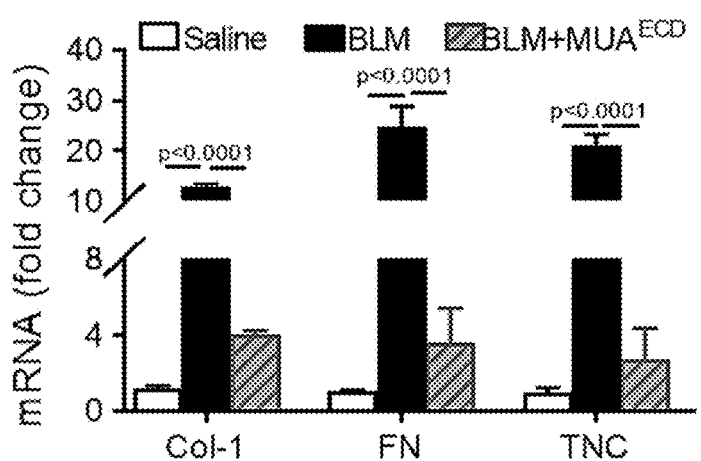
FIG. 25J

COMPOSITIONS AND METHODS FOR TREATMENT OF CHRONIC LUNG DISEASES

CROSS-REFERENCE TO RELATED APPLICATION

This application is a continuation of PCT/US2022/023992 filed Apr. 8, 2022, which claims the benefit of U.S. Provisional Application No. 63/172,980, filed Apr. 9, 2021, the entire contents of which are hereby fully incorporated herein by reference.

STATEMENT REGARDING FEDERALLY SPONSORED RESEARCH

This invention was made with government support under Grant No. R01HL151397 awarded by the National Institutes of Health. The government has certain rights in the invention.

FIELD OF THE INVENTION

The present invention is in the field of biochemistry and medicine and directed to methods and composition for treating, ameliorating, improving or otherwise reducing symptoms of diseases, such as pulmonary conditions.

REFERENCE TO AN ELECTRONIC SEQUENCE LISTING

The entire contents of the electronic sequence listing ("4842-106US2.xml," 98,304 bytes, created on Oct. 5, 2023) are incorporated herein by reference.

BACKGROUND OF THE INVENTION

Interstitial lung diseases (ILDs) are characterized by progressive pulmonary scarring. Idiopathic pulmonary fibrosis (IPF) is one of the most common and fatal forms of ILDs with an incidence of 60 cases/100,000 individuals in the U.S. annually. IPF has a median five-year survival of only 20%. There is presently no cure.

IPF is a poorly understood progressive and fatal lung disease for which no treatment exists other than lung transplantation (Mason D P et al., Ann Thorac Surg 84:1121-8, 2007). Median survival of five years after diagnosis is less than 20%. Most forms of interstitial lung diseases and other forms of pulmonary fibrosis are characterized by fibrotic lesions, progressive distortion of alveolar architecture occurs and replacement with fibrotic or scar tissues with excess extracellular matrix (ECM) deposition (American Thoracic Society, *Am J Respir Crit Care Med* 161:646-664, 2000; Noble P W et al., *Clin Chest Med* 25:749-758, 2004; Selman M et al., *Ann Intern Med* 134:136-151, 2001). This results in progressive dyspnea and loss of lung function. A hallmark morphological lesion is spatial and temporal heterogeneity incorporating areas of normal lung being directly adjacent to areas of fully established fibrosis, microscopic honeycombing, and areas of evolving fibrosis containing actively proliferating and collagen-producing fibroblasts/myofibroblasts, the so called "fibrotic foci".

Increased fibrotic lung fibroblasts (fLfs) (or myofibroblast)) viability, activation, production and deposition of ECM typify IPF lungs (Selman M et al., Expert Opin Emerg Drugs 16:341-62, 2011; Shetty, S et al. *Am J Respir Cell Mol Biol* 15:78-87, 1996; Zhu S et al., Am J Physiol: Lung Cell Mol Physiol 297:L97-108, 2009; Suganuma H et al., Thorax 50:984-9,1995; American Thoracic Society, supra; Noble P W et al., supra).

The pathogenesis of IPF is characterized by loss of alveolar epithelial cell (AEC) renewal capacity due to senescence and apoptosis, proliferation and accumulation of activated fLfs and extracellular matrix deposition. These features lead to progressive lung dysfunction. Morphologic changes include spatial and temporal heterogeneity incorporating areas of normal lung adjacent to diseased areas containing apoptotic AECs, and fLfs.

Previous work by the present inventor and his colleagues as well as by others showed that lung fibroblasts including fL-fibroblasts (fLfs) from the lungs of IPF patients express urokinase-type plasminogen activator (uPA), uPA receptor, (uPAR) and plasminogen activator inhibitor-1 (PAI-1) (Shetty et al., 1996, supra; Shetty S and Idell S. *Am J Physiol* 274:L871-L882, 1998; Chang W et al., J Biol Chem 285: 8196-206, 2010). uPA is mitogenic for both normal lung (nL) and fLfs, and the process involves uPA binding to uPAR through the uPA growth factor domain (Tkachuk V et al., Clin Exp Pharmacol Physiol 23:759-65, 1996; Padró T et al., J Cell Sci 115:1961-71, 2002; Shetty S et al., *Am J Physiol* 268:L972-L982, 1995; Shetty S et al., *Antisense Res Dev* 5:307-314, 1995). In addition, uPA augments uPAR expression (Shetty S et al., J Biol Chem 276:24549-56, 2001; Shetty S et al., Am J Respir Cell Mol Biol 30:69-75, 2004). Several years ago, the present inventor and colleagues reported that fLfs from IPF lungs express significantly more uPA and uPAR, and show a higher rate of basal and uPA-mediated proliferation than the nL-fibroblasts (nLfs) (Shetty et al., 1996, supra; 1998, supra). Other groups confirmed that increased uPAR expression by fLfs from patients with IPF contributes to the migratory behavior (Mace K A et al., J Cell Sci 118:2567-77, 2005; Basire A et al., Thromb Haemost 95:678-88, 2006; Zhu, S. et al., 2009, supra.

Studies by the present inventor and colleagues found that uPA regulates epithelial cell apoptosis/survival through regulation of p53 (Shetty S et al., 2005, supra) which controls reciprocal expression of uPA (Shetty P et al., *Am J Resp Cell Mol Biol,* 39:364-72,2008), its receptor uPAR (Shetty S et al., *Mol Cell Biol* 27:5607-18, 2007) and its major inhibitor PAI-1 (Shetty S et al., *J Biol. Chem* 283: 19570-80, 2008) at the posttranscriptional level and involves a novel cell surface signaling interaction between uPA, uPAR, caveolin-1 ("Cav-1") and β1-integrin (Shetty S et al., 2005, supra).

During lung fibrosis (which term is used interchangeably with "pulmonary" fibrosis), expression of the transcriptional factor p53, known primarily as a tumor suppressor protein, is severely suppressed in fLfs which in turn induces expression of uPA and uPAR while PAI-1 expression is significantly inhibited (Nagaraja et al., 2019). Suppression of PAI-1 expression and concurrent induction of uPA and uPAR expression as a consequence of inhibition of p53 expression leads to fLf proliferation and ECM deposition, i.e., fibrosis.

The present inventor and colleagues found that the caveolin-1 (Cav1) polypeptide was increased in injured AECs while its level was markedly reduced in proliferating fLfs from the lungs of IPF patients and mice with established PF. They identified a 20-mer Cav1 scaffolding domain peptide (CSP), and its truncated 7-mer fragment, CSP7, that inhibited p53, TGF-β, CTGF, AEC apoptosis and fLf expansion. These peptides blocked PF in mice after single (1×) or multi-hit (8×) bleomycin (BLM)-, adenoviral TGF-β1 (Ad-TGF-β1)-, silica- and thoracic radiation-induced lung injury.

CSP7 inhibited degradation of p53 due to increased mdm2 expression in fLfs and blocks their proliferation. CSP7 also inhibited AEC senescence and apoptosis, which are otherwise increased in fibrotic lungs, including in IPF. CSP7 was well-tolerated in mice and could be delivered effectively via the airways (Marudamuthu et al., 2019).

ALG5 is dolichyl-phosphate beta-glucosyltransferase, a member of the family of glycosyltransferases, specifically the hexosyltransferases that catalyzes the chemical reaction between UDP-glucose and UDP with dolichyl phosphate. ALG5 is widely expressed in pancreas, placenta, liver, heart, brain, kidney, skeletal muscle, and lung.

U.S. Pat. No. 7,655,628 (to Plater-Zyberk et al.) discloses a method for treating liver cirrhosis or interstitial pulmonary fibrosis, comprising administering to a patient in need thereof a polypeptide that binds to Wnt protein to competitively inhibit the binding of Wnt protein to its receptor and to treat liver cirrhosis or interstitial pulmonary fibrosis. That polypeptide is selected from a given group of specific Seq IDs.

Ding et al., *Int J Clin Exp Pathol* 11:3835-45 (2018) describes the association of UNC5A expression with the clinicopathologic features and prognosis of radiotherapy in patients with non-small-cell lung cancer.

US Pat. Publ. 2010/0215588 (Skaliter) teaches methods of treating respiratory disorders of all types, including pulmonary disorders, by delivering inhibitory siRNAs or other nucleic acid molecules directly to the respiratory system. Paragraph [0065] notes that the nucleic acids inhibit expression of UNC5A.

Miyamoto Y et al., *Int J Oncol* 36:1253-60 (2010) identified UNC5A as a novel transcriptional target of tumor suppressor p53 and a regulator of apoptosis.

Caveolin-1-Derived Peptides

As noted above, the present inventor and colleagues discovered initially that a 20 residue peptide DGIWKASFTTFTVTKYWFYR (SEQ ID NO: 10) which is the scaffolding domain of caveolin-1 (Cav-1) protected lung epithelial cells (LECs) from bleomycin ("BLM")-induced apoptosis in vitro and in vivo and prevented subsequent pulmonary fibrosis by attenuating lung epithelial damage (Shetty et al., U.S. patent application Ser. No. 12/398,757 published as U.S. 2009-0227515A1 (Sep. 10, 2009) and issued as U.S. Pat. No. 8,697,840 (Apr. 15, 2014)) and Shetty et al., PCT Pub. WO2014/145389 (Sep. 18, 2014), corresponding to U.S. application Ser. No. 14/775,895 published as U.S. Pat. Publ. 2016/0272678 (Sep. 22, 2014) and issued as U.S. Pat. No. 9,630,990 (Apr. 25, 2017), all of which are hereby incorporated by reference in their entirety.

The present inventor and colleagues also found a 17 residue peptide NYHYLESSMTALYTLGH (SEQ ID NO: 105), termed PP-2, that also protected LECs from BLM-induced apoptosis in vitro and in vivo and prevented subsequent pulmonary fibrosis by attenuating lung epithelial damage.

Shetty et al., 2009 and 2014 (supra) also described biologically active substitution, addition an deletion variants of these peptides as well as peptide multimers and deliverable polypeptides comprising the above peptides, and pharmaceutical compositions comprising the foregoing peptides, variants and multimers. Those compositions inhibit apoptosis of injured or damaged lung epithelial cells and treating acute lung injury and consequent pulmonary fibrosis/IPF.

Shetty et al. 2014 (U.S. Pat. No. 9,630,990) identified a particular fragment of CSP now termed CSP7, which has the sequence FTTFTVT (SEQ ID NO: 11) and which has the biological activity of CSP. More recently the present inventor's group has described formulations of CSP7 as an inhaled peptide therapeutic for, inter alia, idiopathic pulmonary fibrosis (Surasaranga et al., *Drug Devel. Indust. Pharmacy*, 44:184-98, 2018;) which are also used in the methods of the present invention.

In view of the poor prognosis and lack of therapeutic approaches for lung diseases such as IPF, there is an urgent need for new interventions to reverse or at least slow the progression of such diseases. This critical therapeutic gap is addressed by the present invention.

SUMMARY OF THE INVENTION

The present disclosure provides methods using antibodies, or polypeptide or fragments thereof for the treatment amelioration of pulmonary conditions such as IPF or pneumonia.

In one aspect, the present disclosure provides a method of treating, reducing, ameliorating or inhibiting symptoms idiopathic pulmonary fibrosis (IPF) or interstitial pneumonia, comprising administering to a subject in need thereof an effective amount of: a) multiple EGF-like-domains-9 (MEGF9) or a biologically active fragment thereof; b) uncoordinated receptor 5A (UNC5A) or a biologically active fragment thereof; c) dolichyl-phosphate beta-glucosyltransferase (ALG5) or a biologically active fragment thereof; d) a combination of two or three of a)-c); e) an antibody specifically binding to a); f) an antibody specifically binding to b); g) an antibody specifically binding to c); h) a combination of two or three of e)-g); or i) a combination of at least one of a)-c) and at least one of e)-g).

In some embodiments, the method comprises administering MEGF9 or a biologically active fragment thereof; and UNC5A or a biologically active fragment thereof. In some embodiments, the method comprises administering UNC5A or a biologically active fragment thereof; and ALG5 or a biologically active fragment thereof. In some embodiments, the method comprises administering MEGF9 or a biologically active fragment thereof; and ALG5 or a biologically active fragment thereof. In some embodiments, the method comprises administering MEGF9 or a biologically active fragment thereof; UNC5A or a biologically active fragment thereof; and ALG5 or a biologically active fragment thereof.

In some embodiments, the MEGF9 comprises the sequence of SEQ ID NO: 1, or a sequence with at least 80%, at least 85%, at least 90%, or at least 95% sequence identity to SEQ ID NO: 1. In some embodiments, the UNC5A comprises the sequence of SEQ ID NO: 5, or a sequence with at least 80%, at least 85%, at least 90%, or at least 95% sequence identity to SEQ ID NO: 5. In some embodiments, the ALG5 comprises the sequence of SEQ ID NO: 9, or a sequence with at least 80%, at least 85%, at least 90%, or at least 95% sequence identity to SEQ ID NO: 9. In some embodiments, the biologically active fragment of the MEGF9 comprises the sequence of SEQ ID NO: 3, or a sequence with at least 80%, at least 85%, at least 90%, or at least 95% sequence identity to SEQ ID NO: 3. In some embodiments, the biologically active fragment of the MEGF9 consists of the sequence of SEQ ID NO: 3, or a sequence with at least 80%, at least 85%, at least 90%, or at least 95% sequence identity to SEQ ID NO: 3. In some embodiments, the biologically active fragment of the MEGF9 comprises the sequence of SEQ ID NO: 4, or a one-amino acid or two-amino acid modification thereof. In some embodiments, the biologically active fragment of the MEGF9 consists of the sequence of SEQ ID NO: 4, or a one-amino acid or two-amino acid modification thereof. In some embodiments, the biologically active fragment of the MEGF9 comprises the sequence of SEQ ID NO: 102, or a sequence with at least 80%, at least 85%, at least 90%, or at least 95% sequence identity to SEQ ID NO: 102. In some embodiments, the biologically active fragment of the MEGF9 consists of the sequence of SEQ ID NO: 102, or a sequence with at least 80%, at least 85%, at least 90%, or at least 95% sequence identity to SEQ ID NO: 102. In some embodiments, the biologically active fragment of the UNC5A comprises the sequence of SEQ ID NO: 7, or a sequence with at least 80%, at least 85%, at least 90%, or at least 95% sequence identity to SEQ ID NO: 7. In some embodiments, the biologically active fragment of the UNC5A consists of the sequence of SEQ ID NO: 7, or a sequence with at least 80%, at least 85%, at least 90%, or at least 95% sequence identity to SEQ ID NO: 7. In some embodiments, the biologically active fragment of the UNC5A comprises the sequence of SEQ ID NO: 8, or a sequence with at least 80%, at least 85%, at least 90%, or at least 95% sequence identity to SEQ ID NO: 8. In some embodiments, the biologically active fragment of the UNC5A consists of the sequence of SEQ ID NO: 8, or a sequence with at least 80%, at least 85%, at least 90%, or at least 95% sequence identity to SEQ ID NO: 8. In some embodiments, the biologically active fragment of the UNC5A comprises the sequence of SEQ ID NO: 103, or a sequence with at least 80%, at least 85%, at least 90%, or at least 95% sequence identity to SEQ ID NO: 103. In some embodiments, the biologically active fragment of the UNC5A consists of the sequence of SEQ ID NO: 103, or a sequence with at least 80%, at least 85%, at least 90%, or at least 95% sequence identity to SEQ ID NO: 103. In some embodiments, the biologically active fragment of the ALG5 comprises the sequence of SEQ ID NO: 104, or a sequence with at least 80%, at least 85%, at least 90%, or at least 95% sequence identity to SEQ ID NO: 104. In some embodiments, the biologically active fragment of the ALG5 consists of the sequence of SEQ ID NO: 104, or a sequence with at least 80%, at least 85%, at least 90%, or at least 95% sequence identity to SEQ ID NO: 104.

In some embodiments, the method further comprises administering a Cav1 scaffolding domain peptide (CSP). In some embodiments, the CSP comprises a sequence of SEQ ID NO: 11 or a one-amino acid modification thereof.

In some embodiments, the method further comprises administering a), b), c), d), e), f), g), h), or i) to the subject in the form of a pharmaceutical composition that further comprises a pharmaceutically acceptable carrier. In some embodiments, the method further comprises administering the pharmaceutical composition via a route selected from the group consisting of intrapulmonary, intravenous, intramuscular, subcutaneous, oral, or in any combination thereof. In some embodiments, the route is intrapulmonary. In some embodiments, the intrapulmonary route is carried out by inhalation. In some embodiments, the route is intravenous. In some embodiments, the route is intratracheal. In some embodiments, the interstitial pneumonia is defined by radiographic and histologic presentation of lung scarring, extracellular matrix deposition, epithelial cell senescence and apoptosis, activation of myofibroblasts of fibrotic lung fibroblasts, M2 macrophage polarization and elaboration of profibrogenic cytokines, or a combination thereof. In some embodiments, the subject is a human.

In some embodiments, the method further comprises administering one or more additional therapeutic agents. In some embodiments, the one or more additional therapeutic agents comprises nintedanib, pirfenidone, or a combination thereof.

In another aspect, the present disclosure provides a vector comprising a nucleic acid molecule comprising one or more polynucleotides encoding: a) MEGF9 or a biologically active fragment thereof; b) UNC5A or a biologically active fragment thereof; c) ALG5 or a biologically active fragment thereof; d) a combination two or three of any of a-c; e) an antibody specifically binding to a); f) an antibody specifically binding to b); g) an antibody specifically binding to c); h) a combination of two or three of e)-g); or i) a combination of at least one of a)-c) and at least one of e)-g).

In another aspect, the present disclosure provides a cell comprising the vector herein.

In another aspect, the present disclosure provides a method of producing a therapeutic protein, comprising: culturing the cell herein in a culture medium under a condition sufficient to produce a therapeutic protein comprising any one of a), b), c), d), e), f), g), h), or i); and recovering the therapeutic protein from the cell or the culture medium. In some embodiments, the method further comprises isolating the therapeutic protein recovered from the cell or the culture medium. In some embodiments, the method further comprises formulating the therapeutic protein into a pharmaceutical composition.

In another aspect, the present disclosure provides a pharmaceutical composition comprising a pharmaceutically acceptable carrier and one of: a) MEGF9 or a biologically active fragment thereof; b) UNC5A or a biologically active fragment thereof; c) ALG5 or a biologically active fragment thereof; d) a combination of two or three of a)-c); e) an antibody specific for a); f) an antibody specific for b); g) an antibody specific for c); h) a combination of two or three of e)-g); or i) a combination of at least one of a)-c) and at least one of e)-g).

In some embodiments, the pharmaceutical composition comprises MEGF9 or a biologically active fragment thereof; and UNC5A or a biologically active fragment thereof. In some embodiments, the pharmaceutical composition comprises UNC5A or a biologically active fragment thereof; and ALG5 or a biologically active fragment thereof. In some embodiments, the pharmaceutical composition comprises MEGF9 or a biologically active fragment thereof; and ALG5 or a biologically active fragment thereof. In some embodiments, the pharmaceutical composition comprises MEGF9 or a biologically active fragment thereof; UNC5A or a biologically active fragment thereof; and ALG5 or a biologically active fragment thereof.

In some embodiments, the MEGF9 comprises the sequence of SEQ ID NO: 1, or a sequence with at least 80%, at least 85%, at least 90%, or at least 95% sequence identity to SEQ ID NO: 1. In some embodiments, the UNC5A comprises the sequence of SEQ ID NO: 5, or a sequence with at least 80%, at least 85%, at least 90%, or at least 95% sequence identity to SEQ ID NO: 5. In some embodiments, the ALG5 comprises the sequence of SEQ ID NO: 9, or a sequence with at least 80%, at least 85%, at least 90%, or at least 95% sequence identity to SEQ ID NO: 9. In some embodiments, the biologically active fragment of the MEGF9 comprises the sequence of SEQ ID NO: 3, or a sequence with at least 80%, at least 85%, at least 90%, or at least 95% sequence identity to SEQ ID NO: 3. In some embodiments, the biologically active fragment of the MEGF9 consists of the sequence of SEQ ID NO: 3, or a sequence with at least 80%, at least 85%, at least 90%, or at least 95% sequence identity to SEQ ID NO: 3. In some embodiments, the biologically active fragment of the MEGF9 comprises the sequence of SEQ ID NO: 4, or a one-amino acid or two-amino acid modification thereof. In some embodiments, the biologically active fragment of the MEGF9 consists of the sequence of SEQ ID NO: 4, or a one-amino acid or two-amino acid modification thereof. In some embodiments, the biologically active fragment of the MEGF9 comprises the sequence of SEQ ID NO: 102, or a sequence with at least 80%, at least 85%, at least 90%, or at least 95% sequence identity to SEQ ID NO: 102. In some embodiments, the biologically active fragment of the MEGF9 consists of the sequence of SEQ ID NO: 102, or a sequence with at least 80%, at least 85%, at least 90%, or at least 95% sequence identity to SEQ ID NO: 102. In some embodiments, the biologically active fragment of the UNC5A comprises the sequence of SEQ ID NO: 7, or a sequence with at least 80%, at least 85%, at least 90%, or at least 95% sequence identity to SEQ ID NO: 7. In some embodiments, the biologically active fragment of the UNC5A consists of the sequence of SEQ ID NO: 7, or a sequence with at least 80%, at least 85%, at least 90%, or at least 95% sequence identity to SEQ ID NO: 7. In some embodiments, the biologically active fragment of the UNC5A comprises the sequence of SEQ ID NO: 8, or a sequence with at least 80%, at least 85%, at least 90%, or at least 95% sequence identity to SEQ ID NO: 8. In some embodiments, the biologically active fragment of the UNC5A consists of the sequence of SEQ ID NO: 8, or a sequence with at least 80%, at least 85%, at least 90%, or at least 95% sequence identity to SEQ ID NO: 8. In some embodiments, the biologically active fragment of the UNC5A comprises the sequence of SEQ ID NO: 103, or a sequence with at least 80%, at least 85%, at least 90%, or at least 95% sequence identity to SEQ ID NO: 103. In some embodiments, the biologically active fragment of the UNC5A consists of the sequence of SEQ ID NO: 103, or a sequence with at least 80%, at least 85%, at least 90%, or at least 95% sequence identity to SEQ ID NO: 103. In some embodiments, the biologically active fragment of the ALG5 comprises the sequence of SEQ ID NO: 104, or a sequence with at least 80%, at least 85%, at least 90%, or at least 95% sequence identity to SEQ ID NO: 104. In some embodiments, the biologically active fragment of the ALG5 consists of the sequence of SEQ ID NO: 104, or a sequence with at least 80%, at least 85%, at least 90%, or at least 95% sequence identity to SEQ ID NO: 104.

In some embodiments, the pharmaceutical composition further comprises administering a Cav1 scaffolding domain peptide (CSP). In some embodiments, the CSP comprises a sequence of SEQ ID NO: 11 or a one-amino acid modification thereof.

In another aspect, the present disclosure provides use of a pharmaceutical composition herein for the treatment of an idiopathic pulmonary fibrosis or interstitial pneumonia in a subject.

In another aspect, the present disclosure provides use of a pharmaceutical composition herein for the manufacture of a medicament for treatment of an idiopathic pulmonary fibrosis or interstitial pneumonia in a subject. In some embodiments, the interstitial pneumonia is defined by radiographic and histologic presentation of lung scarring, extracellular matrix deposition, epithelial cell senescence and apoptosis, activation of myofibroblasts of fibrotic lung fibroblasts, M2 macrophage polarization and elaboration of pro-fibrogenic cytokines, or a combination thereof.

BRIEF DESCRIPTION OF THE DRAWINGS

FIGS. 1A-1B. Differential expression of UNC5A (U5a) and MEGF9 (M9) in injured human AECs and fLfs. Western blotting (FIG. 1A) and qPCR (FIG. 1B) for M9 and U5a protein and mRNA in AECs and Lfs isolated from normal lung of healthy donors (nL) or lung tissue from IPF patient (IPF). M9 was upregulated in IPF fLfs while U5a was highly expressed in injured AECs.

FIG. 7A: Representative micro-CT images on day 21 after BLM. Lung volumes (FIG. 7B) were measured by quantitative-CT renditions, and lung compliance (FIG. 7C) and elastance (FIG. 7D) were measured using a flexiVent system. FIG. 7E: Lung weights presented as a bar graph. FIG. 7F: Trichrome-stained lung sections. Lung homogenates were tested for hydroxyproline (FIG. 7G), soluble collagen (FIG. 7H) and pro-fibrogenic marker protein (FIG. 7I), and respective mRNAs (FIG. 7J), survival (FIG. 7K), and protein levels of additional pro-fibrogenic markers (FIG. 7L). Bars indicate mean±SD. Statistical significance (*P<0.05, P<0.01, *P<0.001 and ****P<0.0001) was assessed by one-way ANOVA with Turkey's multiple comparison. FIG. 7M shows fLfs (IPF) treated with PBS or M9$^{pAb}$ (2 μg/ml) in vitro and tested for pro-fibrogenic proteins and mRNAs.

FIG. 8A: Representative micro-CT images on d. 21 after BLM. Results obtained on d. 21 after BLM. Lung volumes (FIG. 8B) were measured by quantitative-CT renditions. Lung compliance (FIG. 8C) and elastance (FIG. 8D) were measured using a flexiVent system. Lung weights (FIG. 8E), survival curve (FIG. 8F) and body weights (FIG. 8G) are presented as bar graphs. Lung homogenates were tested for hydroxyproline (FIG. 8H), soluble collagen (FIG. 8I), and pro-fibrogenic marker proteins (FIG. 8J) and mRNAs (FIG. 8K). Trichrome-stained lung sections are shown in FIG. 8L. Vertical bars indicate mean±SD. Statistical significance (*P<0.05, P<0.01, *P<0.001 and ****P<0.0001) was assessed by one-way ANOVA with Turkey's multiple comparison.

FIG. 9A: Representative micro-CT images at d21 after BLM exposure.

FIG. 10A: Representative micro-CT images at d21 after BLM exposure. FIG. 10B: Lung volumes were measured by quantitative-CT renditions. Lung compliance (FIG. 10C) and elastance (FIG. 10D) were measured using a flexiVent system. Lung weights (FIG. 10E) and body weights (FIG. 10F) are presented as bar graphs. Lung homogenates were tested for hydroxyproline (FIG. 10G), soluble collagen (FIG. 10H), pro-fibrogenic marker proteins (FIG. 10I) and mRNAs (FIG. 10J). Trichrome staining of lung sections are shown in FIG. 10K. Bars indicate mean±SD. Statistical significance (*P<0.05, P<0.01, *P<0.001 and ****P<0.0001) was assessed by one-way ANOVA with Turkey's multiple comparison.

FIG. 11A: Representative micro-CT images at d21 after BLM exposure. FIG. 11B: Lung volumes were measured by quantitative-CT renditions. Lung compliance (FIG. 11C) and elastance (FIG. 11D) were measured using a flexiVent system. Lung weights (FIG. 11E) and body weights (FIG. 11F) are presented as bar graphs. Lung homogenates were tested for hydroxyproline (FIG. 11G), soluble collagen (FIG. 11H), pro-fibrogenic marker proteins (FIG. 11I) and mRNAs (FIG. 11J). Trichrome staining of lung sections is shown in FIG. 11K. Bars indicate mean±SD. *P<0.05, P<0.01, *P<0.001 and ****P<0.0001 were obtained by one-way ANOVA with Turkey's multiple comparison.

FIGS. 12A-12E. WT mice with BLM-PF were treated with or without rM9$^{ECD}$ (1.5 mg/kg) via intratracheal (IT) instillation daily for 7 d starting d 14 after BLM. Survival (FIG. 12A), body weights (FIG. 12B), lung volumes (FIG. 12C) and lung weights (FIG. 12D) were measured on d 21 post-BLM. Lung homogenates were tested for soluble collagen (FIG. 12E). All tests suggest resolution of existing PF by IT delivered rM9$^{ECD}$ FIGS. 13A-13B. FIG. 13A: fLfs (IPF) treated with PBS or M9$^{mAb}$ (2 μg/ml) or control IgG, tested for pro-fibrogenic proteins (i) and mRNAs (ii). FIG. 13B: WT mice with BLM-PF were left untreated, or intraperitoneal (IP) injected with control IgG or M9$^{mAb}$ (2.5 mg/kg) daily for 7 d starting 14 d after IT BLM. Body weights (i) and total lung hydroxyproline (ii), and soluble collagen (iii) were measured. Like M9$^{pAb}$, M9$^{mAb}$ developed against M9$^{ECD}$ inhibited pro-fibrogenic markers in fLfs and resolved BLM-induced PF in mice.

FIGS. 16A-16J. Recombinant extracellular domain of U5a (U5a$^{ECD}$) protein mitigated BLM-induced pulmonary fibrosis. Mice exposed to saline or 1.0 U/kg BLM by IT instillation were IP injected with or without U5a$^{ECD}$ (7.5 mg/kg) daily for 7 days starting day 14 after BLM injury. Total body weight (FIG. 16A), micro-CT images (FIG. 16B), and lung volumes (FIG. 16C) were measured by quantitative-CT renditions, and lung compliance (FIG. 16D) and elastance (FIG. 16E) were measured using a flexiVent system on day 21 post-BLM. Lung weights (FIG. 16F) were measured on day 21 post-BLM. Lung homogenates were analyzed for total hydroxyproline (FIG. 16G), soluble collagen (FIG. 16H), pro-fibrogenic marker proteins (FIG. 16I) and their mRNAs (FIG. 16J) day 21 after BLM.

FIGS. 17A-17C. A monoclonal antibody (U5a$^{mAb}$) developed against U5a$^{ECD}$ mitigated BLM-induced pulmonary fibrosis. Mice exposed to saline or 1.0 U/kg BLM by intratracheal instillation received intraperitoneal injections with or without U5a$^{mAb}$ (2.5 mg/kg) daily for 7 days starting day 14 after BLM injury. Body weights (FIG. 17A) were measured day 21 after BLM. Lung homogenates were analyzed for hydroxyproline (FIG. 17B) and soluble collagen (FIG. 17C) day 21 after BLM.

FIG. 18. Differential expression of ALG5 (A5) protein in human nLfs and fLfs. Normal lung fibroblasts (nLfs) were isolated from nL tissues from control subjects and fibrotic lung fibroblasts were isolated from fibrotic lung (fL) tissues from patients with IPF. Membrane proteins extracted from nLfs and fLfs were subjected to Western blotting using anti-A5 and anti-β-actin antibodies.

FIGS. 19A-19K. A polyclonal A5 antibody (A5$^{pAb}$) mitigated BLM-induced pulmonary fibrosis. Mice exposed to saline or 1.0 U/kg BLM by intratracheal instillation received intraperitoneal injections with or without A5$^{pAb}$ (2.5 mg/kg) daily for 7 days starting d14 after BLM injury. Percent Survival (FIG. 19A) were shown. Total body weight (FIG. 19B), micro-CT images (FIG. 19C) and lung volumes (FIG. 19D) were measured by quantitative-CT renditions, and lung compliance (FIG. 19E) and elastance (FIG. 19F) were measured using a flexiVent system on day 21 post-BLM. Lung weight (FIG. 19G) were measured on day 21 post-BLM. Lung homogenates were analyzed for total hydroxyproline (FIG. 19H), soluble collagen (FIG. 19I), pro-fibrogenic marker proteins (FIG. 19J) and their mRNAs (FIG. 19K).

FIGS. 20A-20K. Recombinant full length A5 (A5$^{FL}$) protein mitigated BLM-induced pulmonary fibrosis. Mice exposed to saline or 1.0 U/kg BLM by intratracheal instillation were IP injected with or without A5$^{FL}$ (7.5 mg/kg) daily for 7 days starting d14 after BLM injury. Total body weight (FIG. 20A), micro-CT images (FIG. 20B) and lung volumes (FIG. 20C) were measured by quantitative-CT renditions and lung compliance (FIG. 20D) and elastance (FIG. 20E) were measured using a flexiVent system on day 21 post-BLM. Lung weight (FIG. 20F) were measured on day 21 post-BLM. Lung homogenates were analyzed for total hydroxyproline (FIG. 20G), soluble collagen (FIG. 20H), pro-fibrogenic marker proteins (FIG. 20I) and their mRNAs (FIG. 20J) d21 after BLM. Lung sections were subjected H&E and Trichrome staining (FIG. 20K) assess lung architectural distortion and collagen and other extracellular matrix deposition.

FIGS. 21A-21I. Recombinant extracellular domain of A5 (A5$^{ECD}$) protein mitigated BLM-induced pulmonary fibrosis. Mice exposed to saline or 1.0 U/kg BLM by intratracheal instillation were IP injected with or without A5$^{ECD}$ (7.5 mg/kg) daily for 7 days starting d14 after BLM injury. Total body weight (FIG. 21A), micro-CT images (FIG. 21B) and lung volumes (FIG. 21C) were measured by quantitative-CT renditions and lung compliance (FIG. 21D) and elastance (FIG. 21E) were measured using a flexiVent system on day 21 post-BLM. Lung homogenates were analyzed for total hydroxyproline (FIG. 21F), soluble collagen (FIG. 21G), pro-fibrogenic marker proteins (FIG. 21H) and their mRNAs (FIG. 21I) d21 after BLM.

FIGS. 22A-22C. A monoclonal antibody (A5$^{mAb}$) developed against A5$^{ECD}$ mitigated BLM-induced pulmonary fibrosis. Mice exposed to saline or 1.0 U/kg BLM by intratracheal instillation received intraperitoneal injections with or without A5$^{mAb}$ Ab (2.5 mg/kg) daily for 7 days starting day 14 after BLM injury. Body weights (FIG. 22A) were measured day 21 after BLM. Lung homogenates were analyzed for hydroxyproline (FIG. 22B) and soluble collagen (FIG. 22C) day 21 after BLM.

FIGS. 23A to 23J. A combination of polyclonal antibodies against M9, U5a, and A5 respectively (MUA$^{pAb}$) mitigated BLM-induced pulmonary fibrosis. Mice exposed to saline or 1.0 U/kg BLM by intratracheal (IT) instillation received intraperitoneal (IP) injections with or without MUA$^{pAb}$ (2.5 mg/kg) daily for 7 days starting day 14 after BLM injury. Total body weight (FIG. 23A), micro-CT images (FIG. 23B) and lung volumes (FIG. 23C) were measured by quantitative-CT renditions, and lung compliance (FIG. 23D) and elastance (FIG. 23E) were measured using a flexiVent system on day 21 post-BLM. Lung weights (FIG. 23F) were measured on day 21 post-BLM. Lung homogenates were analyzed for total hydroxyproline (FIG. 23G), soluble collagen (FIG. 23H), pro-fibrogenic marker proteins (FIG. 23I) and their mRNAs (FIG. 23J).

FIGS. 24A-24J. Recombinant full length proteins of M9, U5a, and A5 (MUA$^{FL}$) protein mitigated BLM-induced pulmonary fibrosis. Mice exposed to saline or 1.0 U/kg BLM by IT instillation were IP injected with or without MUA$^{FL}$ (7.5 mg/kg together) daily for 7 days starting day 14 after BLM injury. Total body weight (FIG. 24A), micro-CT images (FIG. 24B) and lung volumes (FIG. 24C) were measured by quantitative-CT renditions and lung compliance (FIG. 24D) and elastance (FIG. 24E) were measured using a flexiVent system on day 21 post-BLM. Lung weights (FIG. 24F) were measured on day 21 post-BLM. Lung homogenates were analyzed for total hydroxyproline (FIG. 24G), soluble collagen (FIG. 24H), pro-fibrogenic marker proteins (FIG. 24I) and their mRNAs (FIG. 24J) day 21 after BLM.

FIGS. 25A-25J. Recombinant extracellular domain peptides of M9, U5a, and A5 (MUA$^{ECD}$) protein mitigated BLM-induced pulmonary fibrosis. Mice exposed to saline or 1.0 U/kg BLM by IT instillation were IP injected with or without MUA$^{ECD}$ (7.5 mg/kg together) daily for 7 days starting day 14 after BLM injury. Total body weight (FIG. 25A), micro-CT images (FIG. 25B) and lung volumes (FIG. 25C) were measured by quantitative-CT renditions, and lung compliance (FIG. 25D) and elastance (FIG. 25E) were measured using a flexiVent system on day 21 post-BLM. Lung weights (FIG. 25F) were measured on day 21 post-BLM. Lung homogenates were analyzed for total hydroxyproline (FIG. 25G), soluble collagen (FIG. 25H), pro-fibrogenic marker proteins (FIG. 25I) and their mRNAs (FIG. 25J) day 21 after BLM.

DETAILED DESCRIPTION

Figure 2A:
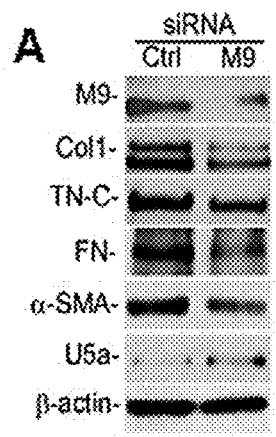
FIGS. 2A-2D. M9 regulated U5a and differentiation of fLfs. Inhibition of M9 using siRNA rescued basal expression of U5a and inhibited pro-fibrogenic marker proteins (FIG. 2A) and mRNAs (FIG. 2B) in fLfs. Overexpression of M9 inhibited U5a and induced pro-fibrogenic proteins (FIG. 2C) and mRNAs (FIG. 2D) in nLfs, suggesting, an intricate link between expression of M9 and U5a, and differentiation of lung fibroblasts (Lfs).

The present disclosure provides compositions and methods for treating pulmonary conditions, e.g., idiopathic pulmonary fibrosis (IPF) and interstitial pneumonia. In one aspect, the present disclosure provides compositions comprising one or more of: multiple EGF-like-domains-9 (MEGF9), uncoordinated receptor 5A (UNC5A), and dolichyl-phosphate beta-glucosyltransferase (ALG5) proteins, biologically active fragments thereof, and antibodies specific for these proteins, as therapeutic agents. In other aspects, the present disclosure provides related pharmaceutical compositions, nucleic acids, vectors, methods of manufacturing the compositions, and methods of using the compositions for treating idiopathic pulmonary fibrosis (IPF) or interstitial pneumonia.

Therapeutic Agents

In some embodiments, the composition comprises one or more therapeutic agents. In some examples, the composition comprises MEGF9 or a biologically active fragment thereof. In some examples, the composition comprises UNC5A or a biologically active fragment thereof. In some examples, the composition comprises ALG5 or a biologically active fragment thereof. In some examples, the composition comprises MEGF9 or a biologically active fragment thereof, and UNC5A or a biologically active fragment thereof. In some examples, the composition comprises MEGF9 or a biologically active fragment thereof, and ALG5 or a biologically active fragment thereof. In some examples, the composition comprises UNC5A or a biologically active fragment thereof, and ALG5 or a biologically active fragment thereof. In some examples, the composition comprises MEGF9 or a biologically active fragment thereof, UNC5A or a biologically active fragment thereof, and ALG5 or a biologically active fragment thereof. In some examples, the composition comprises an antibody specifically binding to MEGF9. In some examples, the composition comprises an antibody specifically binding to UNC5A. In some examples, the composition comprises an antibody specifically binding to ALG5. In some examples, the composition comprises an antibody specifically binding to MEGF9, and an antibody specifically binding to UNC5A. In some examples, the composition comprises an antibody specifically binding to MEGF9, and an antibody specifically binding to ALG5. In some examples, the composition comprises an antibody specifically binding to UNC5A, and an antibody specifically binding to ALG5. In some examples, the composition comprises an antibody specifically binding to MEGF9, an antibody specifically binding to UNC5A, and an antibody specifically binding to ALG5.

A "biologically active fragment" of a protein refers to a peptide whose the amino acid sequence may include less amino acids than the corresponding full-length protein but still enough amino acids to confer the activity or function of the corresponding full-length protein. For example, a biologically active fragment of a protein may have at least 20% of the biological or biochemical activity of the corresponding full-length protein (e.g., as measured by an in vitro or an in vivo assay). In some examples, the biologically active peptide may have an increase biological or biochemical activity as compared to the corresponding full-length protein.

UNC5A and Biologically Active Fragments Thereof

In some embodiments, the composition comprises UNC5A (also referred to as "U5A," "U5a," or "U5"), biologically active fragments thereof, and/or antibodies specifically binding to UNC5A or biologically active fragments thereof. The UNC5A may be a human UNC5A. In one example, the UNC5A may comprise the sequence of SEQ ID NO: 5 (full-length human UNC5A with signal peptide, Accession Number Q6ZN44, see uniprot.org/uniprot/Q6ZN44). The protein of SEQ ID NO: 5 comprises the following domains: signal peptide (amino acids 1-25), Ig-like domain (amino acids 44-141 of SEQ ID NO: 5), Ig-like C2-type domain (amino acids 155-234 of SEQ ID NO: 5), TSP type-1 domain (amino acids 242-294 of SEQ ID NO: 5), ZU (interacting with Netrin receptor DCC) (amino acids 441-584 of SEQ ID NO: 5), and death domain (amino acids 761-841 of SEQ ID NO: 5). In some examples, the biologically active fragment of the UNC5A may comprise a sequence in the ECD of UNC5A, e.g., amino acids 26-306 of SEQ ID NO: 5. In some aspects, the present disclosure includes the polypeptide having SEQ ID NO: 103.

In some examples, the UNC5A may comprise a sequence with at least 80%, e.g., at least 85%, at least 90%, at least 95%, or at least 99% identity to SEQ ID NO: 5. In some examples, the UNC5A may consist of the sequence of SEQ ID NO: 5. In some examples, the UNC5A may consist of a sequence with at least 80%, e.g., at least 85%, at least 90%, at least 95%, or at least 99% identity to SEQ ID NO: 5.

In some examples, the UNC5A may comprise a mature protein without the signal peptide (SEQ ID NO: 6). In some examples, the UNC5A may comprise a sequence with at least 80%, e.g., at least 85%, at least 90%, at least 95%, or at least 99% identity to SEQ ID NO: 6. In some examples, the UNC5A may consist of the sequence of SEQ ID NO: 6. In some examples, the UNC5A may consist of a sequence with at least 80%, e.g., at least 85%, at least 90%, at least 95%, or at least 99% identity to SEQ ID NO: 6.

In some examples, a biologically active fragment of the UNC5A may comprise the sequence of SEQ ID NO: 7. In some examples, the biologically active fragment of the UNC5A may comprise a sequence with at least 80%, e.g., at least 85%, at least 90%, at least 95%, or at least 99% identity to SEQ ID NO: 7. In some examples, the biologically active fragment of the UNC5A may consist of the sequence of SEQ ID NO: 7. In some examples, the biologically active fragment of the UNC5A may consist of a sequence with at least 80%, e.g., at least 85%, at least 90%, at least 95%, or at least 99% identity to SEQ ID NO: 7.

In some examples, the biologically active fragment of the UNC5A may comprise the sequence of SEQ ID NO: 8. In some examples, the biologically active fragment of the UNC5A may comprise a sequence with at least 80%, e.g., at least 85%, at least 90%, at least 95%, or at least 99% identity to SEQ ID NO: 8. In some examples, the biologically active fragment of the UNC5A may consist of the sequence of SEQ ID NO: 8. In some examples, the biologically active fragment of the UNC5A may consist of a sequence with at least 80%, e.g., at least 85%, at least 90%, at least 95%, or at least 99% identity to SEQ ID NO: 8.

In some examples, the biologically active fragment of the UNC5A may comprise the sequence of SEQ ID NO: 103. In some examples, the biologically active fragment of the UNC5A may comprise a sequence with at least 80%, e.g., at least 85%, at least 90%, at least 95%, or at least 99% identity to SEQ ID NO: 103. In some examples, the biologically active fragment of the UNC5A may consist of the sequence of SEQ ID NO: 103. In some examples, the biologically active fragment of the UNC5A may consist of a sequence with at least 80%, e.g., at least 85%, at least 90%, at least 95%, or at least 99% identity to SEQ ID NO: 103.

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software. A protein or peptide has a certain percentage (for example, 80%, 85%, 90%, or 95%) of "sequence identity" or "homology" to another sequence means that, when aligned, that percentage of bases (or amino acids) are the same in comparing the two sequences. This alignment and the percent homology or sequence identity may be determined using software programs known in the art, for example those described in Current Protocols In Molecular Biology (F. M. Ausubel et al., eds., 1987) Supplement 30, section 7.7.18, Table 7.7.1.

MEGF9 and Biologically Active Fragments Thereof

In some embodiments, the composition comprises a MEGF9 (also referred to as "M9"), biologically active fragments thereof, and/or antibodies specifically binding to MEGF9 or biologically active fragments thereof. The MEGF9 may be a human MEGF9. In one example, the MEGF9 may comprise the sequence of SEQ ID NO: 1 (full-length human MEGF9 with signal peptide, Accession Number Q9H1U4, see uniprot.org/uniprot/Q9H1U4). The protein of SEQ ID NO: 1 comprises the following domains: signal peptide (amino acids 1-30 of SEQ ID NO: 1), extracellular domain (ECD) (amino acids 31-514 of SEQ ID NO: 1), Transmembrane (helical) domain (amino acids 515-535 of SEQ ID NO: 1), cytoplasmic domain (amino acids 536-602 of SEQ ID NO: 1), and the polypeptide having SEQ ID NO: 102.

In some examples, the MEGF9 may comprise a sequence with at least 80%, e.g., at least 85%, at least 90%, at least 95%, or at least 99% identity to SEQ ID NO: 1. In some examples, the MEGF may consist of the sequence of SEQ ID NO: 1. In some examples, the MEGF may consist of a sequence with at least 80%, e.g., at least 85%, at least 90%, at least 95%, or at least 99% identity to SEQ ID NO: 1.

In some examples, the MEGF9 may comprise a mature protein without the signal peptide (SEQ ID NO: 2). In one example, the MEGF9 may comprise a sequence with at least 80%, e.g., at least 85%, at least 90%, at least 95%, or at least 99% identity to SEQ ID NO: 2. In some examples, the MEGF9 may consist of the sequence of SEQ ID NO: 2. In some examples, the MEGF9 may consist of a sequence with at least 80%, e.g., at least 85%, at least 90%, at least 95%, or at least 99% identity to SEQ ID NO: 2.

In some embodiments, a biologically active fragment of the MEGF9 may comprise a sequence in the ECD of MEGF9. In some examples, the biologically active fragment of the MEGF9 may comprise the sequence of SEQ ID NO: 3. In some examples, the biologically active fragment of the MEGF9 may comprise a sequence with at least 80%, e.g., at least 85%, at least 90%, at least 95%, or at least 99% identity to SEQ ID NO: 3. In some examples, the biologically active fragment of the MEGF9 may consist of the sequence of SEQ ID NO: 3. In some examples, the biologically active fragment of the MEGF9 may consist of a sequence with at least 80%, e.g., at least 85%, at least 90%, at least 95%, or at least 99% identity to SEQ ID NO: 3.

In some examples, the biologically active fragment of the MEGF9 may comprise a portion of the ECD. In some examples, the biologically active fragment of the MEGF9 may comprise the sequence of SEQ ID NO: 4. In some examples, the biologically active fragment of the MEGF9 may comprise a sequence with a one-amino acid, two-amino acid, three-amino acid, four-amino acid, five-amino acid, or six-amino acid modification of SEQ ID NO: 4.

In some examples, the biologically active fragment of the MEGF9 may consist of a portion of the ECD. In some examples, the biologically active fragment of the MEGF9 may consist of the sequence of SEQ ID NO: 4. In some examples, the biologically active fragment of the MEGF9 may consist of a sequence with a one-amino acid, two-amino acid, three-amino acid, four-amino acid, five-amino acid, or six-amino acid modification of SEQ ID NO: 4.

In some examples, the biologically active fragment of the MEGF9 may comprise the sequence of SEQ ID NO: 102. In some examples, the biologically active fragment of the MEGF9 may comprise a sequence with at least 80%, e.g., at least 85%, at least 90%, at least 95%, or at least 99% identity to SEQ ID NO: 102. In some examples, the biologically active fragment of the MEGF9 may consist of the sequence of SEQ ID NO: 102. In some examples, the biologically active fragment of the MEGF9 may consist of a sequence with at least 80%, e.g., at least 85%, at least 90%, at least 95%, or at least 99% identity to SEQ ID NO: 102.

ALG5 and Biologically Active Fragments Thereof

In some embodiments, the composition comprises ALG5 (also referred to as "A5"), biologically active fragments thereof, and/or antibodies specifically binding to ALG5 or biologically active fragments thereof. The ALG5 may be a human ALG5. In one example, the ALG5 may comprise the sequence of SEQ ID NO: 9 (full-length human ALG5, Accession Number Q9Y673, see www.uniprot.org/uniprot/Q9Y673). The protein of SEQ ID NO: 9 comprises the following domains: cytoplasmic domain (amino acids 1-7), transmembrane (helical) domain (amino acids 8-28), and lumenal domain (amino acids 29-324). In some aspects, the present disclosure includes the polypeptide having SEQ ID NO: 104.

In some examples, the ALG5 may comprise a sequence with at least 80%, e.g., at least 85%, at least 90%, at least 95%, or at least 99% identity to SEQ ID NO: 9. In some examples, the ALG5 may consist of the sequence of SEQ ID NO: 9. In some examples, the ALG5 may consist of a sequence with at least 80%, e.g., at least 85%, at least 90%, at least 95%, or at least 99% identity to SEQ ID NO: 9.

In some examples, the biologically active fragment of the ALG5 may comprise the sequence of SEQ ID NO: 104. In some examples, the biologically active fragment of the ALG5 may comprise a sequence with at least 80%, e.g., at least 85%, at least 90%, at least 95%, or at least 99% identity to SEQ ID NO: 104. In some examples, the biologically active fragment of the ALG5 may consist of the sequence of SEQ ID NO: 104. In some examples, the biologically active fragment of the ALG5 may consist of a sequence with at least 80%, e.g., at least 85%, at least 90%, at least 95%, or at least 99% identity to SEQ ID NO: 104.

Caveolin-1 Scaffolding Domain Peptides

In some embodiments, the compositions may further comprise a caveolin-1 (Cav-1) scaffolding domain peptide (CSP). The Caveolin-1 (Cav-1) scaffolding domain or polypeptide interferes with Cav-1 interaction with Src kinases mimics the combined effect of uPA and anti-β1-integrin antibody. In some examples, the CSP may be comprised in the same pharmaceutical composition that comprises the MEGF9, UNC5A, ALG5, and/or biologically active fragment thereof, and/or antibodies specifically binding to the proteins. In some examples, the CSP may be comprised in a pharmaceutical composition different from the one comprising the MEGF9, UNC5A, ALG5, and/or biologically active fragment thereof, and/or antibodies specifically binding to the proteins. In some examples, the CSP may be administered at the same time as the MEGF9, UNC5A, ALG5, and/or biologically active fragment thereof, and/or antibodies specifically binding to the proteins. In some examples, the CSP may be administered prior to the administration of the MEGF9, UNC5A, ALG5, and/or biologically active fragment thereof, and/or antibodies specifically binding to the proteins. In some examples, the CSP may be administered after the administration of the MEGF9, UNC5A, ALG5, and/or biologically active fragment thereof, and/or antibodies specifically binding to the proteins.

In some examples, the CSP may comprise the sequence of SEQ ID NO: 10. In some examples, the CSP may comprise a sequence with at least 80%, e.g., at least 85%, at least 90%, at least 95%, or at least 99% identity to SEQ ID NO: 10. In some examples, the CSP may consist of the sequence of SEQ ID NO: 10. In some examples, the CSP may consist of a sequence with at least 80%, e.g., at least 85%, at least 90%, at least 95%, or at least 99% identity to SEQ ID NO: 10.

In some examples, the CSP may comprise the sequence of SEQ ID NO: 11. In some examples, the CSP may comprise a sequence with a one-amino acid, two-amino acid, three-amino acid, or four-amino acid modification of SEQ ID NO: 11. In some examples, the CSP may consist of the sequence of SEQ ID NO: 11. In some examples, the CSP may consist of a sequence with a one-amino acid, two-amino acid, three-amino acid, or four-amino acid modification of SEQ ID NO: 11.

In some examples, the CSP may comprise or consist of any one of sequences shown in Table 1.

TABLE 1

Exemplary Cav-1 peptides

| SEQ ID NO: | Sequences |
| --- | --- |
| 12 | SFTTFTVT |
| 13 | SFTTFTVTK |
| 14 | FTTFTVTKYW |
| 15 | ASFTTFTVTK |
| 16 | FTTFTVTKYWF |
| 17 | ASFTTFTVTKY |
| 18 | WKASFTTFTVT |
| 19 | SFTTFTVTKYWF |
| 20 | KASFTTFTVTKY |
| 21 | IWKASFTTFTVT |
| 22 | SFTTFTVTKYWFY |
| 23 | KASFTTFTVTKYW |
| 24 | IWKASFTTFTVTK |

TABLE 1-continued

Exemplary Cav-1 peptides

| SEQ ID NO: | Sequences |
| --- | --- |
| 25 | FTTFTVTKYWFYRL |
| 26 | ASFTTFTVTKYWFY |
| 27 | WKASFTTFTVTKYW |
| 28 | GIWKASFTTFTVTK |
| 29 | FTTFTVTKYWFYRLL |
| 30 | ASFTTFTVTKYWFYR |
| 31 | WKASFTTFTVTKYWF |
| 32 | GIWKASFTTFTVTKY |
| 33 | FDGIWKASFTTFTVT |
| 34 | SFTTFTVTKYWFYRLL |
| 35 | KASFTTFTVTKYWFYR |
| 36 | IWKASFTTFTVTKYWF |
| 37 | DGIWKASFTTFTVTKY |
| 38 | SFDGIWKASFTTFTVT |
| 39 | SFTTFTVTKYWFYRLLS |
| 40 | KASFTTFTVTKYWFYRL |
| 41 | IWKASFTTFTVTKYWFY |
| 42 | DGIWKASFTTFTVTKYW |
| 43 | SFDGIWKASFTTFTVTK |
| 44 | FTTFTVTKYWFYRLLSAL |
| 45 | ASFTTFTVTKYWFYRLLS |
| 46 | WKASFTTFTVTKYWFYRL |
| 47 | GIWKASFTTFTVTKYWFY |
| 48 | FDGIWKASFTTFTVTKYW |
| 49 | HSFDGIWKASFTTFTVTK |
| 50 | FTTFTVTKYWFYRLLSALF |
| 51 | ASFTTFTVTKYWFYRLLSA |
| 52 | WKASFTTFTVTKYWFYRLL |
| 53 | GIWKASFTTFTVTKYWFYR |
| 54 | FDGIWKASFTTFTVTKYWF |
| 55 | HSFDGIWKASFTTFTVTKY |
| 56 | GTHSFDGIWKASFTTFTVT |
| 57 | FTTFTVTK |
| 58 | FTTFTVTKY |
| 59 | ASFTTFTVT |
| 60 | SFTTFTVTKY |
| 61 | KASFTTFTVT |
| 62 | SFTTFTVTKYW |

TABLE 1-continued

Exemplary Cav-1 peptides

| SEQ ID NO: | Sequences |
|---|---|
| 63 | KASFTTFTVTK |
| 64 | FTTFTVTKYWFY |
| 65 | ASFTTFTVTKYW |
| 66 | WKASFTTFTVTK |
| 67 | FTTFTVTKYWFYR |
| 68 | ASFTTFTVTKYWF |
| 69 | WKASFTTFTVTKY |
| 70 | GIWKASFTTFTVT |
| 71 | SFTTFTVTKYWFYR |
| 72 | KASFTTFTVTKYWF |
| 73 | IWKASFTTFTVTKY |
| 74 | DGIWKASFTTFTVT |
| 75 | SFTTFTVTKYWFYRL |
| 76 | KASFTTFTVTKYWFY |
| 77 | IWKASFTTFTVTKYW |
| 78 | DGIWKASFTTFTVTK |
| 79 | FTTFTVTKYWFYRLLS |
| 80 | ASFTTFTVTKYWFYRL |
| 81 | WKASFTTFTVTKYWFY |
| 82 | GIWKASFTTFTVTKYW |
| 83 | FDGIWKASFTTFTVTK |
| 84 | FTTFTVTKYWFYRLLSA |
| 85 | ASFTTFTVTKYWFYRLL |
| 86 | WKASFTTFTVTKYWFYR |
| 87 | GIWKASFTTFTVTKYWF |
| 88 | FDGIWKASFTTFTVTKY |
| 89 | HSFDGIWKASFTTFTVT |
| 90 | SFTTFTVTKYWFYRLLSA |
| 91 | KASFTTFTVTKYWFYRLL |
| 92 | IWKASFTTFTVTKYWFYR |
| 93 | DGIWKASFTTFTVTKYWF |
| 94 | SFDGIWKASFTTFTVTKY |
| 95 | THSFDGIWKASFTTFTVT |
| 96 | SFTTFTVTKYWFYRLLSAL |
| 97 | KASFTTFTVTKYWFYRLLS |
| 98 | IWKASFTTFTVTKYWFYRL |
| 99 | DGIWKASFTTFTVTKYWFY |
| 100 | SFDGIWKASFTTFTVTKYW |
| 101 | THSFDGIWKASFTTFTVTK |

The CSP may have the activity of the native CAV-1 polypeptide in in vitro or in vivo assays of binding or of biological activity. For example, the CSP may inhibit or prevent apoptosis of LECs induced by BLM in vitro or in vivo with activity at least about 20% of the activity of the native CAV-1 polypeptide, or at least about 30%, 40%, 50%, 60%, 65%, 70%, 75%, 80%, 85%, 90%, about 95%, 97%, 99%, and any range derivable therein, such as, for example, from about 70% to about 80%, from about 81% to about 90%; or from about 91% to about 99%. The CSP may have 100% or even greater activity than the native Cav-1 polypeptide. Assays for testing biological activity, e.g., antifibrotic activity, the ability to affect expression of uPA, uPAR and PAI-1 mRNAs, or inhibit proliferation of lung fibroblasts, are well-known in the art.

Antibodies Specifically Binding to MEGF9, UNC5A and ALG5

In some embodiments, the composition comprises an antibody specifically binding to MEGF9, an antibody specifically binding to UNC5A, an antibody specifically binding to ALG5, or any combination thereof. In some examples, the antibody is a polyclonal antibody. In some examples, the antibody is a monoclonal antibody.

In some examples, the composition comprises an antibody specifically binding to MEGF9. The antibody may be generated against any one of SEQ ID NOs: 1-4 and 102 and fragments thereof. In one example, the anti-MEGF9 antibody is a rabbit polyclonal antibody generated using an 11 amino acid peptide SEQ ID NO: 4 as an antigen. Examples of anti-MEGF9 antibodies include Mybiosource: Catalog #MBS9605643 (Clonality: Polyclonal, Isotype: IgG, Host: Rabbit) and Invitrogen: #PA5-106685 (Clonality: Polyclonal, Isotype: IgG, Host: Rabbit).

In some examples, the composition comprises an antibody specifically binding to UNC5A. The antibody may be generated against any one of SEQ ID NOs: 5-8 and 103 and fragments thereof. In one example, the anti-U5A antibody may be induced using either the 279 amino acid peptide SEQ ID NO: 7 or the 50 amino acid peptide SEQ ID NO: 8 as antigen. Examples of anti-U5A antibodies include Protein-Tech, #22068-1-AP (Clonality: Polyclonal, Isotype: IgG, Host: Rabbit) and Sigma, #SAB2108252, Lot #QC23528 (Clonality: Polyclonal, Isotype: IgG, Host: Rabbit).

In some examples, the composition comprises an antibody specifically binding to ALG5. The antibody may be generated against any one of SEQ ID NOs: 9 and 104 and fragments thereof. For example, a polyclonal anti-ALG5 antibody ("ALG5 Ab") may be induced using the full length protein as antigen (MW of protein is 36.9 kDa).

Examples of anti-ALG5 antibodies include those offered by a number of suppliers. Examples of anti-ALG5 antibodies include those in the following sources:
novusbio.com/products/alg5-antibody_nbp1-88767
thermofisher.com/antibody/product/ALG5-Antibody-Polyclonal/PA5-52496
ptglab.com/products/ALG5-Antibody-16046-1-AP.htm thermofisher.com/antibody/product/ALG5-Antibody-Polyclonal/PA5-109380
thermofisher.com/antibody/product/ALG5-Antibody-Polyclonal/PA5-114185
sigmaaldrich.com/catalog/product/sigma/sab1410599?lang=en&region=US
atlasantibodies.com/products/antibodies/primary-antibodies/triple-a-polyclonals/alg5-antibody-hpa007989/

The term "antibody" is meant to include both intact immunoglobulin (Ig) molecules as well as fragments and derivative thereof, that may be produced by proteolytic cleavage of Ig molecules or engineered genetically or chemically. Fragments include, for example, Fab, Fab', F(ab')$_2$ and Fv, each of which is capable of binding antigen. These fragments lack the Fc fragment of intact Ab and have an additional advantage, if used therapeutically, of clearing more rapidly from the circulation and undergoing less non-specific tissue binding than intact antibodies. Papain treatment of Ig's produces Fab fragments; pepsin treatment produces F(ab')$_2$ fragments. These fragments may also be produced by genetic or protein engineering using methods well known in the art. A Fab fragment is a multimeric protein consisting of the portion of an Ig molecule containing the immunologically active portions of an Ig heavy (H) chain and an Ig light (L) chain covalently coupled together and capable of specifically combining with antigen. Fab fragments are typically prepared by proteolytic digestion of substantially intact Ig molecules with papain using methods that are well known in the art. However, a Fab fragment may also be prepared by expressing in a suitable host cell the desired portions of Ig H chain and L chain using methods well known in the art. A (Fab')$_2$ fragment is a tetramer that includes a fragment of two H and two L chains. The Fv fragment is a multimeric protein consisting of the immunologically active portions of an Ig H chain variable (V) region ($V_H$) and an Ig L chain V region ($V_L$) covalently coupled together and capable of specifically combining with antigen. Fv fragments are typically prepared by expressing in suitable host cell the desired portions of Ig $V_H$ region and $V_L$ region using methods well known in the art.

Single-chain antigen-binding protein or single chain Ab, also referred to as "scFv," is a polypeptide composed of an Ig $V_L$ amino acid sequence tethered to an Ig $V_H$ amino acid sequence by a peptide that links the C-terminus of the $V_L$ sequence to the N-terminus of the $V_H$ sequence.

In some embodiment, the antibody is a monoclonal antibody specifically binding to MEGF9, UNC5A or ALG5 or a peptide epitope thereof, e.g., SEQ ID NO: 8 in the case of UNC5A or SEQ ID NO: 4 in the case of MEGF9.

Chimeric Antibodies

In some embodiments, the antibodies may be chimeric antibodies. The chimeric antibodies may comprise individual chimeric H and L Ig chains. The chimeric H chain may comprise an antigen-binding region derived from the H chain of a non-human antibody specific for either M9, or UNC5A or ALG5, which is linked to at least a portion of a human $C_H$ region. A chimeric L chain may comprise an antigen-binding region derived from the L chain of a non-human antibody specific for the target antigen linked to at least a portion of a human $C_L$ region. As used herein, the term "antigen-binding region" refers to that portion of an antibody molecule, which contains the amino acid residues that interact with an antigen and confer on the antibody its specificity and affinity for the antigen. The antibody region may include the "framework" amino acid residues necessary to maintain the proper conformation of the antigen-binding (or "contact") residues.

As used herein, the term "chimeric antibody" includes monovalent, divalent or polyvalent Igs. A monovalent chimeric antibody may be an HL dimer formed by a chimeric H chain associated through disulfide bridges with a chimeric L chain. A divalent chimeric antibody may be tetramer $H_2L_2$ formed by two HL dimers associated through at least one disulfide bridge. A polyvalent chimeric antibody can also be produced, for example, by employing a $C_H$ region that aggregates (e.g., from an IgM H chain, termed the μ chain).

Antibodies, fragments or derivatives having chimeric H chains and L chains of the same or different V region binding specificity, can be prepared by an appropriate association of the individual polypeptide chains, as taught, for example by Sears et al., *Proc. Natl. Acad. Sci. USA* 72:353-357 (1975). With this approach, hosts expressing chimeric H chains (or their derivatives) are separately cultured from hosts expressing chimeric L chains (or their derivatives), and the Ig chains are separately recovered and then associated. Alternatively, the hosts can be co-cultured and the chains allowed to associate spontaneously in the culture medium, followed by recovery of the assembled Ig, fragment or derivative.

The antigen-binding region of the chimeric antibody (or a human monoclonal antibody) of the present invention may be derived preferably from a non-human antibody specific for the described polypeptides. The non-human antibody producing cell from which the V region of the antibody may be derived may be a B lymphocyte obtained from the blood, spleen, lymph nodes or other tissue of an animal immunized with one of the polypeptides or a peptide or a relevant epitope thereof. The antibody-producing cell contributing the nucleotide sequences encoding the antigen-binding region of the chimeric antibody of the present invention may also be produced by transformation of a non-human, such as a primate, or a human cell. For example, a B lymphocyte (Kozbor et al. *Immunol. Today* 4:72-79 (1983)). Alternatively, the B lymphocyte may be transformed by providing a transforming gene or transforming gene product, as is well-known in the art. For example, the antigen-binding region may be of murine origin. In other embodiments, the antigen-binding region may be derived from other animal species, in particular, rodents such as rat or hamster.

The murine or chimeric monoclonal antibody of the present invention may be produced in large quantities by injecting hybridoma or transfectoma cells secreting the antibody into the peritoneal cavity of mice and, after an appropriate time, harvesting the ascites fluid, which contains a high titer of the monoclonal antibody. Alternatively, the antibodies may be produced by culturing hybridoma (or transfectoma) cells in vitro and isolating secreted monoclonal antibody from the cell culture medium.

Human genes that encode the constant C regions of the chimeric antibodies of the present invention may be derived from a human fetal liver library or from any human cell including those that express and produce human Igs. The human $C_H$ region can be derived from any of the known classes or isotypes of human H chains, including γ, μ, α, δ or ε, and subtypes thereof, such as G1, G2, G3 and G4. Since the H chain isotype is responsible for the various effector functions of an Ab, the choice of $C_H$ region will be guided by the desired effector functions. For example, the $C_H$ region is derived from γ1 (IgG1), γ3 (IgG3), γ4 (IgG4), or μ(IgM). The human $C_L$ region can be derived from either human L chain isotype, κ or λ.

Genes encoding human Ig C regions are obtained from human cells by standard cloning techniques (Sambrook, J. et al., *Molecular Cloning: A Laboratory Manual*, 2nd Edition (or later edition), Cold Spring Harbor Press, Cold Spring Harbor, NY (1989)). Human C region genes are readily available from known clones containing genes representing the two classes of L chains, the five classes of H chains and subclasses thereof. Chimeric antibody fragments, such as F(ab')$_2$ and Fab, can be prepared by designing a chimeric H chain gene which is appropriately truncated. For example, a chimeric gene encoding an H chain portion of an F(ab')$_2$ fragment would include DNA sequences encoding the CH$_1$ domain and hinge region of the H chain, followed by a translational stop codon to yield the truncated molecule.

The chimeric Ig coding sequences or genes of the present invention can also be expressed in nonlymphoid mammalian cells or in other eukaryotic cells, such as yeast, or in prokaryotic cells, in particular bacteria. Yeast provides substantial advantages over bacteria for the production of Ig H and L chains. Yeasts carry out post-translational peptide modifications including glycosylation. A number of recombinant DNA strategies now exist which utilize strong promoter sequences and high copy number plasmids that can be used for the production of the desired proteins in yeast. Yeast recognizes leader sequences of cloned mammalian gene products and secretes peptides bearing leader sequences (i.e., pre-peptides). Yeast gene expression systems can be routinely evaluated for the levels of production, secretion and the stability of chimeric H and L chain proteins and assembled chimeric Abs. Any of a series of yeast gene expression systems incorporating promoter and termination elements from the actively expressed genes coding for glycolytic enzymes produced in large quantities when yeasts are grown in media rich in glucose can be utilized. Bacterial strains may also be utilized as hosts for the production of antibody molecules or antibody fragments described by this invention. The hosts may be mammalian cells, grown in vitro or in vivo. Mammalian cells provide post-translational modifications to Ig protein molecules including leader peptide removal, folding and assembly of H and L chains, glycosylation of the Ab molecules, and secretion of functional Ab protein. Mammalian cells which may be useful as hosts for the production of antibody proteins, in addition to the cells of lymphoid origin described above, include cells of fibroblast origin, such as Vero (ATCC CRL 81) or CHO-K1 (ATCC CRL 61). Many vector systems are available for the expression of cloned H and L chain genes in mammalian cells (see Glover, supra). Different approaches can be followed to obtain complete H$_2$L$_2$ Abs.

For in vivo use, particularly for administration into humans, it is desirable to decrease the immunogenicity of the antibody by making mouse-human (or rodent-human) chimeric antibodies as above, or by humanizing the antibodies using methods known in the art. The humanized antibody may be the product of an animal having transgenic human Ig Constant region genes (see for example WO90/10077 and WO90/04036). Alternatively, the antibody of interest may be genetically engineered to substitute the CH$_1$, CH$_2$, CH$_3$, hinge domains, and/or the framework domain with the corresponding human sequence (see WO92/02190).

Single Chain Antibodies

The antibody of the present invention may be produced as a single chain Ab or scFv instead of the normal multimeric structure. Single chain Abs include the hypervariable regions from an Ig of interest and recreate the antigen binding site of the native Ig while being a fraction of the size of the intact Ig (Skerra, A. et al. (1988) *Science*, 240: 1038-1041; Pluckthun, A. et al. (1989) *Methods Enzymol.* 178: 497-515; Winter, G. et al. (1991) *Nature*, 349: 293-299); Bird et al., (1988) *Science* 242:423; Huston et al. (1988) *Proc. Natl. Acad. Sci. USA* 85:5879; Jost C R et al., *J Biol Chem*. 1994 269:26267-26273; U.S. Pat. Nos. 4,704, 692, 4,853,871, 4,94,6778, 5,260,203, 5,455,030). DNA sequences encoding the V regions of the H chain and the L chain are ligated to a linker encoding at least about 4 amino acids (typically small neutral amino acids). The protein encoded by this fusion allows assembly of a functional variable region that retains the specificity and affinity of the original antibody.

Antibodies can be selected for particular desired properties. In the case of an antibody to be used in vivo, antibody screening procedures can include any of the in vitro or in vivo bioassays that measure binding to MEGF9, UNC5A or ALG5 or a peptide epitope thereof, or to cells expressing the relevant polypeptide or peptide epitope.

Modifications

The present disclosure also includes modifications of the exemplary proteins and peptides described herein. Modifications may be made to amino acids on the N-terminus, C-terminus, or internally. The proteins and biologically active fragments thereof may include conservative or non-conservative amino acid changes, as described below. Examples of the modifications include amino acid substitutions, additions, deletions, fusions and truncations in the original proteins or peptide. The proteins and biologically active fragments thereof may also include insertions, deletions or substitutions of amino acids, including insertions and substitutions of amino acids (and other molecules) that do not normally occur in the peptide sequence that may be the basis of the modified variant, for example but not limited to insertion L-amino acids, or non-standard amino acids such as ornithine, which do not normally occur in human proteins.

Derivatives

In some aspects, the proteins or biologically active fragments thereof may be derivatives of any of SEQ ID NOs: 1-11 and 102-104. The term "derivative" as used herein refers to proteins and biologically active fragments thereof that are chemically modified, for example but not limited to by techniques such as acetylation, ubiquitination, labeling, pegylation (derivatization with polyethylene glycol), lipidation, glycosylation, amidation, cyclization, or addition of other molecules. The proteins and biologically active fragments thereof may be provided in a cyclic form, e.g., as a cyclic peptide or as a lactam. Alternatively, or in addition, proteins and biologically active fragments thereof may be provided as a branched peptide. A molecule may be also a "derivative" of another molecule when it contains additional chemical moieties not normally a part of the molecule. Such moieties may alter the pH or improve the molecule's solubility, absorption, biological half-life, etc. The moieties may alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, PA (1990), incorporated herein, by reference, in its entirety.

The term "functional" when used in conjunction with "derivative" or "variant" refers to a polypeptide of the invention that possesses a biological activity (either functional or structural) that may be substantially similar to a biological activity of the entity or molecule it may be a functional derivative or functional variant thereof. The term functional derivative may be intended to include the fragments, analogues or chemical derivatives of a molecule.

The modified proteins and biologically active fragments thereof may comprise co-translational and post-translational (e.g., C-terminal peptide cleavage) modifications, such as, for example, disulfide-bond formation, glycosylation, acetylation, phosphorylation, proteolytic cleavage (e.g., cleavage by furins or metalloproteases), and the like to the extent that such modifications do not affect the function of the peptides.

In yet a further aspect, the proteins or biologically active fragments thereof may be "retro-inverso peptides." A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide may contain L-amino acids or D-amino acids, or a mixture of L-amino acids and D-amino acids, up to all of the amino acids being the D-isomer. Partial retro-inverso peptide analogues may be polypeptides in which only part of the sequence may be reversed and replaced with enantiomeric amino acid residues. Since the retro-inverted portion of such an analogue has reversed amino and carboxyl termini, the amino acid residues flanking the retro-inverted portion may be replaced by side-chain-analogous a-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., *Int J Pept Protein Res.* 24(6):553-6 (1984); Verdini, A and Viscomi, G. C, *J. Chem. Soc. Perkin Trans.* 1:697-701 (1985); and U.S. Pat. No. 6,261,569, which are incorporated herein in their entirety by reference. Processes for the solid-phase synthesis of partial retro-inverso peptide analogues have been described (EP 97994-B) which may be also incorporated herein in its entirety by reference.

Terminal Modifications

The proteins and biologically active fragments thereof may be modified (at its amino terminus or carboxy terminus. Examples of amino terminal modifications include, e.g., N-glycated, N-alkylated, N-acetylated or N-acylated amino acid. A terminal modification may include a pegylation. An example of a carboxy terminal modification may be a C-terminal amidated amino acid. The proteins and peptides may be cross-linked or have a cross-linking site (for example, the protein or biologically active fragments thereof may a cysteinyl residue and thus forms cross-linked dimers in culture or in vivo. One or more peptidyl bonds may be replaced by a non-peptidyl linkage; the N-terminus or the C-terminus may be replaced, and individual amino acid moieties may be modified through treatment with agents capable of reacting with selected side chains or terminal residues, and so forth. Either the C-terminus or the N-terminus of the sequences, or both, may be linked to a carboxylic acid functional groups or an amine functional group, respectively.

Examples of N-terminal protecting groups include acyl groups (—CO— R1) and alkoxy carbonyl or aryloxy carbonyl groups (—CO—O—R1), wherein R1 may be an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO and (substituted benzyl)-CO—. Examples of alkoxy carbonyl and aryloxy carbonyl groups include CH3-O—CO, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO and benzyl-O CO—, (substituted benzyl)-O—CO—, Adamantan, naphtalen, myristoleyl, toluen, biphenyl, cinnamoyl, nitrobenzoy, toluoyl, furoyl, benzoyl, cyclohexane, norbornane, or Z-caproic. In order to facilitate the N-acylation, one to four glycine residues may be present at the N-terminus of the molecule.

Carboxy terminal modifications include acylation with carboxylic acids: formic, acetic, propionic, fatty acids (myristic, palmitic, stearic), succinic, benzoic, carbobenzoxy (Cbz); acetylation and biotinylation. Amino terminal modifications include: (i) acylation with carboxylic acids: formic, acetic, propionic, fatty acids (myristic, palmitic, stearic, etc) succinic, benzoic, carbobenzoxy (Cbz); (ii) biotinylation; (iii) amidation; (iv) attachment of dyes such as fluorescein (FITC, FAM, etc.), 7-hydroxy-4-methylcoumarin-3-acetic acid, 7-hydroxycoumarin-3-acetic acid, 7-metoxycoumarin-3-acetic acid and other coumarins; rhodamines (5-carboxyrhodamine 110 or 6G, 5(6)-TAMRA, ROX); N-[4-(4-dimethylamino)phenylazo]bezoic acid (Dabcyl), 2,4-dinitrobenzene (Dnp), 5-dimethylaminonaphthalene-1-sulfonic acid (Dansyl) and other dyes; and (v) polyethyleneglycol.

The carboxyl group at the C-terminus of a protein or biologically active fragments thereof may be protected, for example, by a group including but not limited to an amide (i.e., the hydroxyl group at the C-terminus may be replaced with —NH2, —NHR2 and —NR2R3) or ester (i.e. the hydroxyl group at the C-terminus may be replaced with —OR2). R2 and R3 may be optionally independently an aliphatic, substituted aliphatic, benzyl, substituted benzyl, aryl or a substituted aryl group. In addition, taken together with the nitrogen atom, R2 and R3 may optionally form a C4 to C8 heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include-NH2, —NHCH3, —N(CH3)2, —NH(ethyl), N(ethyl)2, N(methyl) (ethyl), —NH(benzyl), —N(C1-C4 alkyl)(benzyl), —NH(phenyl), —N(C1-C4 alkyl) (phenyl), —OCH3, —O-(ethyl), O-(n-propyl), —O-(n-butyl), O-(isopropyl), —O-(sec-butyl), —O-(t-butyl), —O-benzyl and —O-phenyl.

Side Chain Modifications

The amino acids of the proteins and biologically active fragments thereof may optionally be modified according to any one of the following exemplary types of modification. Non-limiting exemplary types of modification include carboxymethylation, acylation, phosphorylation, glycosylation or fatty acylation. Ether bonds may optionally be used to join the serine or threonine hydroxyl to the hydroxyl of a sugar. Amide bonds may optionally be used to join the glutamate or aspartate carboxyl groups to an amino group on a sugar (Gang and Jeanloz, *Advances in Carbohydrate Chemistry and Biochemistry*, Vol. 43, Academic Press (1985); Kunz, *Ang. Chem. Int. Ed. English* 26:294-308 (1987)). Acetal and ketal bonds may also optionally be formed between amino acids and carbohydrates. Fatty acid acyl derivatives may optionally be made, for example, by acylation of a free amino group (e.g., lysine) (Toth et al., *Peptides: Chemistry, Structure and Biology*, Rivier and Marshal, eds., ESCOM Publ., Leiden, 1078-1079 (1990)).

As used herein the term "chemical modification", when referring to a protein or biologically active fragments thereof herein, refers to a protein or biologically active fragments thereof where at least one of its amino acid residues may be modified either by natural processes, such as processing or other post-translational modifications, or by chemical modification techniques which are well known in the art. Examples of the numerous known modifications typically include acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications may optionally include the addition of a cycloalkane moiety to a biological molecule, such as a protein, as described in PCT Application No. WO 2006/050262, hereby incorporated by reference as if fully set forth herein. These moieties may be designed for use with biomolecules and may optionally be used to impart various properties to proteins.

Furthermore, optionally any point on a protein or biologically active fragments thereof may be modified. For example, pegylation of a glycosylation moiety on a protein or biologically active fragments thereof may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein or biologically active fragments thereof through a glycosyl linker.

Covalent modifications of the proteins and biologically active fragments thereof are included within the scope of this invention. Other types of covalent modifications of the proteins or biologically active fragments thereof may be introduced into the molecule by reacting targeted amino acid residues with an organic derivatizing agent that may be capable of reacting with selected side chains or the N- or C-terminal residues.

Cysteinyl residues may be reacted with α-haloacetates (and corresponding amines), such as chloroacetic acid or chloroacetamide, to give carboxymethyl or carboxyamidomethyl derivatives. Cysteinyl residues also may be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with diethylpyrocarbonate at pH 5.5-7.0 because this agent may be relatively specific for the histidyl side chain. Parabromophenacyl bromide also may be useful; the reaction may be preferably performed in 0.1M sodium cacodylate at pH 6.0.

Lysinyl and amino-terminal residues may be reacted with succinic or other carboxylic acid anhydrides. Derivatization with these agents may have the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin. Derivatization of arginine residues may need the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. For example, N-acetylimidizole and tetranitromethane may be used to form O-acetyl tyrosyl species and 3-nitro derivatives, respectively. Tyrosyl residues may be iodinated using $^{125}I$ or $^{131}I$ to prepare labeled proteins or peptides for use in radioimmunoassay.

Carboxyl side groups (aspartyl or glutamyl) may be selectively modified by reaction with carbodiimides (R—N=C=N—R'), where R and R' may be different alkyl groups, such as 1-cyclohexyl-3-(2-morpholinyl-4-ethyl)carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Derivatization with bifunctional agents may be useful for crosslinking to a water-insoluble support matrix or surface for use in the method for purifying anti-CHF antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that may be capable of forming crosslinks in the presence of light. Alternatively or additionally, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 may be employed for protein immobilization.

Glutaminyl and asparaginyl residues may be frequently deamidated to the corresponding glutamyl and aspartyl residues, respectively. These residues may be deamidated under neutral or basic conditions.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, pp. 79-86 [1983]), acetylation of the N-terminal amine, and amidation of any C-terminal carboxyl group.

Capping

The proteins and biologically active fragments thereof may be capped at the N- and/or C-termini with an acyl (abbreviated "Ac") and an amido (abbreviated "Am") group, respectively, for example acetyl ($CH_3CO$—) at the N-terminus and amido (—$NH_2$) at the C-terminus. A broad range of N-terminal capping functions, preferably in a linkage to the terminal amino group, is contemplated, for example:
formyl;
   alkanoyl, having from 1 to 10 carbon atoms, such as acetyl, propionyl, butyryl;
   alkenoyl, having from 1 to 10 carbon atoms, such as hex-3-enoyl;
   alkynoyl, having from 1 to 10 carbon atoms, such as hex-5-ynoyl;
   aroyl, such as benzoyl or 1-naphthoyl;
   heteroaroyl, such as 3-pyrroyl or 4-quinoloyl;
   alkylsulfonyl, such as methanesulfonyl;
   arylsulfonyl, such as benzenesulfonyl or sulfanilyl;

heteroarylsulfonyl, such as pyridine-4-sulfonyl;
substituted alkanoyl, having from 1 to 10 carbon atoms, such as 4-aminobutyryl;
substituted alkenoyl, having from 1 to 10 carbon atoms, such as 6-hydroxy-hex-3-enoyl;
substituted alkynoyl, having from 1 to 10 carbon atoms, such as 3-hydroxy-hex-5-ynoyl;
substituted aroyl, such as 4-chlorobenzoyl or 8-hydroxy-naphth-2-oyl;
substituted heteroaroyl, such as 2,4-dioxo-1,2,3,4-tetrahydro-3-methyl-quinazolin-6-oyl;
substituted alkylsulfonyl, such as 2-aminoethanesulfonyl;
substituted arylsulfonyl, such as 5-dimethylamino-1-naphthalenesulfonyl;
substituted heteroarylsulfonyl, such as 1-methoxy-6-isoquinolinesulfonyl;
carbamoyl or thiocarbamoyl;
substituted carbamoyl (R'—NH—CO) or substituted thiocarbamoyl (R'—NH—CS) wherein R' may be alkyl, alkenyl, alkynyl, aryl, heteroaryl, substituted alkyl, substituted alkenyl, substituted alkynyl, substituted aryl, or substituted heteroaryl;
substituted carbamoyl (R'—NH—CO) and substituted thiocarbamoyl (R'—NH—CS) wherein R' may be alkanoyl, alkenoyl, alkynoyl, aroyl, heteroaroyl, substituted alkanoyl, substituted alkenoyl, substituted alkynoyl, substituted aroyl, or substituted heteroaroyl, all as above defined.

The C-terminal capping function may either be in an amide or ester bond with the terminal carboxyl. Capping functions that provide for an amide bond are designated as $NR^1R^2$ wherein $R^1$ and $R^2$ may be independently drawn from the following group: hydrogen;
alkyl, preferably having from 1 to 10 carbon atoms, such as methyl, ethyl, isopropyl;
alkenyl, preferably having from 1 to 10 carbon atoms, such as prop-2-enyl;
alkynyl, preferably having from 1 to 10 carbon atoms, such as prop-2-ynyl;
substituted alkyl having from 1 to 10 carbon atoms, such as hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl;
substituted alkenyl having from 1 to 10 carbon atoms, such as hydroxyalkenyl, alkoxyalkenyl, mercaptoalkenyl, alkylthioalkenyl, halogenoalkenyl, cyanoalkenyl, aminoalkenyl, alkylaminoalkenyl, dialkylaminoalkenyl, alkanoylalkenyl, carboxyalkenyl, carbamoylalkenyl;
substituted alkynyl having from 1 to 10 carbon atoms, such as hydroxyalkynyl, alkoxyalkynyl, mercaptoalkynyl, alkylthioalkynyl, halogenoalkynyl, cyanoalkynyl, aminoalkynyl, alkylaminoalkynyl, dialkylaminoalkynyl, alkanoylalkynyl, carboxyalkynyl, carbamoylalkynyl;
aroylalkyl having up to 10 carbon atoms, such as phenacyl or 2-benzoylethyl;
aryl, such as phenyl or 1-naphthyl;
heteroaryl, such as 4-quinolyl;
alkanoyl having from 1 to 10 carbon atoms, such as acetyl or butyryl;
aroyl, such as benzoyl;
heteroaroyl, such as 3-quinoloyl;
OR' or NR'R" where R' and R" may be independently hydrogen, alkyl, aryl, heteroaryl, acyl, aroyl, sulfonyl, sulfinyl, or $SO_2$—R''' or SO—R''' where R''' may be substituted or unsubstituted alkyl, aryl, heteroaryl, alkenyl, or alkynyl.

Capping functions that provide for an ester bond are designated as OR, wherein R may be: alkoxy; aryloxy; heteroaryloxy; aralkyloxy; heteroalkyloxy; substituted alkoxy; substituted aryloxy; substituted heteroaryloxy; substituted aralkyloxy; or substituted heteroaralkyloxy.

Either the N-terminal or the C-terminal capping function, or both, may be of such structure that the capped molecule functions as a prodrug (a pharmacologically inactive derivative of the parent drug molecule) that undergoes spontaneous or enzymatic transformation within the body in order to release the active drug and that has improved delivery properties over the parent drug molecule (Bundgaard H, Ed: *Design of Prodrugs*, Elsevier, Amsterdam, 1985).

Judicious choice of capping groups may allow the addition of other activities on the protein or biologically active fragments thereof. For example, the presence of a sulfhydryl group linked to the N- or C-terminal cap may permit conjugation of the derivatized peptide to other molecules.

Multimerization

In some embodiments, the proteins or biologically active fragments thereof may be longer molecules built from multimerizing (e.g., repeating) units of a protein or biologically active fragments thereof described herein. A multimer may comprise different combinations of proteins or biologically active fragments thereof. Such multimeric protein or peptide may be made by chemical synthesis or by recombinant DNA techniques as discussed herein. When produced by chemical synthesis, the oligomers may have from 2-5 repeats of a core polypeptide sequence, and the total number of amino acids in the multimer may be less than about 160 residues, e.g., not more than 100 residues (or their equivalents, when including linkers or spacers).

Peptidomimetics

The proteins or biologically active fragments thereof herein may be a peptidomimetic compound, which mimics the biological effects of the corresponding native protein or peptide. A peptidomimetic agent may be an unnatural peptide or a non-peptide agent that recreates the stereospatial properties of the binding elements of the native protein or peptide such that it has the binding activity and biological activity of the native protein or peptide. Similar to a native protein or biologically active fragments thereof, or multimer, a peptidomimetic will have a binding face (which interacts with any ligand to which native protein or peptide binds) and a non-binding face.

In some aspects, the present disclosure also includes compounds that retain partial peptide characteristics. For example, any proteolytically unstable bond within a protein or peptide may be selectively replaced by a non-peptidic element such as an isostere (N-methylation; D-amino acid) or a reduced peptide bond while the rest of the molecule retains its peptidic nature.

The peptidomimetic compounds, either agonists, substrates or inhibitors, included those described for a number of bioactive peptides/polypeptides such as opioid peptides, VIP, thrombin, HIV protease, etc. Methods for designing and preparing peptidomimetic compounds are known in the art (Hruby, V J, Biopolymers 33:1073-1082 (1993); Wiley, R A et al., Med. Res. Rev. 13:327-384 (1993); Moore et al., Adv. in Pharmacol 33:91-141 (1995); Giannis et al., Adv. in Drug Res. 29:1-78 (1997). Certain mimetics that mimic secondary structure are described in Johnson et al., In: Biotechnology and Pharmacy, Pezzuto et al., Chapman and Hall (Eds.), NY, 1993. These methods may be used to make peptidomimetics that possess at least the binding capacity and specificity of the native protein or peptide and may possess the biological activity. Knowledge of peptide chemistry and general organic chemistry available to those skilled in the art may be sufficient, in view of the present disclosure, for designing and synthesizing such compounds.

For example, such peptidomimetics may be identified by inspection of the three-dimensional structure of a protein or peptide either free or bound in complex with a ligand (e.g., soluble uPAR or a fragment thereof). Alternatively, the structure of a protein or peptide bound to its ligand may be gained by the techniques of nuclear magnetic resonance spectroscopy. Greater knowledge of the stereochemistry of the interaction of the protein or peptide with its ligand or receptor may permit the rational design of such peptidomimetic agents. The structure of a protein or peptide in the absence of ligand may also provide a scaffold for the design of mimetic molecules.

PEGylation

The proteins or biologically active fragments thereof may be conjugated with heterologous polypeptide segments or polymers, such as polyethylene glycol. The protein or biologically active fragments thereof may be linked to PEG to increase the hydrodynamic radius of the enzyme and hence increase the serum persistence. The protein or biologically active fragments thereof may be conjugated to any targeting agent, such as a ligand having the ability to specifically and stably bind to an external receptor (see e.g., U.S. Patent Publ. 2009/0304666).

In certain aspects, methods and compositions of the embodiments related to PEGylation of the protein or biologically active fragments thereof. PEGylation may be the process of covalent attachment of poly(ethylene glycol) polymer chains to another molecule, normally a drug or therapeutic protein. PEGylation may be achieved by incubation of a reactive derivative of PEG with the target macromolecule. The covalent attachment of PEG to a drug or therapeutic protein may "mask" the agent from the host's immune system (reduced immunogenicity and antigenicity) or increase the hydrodynamic size (size in solution) of the agent, which may prolong its circulatory time by reducing renal clearance. PEGylation may also provide water solubility to hydrophobic drugs and proteins.

The first step of the PEGylation may be the suitable functionalization of the PEG polymer at one or both terminals. PEGs that are activated at each terminus with the same reactive moiety are known as "homobifunctional," whereas if the functional groups present may be different, then the PEG derivative may be referred as "heterobifunctional" or "heterofunctional." The chemically active or activated derivatives of the PEG polymer may be prepared to attach the PEG to the desired molecule.

The choice of the suitable functional group for the PEG derivative may be based on the type of available reactive group on the molecule that may be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid may also be used.

The techniques used to form first generation PEG derivatives may be generally reacting the PEG polymer with a group that may be reactive with hydroxyl groups, typically anhydrides, acid chlorides, chloroformates, and carbonates. In the second generation PEGylation chemistry more efficient functional groups, such as aldehyde, esters, amides, etc., may be made available for conjugation.

As applications of PEGylation have become more and more advanced and sophisticated, there has been an increase in need for heterobifunctional PEGs for conjugation. These heterobifunctional PEGs may be very useful in linking two entities, where a hydrophilic, flexible, and biocompatible spacer may be needed. Preferred end groups for heterobifunctional PEGs may be maleimide, vinyl sulfones, pyridyl disulfide, amine, carboxylic acids, and NHS esters.

The most common modification agents, or linkers, may be based on methoxy PEG (mPEG) molecules. Their activity depends on adding a protein-modifying group to the alcohol end. In some instances, polyethylene glycol (PEG diol) may be used as the precursor molecule. The diol may be subsequently modified at both ends in order to make a hetero- or homo-dimeric PEG-linked molecule.

Protein or biologically active fragments thereof may PEGylated at nucleophilic sites, such as unprotonated thiols (cysteinyl residues) or amino groups. Examples of cysteinyl-specific modification reagents include PEG maleimide, PEG iodoacetate, PEG thiols, and PEG vinylsulfone. All four may be strongly cysteinyl-specific under mild conditions and neutral to slightly alkaline pH but each has some drawbacks. The thioether formed with the maleimides may be somewhat unstable under alkaline conditions so there may be some limitation to formulation options with this linker. The carbamothioate linkage formed with iodo PEGs may be more stable, but free iodine may modify tyrosine residues under some conditions. PEG thiols form disulfide bonds with protein thiols, but this linkage may also be unstable under alkaline conditions. PEG-vinylsulfone reactivity may be relatively slow compared to maleimide and iodo PEG; however, the thioether linkage formed may be quite stable. Its slower reaction rate also may make the PEG-vinylsulfone reaction easier to control.

Site-specific PEGylation at native cysteinyl residues may be carried out. On the other hand, site-directed mutagenesis may be used to incorporate cysteinyl PEGylation sites for thiol-specific linkers. The cysteine mutation may be designed such that it may be accessible to the PEGylation reagent and may be still biologically active after PEGylation.

The proteins and peptides may be modified by amine-specific modification agents, e.g., PEG NHS ester, PEG tresylate, PEG aldehyde, PEG isothiocyanate, and several others. All may react under mild conditions and may be specific for amino groups. The PEG NHS ester may be one of the more reactive agents; however, its high reactivity may make the PEGylation reaction difficult to control on a large scale. PEG aldehyde forms an imine with the amino group, which may be then reduced to a secondary amine with sodium cyanoborohydride. Unlike sodium borohydride, sodium cyanoborohydride may not reduce disulfide bonds. However, this chemical may be highly toxic and may need to be handled cautiously, particularly at lower pH where it becomes volatile.

Because these reagents react with unprotonated amino groups, it may be possible to direct the PEGylation to lower-pK amino groups by performing the reaction at a lower pH. Generally the pK of the alpha-amino group may be 1-2 pH units lower than the epsilon-amino group of lysine residues. By PEGylating the molecule at pH 7 or below, high selectivity for the N-terminus frequently may be attained. This may be if the N-terminal portion of the protein may be not required for biological activity. Still, the pharmacokinetic benefits from PEGylation may result in a product with much greater in vivo bioactivity regardless of PEGylation chemistry.

There may be several parameters to consider when developing a PEGylation procedure. The "design of experiments" approach to optimization of PEGylation conditions may be very useful. For thiol-specific PEGylation reactions, parameters to consider include: protein concentration, PEG-to-protein ratio (on a molar basis), temperature, pH, reaction time, and in some instances, the exclusion of oxygen. For example, oxygen may contribute to intermolecular disulfide formation by the protein, which may reduce the yield of the PEGylated product. The same factors may be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker may need to be known before starting the PEGylation reaction. For example, if the PEGylation agent may be only 70 percent active, the amount of PEG used may ensure that only active PEG molecules may be counted in the protein-to-PEG reaction stoichiometry.

Fusion Proteins

In some embodiments, the proteins and biologically active fragments thereof may be fusion proteins of multiple proteins or peptides (e.g., fusion proteins of one or more sequences described in SEQ ID NOs: 1-11, 102-104). The fusion protein may have the protein or peptides of the embodiments linked at the N- or C-terminus to a heterologous peptide or protein. For example, the fusion proteins may also employ leader sequences from other species to permit the recombinant expression of a protein in a heterologous host. Fusion proteins may comprise a half-life extender. Another useful fusion includes the addition of a protein affinity tag, such as a serum albumin affinity tag or six histidine residues, or an immunologically active domain, such as an antibody epitope, preferably cleavable, to facilitate purification of the fusion protein. Examples of affinity tags include polyhistidine, chitin binding protein (CBP), maltose binding protein (MBP), and glutathione-S-transferase (GST).

In some embodiments, the proteins or biologically active fragments thereof of the embodiments may be linked to a peptide that increases the in vivo half-life, such as an XTEN® polypeptide (Schellenberger et al., 2009), IgG Fc domain, albumin, or albumin binding peptide.

Methods of generating fusion proteins are well known to those of skill in the art. Such proteins may be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that may be spliced between the polypeptides connected in tandem. The linker would be of sufficient length to allow proper folding of the resulting fusion protein.

Linkers

In certain embodiments, the proteins or biologically active fragments thereof may be chemically conjugated using bifunctional cross-linking reagents or fused at the protein level with peptide linkers. Bifunctional cross-linking reagents may be used for a variety of purposes, including preparation of affinity matrices, modification and stabilization of diverse structures, identification of ligand and receptor binding sites, and structural studies. Suitable peptide linkers may also be used to link the polypeptide of the embodiments, such as Gly-Ser linkers.

Homobifunctional reagents that carry two identical functional groups may provide highly efficient in inducing cross-linking between identical and different macromolecules or subunits of a macromolecule, and linking of polypeptide ligands to their specific binding sites. Heterobifunctional reagents may contain two different functional groups. By taking advantage of the differential reactivities of the two different functional groups, cross-linking may be controlled both selectively and sequentially. The bifunctional cross-linking reagents may be divided according to the specificity of their functional groups, e.g., amino-, sulfhydryl-, guanidine-, indole-, carboxyl-specific groups. Reagents directed to free amino groups may be used because of their commercial availability, ease of synthesis, and the mild reaction conditions under which they may be applied.

Heterobifunctional cross-linking reagents may contain a primary amine-reactive group and a thiol-reactive group. In some examples, heterobifunctional cross-linking reagents and methods of using the cross-linking reagents may be those described in U.S. Pat. No. 5,889,155, incorporated herein by reference in its entirety. The cross-linking reagents may combine a nucleophilic hydrazide residue with an electrophilic maleimide residue, allowing coupling, in one example, of aldehydes to free thiols. The cross-linking reagent may be modified to cross-link various functional groups.

Additionally, any other linking/coupling agents and/or mechanisms known to those of skill in the art may be used to combine polypeptides of the embodiments, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

A cross-linker having reasonable stability in blood may be used. Numerous types of disulfide-bond containing linkers are known that may be successfully employed to conjugate targeting and therapeutic/preventative agents. Linkers that contain a disulfide bond that may be sterically hindered may prove to give greater stability in vivo. These linkers may be thus one group of linking agents.

Non-hindered linkers may also be employed in accordance herewith. Other useful cross-linkers, not considered to contain or generate a protected disulfide, include SATA, SPDP, and 2-iminothiolane (Wawrzynczak and Thorpe, 1987). The use of such cross-linkers is well understood in the art. Another embodiment involves the use of flexible linkers.

Once chemically conjugated, the proteins and biologically active fragments thereof may be purified to separate the conjugate from unconjugated agents and from other contaminants. A large number of purification techniques are available for use in providing conjugates of a sufficient degree of purity to render them clinically useful. Examples of purification methods include those based upon size separation, such as gel filtration, gel permeation, or high performance liquid chromatography. Other chromatographic techniques, such as Blue-Sepharose separation, may also be used. Conventional methods to purify the fusion proteins from inclusion bodies may be useful, such as using weak detergents, such as sodium N-lauroyl-sarcosine (SLS).

Cell Penetrating and Membrane Translocation Peptides

In some embodiments, the proteins and biologically active fragments thereof may further comprise a cell-binding domain or cell penetrating peptide (CPP). As used herein the terms "cell penetrating peptide" and "membrane translocation domain" and "protein transduction domain" are used interchangeably and refer to segments of polypeptide sequence that allow a polypeptide to cross the cell membrane (e.g., the plasma membrane in the case a eukaryotic cell). Examples of CPPs include segments derived from HIV-binding peptides, HIV-1 Tat (HIV), Tat-derived peptides, Penetratin, VP22 derived or analog peptides, HSV VP22 (Herpes simplex), protegrin I, MAP, KALA or protein transduction domains (PTDs), PpT620, proline-rich peptides, arginine-rich peptides, lysine-rich peptides, MPG-peptide(s), Pep-1, L-oligomers, Calcitonin peptide(s), Antennapedia-derived peptides (particularly from *Drosophila* Antennapedia), pAntp, T1, T2, peptide 26, INF7, pIs1, FGF, Lactoferrin, Transportan, Buforin-2, Bac715-24, SynB, SynB(1), pVEC, hCT-derived peptides, SAP, or histones.

Cell penetrating peptides may have an amino acid composition that either contains a high relative abundance of positively charged amino acids such as lysine or arginine or have a sequence that contains an alternating pattern of polar/charged amino acids and non-polar, hydrophobic amino acids. These two types of structures are referred to as polycationic or amphipathic, respectively. In some examples, cell penetrating peptides (CPPs) may be peptides of 8 to 50 residues that have the ability to cross the cell membrane and enter into most cell types. In some examples, CPPs also include protein transduction domain (PTDs) reflecting their origin as occurring in natural proteins. Frankel and Pabo simultaneously to Green and Lowenstein described the ability of the trans-activating transcriptional activator from the human immunodeficiency virus 1 (HIV-TAT) to penetrate into cells (Frankel, A. D. and C. O. Pabo, Cellular uptake of the tat protein from human immunodeficiency virus. Cell, 1988. 55(6): p. 1189-93). In 1991, transduction into neural cells of the Antennapedia homeodomain (DNA-binding domain) from *Drosophila melanogaster* was described (Joliot, A., et al., Antennapedia homeobox peptide regulates neural morphogenesis. Proc Natl Acad Sci USA, 1991. 88(5): p. 1864-8). In 1994, the first 16-mer peptide CPP called Penetratin was characterized from the third helix of the homeodomain of *Drosophila* Antennapedia homeobox gene product (Derossi, D., et al., The third helix of the Antennapedia homeodomain translocates through biological membranes. J Biol Chem, 1994. 269(14): p. 10444-50), followed in 1998 by the identification of the minimal domain of TAT required for protein transduction (Vives, E. P. Brodin, and B. Lebleu, A truncated HIV-1 Tat protein basic domain rapidly translocates through the plasma membrane and accumulates in the cell nucleus. J Biol Chem, 1997. 272(25): p. 16010-7). Over the past two decades, dozens of peptides were described from different origins including viral proteins, e.g. herpes virus VP22 (Elliott, G. and P. O'Hare, Intercellular trafficking and protein delivery by a herpesvirus structural protein. Cell, 1997. 88(2): p. 223-33), or from venoms, e.g. melittin (Dempsey, C. E., The actions of melittin on membranes. Biochim Biophys Acta, 1990. 1031 (2): p. 143-61), mastoporan (Konno, K., et ah, Structure and biological activities of eumenine mastoparan-AF (EMP-AF), a new mast cell degranulating peptide in the venom of the solitary wasp (Anterhynchium flavomarginatum micado). Toxicon, 2000. 38(11):1505-15), maurocalcin (Esteve, E., et al., Transduction of the scorpion toxin maurocalcine into cells. Evidence that the toxin crosses the plasma membrane. J Biol Chem, 2005. 280(13): p. 12833-9), crotamine (Nascimento, F. D., et al., Crotamine mediates gene delivery into cells through the binding to heparan sulfate proteoglycans. J Biol Chem, 2007. 282(29): p. 21 349-60) or buforin (Kobayashi, S., et al., Membrane translocation mechanism of the antimicrobial peptide buforin 2. Biochemistry, 2004. 43(49): p. 15610-6). Synthetic CPPs were also designed including the poly-arginine (R8, R9, R10 and R12) (Futaki, S., et al., Arginine-rich peptides. An abundant source of membrane-permeable peptides having potential as carriers for intracellular protein delivery. J Biol Chem, 2001. 276(8): p. 5836-40) or transportan (Pooga, M., et al., Cell penetration by transportan. FASEB J, 1998. 12(1): p. 67-77). Any of the above-described CPPs may be used as cell penetrating peptide in the protein or biologically active fragments thereof according to the present invention. Various CPPs, which may be used as cell penetrating peptide in the protein or biologically active fragments thereof herein include those disclosed in the review: Milletti, F., Cell-penetrating peptides: classes, origin, and current landscape. Drug Discov Today 17 (15-16): 850-60, 2012.

Methods of Use

In another aspect, the present disclosure provides methods of using the proteins, biologically active fragments thereof, and/or antibodies described herein. The methods may relate to administering a composition (e.g., pharmaceutical composition) comprising one or more of the proteins biologically active fragments thereof, and/or antibodies described herein or their pharmaceutically acceptable modifications in a pharmaceutically acceptable carrier to a subject, for treating or preventing a lung disease. In some examples, the lung disease is pulmonary fibrosis such as idiopathic pulmonary fibrosis. In some examples, the lung disease is pneumonia, e.g., interstitial pneumonia. The interstitial pneumonia may be one defined radiographic and histologic presentation of lung scarring, extracellular matrix deposition, epithelial cell senescence and apoptosis, activation of myofibroblasts of fibrotic lung fibroblasts, M2 macrophage polarization and elaboration of pro-fibrogenic cytokines, or a combination thereof. The composition (e.g., pharmaceutical composition) may further comprise the proteins and/or peptides in a pharmaceutically acceptable carrier.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. In addition to being useful as methods of treatment, the methods described herein may be useful for the prevention or prophylaxis of disease.

The terms "subject" and "individual" and "patient" are used interchangeably herein, and refer to an animal, for example a human or non-human animal (e.g., a mammal), to whom treatment, including prophylactic treatment, with a pharmaceutical composition as disclosed herein, is provided. The term "subject" as used herein refers to human and non-human animals. The term "non-human animals" includes all vertebrates, e.g., mammals, such as non-human primates (particularly higher primates), sheep, dogs, rodents (e.g. mouse or rat), guinea pigs, goats, pigs, cats, rabbits, cows, and non-mammals such as chickens, amphibians, reptiles etc. In one embodiment, the subject is human. In another embodiment, the subject is an experimental animal or animal substitute as a disease model. In another embodiment, the subject is a farm animal. Non-human mammals include mammals such as non-human primates (particularly higher primates), sheep, dogs, rodents (e.g. mouse or rat), guinea pigs, goats, pigs, cats, rabbits, horses, and cows. In some aspects, the non-human animal is a companion animal such as a dog or a cat.

Pharmaceutical Compositions

In addition to MEGF9, UNC5A, and/or ALG5 proteins, biologically active fragments thereof, or specific antibodies, the present pharmaceutical compositions/preparations may contain suitable pharmaceutically acceptable carriers comprising excipients and auxiliaries which facilitate the processing of the active compounds into preparations which can be used pharmaceutically as is well known in the art. Suitable solutions for administration by injection, may contain from about 0.01 to 99% active compound(s) together with the excipient.

The phrases "pharmaceutical composition" or "pharmacologically acceptable composition" refers to molecular entities and compositions that do not produce an adverse, allergic, or other untoward reaction when administered to an animal, such as a human, as appropriate. Moreover, for animal (e.g., human) administration, it will be understood that preparations should meet bioburden, sterility, pyrogenicity, general safety, and/or purity standards as required by the FDA or other recognized regulatory authority.

As used herein, "pharmaceutically acceptable carrier" includes any and all excipients, buffers, co-solvents, tonicity agents, processing aids, aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, disintegration agents, lubricants, flavor modifiers (e.g., sweetening agents, flavoring agents), such like materials and combinations thereof. The pH and exact concentration of the various components in a pharmaceutical composition may be adjusted according to well-known parameters. In some aspects, the carrier may encapsulate a therapeutic agent, but not itself be consumed or administered to a subject (e.g., a shell capsule encasing a dry powder composition, such as for use in a dry powder inhaler).

As used herein, "excipient" refers to pharmaceutically acceptable carriers that are relatively inert substances used to facilitate administration or delivery of an Active Pharmaceutical Ingredient (API) into a subject or used to facilitate processing of an API into drug formulations that may be used pharmaceutically for delivery to the site of action in a subject. Excipients or pharmaceutically acceptable carriers include all of the inactive components of the dosage form except for the active ingredient(s). Non-limiting examples of excipients include carrier agents, bulking agents, stabilizing agents, surfactants, surface modifiers, solubility enhancers, buffers, encapsulating agents, antioxidants, preservatives, nonionic wetting or clarifying agents, viscosity-increasing agents, and absorption-enhancing agents. "Excipient free" refers to the pharmaceutical composition of interest in a formulation free of any excipients.

Other pharmaceutically acceptable carriers the present composition are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension.

The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

In some embodiments, the components in the pharmaceutical composition may be combined with the carrier in any convenient and practical manner, e.g., by solution, suspension, emulsification, admixture, encapsulation, absorption, and the like. Such procedures may be routine for those skilled in the art. In some examples, the composition may be combined or mixed thoroughly with a semi-solid or solid carrier. The mixing may be carried out in any convenient manner, such as grinding. Stabilizing agents may be also added in the mixing process in order to protect the composition from loss of therapeutic activity, e.g., denaturation in the stomach. Examples of stabilizers for use in a composition include buffers, amino acids, such as glycine and lysine, carbohydrates or lyoprotectants, such as dextrose, mannose, galactose, fructose, lactose, sucrose, maltose, sorbitol, mannitol, etc.

In some embodiments, a pharmaceutical composition may comprise one or more surfactants. Surfactants used in accordance with the disclosed methods include ionic and non-ionic surfactants. Examples of non-ionic surfactants include polysorbates such as TWEEN®-20 and TWEEN-80® surfactants (ICI Americas Inc. of Bridgewater, N.J.); poloxamers (e.g., poloxamer 188); TRITON® surfactants (Sigma of St. Louis, Mo.); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palnidopropyl-, or (e.g., lauroamidopropyl); myristamidopropyl-, palmidopropyl-, or isosteaaramidopropyl-dimethylamine; sodium methyl cocoyl-, or disodium methyl oleyl-taurate; MONAQUAT™ surfactants (Mona Industries Inc. of Paterson, N.J.); polyethyl glycol; polypropyl glycol; block copolymers of ethylene and propylene glycol such as PLURONIC® surfactants (BASF of Mt. Olive, N.J.); oligo (ethylene oxide) alkyl ethers; alkyl (thio) glucosides, alkyl maltosides; and phospholipids. For example, the surfactant may be present in a formulation in an amount from about 0.01% to about 0.5% (weight of surfactant relative to total weight of other solid components of the formulation; "w/w"), from about 0.03% to about 0.5% (w/w), from about 0.05% to about 0.5% (w/w), or from about 0.1% to about 0.5% (w/w). In some examples, the pharmaceutical composition may be essentially free of non-ionic surfactants or essentially free of all surfactants.

The pharmaceutical compositions may be manufactured in a manner, which is itself known, for example, by means of conventional mixing, granulating, dissolving, or lyophilizing processes. Suitable excipients may include fillers binders, disintegrating agents, auxiliaries and stabilizers, all of which are known in the art. Suitable formulations for parenteral administration include aqueous solutions of the antibody in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances that increase the viscosity of the suspension.

The pharmaceutical formulation for systemic administration may be formulated for parenteral administration and various types of the formulation may be used simultaneously to achieve systemic administration of the active ingredient.

The one or more proteins, peptides and/or antibodies may be formulated into a composition in a pharmaceutically acceptable free base, neutral, or salt form. Pharmaceutically acceptable salts include the acid addition salts, e.g., those formed with the free amino groups of a proteinaceous composition, or which may be formed with inorganic acids, such as, for example, hydrochloric or phosphoric acids, or such organic acids as acetic, oxalic, tartaric, or mandelic acid. Salts formed with the free carboxyl groups may also be derived from inorganic bases, such as, for example, sodium, potassium, ammonium, calcium, or ferric hydroxides; or such organic bases as isopropylamine, trimethylamine, histidine, or procaine. Upon formulation, solutions will be administered in a manner compatible with the dosage formulation and in such amount as may be therapeutically effective. The formulations may be administered in a variety of dosage forms, such as formulated for parenteral administrations, such as injectable solutions, or aerosols for delivery to the lungs, or formulated for alimentary administrations, such as drug release capsules and the like.

The methods may be used to treat, reduce or ameliorate IPF (or another fibrotic condition) in a subject in need thereof. The active protein, peptide, antibody, or small organic molecule mimic thereof, or a pharmaceutically acceptable salt thereof may be administered in the form of a pharmaceutical composition as described above.

Doses preferably include pharmaceutical dosage units comprising an effective amount of the therapeutic agent. Dosage unit form refers to physically discrete units suited as unitary dosages for a mammalian subject; each unit contains a predetermined quantity of active material calculated to produce the desired therapeutic effect, in association with the required pharmaceutical carrier. The specification for the dosage unit forms may be dictated by and directly dependent on (a) the unique characteristics of the active material and the particular therapeutic effect to be achieved, and (b) the limitations inherent in the art of compounding such an active compound for the treatment of, and sensitivity of, individual subjects.

By an effective amount is meant an amount sufficient to achieve a regional concentration or a steady state systemic concentration in vivo, which results in a measurable reduction in any relevant parameter of disease. The desired therapeutic result may be improvement in the condition to be treated by a claimed method, use, or composition.

The amount of antibody, polypeptide or peptide to be administered depends on the antibody that is selected, the state of the disease or condition, the route of administration, the health and weight of the recipient, the existence of other concurrent treatment, if any, the frequency of treatment, the nature of the effect desired, and the judgment of the skilled practitioner.

A preferred single dose, given once daily for treating a subject, preferably a mammal, more preferably human who his suffering from IPF is between about 0.1 mg/kg and about 50 mg/kg, preferably between about 0.5 mg/kg and about 5 mg/kg, for example. Such a dose can be administered daily for anywhere from about 3 days to one or more weeks. Chronic administration is also possible, though the dose may need to be adjusted downward. The foregoing ranges are, however, suggestive, as the number of variables in an individual treatment regime is large, and considerable excursions from these preferred values are expected.

The pharmaceutical composition may be administered to the patient in a single dose or in multiple doses. When multiple doses are administered, the doses may be separated from one another by, for example, one hour, three hours, six hours, eight hours, one day, two days, one week, two weeks, or one month. For example, the pharmaceutical composition may be administered for, e.g., 1, 2, 3, 4, 5, 6, 7, 8, 10, 15, 20, or more weeks. It may be to be understood that, for any particular subject, specific dosage regimes may be adjusted over time according to the individual need and the professional judgment of the person administering or supervising the administration of the compositions. For example, the dosage of the pharmaceutical composition may be increased if the lower dose does not provide sufficient therapeutic activity.

Therapeutically effective amounts of the one or more proteins and peptides as disclosed herein or a mutant, variant, analog or derivative thereof may be provided at a dose of 0.0001, 0.01, 0.01, 0.1, 1, 5, 10, 25, 50, 100, 500, or 1,000 mg/kg or g/kg. Effective doses may be extrapolated from dose-response curves derived from in vitro or animal model test bioassays or systems.

Dosages for a particular patient or subject may be determined by one of ordinary skill in the art using conventional considerations, (e.g., by means of an appropriate, conventional pharmacological protocol). A physician may, for example, prescribe a relatively low dose at first, subsequently increasing the dose until an appropriate response may be obtained. The dose administered to a patient may be sufficient to affect a beneficial therapeutic response in the patient over time, or, e.g., to reduce symptoms, or other appropriate activity, depending on the application. The dose may be determined by the efficacy of the particular formulation, and the activity, stability or serum half-life of the one or more proteins and peptides as disclosed herein or a mutant, variant, analog or derivative thereof and the condition of the patient, as well as the body weight or surface area of the patient to be treated.

In some embodiments, a subject may be given a single dose, given once daily for treating a subject, preferably a mammal, more preferably human who his suffering from or susceptible to pulmonary fibrosis resulting therefrom may be between about 0.2 mg/kg and about 250 mg/kg, such as between about 10 mg/kg and about 50 mg/kg, for example, via instillation (by inhalation). Such a dose may be administered daily for anywhere from about 3 days to one or more weeks. Chronic administration may be also possible, though the dose may need to be adjusted downward as is well-understood in the art. The foregoing ranges are, however, suggestive, as the number of variables in an individual treatment regime may be large, and considerable excursions from these preferred values may be expected.

For continuous administration, e.g., by a pump system such as an osmotic pump, a total dosage for a time course of about 1-2 weeks may be preferably in the range of 1 mg/kg to 1 g/kg, preferably 20-300 mg/kg, more preferably 50-200 mg/kg. After such a continuous dosing regimen, the total concentration of the active compound may be in the range of about 0.5 to about 50 µM, preferably about 1 to about 10 µM.

An effective concentration of the one or more proteins and peptides for inhibiting or preventing inhibiting apoptosis in vitro may be in the range of about 0.5 nM to about 100 nM, more preferably from about 2 nM to about 20 nM. Effective doses and optimal dose ranges may be determined in vitro using the methods described herein.

The pharmaceutical composition may be administered by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrathecal, intra-Ommaya, intravitreous, intraocular, intrasynovial, intrathoracic, intrauterine, intravesical, bolus, vaginal, rectal, buccal, sublingual, intranasal, or transdermal. For example, a dry powder formulation may be administered by installation into a subject (e.g., subcutaneous installation) or may be reconstituted in a liquid prior to injection. In some examples, the pharmaceutical composition may be delivered locally to the airway, such as administration of a nebulized formulation or a dry powder formulation using a dry powder inhaler. They may be administered alone or in combination with anti-fibrotic compounds. The term "airway" refers herein to any portion of the respiratory tract including the upper respiratory tract, the respiratory airway, and the lungs. The upper respiratory tract includes the nose and nasal passages, mouth, and throat. The respiratory airway includes the larynx, trachea, bronchi and bronchioles. The lungs include the respiratory bronchioles, alveolar ducts, alveolar sacs and alveoli.

The terms "nebulizing," "nebulized" and other grammatical variations, refer herein to the process of converting a liquid into small aerosol droplets. In some embodiments, the aerosol droplets have a median diameter of approximately 2-10 μm. In some embodiments, the aerosol droplets have a median diameter of approximately 2-4 μm.

In some embodiments, administration may be by parenteral, subcutaneous (sc), intravenous (iv), intramuscular, intraperitoneal, transdermal routes or by intrapulmonary or intratracheal administration which includes intranasal (i.n.) administration, inhalation or lung instillation, or any combination thereof. Alternatively, or concurrently, administration may be by the oral route. The dosage administered will be dependent upon the age, health, and weight of the recipient, kind of concurrent treatment, if any, frequency of treatment, and the nature of the effect desired. In one example, the administration is by intratracheal administration. In one example, the administration is by intravenous administration.

Dry Powder and Inhalation Devices

In some embodiments, the pharmaceutical composition may be in a form of dry powder. In some examples, for effective inhalation and deposition of a powder into a subject (e.g., into the lungs), the particle size of the dry powder may have a mass median aerodynamic diameter of less than about 5 μm. The particle sizes of the formulations may be reduced by any suitable method, including but not limited to milling, grinding, thin film freezing, spray drying, or crushing. Milling may be performed by any method known in the art, such as by air jet mill, ball mill, wet mill, media mill, high-pressure homogenization, or cryogenic mill. See WO2020/055824, which is incorporated by reference herein in its entirety.

The stability of the proteins and/or peptides and/or antibodies following particle size reduction may be assessed using known techniques in the art, including size exclusion chromatography; electrophoretic techniques; HPLC; mass spectrometry; spectroscopic techniques such as UV spectroscopy and circular dichroism spectroscopy, and activity (measured in vitro or in vivo). To perform in vitro assays of protein stability, an aerosol composition may be collected and then distilled or absorbed onto a filter. To perform in vivo assays, or for pulmonary administration of a pharmaceutical composition to a subject, a device for dry powder dispersion may be adapted for inhalation by the subject. For example, protein stability may be assessed by determining the level of protein aggregation. Preferably, a dry powder composition of the invention may be substantially free of protein aggregates. The presence of soluble aggregates may be determined qualitatively using dynamic light scattering (DLS) (DynaPro-801TC, Protein Solutions Inc. of Charlottesville, Va.) and/or by UV spectrophotometry.

In some embodiments, the methods may comprise modulating the drug release. In some embodiments, the pharmaceutical composition may be formulated for slow- or delayed-release. In some embodiments, the pharmaceutical composition may be formulated for fast-release. In further embodiments, the pharmaceutical composition may be formulated for both slow and fast release (e.g., dual release profile).

In some embodiments, the present disclosure provides methods for the administration of the inhalable pharmaceutical composition provided herein. Administration may be, but is not limited, to inhalation of the pharmaceutical composition using an inhaler. In some embodiments, an inhaler may be a passive dry powder inhaler (DPI), such as a Plastiape RSO1 monodose DPI. In a dry powder inhaler, dry powder may be stored in a reservoir and may be delivered to the lungs by inhalation without the use of propellants.

In some embodiments, an inhaler may be a single-dose DPI, such as a DoseOne™ Spinhaler, Rotohaler®, Aerolizer®, or Handihaler. In some embodiments, an inhaler may be a multidose DPI, such as a Plastiape RSO2, Turbuhaler®, Twisthaler™, Diskhaler®, Diskus®, or Ellipta™. In some embodiments, an inhaler may be a plurimonodose DPI for the concurrent delivery of single doses of multiple medications, such as a Plastiape RSO4 plurimonodose DPI. In some examples, dry powder inhalers have medication stored in an internal reservoir, and medication may be delivered by inhalation with or without the use of propellants. Other types of dry powder inhalers may have medication in pre-divided doses stored in a capsule (e.g., cellulose or gelatin base) or foil pouch, each of which may be punctured by the device to release the dose to the patient. Dry powder inhalers may require an inspiratory flow rate greater than 30 L/min for effective delivery, such as between about 30-120 L/min. In some embodiments, efficient aerosolization of the pharmaceutical composition is independent of inspiratory force. In some embodiments, the dry powder inhaler has a flow resistance of between 0.01 $kPa^{0.5}$ min/L and 0.05 $kPa^{0.5}$ min/L, such as between 0.02 $kPa^{0.5}$ min/L and 0.04 $kPa^{0.5}$ min/L. The dry powder inhaler (e.g., high resistance, low resistance, passive, active) may be chosen based on the patient population and their inspiratory capabilities.

In some embodiments, the inhaler may be a metered dose inhaler. Metered dose inhalers deliver a defined amount of medication to the lungs in a short burst of aerosolized medicine aided by the use of propellants. Metered dose inhalers comprise three major parts: a canister, a metering valve, and an actuator, and may utilize a spacer device to de-accelerate the emitted particles and facilitate inhalation of the aerosolized cloud by the patient. The medication formulation, including propellants and any required excipients, may be stored in the canister. The metering valve allows a defined quantity of the medication formulation to be dispensed. The actuator of the metered dose inhaler, or mouthpiece, contains the mating discharge nozzle and typically includes a dust cap to prevent contamination. The required inspiratory flow rate required for the use of a metered dose inhaler may be less than 90 L/min, such as between about 15-90 L/min, preferably about 30 L/min. In some embodiments, efficient aerosolization of pharmaceutical composition may be independent of inspiratory force.

In some embodiments, an inhaler may be a nebulizer. A nebulizer may be used to deliver medication in the form of an aerosolized mist inhaled into the lungs. The medication formulation may be aerosolized by compressed gas, or by ultrasonic waves. A jet nebulizer may be connected to a compressor. The compressor emits compressed gas through a liquid medication formulation at a high velocity, causing the medication formulation to aerosolize. Aerosolized medication may be then inhaled by the patient. An ultrasonic wave nebulizer generates a high frequency ultrasonic wave, causing the vibration of an internal element in contact with a liquid reservoir of the medication formulation, which causes the medication formulation to aerosolize. Aerosolized medication may be then inhaled by the patient. A nebulizer may utilize a flow rate of between about 3-12 L/min, such as about 6 L/min. In some examples, the milled active may be suspended in a pharmaceutically acceptable liquid carrier vehicle and administered by nebulization (e.g., air jet nebulization). In further aspects, a composition of the embodiments may be administered by a vaporization method (e.g., rapid vaporization) such as by an e-cigarette device.

In some embodiments, the pharmaceutical composition may be administered on a routine schedule. As used herein, a routine schedule refers to a predetermined designated period of time. The routine schedule may encompass periods of time which may be identical or which differ in length, as long as the schedule may be predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In some embodiments, a one or more of the proteins and peptides may be administered once per day. In preferred embodiments, a protein or biologically active fragments thereof may be administered less than once per day, such as every other day, every third day, or once per week. In some embodiments, a complete dose of pharmaceutical composition is between 1-100 mg, such as 20-100, 50-100, 10-20, 20-40, 50-70, or 80-90 mg.

In some embodiments, the one or more proteins and peptides may be provided in a unit dosage form (e.g., pre-divided dose), such as in a capsule, blister or a cartridge, wherein the unit dose comprises at least 1 mg of a protein or biologically active fragments thereof, such as at least 5 mg, 10 mg, 15 mg or 20 mg of the one or more proteins and peptides per dose. In some aspects, the unit dose may be 1-10 mg (e.g., about 5 mg) of the one or more proteins and peptides. In particular aspects, the unit dosage form does not comprise the administration or addition of any excipient and may be merely used to hold the powder for inhalation (e.g., the capsule, blister, or cartridge may be not administered). In some aspects, more than one of the unit dose forms is administered to a subject. For example, in the case of a dry powder inhaler, proteins and peptides of the embodiments may be provided in unit dose capsules and more than one unit dose capsules (e.g., 3-4) may be administered to a subject by inhalation. In some embodiments, the one or more proteins and peptides may be administered in a high emitted dose, such as at least 10 mg, preferably at least 15 mg, even more preferably 20 mg. In some embodiments, administration of the one or more proteins and peptides may result in a high fine particle dose into the deep lung such as greater than 5 mg. In some examples, the fine particle dose into the deep lung may be at least 10 mg, even more preferably at least 15 mg. In some examples, the particle dose may be produced from 1, 2, 3, 4 or 5 or more capsules comprising doses of the one or more proteins and peptides. In some aspects, the fine particle dose may be at least, 50%, such as at least 60, 65, 70, 75, or 80% of the emitted dose.

In some embodiments, changes in inhalation pressure drop may result in a change in emitted dose. In some embodiments, changes in inhalation pressure of 3 kPa, such as from 4 kPa to 1 kPa, may result in a reduction of emitted dose of less than 25%, such as 24%, 23%, 22%, 21%, 20%, 19%, 18%, 17%, 16%, 15%, 14%, 13%, 12%, 11%, 10%, 9%, 8%, 7%, 6%, 5% or less. In some embodiments, changes in inhalation pressure may result in a change in fine particle dose. In some embodiments, changes in inhalation pressure of 3 kPa, such as from 4 kPa to 1 kPa may result in a reduction of fine particle dose of less than 15%, such as 14%, 13%, 12%, 11%, 10%, 9%, 8%, 7%, 6%, 5% or less.

Combination Therapy

In some embodiments, the methods herein comprise administering the composition described herein in combination with one or more additional therapeutic agents. An additional therapeutic agent may be comprised in the pharmaceutical composition comprising the one or more of the proteins and/or antibodies. Alternatively or additionally, an additional therapeutic agent may be in another pharmaceutical composition different from the pharmaceutical composition comprising the one or more of the proteins and/or antibodies.

In some embodiments, the additional therapeutic agent is an inhibitor of vascular endothelial growth factor receptor, fibroblast growth factor receptor, and/or platelet derived growth factor receptor. In one example, the additional therapeutic agent is nintedanib (Ofev®). For example, the method herein comprises administering the composition described herein in combination with nintedanib.

In some embodiments, the additional therapeutic agent is a molecule that reduces fibroblast proliferation, inhibits transforming growth factor beta stimulated collagen production, and/or reduces the production of fibrogenic mediators such as transforming growth factor beta. In one example, the additional therapeutic is pirfenidone (Esbriet®). For example, the method herein comprises administering the composition described herein in combination with pirfenidone. In another example, the method herein comprises administering the composition described herein in combination with nintedanib and pirfenidone.

Further examples of the additional therapeutic agents include an NSAID, steroid, DMARD, immunosuppressive, biologic response modulators, bronchodilator or antifibrotic agent such as pirfenedone, an agent whose antifibrotic mechanism of action may be not fully understood but may involve blockade of TGF-beta, nintedanib, a broad tyrosine kinase blocker or any other antifibrotic agent. Examples of NSAIDS include the non-selective COX-inhibitors acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lornoxicam and nimesulide and the pharmaceutically acceptable salts thereof, the selective COX 2-inhibitors meloxicam, celecoxib and rofecoxib and the pharmaceutically acceptable salts thereof. Examples of steroids include prednisone, prednisolone, methylprednisolone, dexamethasone, budenoside, fluocortolone and triamcinolone. Suitable DMARDs may be sulfasalazine, olsalazine, chloroquin, gold derivatives (Auranofin), D-penicillamine and cytostatics such as methotrexate and cyclophosphamide. Examples of immunsuppressives include cyclosporine A and derivatives thereof, mycophenolatemofetil, FK 506, OKT-3, ATG, 15-desoxyspergualin, mizoribine, misoprostol, rapamycin, reflunomide and azathioprine. Examples of biologic response modifiers include interferon 3, anti-TNF-α (Etanercept), IL-10, anti-CD3 or anti-CD25. Suitable bronchodilators may be ipratropiumbromide, oxytropiumbromide, tiotropiumbromide, epinephrinehydrochloride, salbutamole, terbutalinsulfate, fenoterolhydrobromide, salmeterole and formoterole. In some examples, in such combinations each active ingredient may be administered either in accordance with its usual dosage range or a dose below its usual dosage range. The dosage for the combined NSAIDs, steroids, DMARDs, immunosuppressives and biologic response modifiers may be appropriately 1/50 of the lowest dose normally recommended up to 1/1 of the normally recommended dosage, preferably 1/20 to 1/2 and more preferably 1/10 to 1/5. The normally recommended dose for the combined drug may be the dose disclosed for example in Rote Liste® 2002, Editio Cantor Verlag Aulendorf, Germany, or in Physician's Desk Reference.

As used herein, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one aspect, the degree of flexibility can be within about ±10% of the numerical value. In another aspect, the degree of flexibility can be within about ±5% of the numerical value. In a further aspect, the degree of flexibility can be within about ±2%, ±1%, or ±0.05%, of the numerical value. Numerical quantities given are approximate, meaning that the term "around," "about" or "approximately" can be inferred if not expressly stated.

The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

As used herein, a plurality of compounds, elements, or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Furthermore, certain compositions, elements, excipients, ingredients, disorders, conditions, properties, steps, or the like may be discussed in the context of one specific embodiment or aspect or in a separate paragraph or section of this disclosure. It is understood that this is merely for convenience and brevity, and any such disclosure is equally applicable to and intended to be combined with any other embodiments or aspects found anywhere in the present disclosure and claims, which all form the application and claimed invention at the filing date. For example, a list of method steps, active agents, kits, or compositions described with respect to a formulation or method of treating a certain subject is intended to and does find direct support for embodiments related to compositions, formulations, and methods described in any other part of this disclosure, even if those method steps, active agents, kits, or compositions are not re-listed in the context or section of that embodiment or aspect.

Having now generally described the invention, the same will be more readily understood through reference to the following examples that are provided by way of illustration, and are not intended to be limiting of the present invention, unless specified. The examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Differential Expression of U5A and M9 in Injured Human AECs and fLfs.

M9 was upregulated in IPF fLfs and M2 macrophages while U5a was highly expressed in injured AECs. See FIGS. 1A-1B, which show results of Western blotting and qPCR for MEGF9 (M9) and UNC5a (U5A)) protein and mRNA in AECs and Lfs isolated from normal lung of healthy donors (nL) or lung tissue from IPF patient (IPF).

Example 2

M9 Regulated U5A and Differentiation of fLfs.

Figure 2B:
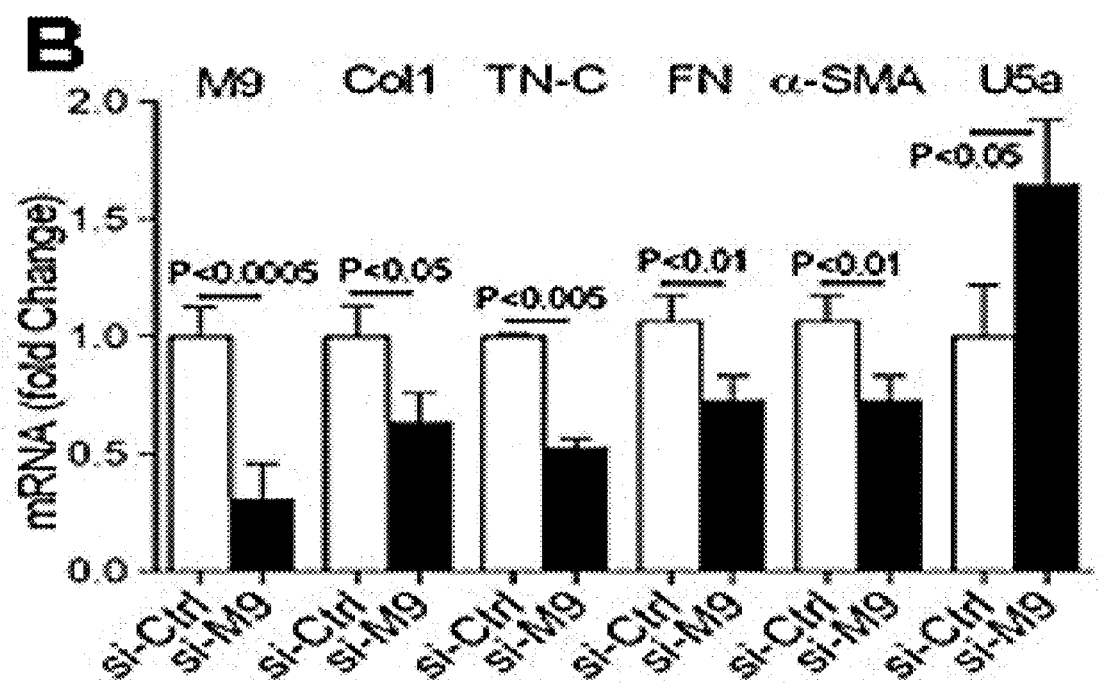
Figure 2C:
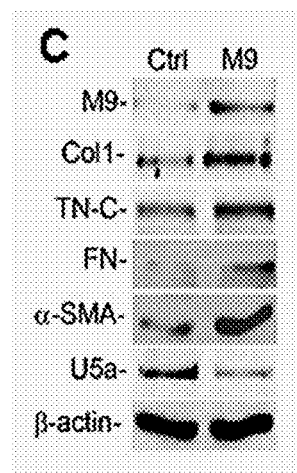
Figure 2D:
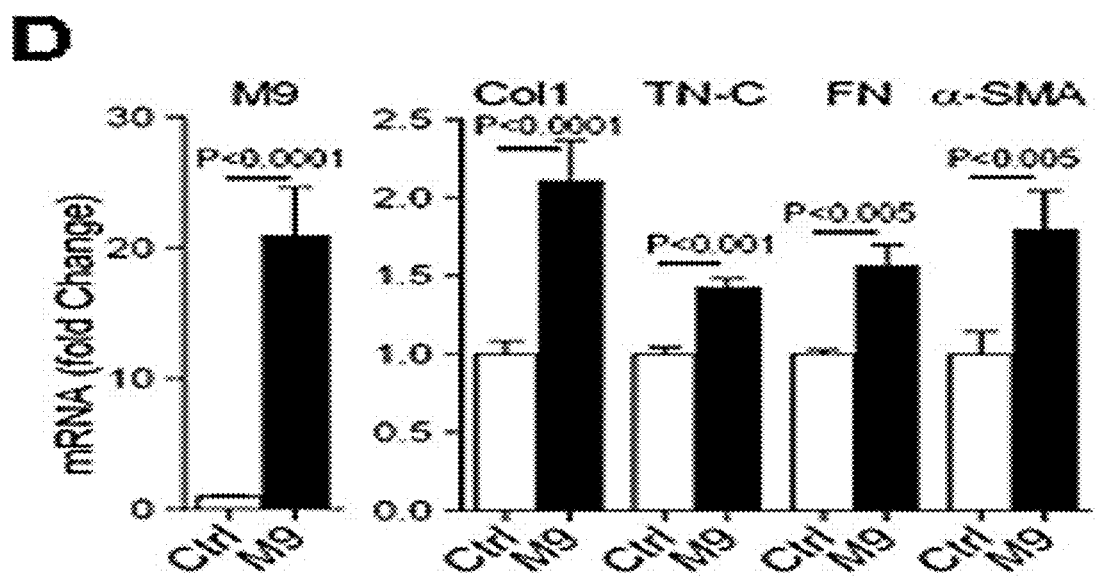

Inhibition of M9 using siRNA rescued basal expression of U5A and inhibited pro-fibrogenic marker proteins (FIG. 2A) and mRNAs (FIG. 2B) in fLfs. Overexpression of M9 inhibited U5A and induced pro-fibrogenic proteins (FIG. 2C) and (mRNAs (FIG. 2D) in nLfs. These results indicate an intricate link between expression of M9 and U5A, and differentiation of lung fibroblasts (Lfs).

The M9, U5A and ALG5 have never been explored for their roles in fibrosis in any fibrotic disease. The present inventor found increased expression of UNC5a, a member of a neuronal guidance protein, netrin-1 (NTN-1) family of receptors in injured AECs that were undergoing senescence and apoptosis. In addition, increased expression of MEGF9 and ALG5 along with loss of UNC5A in fLfs promoted myofibroblast activation and expansion. Inhibition of MEGF9 expression in fLfs (a) rescued basal expression of UNC5A, which was otherwise lost in fLfs and (b) reversed pro-fibrogenic phenotypes. In contrast, overexpression of MEGF9 in normal lung fibroblasts (nLfs) inhibited basal UNC5A expression and increased expression of pro-fibrogenic marker proteins and their mRNAs, suggesting transformation of nLfs into fLfs.

Example 3

Anti-M9 Antibody (M9Ab) Inhibited Pro-Fibrogenic Markers Expression in fLfs In Vitro.

Figure 3A:
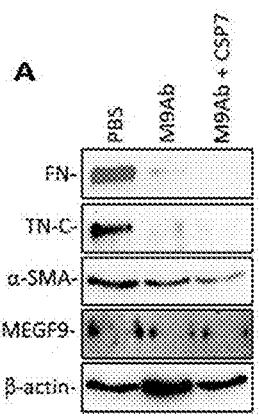
FIGS. 3A-3B. Antibodies specific for M9 inhibited pro-fibrogenic markers expression in fLfs in vitro. hfLfs were serum starved and treated with PBS or 2 µg/ml M9 antibody (M9Ab), or 2 µg/ml M9Ab plus 20 µM CSP7 for 48 hours (FIG. 3A). After treatment, cells were harvested and cell lysates were immunoblotted for pro-fibrogenic markers and M9, and 3-actin was used as loading control. Similar results were observed using mRNA (FIG. 3B).
Figure 3B:
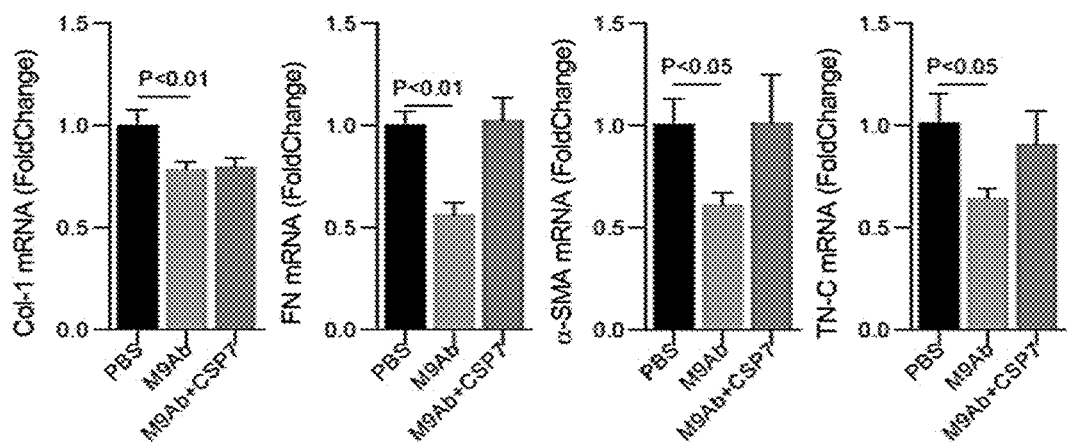

Serum starved hfLfs were treated with PBS or 2 µg/ml anti-MEGF9 antibody (M9Ab) (Mybiosource, Catalog #MBS9605643 and Invitrogen, Catalog #PA5-106685), or 2 µg/ml M9Ab plus 20 µM CSP7 for 48 hours. After treatment, the cells were harvested and cell lysates were immunoblotted for pro-fibrogenic markers, M9 (0-actin was used as loading control). See FIGS. 3A-3B for results. Similar results were observed using mRNA.

Example 4

Figure 4:
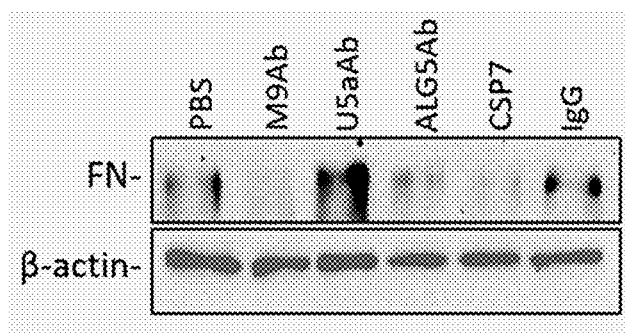
FIG. 4. Antibodies specific for M9 and for ALG5 inhibited pro-fibrogenic marker protein expression in fLfs. hfLfs were treated with or without: 2 µg/ml anti-rabbit M9 polyclonal antibody (M9 Ab), 1 µg/ml anti-rabbit polyclonal U5a antibody (U5a Ab), or 1 µg/ml anti-rabbit polyclonal ALG5 antibody (ALG5 Ab), with CSP7 as a positive control and purified rabbit IgG as a negative control and for 48 hours. Cell lysates were immunoblotted for pro-fibrotic marker fibronectin (FN), with 3-actin as loading control.

Anti-M9 and Anti ALG5 Antibodies Inhibited Pro-Fibrotic Marker Protein Expression in fLfs.

hfLfs were treated with or without: 2 µg/ml anti-rabbit MEGF9 polyclonal antibody (M9 Ab) (Mybiosource, Catalog #MBS9605643 and Invitrogen, Catalog #PA5-106685), 1 µg/ml rabbit anti-U5a polyclonal antibody (U5A Ab) (ProteinTech, Catalog #22068-1-AP and Sigma, Catalog #SAB2108252), or 1 µg/ml anti-rabbit anti-ALG5 polyclonal Ab (ALG5 Ab), or with CSP7 as a positive control or with purified rabbit IgG as a negative control for 48 hours. Cell lysates were immunoblotted for pro-fibrotic marker fibronectin (FN), with 3-actin as loading control. Results shown in FIG. 4 indicate that anti-M9-Ab and anti ALG5 Ab inhibited pro-fibrotic marker expression in fLfs.

Example 5

Anti-UNC5A Antibody Inhibited BLM-Induced AECs Apoptosis In Vitro.

Figure 5:
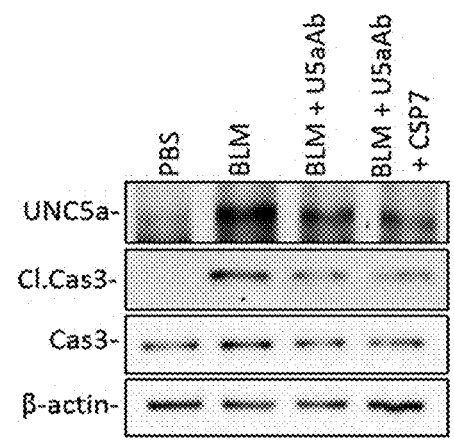
FIG. 5. An antibody specific for U5a inhibited BLM-induced AECs apoptosis in vitro. AECs were serum starved and treated with 40 µg/ml BLM to induce apoptosis. 24 hours later, cells were treated with or without 1 µg/ml U5a polyclonal antibody (U5a Ab) or 1 µg/ml U5a Ab+20 µM CSP7 for 24 hours. Cells lysates were immunoblotted for U5a, cleaved-caspase3 (Cl.Cas3), caspase3 (Cas3), and 3-actin (used as a loading control). BLM upregulated U5a expression. BLM induced Cl.Cas3 in AECs, whereas U5a Ab treatment inhibited Cl.Cas3 in AECs.

Serum-starved AECs were treated with 40 µg/ml BLM to induce apoptosis. 24 hours later, cells were treated with or without 1 µg/ml anti-U5A polyclonal rabbit antibody (U5A Ab) (ProteinTech, Catalog #22068-1-AP and Sigma, Catalog #SAB2108252) or 1 µg/ml U5A Ab+20 µM CSP7 for 24 hours. Cells lysates were immunoblotted for U5A, cleaved-caspase3 (Cl.Cas3), caspase3 (Cas3). β-actin was used as a loading control. Results are shown in FIG. 5. BLM induced UNC5A expression was upregulated. BLM also induced Cl.Cas3 in AECs, whereas U5A Ab treatment inhibited Cl.Cas3 in AECs.

Example 6

U5a and ALG5 Antibodies Inhibited BLM-Induced AECs Apoptosis In Vitro.

Figure 6:
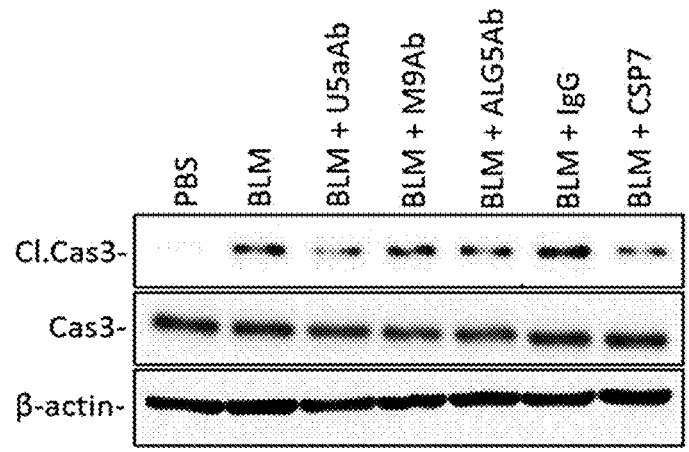
FIG. 6. Antibodies specific for U5a and ALG5 inhibited BLM-induced AECs apoptosis in vitro. AECs were treated with BLM to induce apoptosis. 24 hours later, cells were treated for 24 hours with or without: 1 µg/ml anti-rabbit polyclonal U5a antibody (U5a Ab), 2 µg/ml anti-rabbit polyclonal MEGF9 antibody (M9 Ab), or 1 µg/ml anti-rabbit polyclonal ALG5 antibody (ALG5 Ab). Purified rabbit IgG, 2 µg/ml, served as a negative control, and 20 µM CSP7 served as a positive control. Cell lysates were immunoblotted for apoptosis marker cleaved-caspase3 (Cl.Cas3), with caspase3 (Cas3) and 3-actin as loading controls.

AECs were treated with BLM to induce apoptosis. 24 hours later, cells were treated for 24 hrs with or without: 1 µg/ml anti-rabbit polyclonal anti-U5A antibody (U5A Ab), 2 µg/ml rabbit polyclonal anti-MEGF9 antibody (M9 Ab) (Mybiosource, Catalog #MBS9605643 and Invitrogen, Catalog #PA5-106685), or 1 µg/ml anti-rabbit polyclonal anti ALG5 antibody (ALG5 Ab) (Invitrogen, Catalog #PA5-52496). Purified rabbit IgG, 2 µg/ml, served as a negative control, and 20 µM CSP7 served as a positive control. Cell lysates were immunoblotted for apoptosis marker cleaved-caspase3 (Cl.Cas3), with caspase3 (Cas3) and β-actin as loading controls. Results shown in FIG. 6 indicate that anti-U5A and anti ALG5 Abs inhibited BLM-induced AECs apoptosis.

Example 7

Anti M9 Antibody (M9 Ab) Mitigated BLM-Induced Established Pulmonary Fibrosis.

Mice exposed to saline or 1.0 U/kg BLM by intratracheal instillation received intraperitoneal injections of treatment agent polyclonal M9 Ab (Mybiosource, Catalog #MBS9605643 and Invitrogen, Catalog #PA5-106685) (2.5 mg/kg) or controls daily for 7 days starting d.14 after BLM injury. Results are shown in FIGS. 7A-7F that include representative micro-CT images on d. 21 after BLM, lung volumes, lung compliance, lung elastance. Also shown are survival, lung weights, and body weights, along with Trichrome-stained lung sections. Lung homogenates were tested for hydroxyproline, soluble collagen and pro-fibrogenic marker protein and respective mRNAs.

Figure 7A:
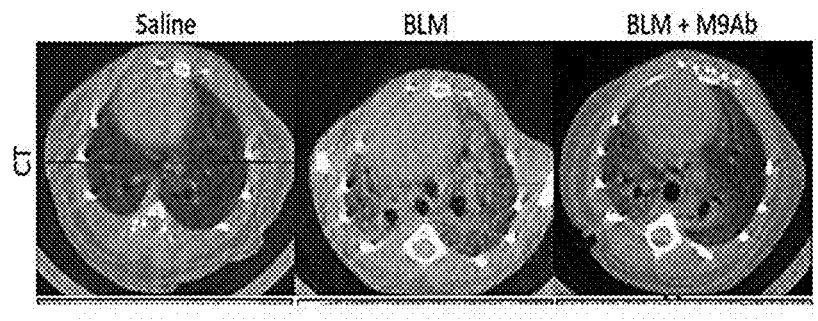
FIGS. 7A-7M. An antibody specific for M9 (M9 Ab) mitigated BLM-induced established pulmonary fibrosis. Mice exposed to saline or 1.0 U/kg BLM by intratracheal instillation received intraperitoneal injections of treatment agents an controls; M9 Ab (2.5 mg/kg) daily for 7 days starting d14 after BLM injury.
Figures 7B, 7C:
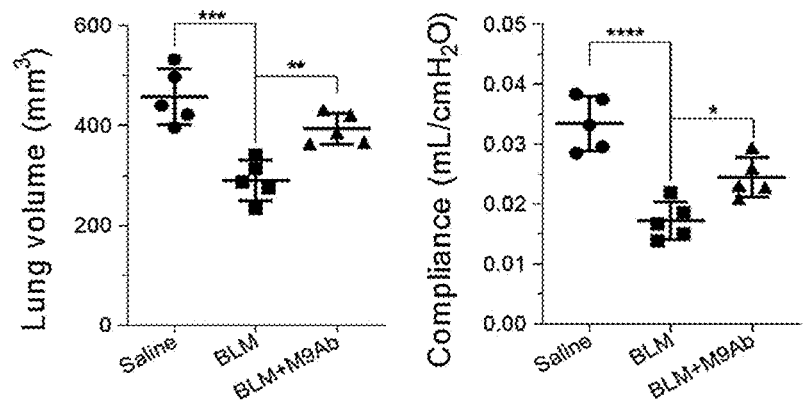
Figure 7D:
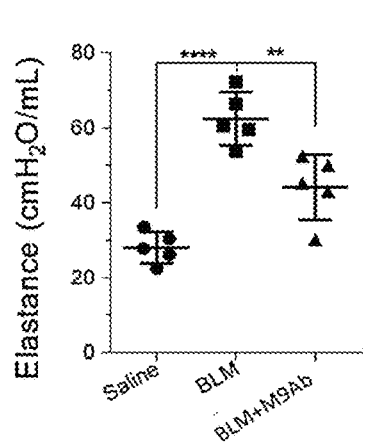
Figure 7E:
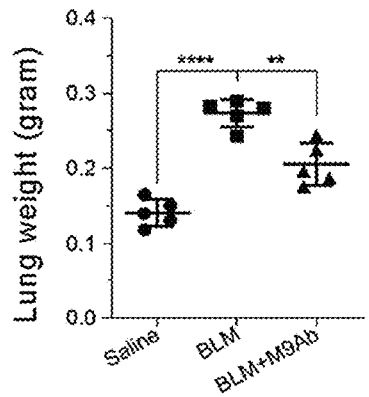
Figure 7F:
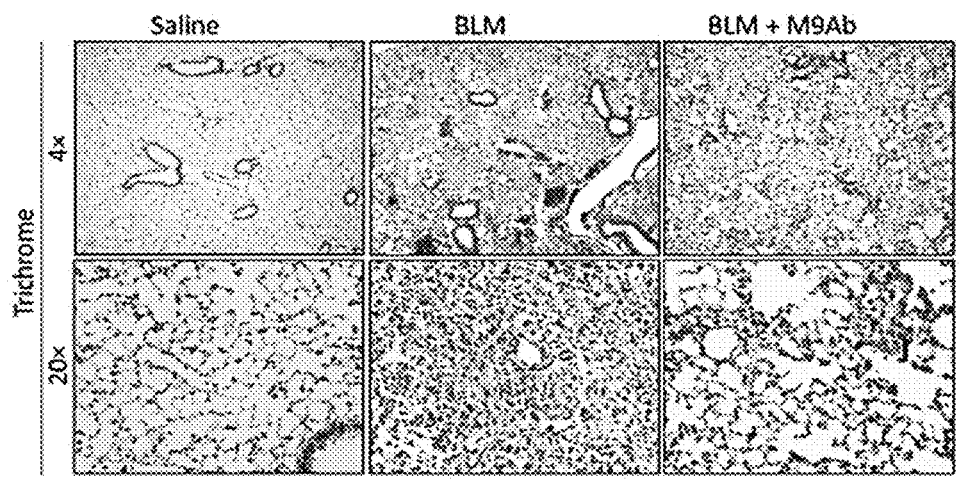
Figure 7G:
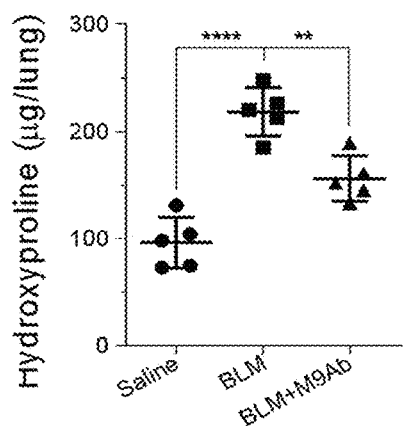
Figure 7H:
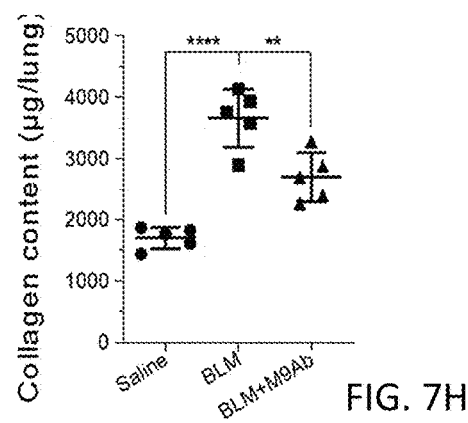
Figure 7I:
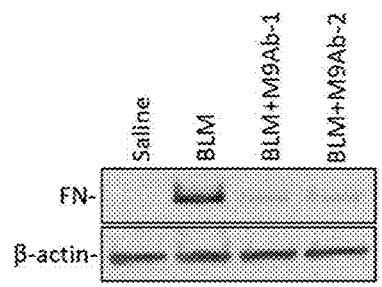
Figure 7J:
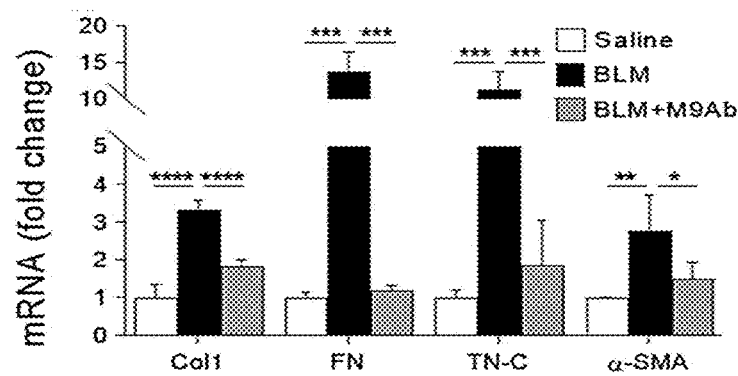
Figure 7K:
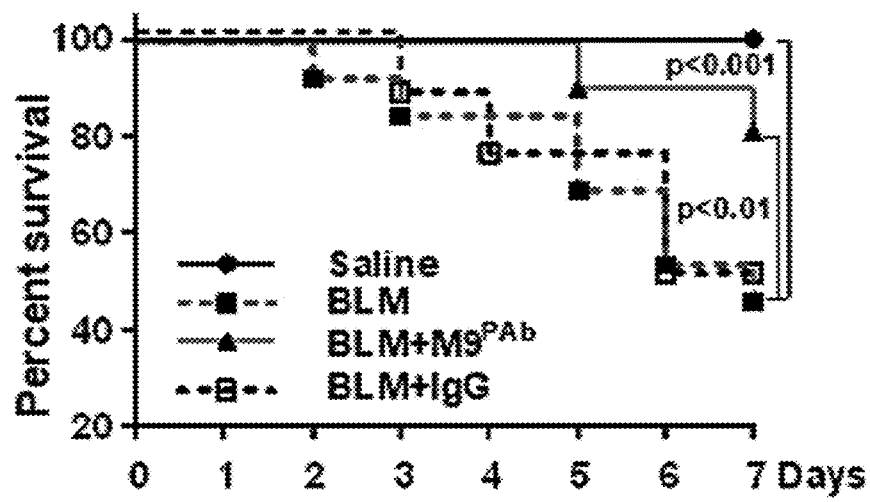
Figure 7L:
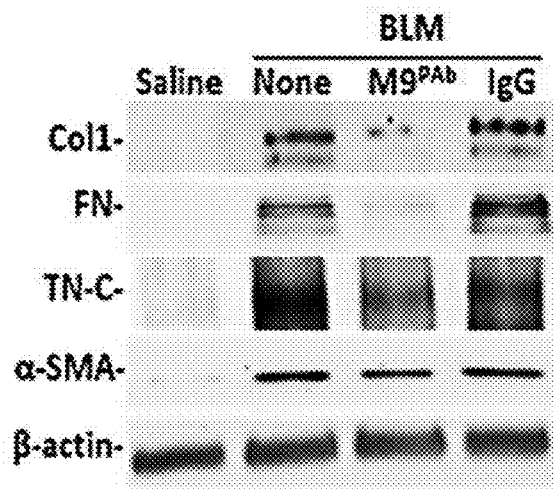
Figure 7M:
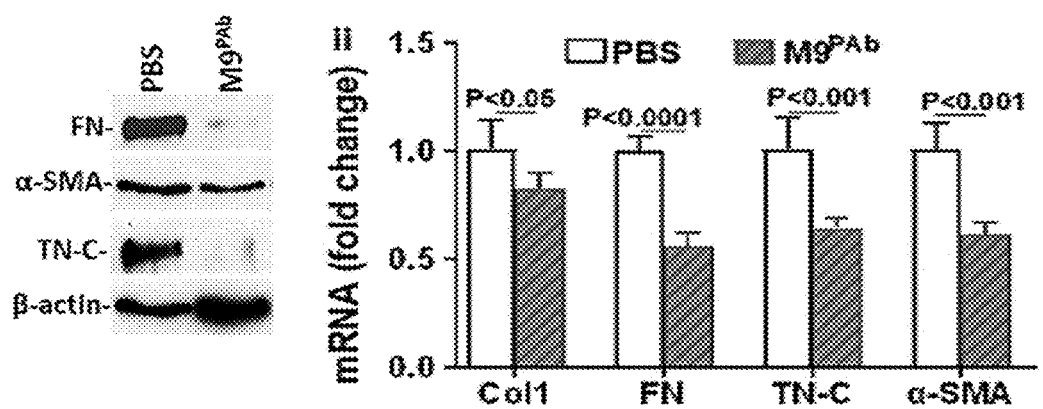
Figure 8A:
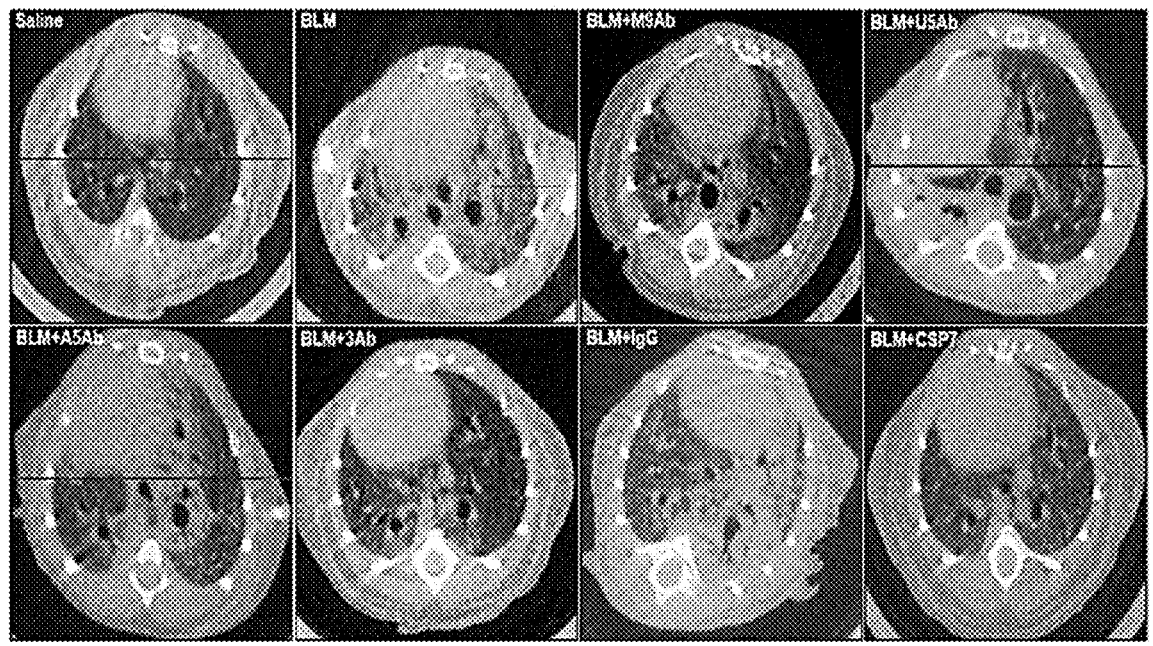
FIGS. 8A-8L. Antibodies specific for M9, UNC5A ("U5"), ALG-5 ("A5") and the combination of all 3 Abs mitigated existing BLM-induced pulmonary fibrosis. Mice exposed to saline or 1.0 U/kg BLM by intratracheal instillation received intraperitoneal injections with or without the Ab (2.5 mg/kg) daily for 7 days starting on d. 14 after BLM injury. CSP7 is a positive control and purified rabbit IgG is a negative control.
Figure 8B:
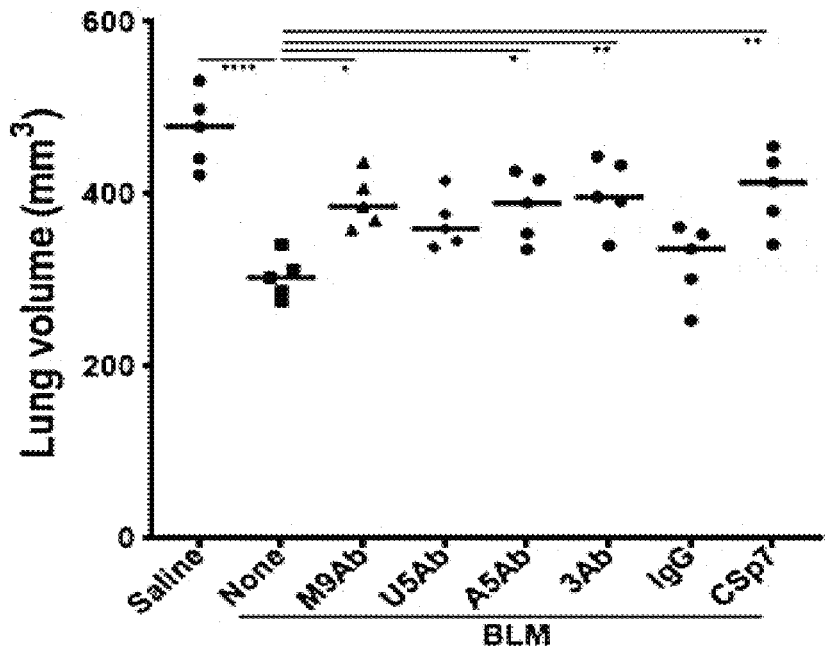
Figure 8C:
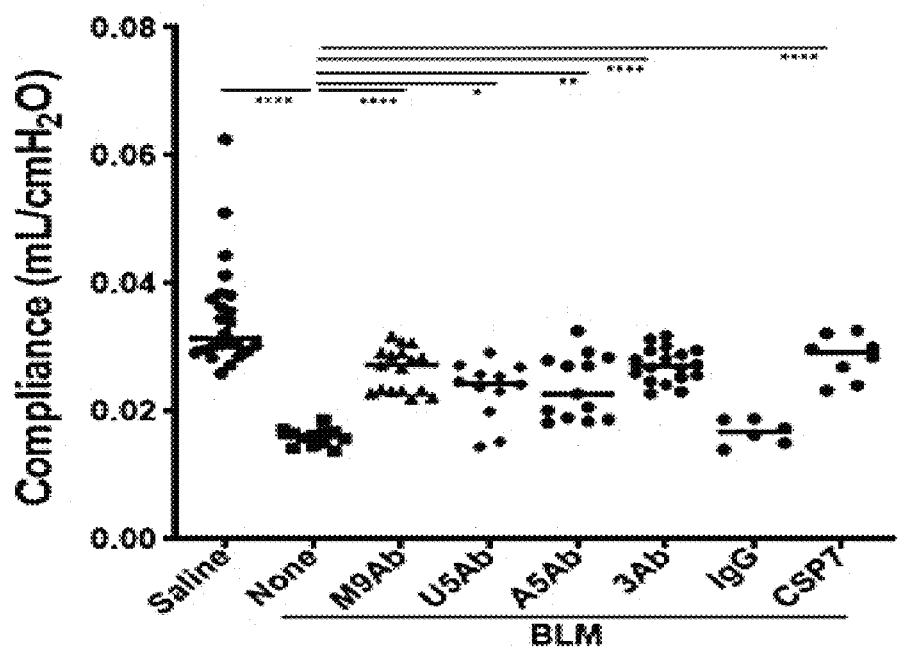
Figure 8D:
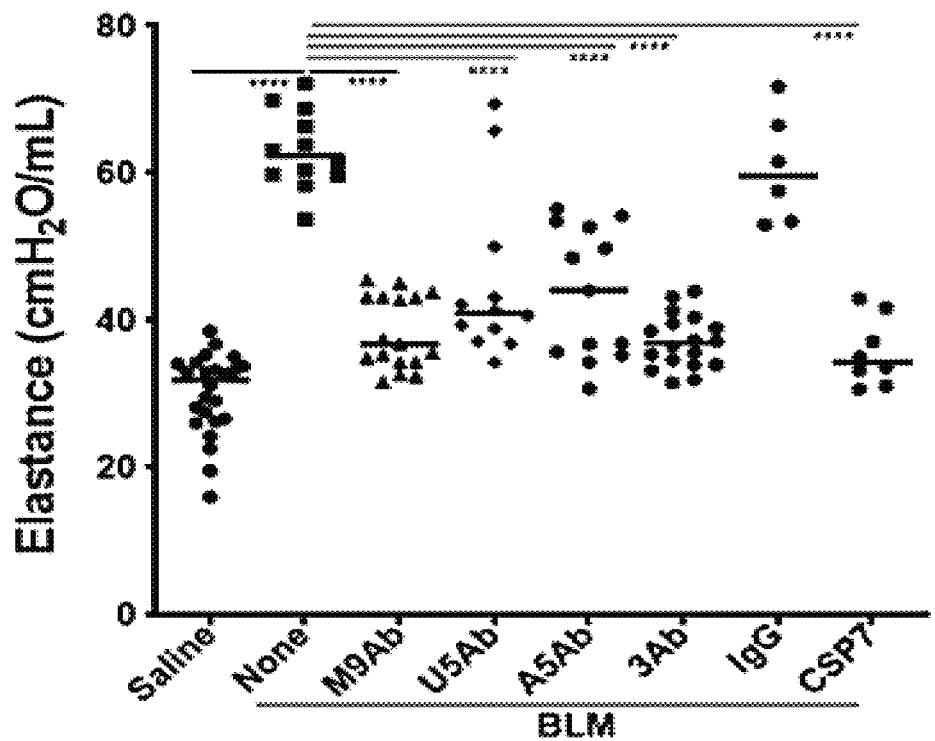
Figure 8E:
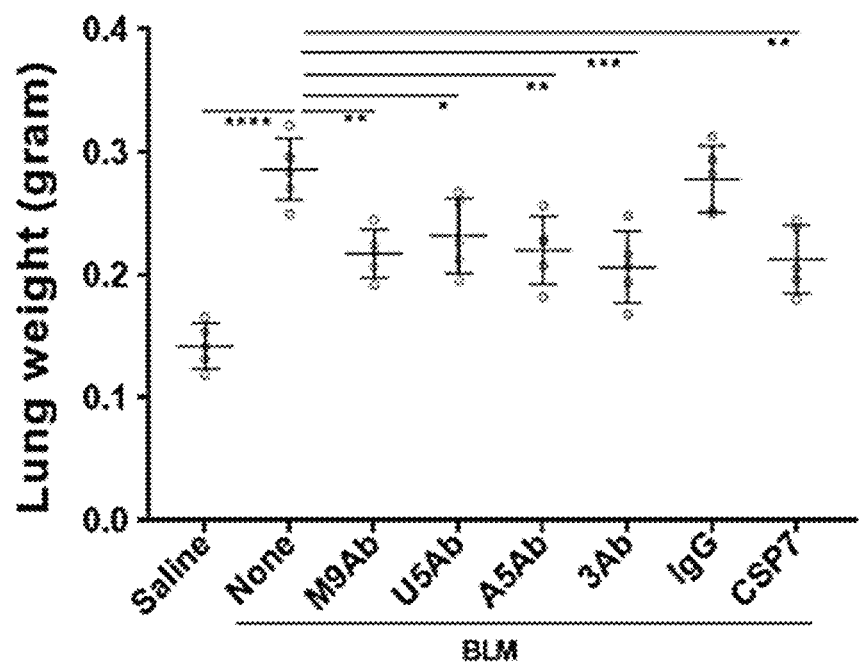
Figure 8F:
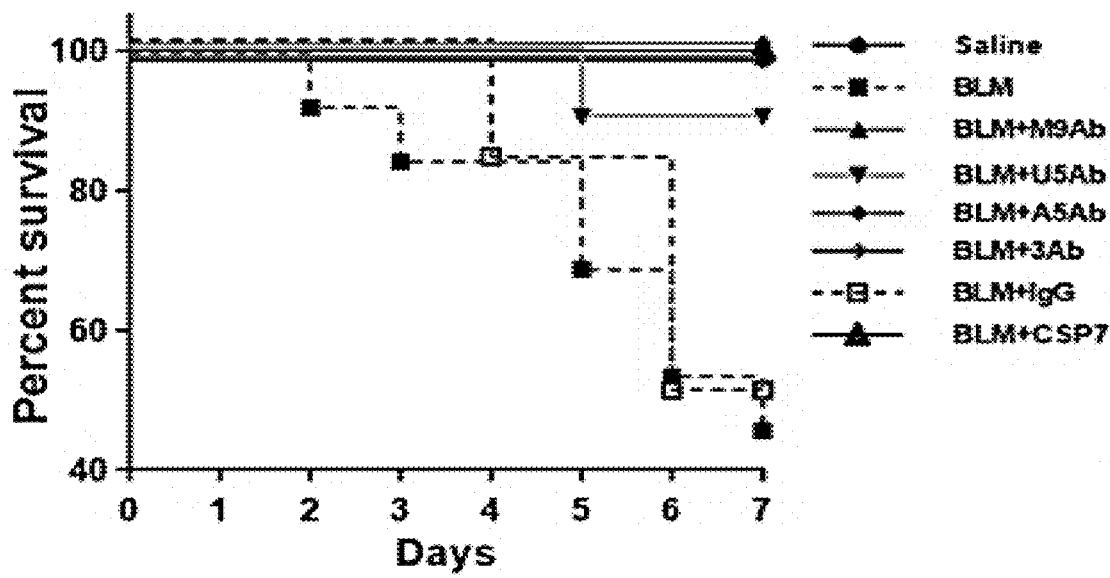
Figure 8G:
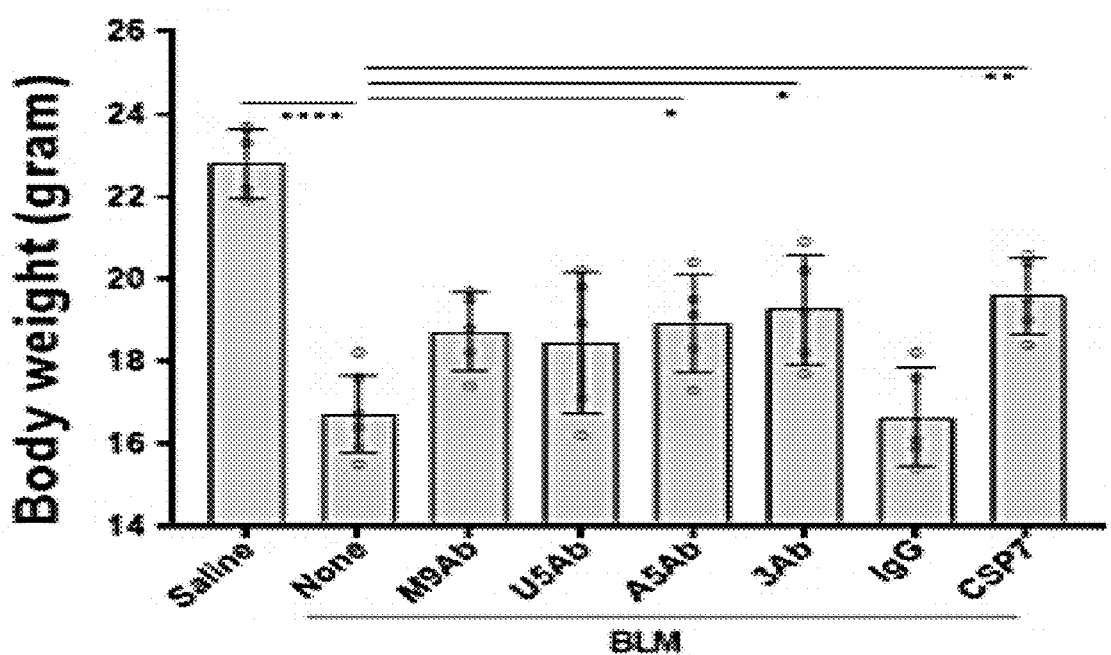
Figure 8H:
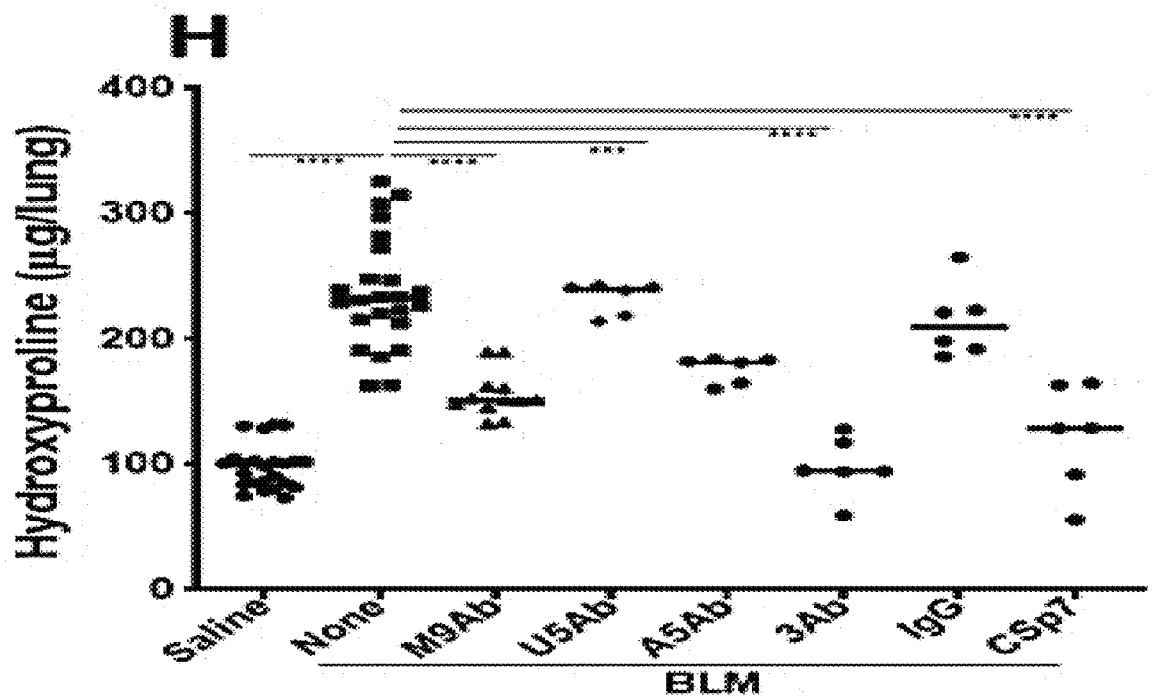
Figure 8I:
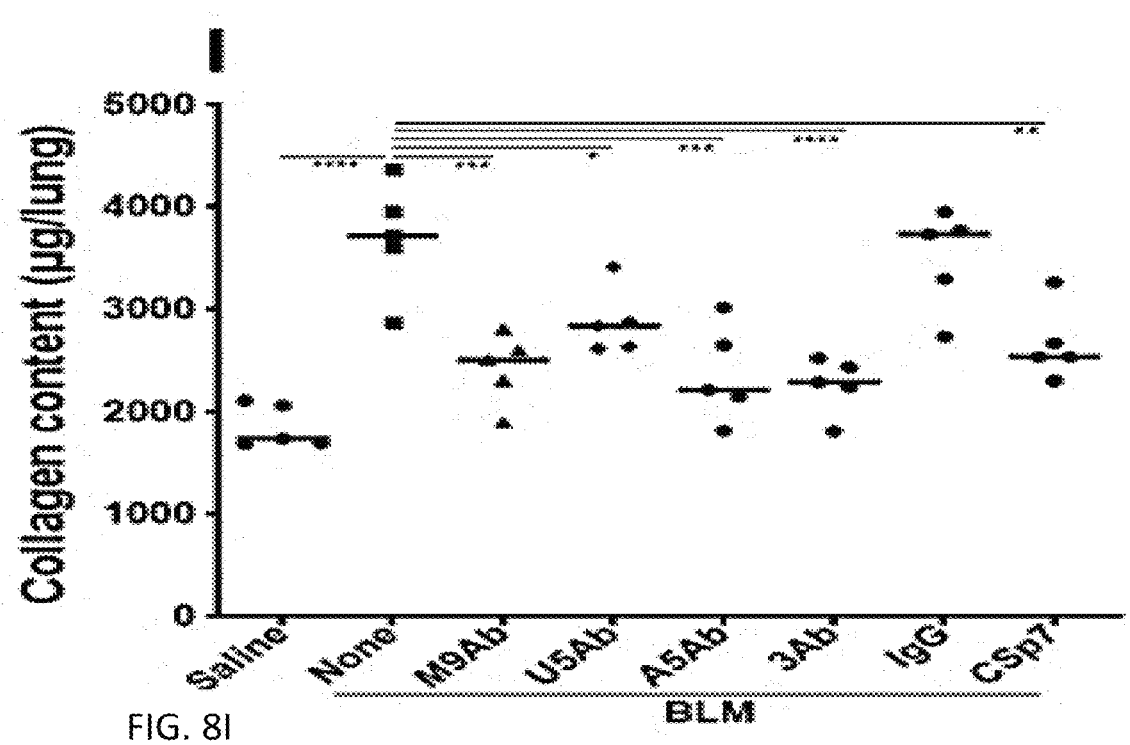
Figure 8J:
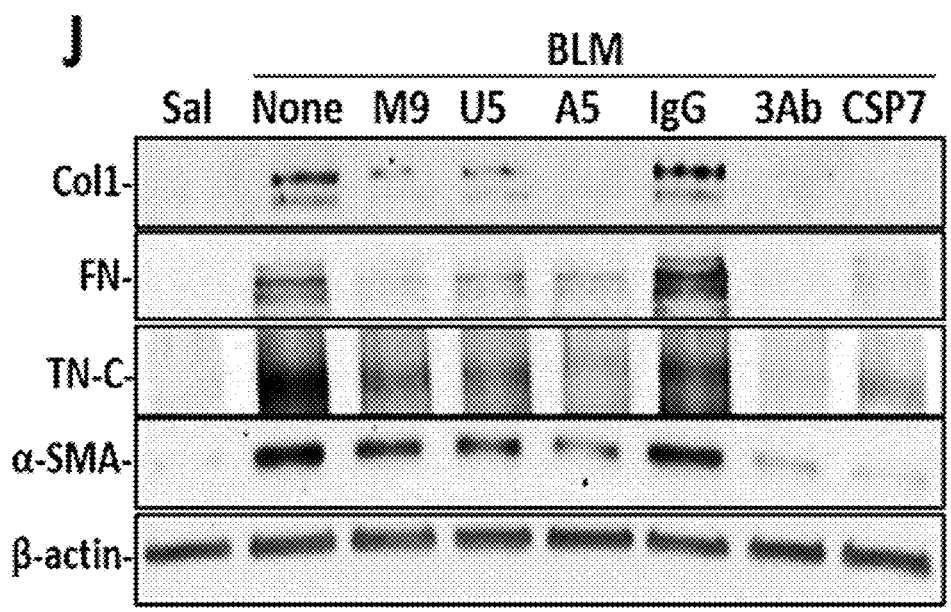
Figure 8K:
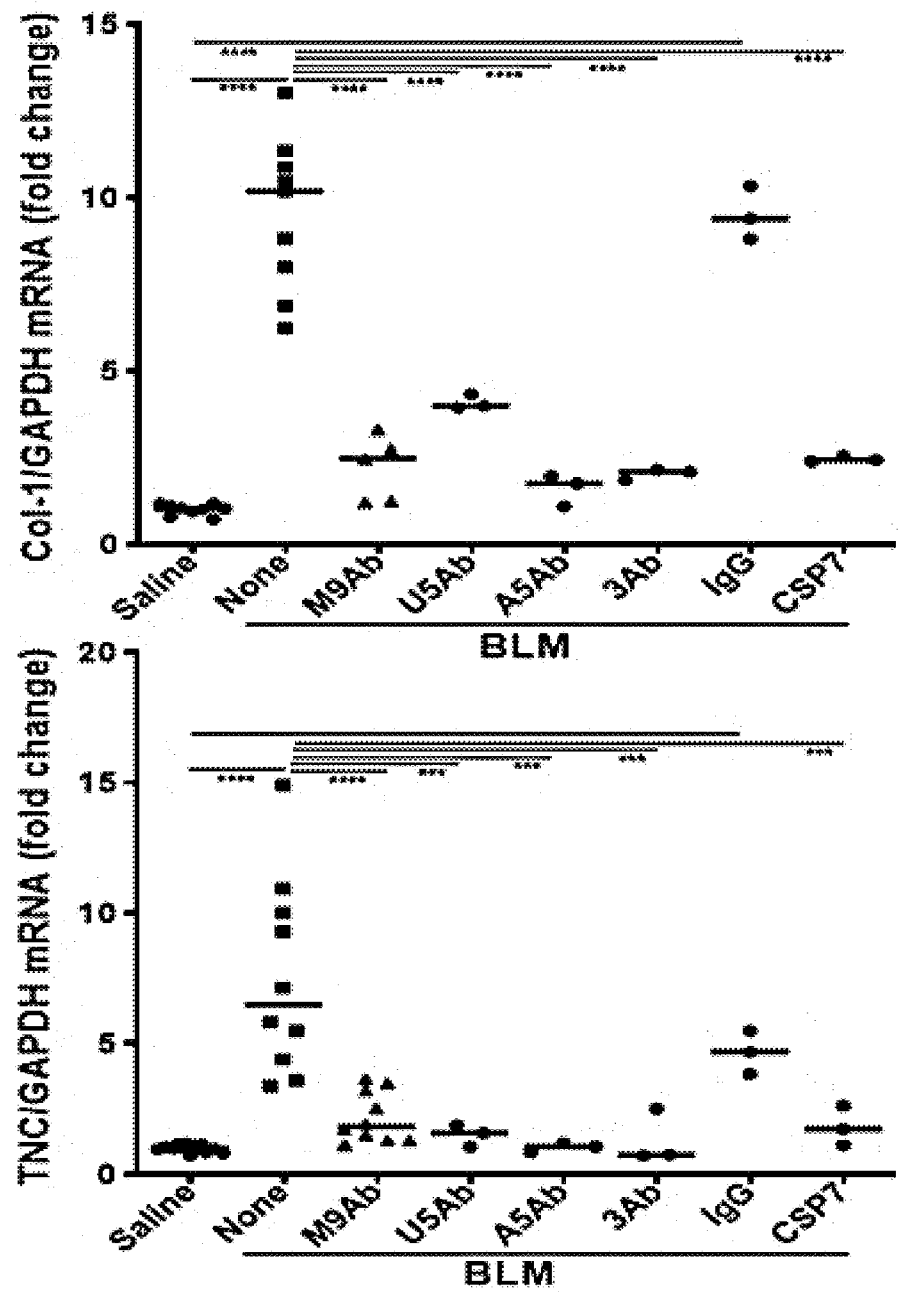
Figure 8K:
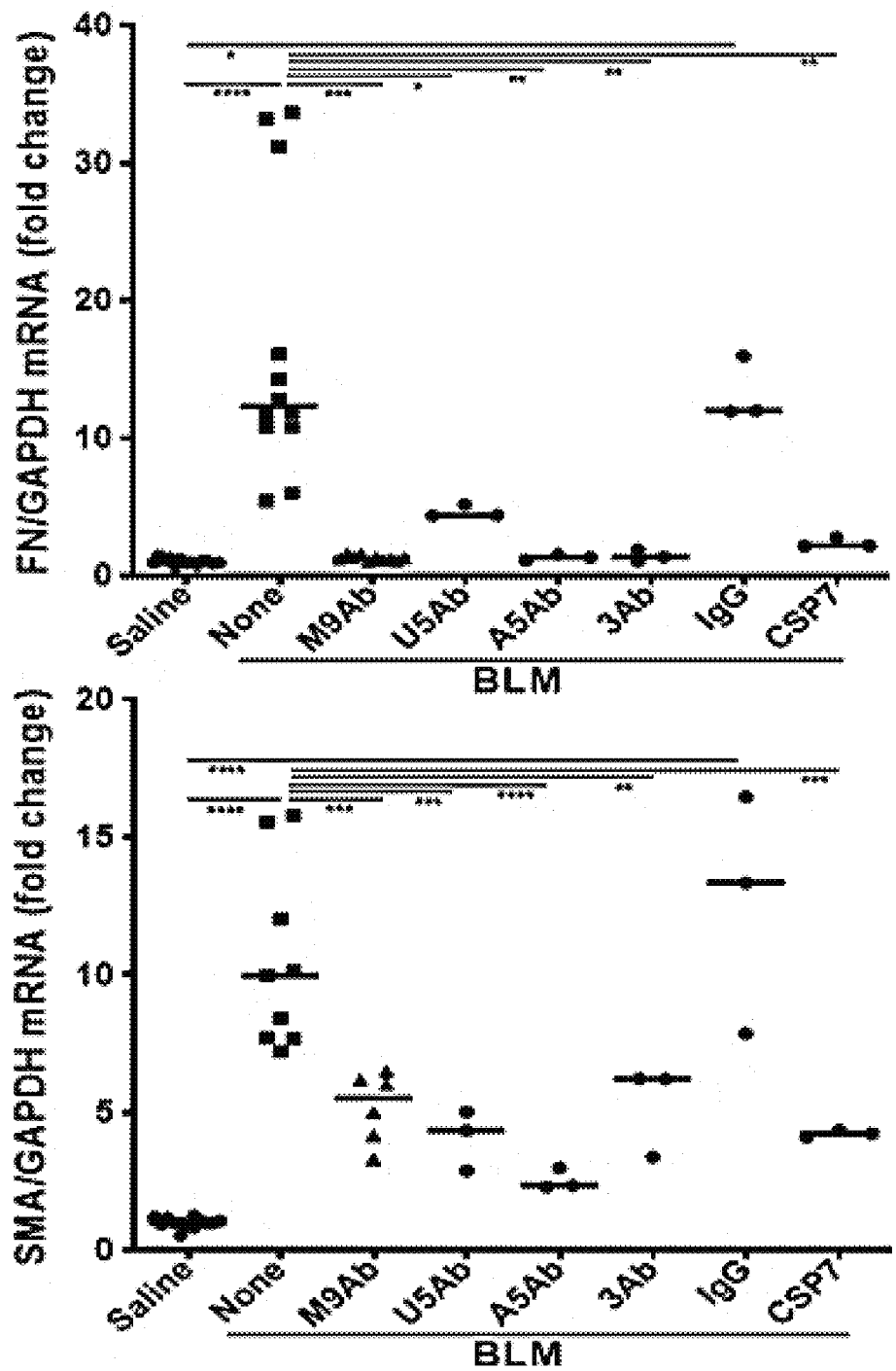
Figure 8L:
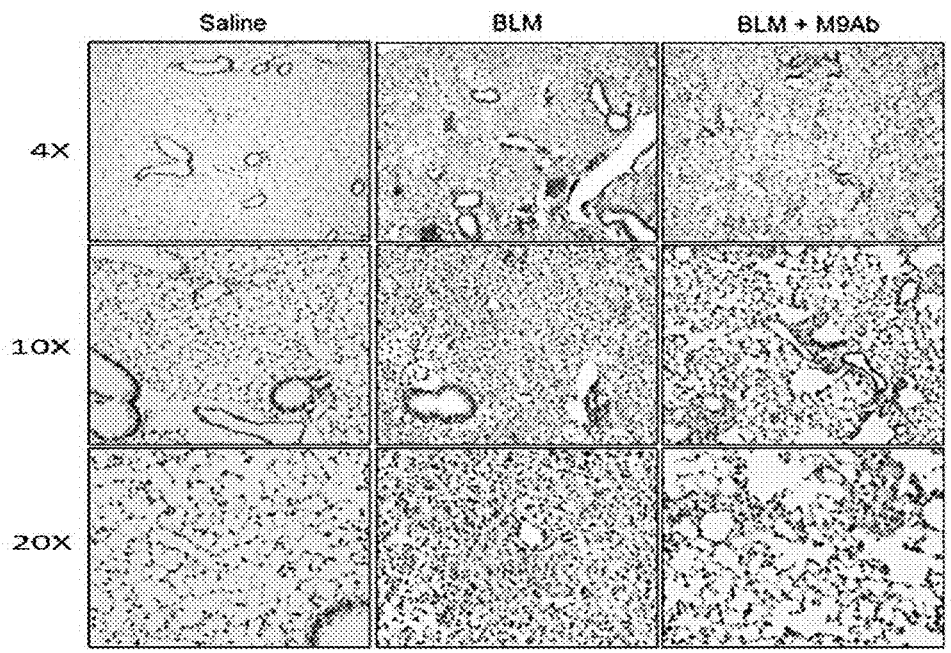

Treatment of the BLM-PF mice with the polyclonal M9 antibody also extended the survival (FIG. 7K) and suppressed the protein levels of pro-fibrogenic markers (FIG. 7L). Treatment of fLfs with $M9^{PAb}$ suppressed Coll, FN, TN-C and α-SMA protein and mRNA in IPF fLfs in vitro (FIG. 7M). The results show that the polyclonal M9Ab was able to mitigate established pulmonary fibrosis.

Anti M9Ab inhibited (IPF fibroblasts with no effect on BLM-induced AEC apoptosis in vitro. Anti-M9 Ab inhibited established lung fibrosis in mice and improved lung function and survival by 100% in animals given bleomycin (BLM) and treated with anti-M9 Ab whereas ⅔ of animals with BLM-induced lung fibrosis left untreated died. Anti-M9 Ab inhibited pro-fibrotic markers (Col, FN, TN-C and α-SMA) in IPF fibroblasts in vitro and resolved existing bleomycin-induced lung fibrosis in vivo. Anti-M9 did not have any anti-apoptotic effect on AECs tested in vitro. M9 proteins are not detectable in AECs.

Example 8

The Combination of Antibodies Specific for MEGF9 ("M9"), UNC5A ("U5"), ALG-5 ("A5") Mitigated BLM-Induced Pulmonary Fibrosis.

Mice exposed to saline or 1.0 U/kg BLM by intratracheal instillation received intraperitoneal injections of antibodies (as described in Examples 4-6) (2.5 mg/kg) or controls daily for 7 days starting on d. 14 after BLM injury. Results are shown in FIGS. 8A-8K that include representative micro-CT images on d. 21 after BLM, lung volumes, lung compliance, and lung elastance. Also shown are lung weights survival curves and body weights). Lung homogenates were tested for hydroxyproline, soluble collagen, pro-fibrogenic marker proteins and mRNAs. Trichrome-stained lung sections are also shown. The results show that all the above 3 Abs, as well as their combination were able to mitigate established pulmonary fibrosis.

Anti-U5A antibody inhibited BLM-induced AEC apoptosis in vitro with no effect on IPF fibroblasts. Anti-U5A Ab treatment for 7 days starting day 14 post-BLM injury inhibited established lung fibrosis in mice (see relevant sections of FIG. 8).

Interestingly, anti-ALG5 antibody inhibited apoptosis in AECs and also inhibited pro-fibrogenic markers (Col, FN, TN-C and α-SMA) in IPF fibroblasts in vitro. Anti-ALG5 antibody inhibited BLM-induced lung fibrosis in mice (see relevant sections of FIG. 8).

In vivo experiments using the three antibodies, showed reversal of established lung fibrosis in mice. Based on the in vitro and in vivo results described herein, each of the three antibodies (M9, U5A and ALG5), alone or in combination of two or three, and also each antibody alone, in combination of two, or in combination of all three when combined with the peptide CSP7 inhibited established lung fibrosis by inhibiting both AEC apoptosis and fibrotic fibroblast expansion In this experiment, the efficacy of M9 antibody was comparable to that of CSP7 peptide in resolving existing pulmonary fibrosis. The efficacy of combination of M9 Ab, U5A Ab, and ALG5 Ab treatment for 7 days starting day 14 post-bleomycin pulmonary fibrosis was greater than that of CSP7 in terms of survival, body weight, lung weight, hydroxyproline, soluble collagen, levels of pro-fibrogenic marker proteins (collagen, α-smooth muscle actin, fibronectin and tenascin-C) and their mRNAs, pulmonary function parameters (lung volume, lung resistance, elastance and compliance) and trichrome staining for matrix protein deposition. Most importantly, daily treatment with recombinant M9 protein (SEQ ID NO: 1) or a 12 amino acid sequence therefrom (SEQ ID NO: 4) for 7 days itself resolved existing pulmonary fibrosis.

Example 9

An M9 12-Mer Peptide HGHVDPVKTPKI (SEQ ID NO: 4) Mitigated BLM-Induced Pulmonary Fibrosis.

Mice that were exposed to saline or 1.0 U/kg BLM by intratracheal instillation received intraperitoneal injections of the above M9 peptide (10 mg/kg) and the full length M9 protein (7.5 mg/kg) daily for 7 days starting d. 14 after BLM injury. Results were obtained on d. 21 after BLM. Results are shown in FIGS. 9A-9K.

Figure 9A:
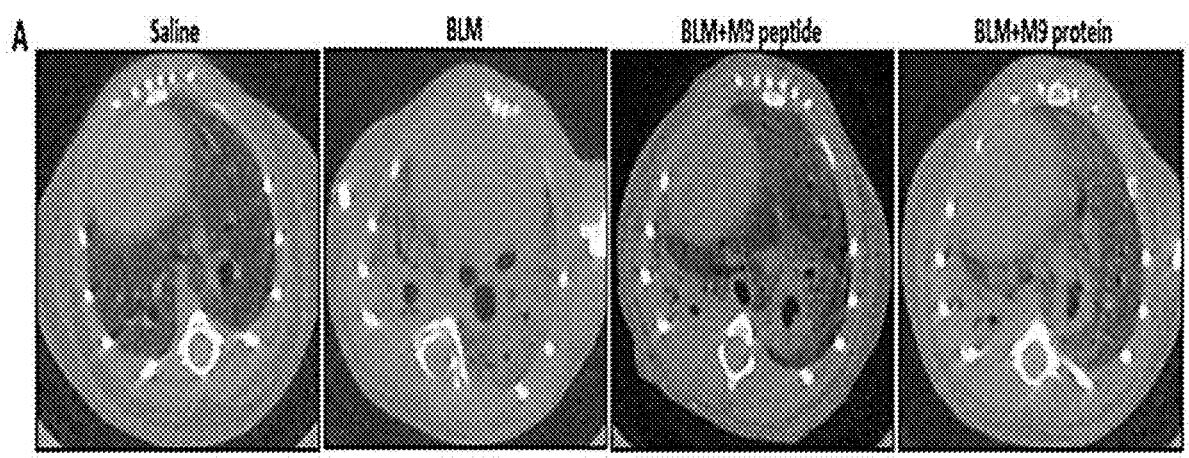
FIGS. 9A-9O. M9 peptide and protein mitigated BLM-induced pulmonary fibrosis. Mice exposed to saline or 1.0 U/kg BLM by intratracheal instillation were treated with or without M9 peptide HGHVDPVKTPKI (SEQ ID NO: 4) (10 mg/kg/d) and M9 protein (SEQ ID NO: 1) 7.5 mg/kg/d) via IP injection daily for 7 days starting d14 after BLM injury.
Figure 9B:
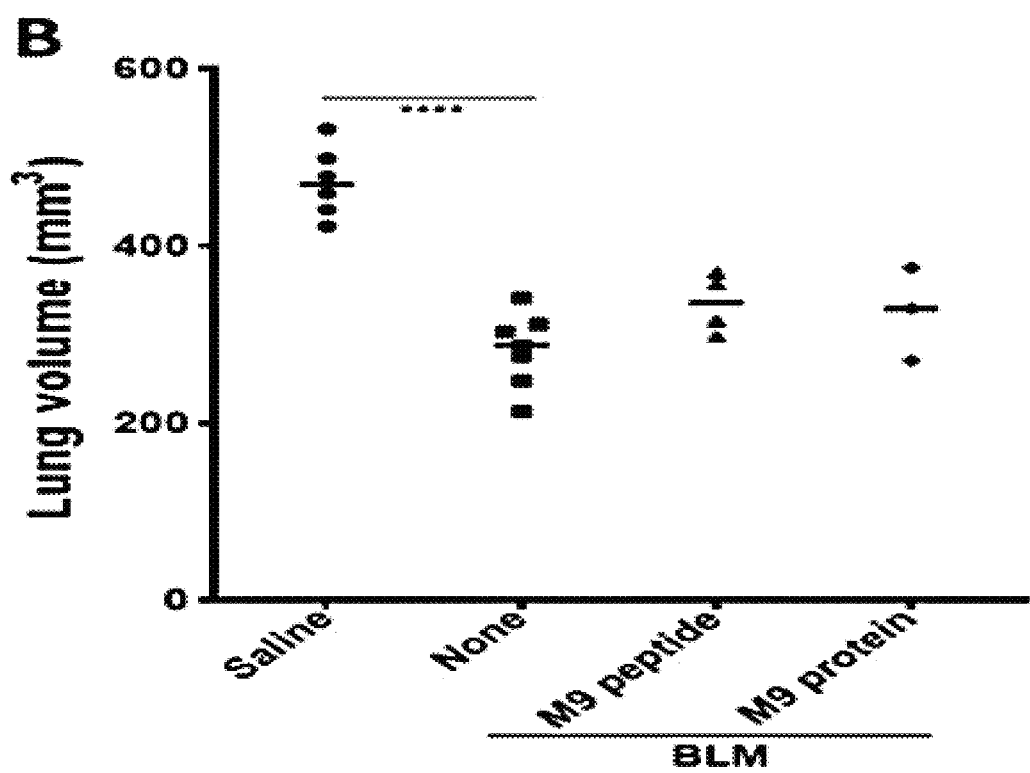
FIG. 9B: Lung volumes were measured by quantitative-CT renditions. Lung compliance (FIG. 9C) and elastance (FIG. 9D) were measured using a flexiVent system. Lung weights (FIG. 9E) and body weights (FIG. 9F) are presented as bar graphs. Lung homogenates were tested for hydroxyproline (FIG. 9G), soluble collagen (FIG. 9H), pro-fibrogenic marker proteins (FIG. 9I) and mRNAs (FIG. 9J). Trichrome staining of lung sections shown in FIG. 9K. Bars indicate mean±SD. Statistical significance (*P<0.05, P<0.01, *P<0.001 and ****P<0.0001) was assessed by one-way ANOVA with Turkey's multiple comparison. fLfs isolated from IPF lungs treated with PBS or recombinant full length M9 (rM9$^{FL}$) protein (2 μg/ml) for 48 h in vitro were tested for pro-fibrogenic proteins (FIG. 9L). fLfs (from IPF lungs) treated with PBS or extracellular domain of rM9$^{FL}$ protein (rM9$^{ECD}$) as in FIG. 9L were tested for pro-fibrogenic proteins (FIG. 9N). The survival the mice treated with rM9$^{FL}$ is shown FIG. 9M. The survival of the mice treated with rM9$^{ECD}$ is shown in FIG. 9O. The results indicate that the M9 protein and peptide mitigated BLM-induced pulmonary fibrosis.
Figure 9C:
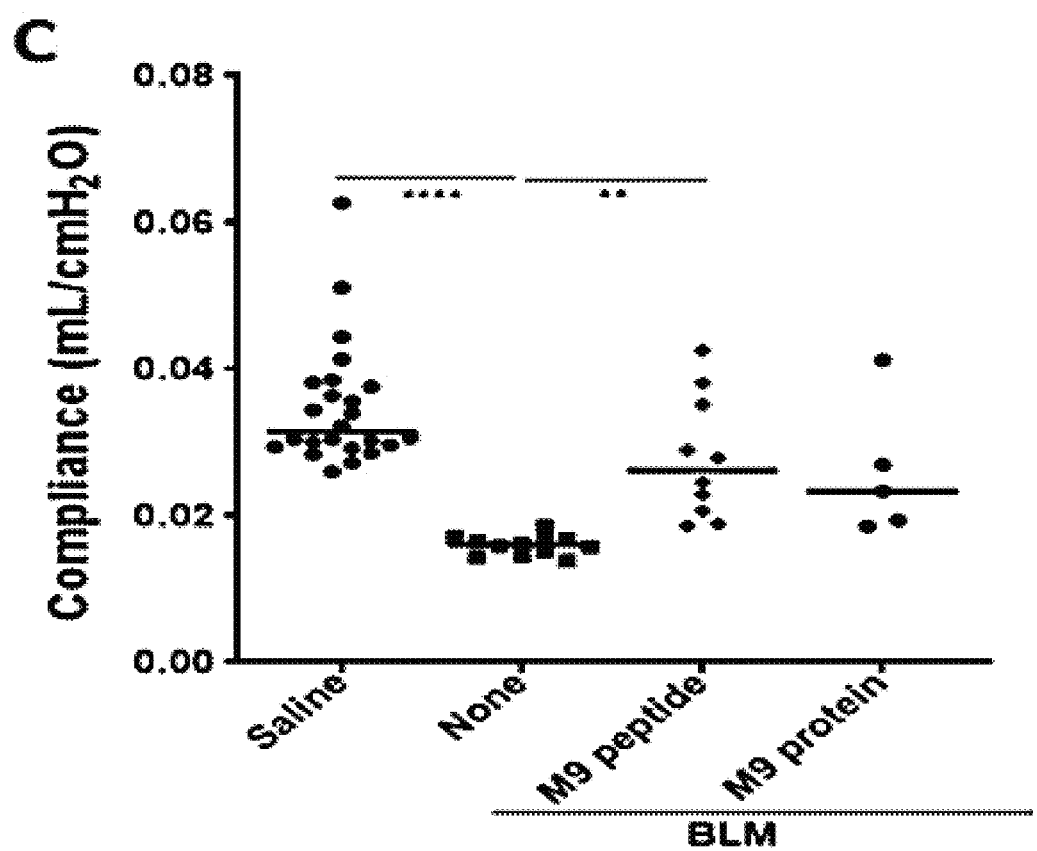
Figure 9D:
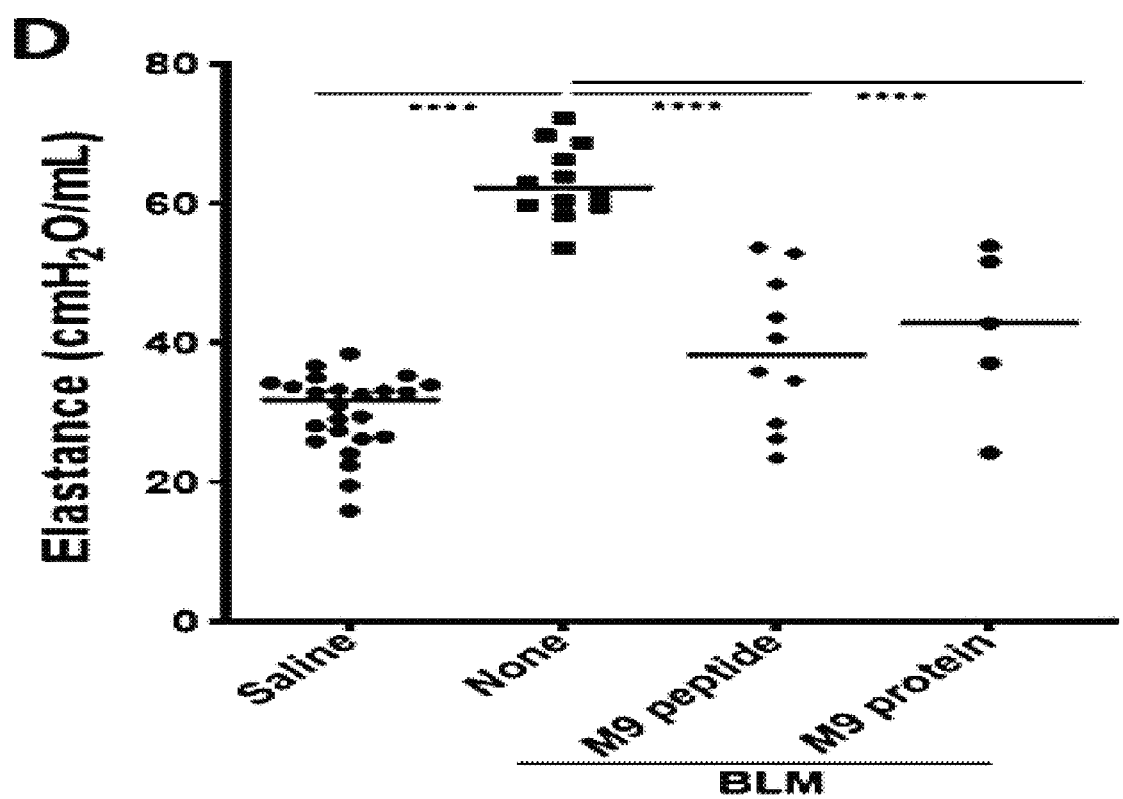
Figure 9E:
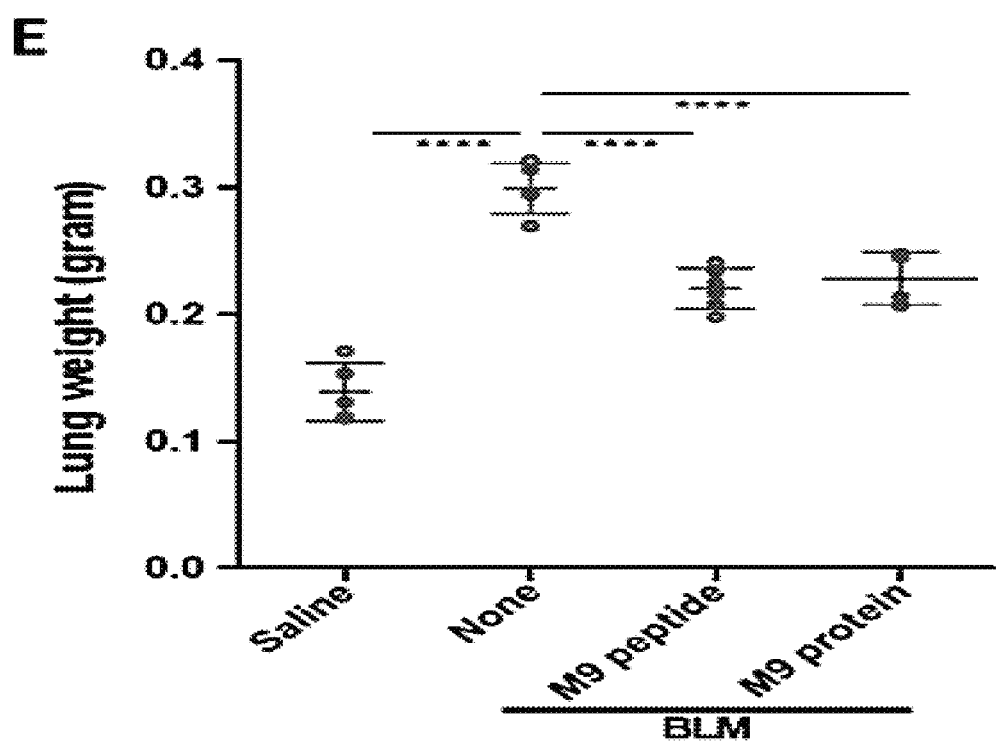
Figure 9F:
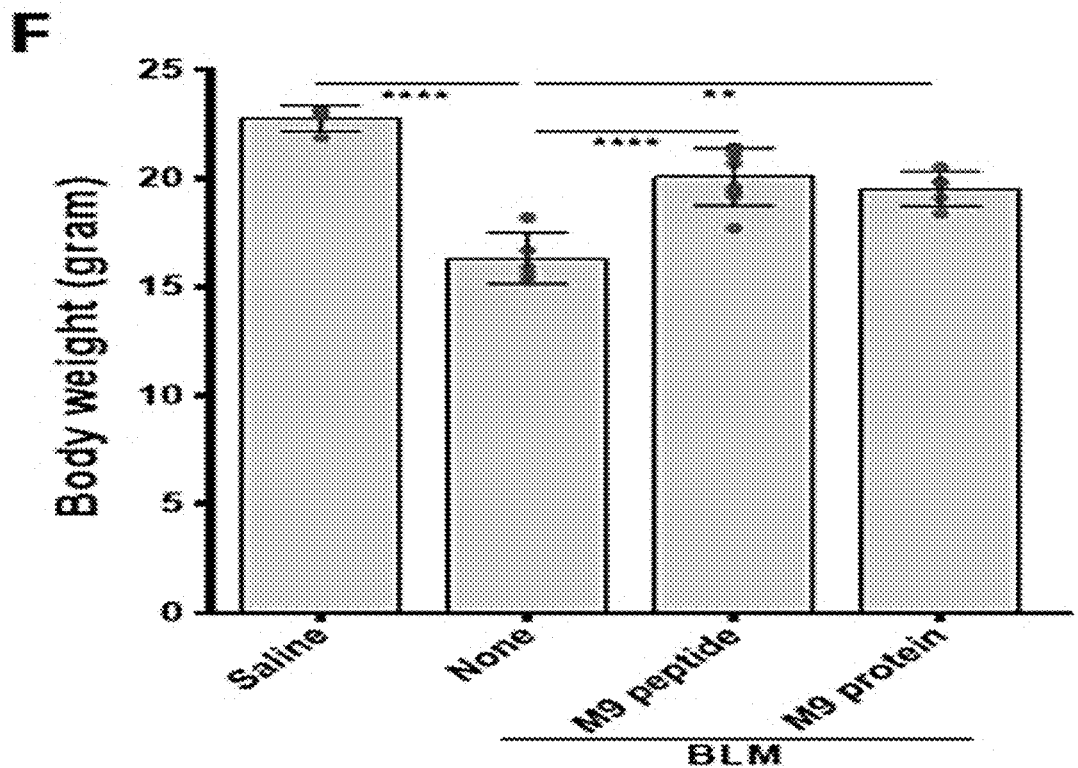
Figure 9G:
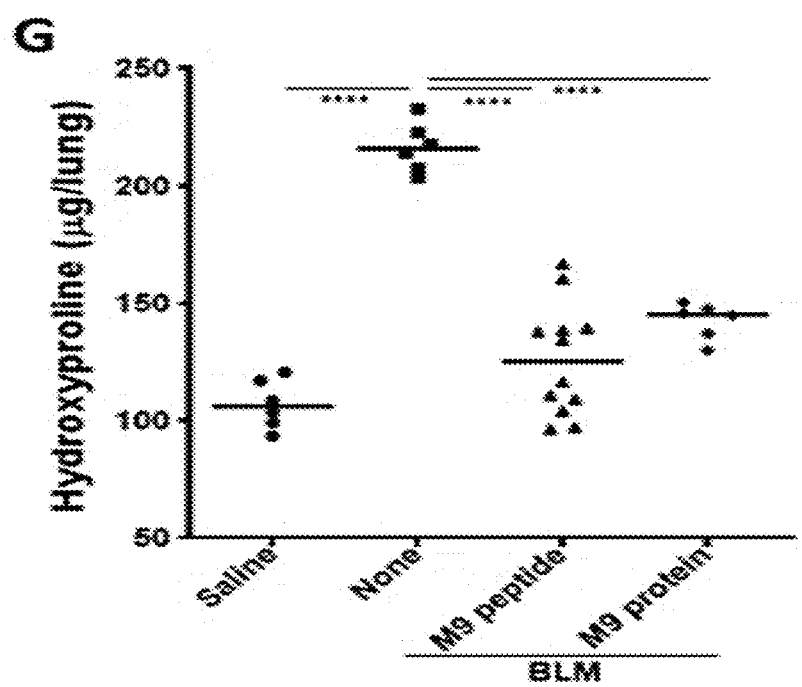
Figure 9H:
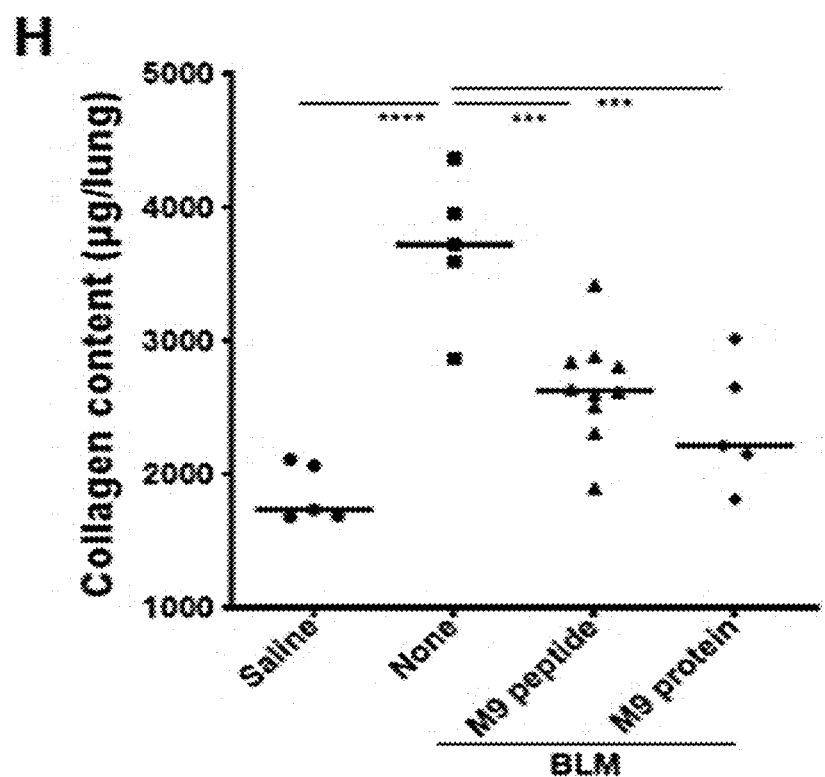
Figure 9I:
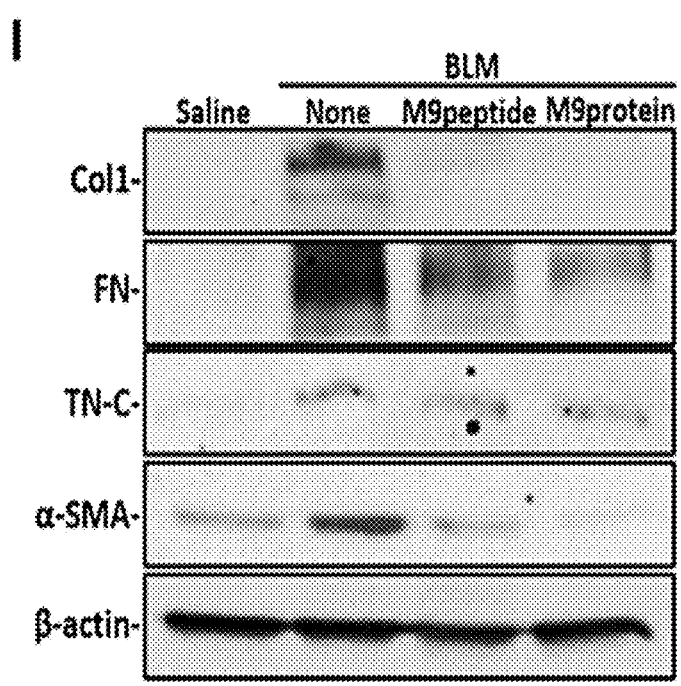
Figure 9J:
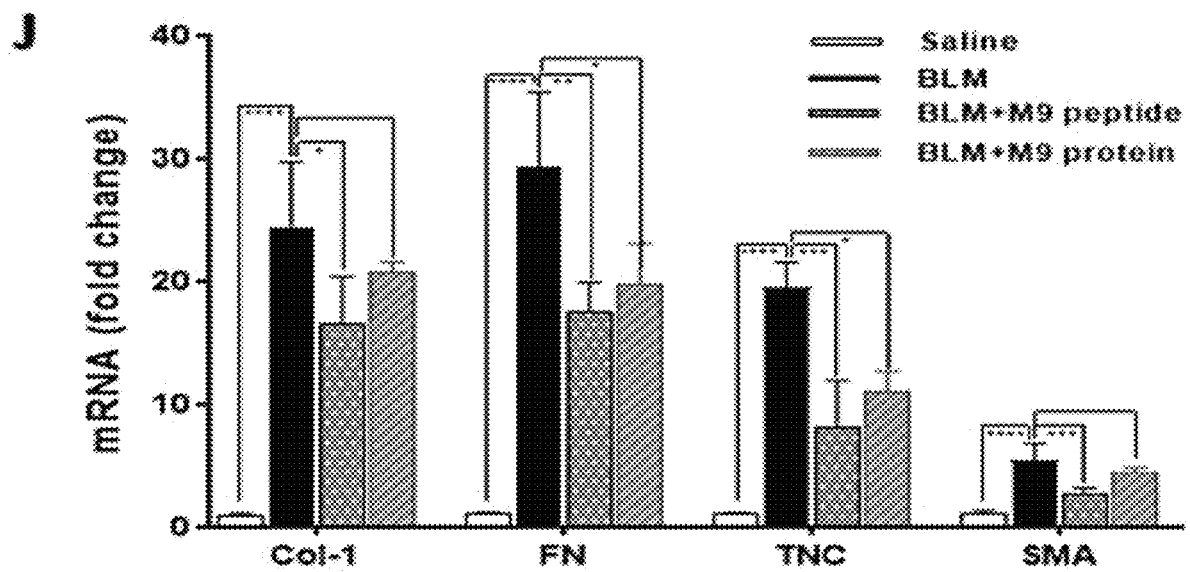
Figure 9K:
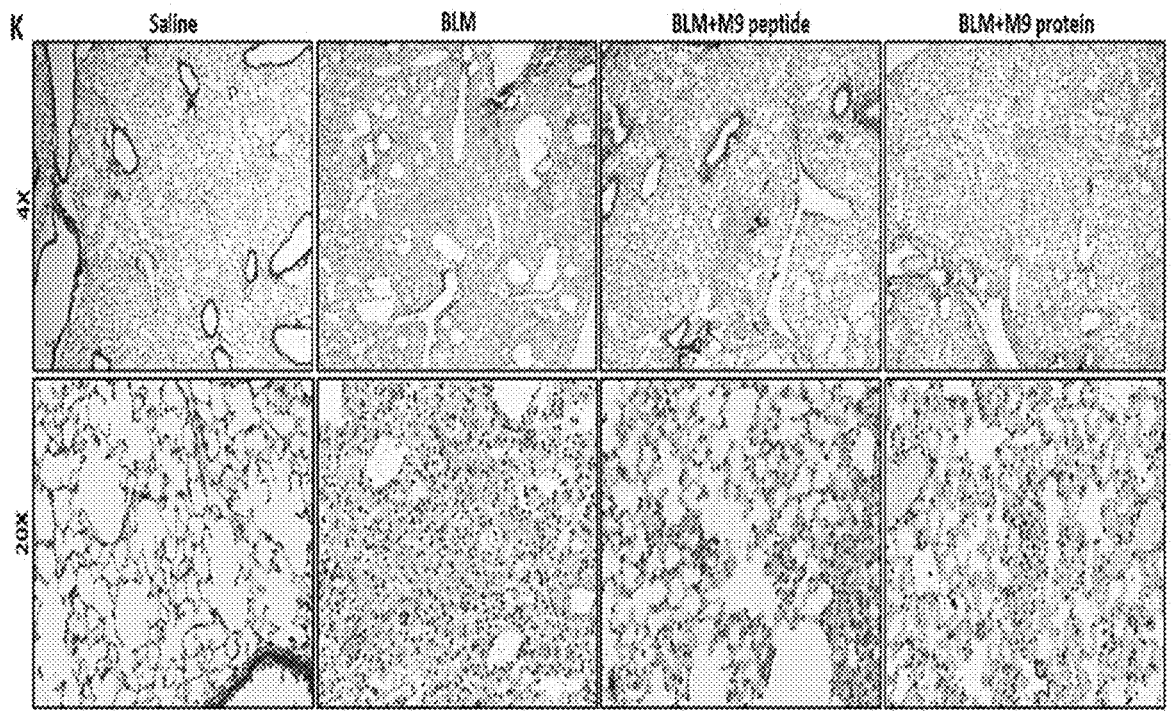
Figure 9L:
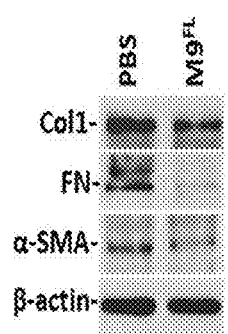
Figure 9M:
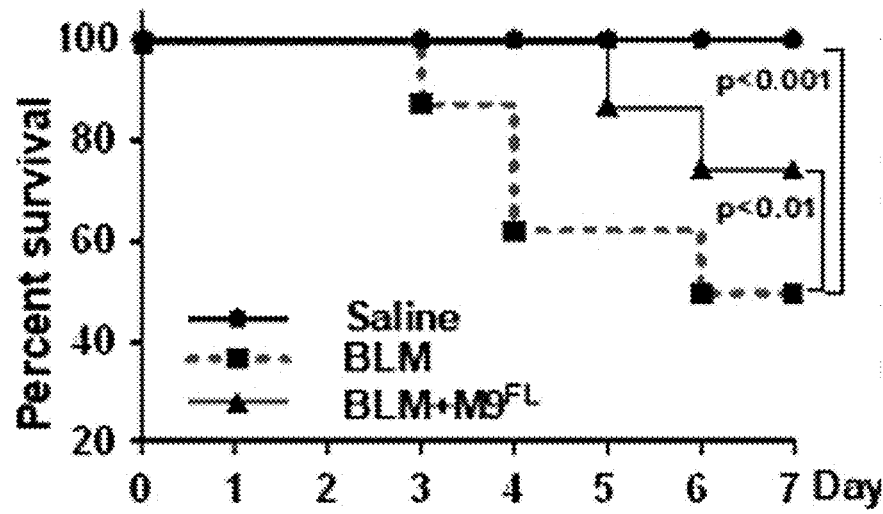
Figure 9N:
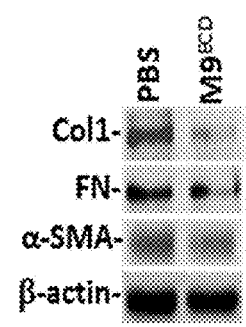
Figure 9O:
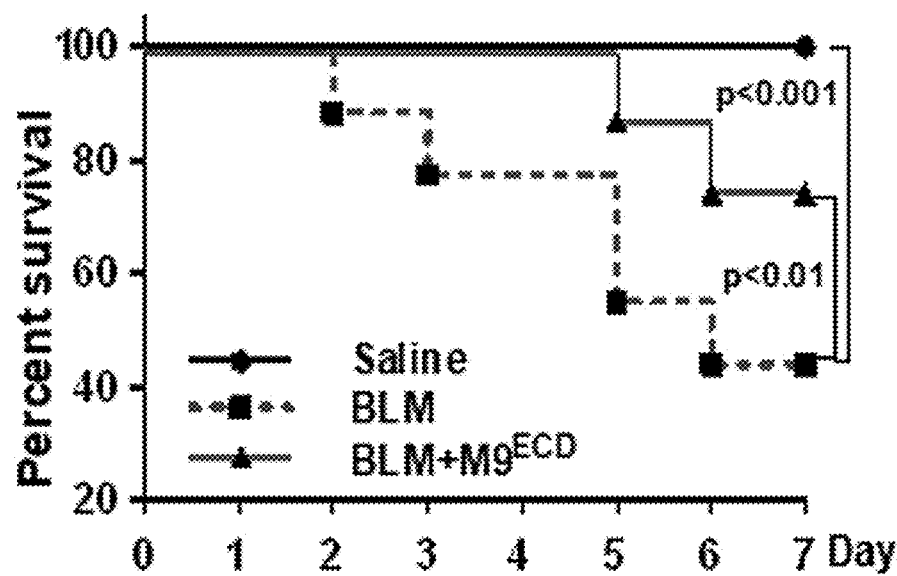

Treatment of mice with established PF for 7 days with recombinant M9 protein (SEQ ID NO: 1 or M9 peptide (SEQ ID NO: 4) improved lung volume, lung compliance and elastance, indications of improved pulmonary function, which is otherwise affected by existing pulmonary fibrosis (FIGS. 9A-9D). These changes were associated with parallel reduction in lung weight (FIG. 9E) and improvement in body weight (FIG. 9F), indicating improvement in overall health due to reduction in collagen and other matrix proteins, which are often observed in lung fibrosis. This was further confirmed by significant inhibition in whole lung total hydroxyproline (FIG. 9G) and soluble collagen (FIG. 9H) content reflecting resolution of existing lung fibrosis by M9 protein or M9 peptide treatment for 7 days. These findings are consistent with marked inhibition of bleomycin-induced fibrogenic markers such as Col1, FN, TN-C and α-SMA proteins (FIG. 9I) and their transcripts (FIG. 9J) in whole lung homogenates of BLM treated mice exposed to M9 protein or M9 peptide. Consistently, treatment of fLfs isolated from IPF lungs with rM9$^{FL}$ or rM9$^{ECD}$ reduced the expression of pro-fibrogenic markers (Col1, FN, TN-C and α-SMA), suggesting de-differentiation of fLfs (FIGS. 9L and 9M). Trichrome staining of lungs sections after treatment with M9 protein or M9 peptide showed remarkable reduction collagen and other extracellular matrix deposits that are otherwise prevalent in fibrotic lung tissues, thereby demonstrating resolution of pulmonary fibrosis. In addition, treatment of mice with BLM-induced existing PF with rM9$^{FL}$ or rM9$^{ECD}$ significantly increased the survival rate (FIGS. 9N and 9O). These findings collectively indicate that recombinant M9 protein or a fragment thereof, just like specific anti-M9 antibody (FIGS. 3, 4, 7A-7M and 8A-8K) can mitigate fibrosis by competing with M9 protein, which was overexpressed on fLf and M2 macrophage surfaces in fibrotic lung tissues, including in IPF tissues (FIG. 1).

Therefore, in addition to (or in combination with) anti-M9 Abs (polyclonal antibodies, monoclonal antibodies, or as otherwise defined here), M9 protein or peptide is useful for treating pulmonary fibrosis.

Example 10

A U5A 50-Mer Peptide (SEQ ID NO: 8) and Full Length U5A Protein (SEQ ID NO: 5) Mitigated BLM-Induced Pulmonary Fibrosis.

Figure 10A:
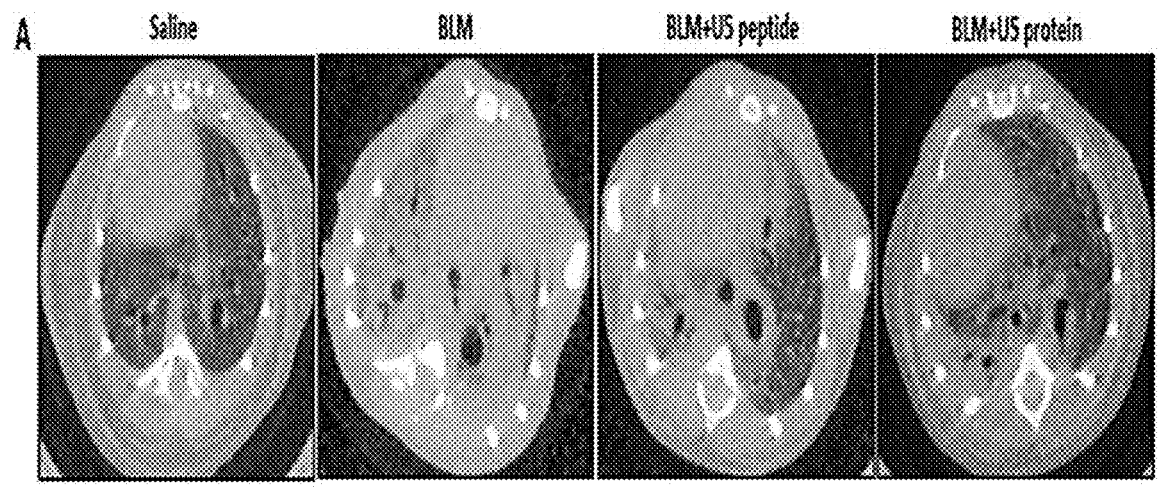
FIGS. 10A-10K. UNC5A ("U5") peptide/protein mitigated BLM-induced pulmonary fibrosis. Mice exposed to saline or 1.0 U/kg BLM by intratracheal instillation were treated with or without U5 peptide (50 residues, SEQ ID NO: 7) (10 mg/kg/d) and full length U5 protein (SEQ ID NO: 5) (7.5 mg/kg/d) via IP injection daily for 7 days starting d14 after BLM injury.
Figure 10B:
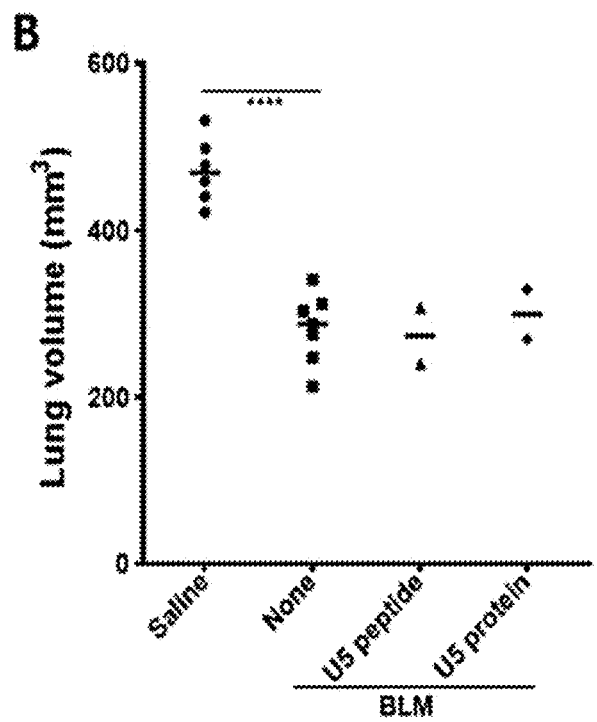
Figure 10C:
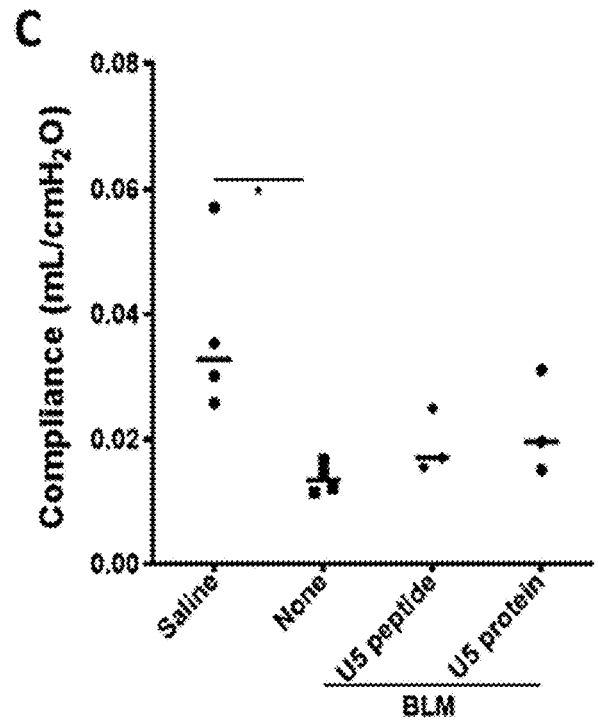
Figure 10D:
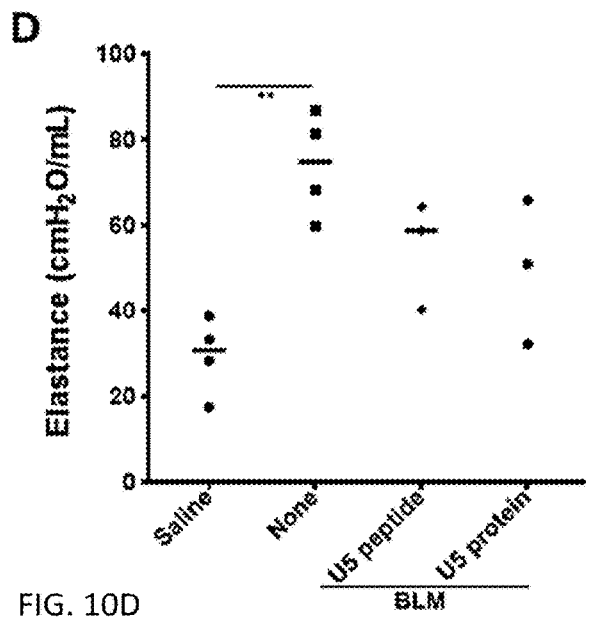
Figure 10E:
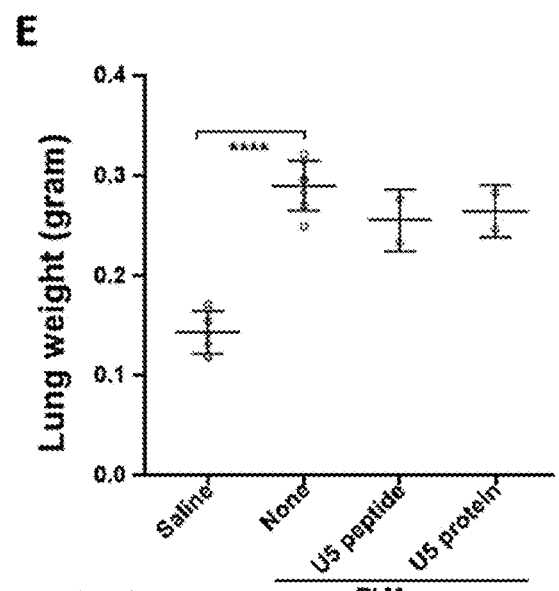
Figure 10F:
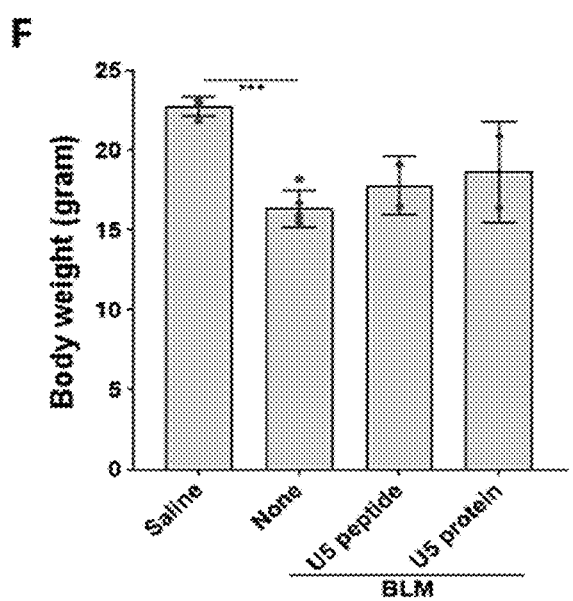
Figure 10G:
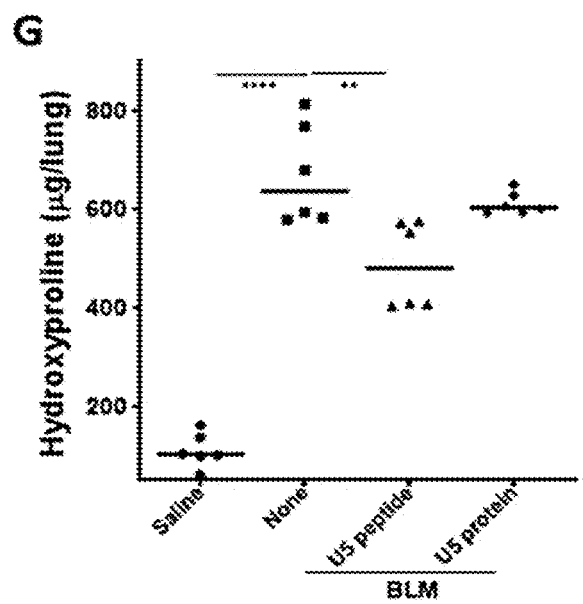
Figure 10H:
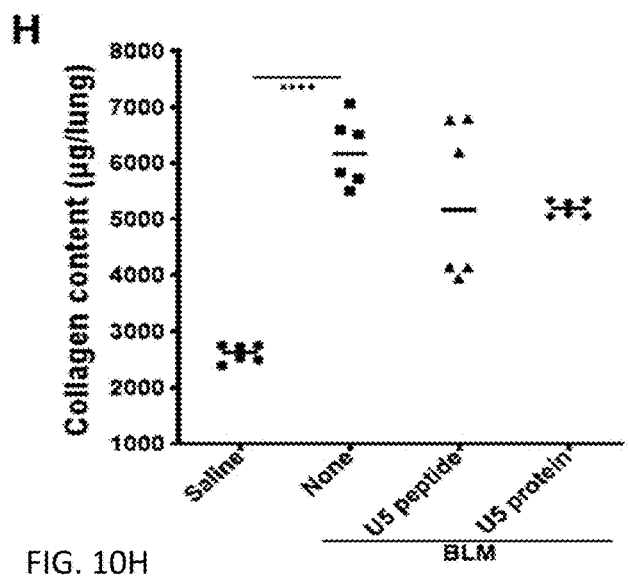
Figure 10I:
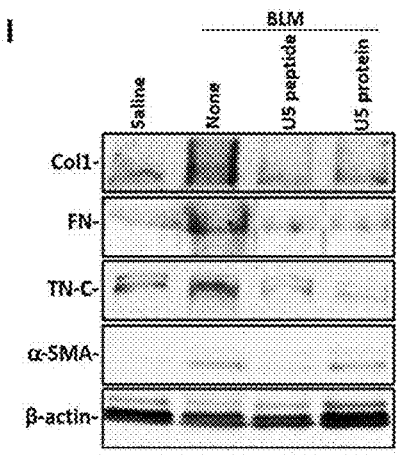
Figure 10J:
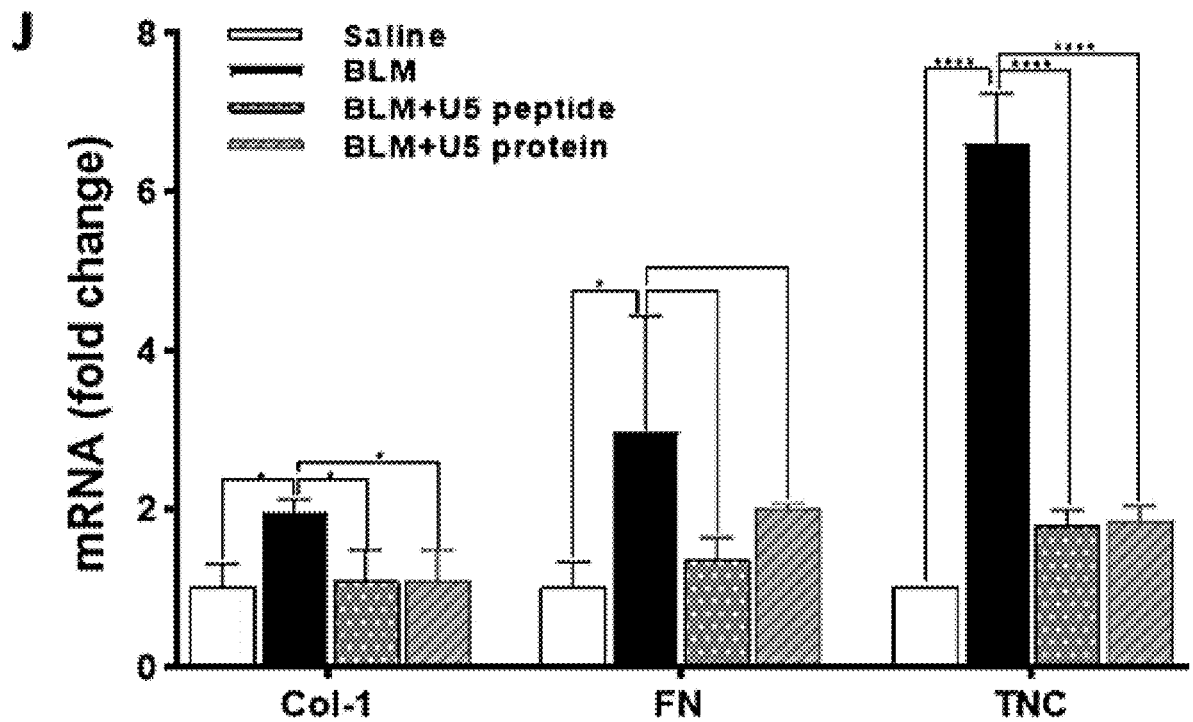
Figure 10K:
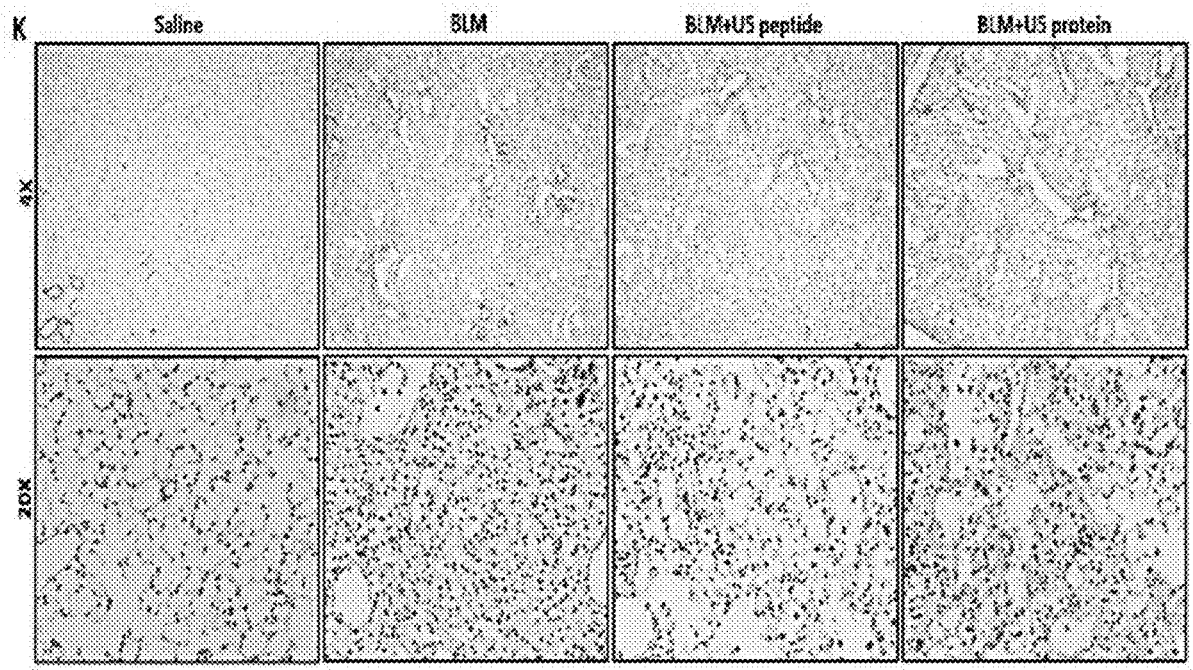

Treatment of mice with established PF for 7 days with recombinant U5A protein or a 50-mer U5A peptide improved lung compliance and elastance indicating improvement in pulmonary function, which was otherwise affected by existing pulmonary fibrosis (FIGS. 10A-10D). These changes were associated with parallel reduction in lung weight (FIG. 10E) and improvement in body weight (FIG. 10F), which was affected by bleomycin-induced lung fibrosis. This was further confirmed by reduction in whole lung total hydroxyproline (FIG. 10G) and soluble collagen (FIG. 10H) content reflecting inhibition of existing lung fibrosis after exposure to the U5A protein or U5A peptide for 7 days. These findings are consistent with inhibition of BLM-induced fibrogenic markers such as Col1, FN, TN-C and α-SMA proteins (FIG. 10I) and their transcripts (FIG. 10J) in whole lung homogenates of BLM-exposed mice treated with the U5A protein or U5A peptide. Trichrome staining of lungs sections after treatment with U5A protein or U5A peptide showed reduction collagen and other extracellular matrix deposits, which were otherwise prevalent in lung fibrosis, thereby demonstrating resolution of pulmonary fibrosis. Collectively, these findings indicate that recombinant U5A protein or fragments thereof acted like specific antibodies against U5A protein (FIGS. 5, 6 and 8A-8K) in mitigating fibrosis by competing with U5A protein which was overexpressed on the surface of injured type II alveolar epithelial (ATII) cells in fibrotic lung tissues of BLM-induced PF (FIGS. 5 and 6), and presumably, in IPF tissues.

Therefore, in addition to (or in combination with) anti-U5A antibodies (polyclonal antibodies, monoclonal antibodies, or as otherwise defined here), U5A protein or peptide is useful for treating pulmonary fibrosis.

Example 11

ALG5 (A5) Protein (SEQ ID NO: 9) Mitigated BLM-Induced Pulmonary Fibrosis.

Figure 11A:
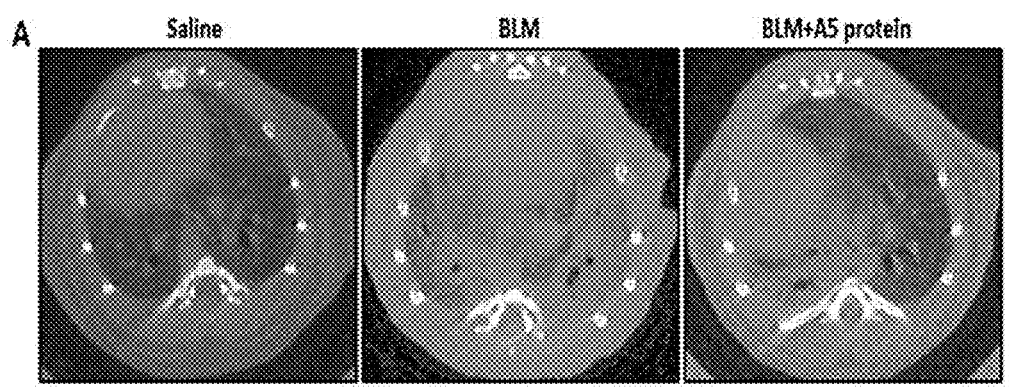
FIGS. 11A-11K. ALG5 ("A5") protein mitigated BLM-induced pulmonary fibrosis. Mice exposed to saline or 1.0 U/kg BLM by intratracheal instillation were treated with or without A5 protein (SEQ ID NO: 9) (7.5 mg/kg/d) via IP injection daily for 7 days starting d14 after BLM injury.
Figure 11B:
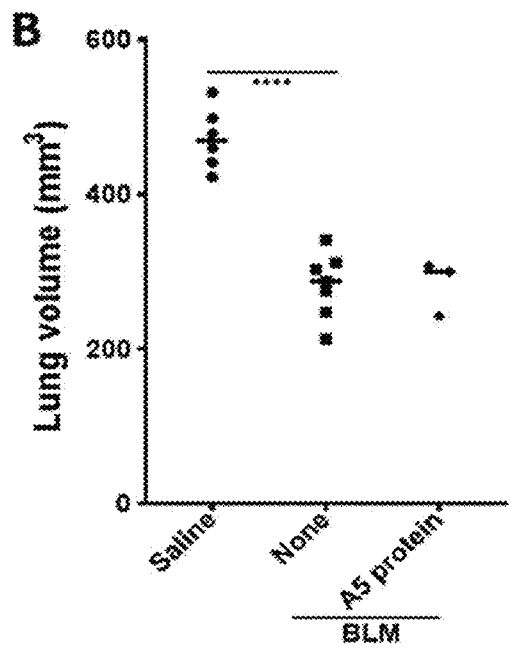
Figure 11C:
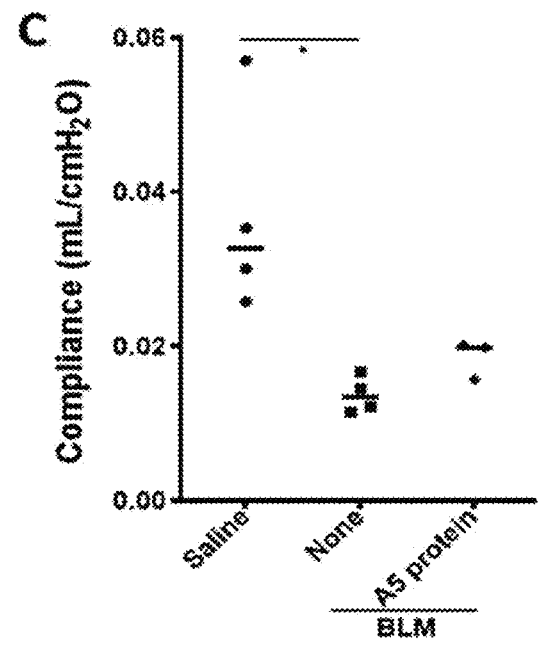
Figure 11D:
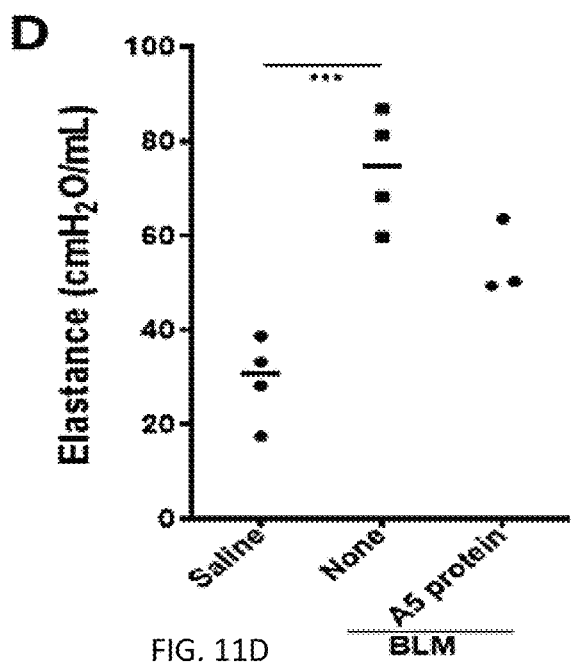
Figure 11E:
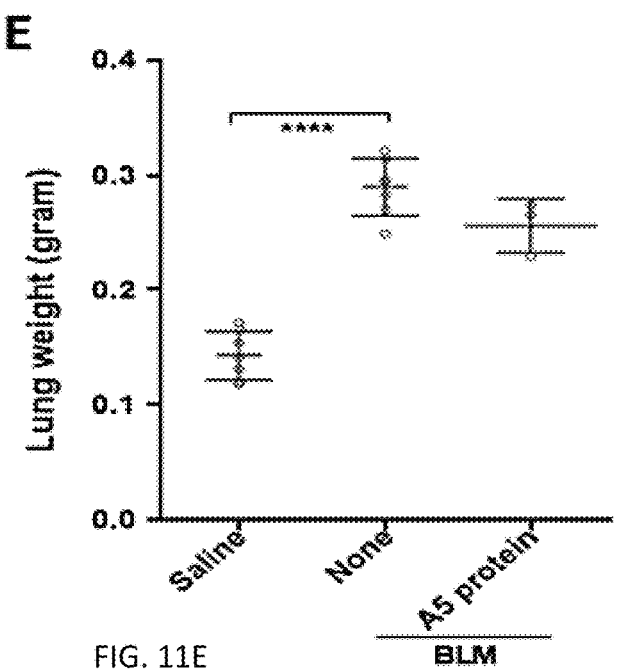
Figure 11F:
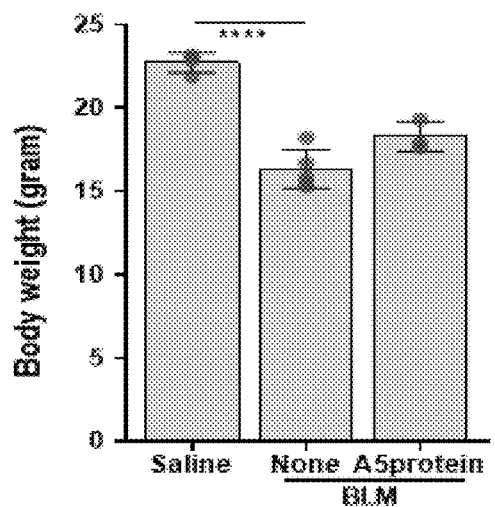
Figure 11G:
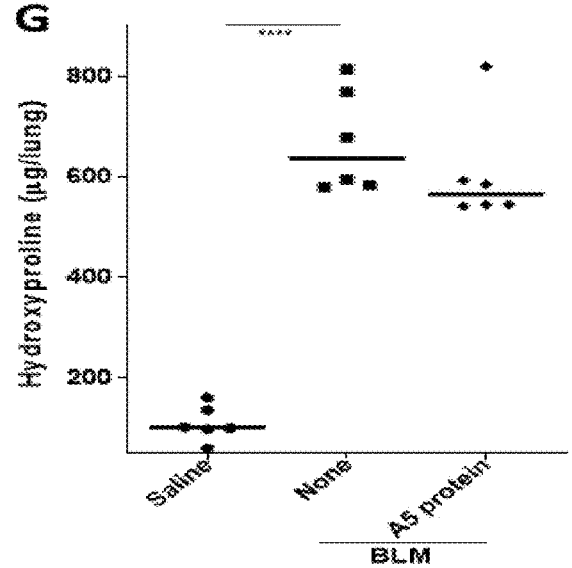
Figure 11H:
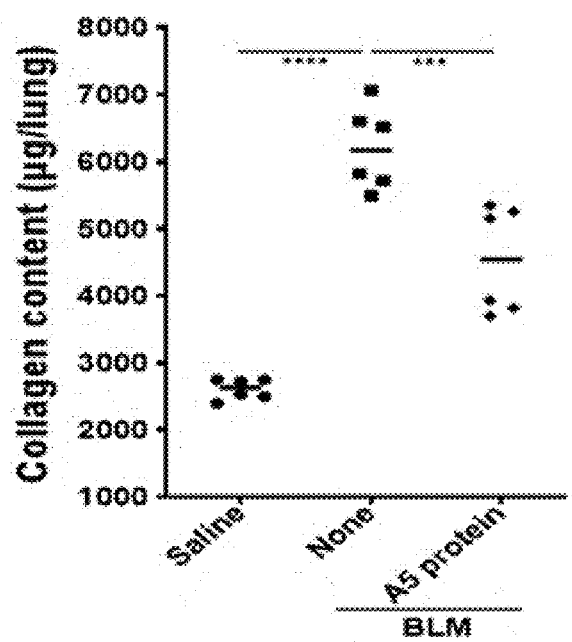
Figure 11I:
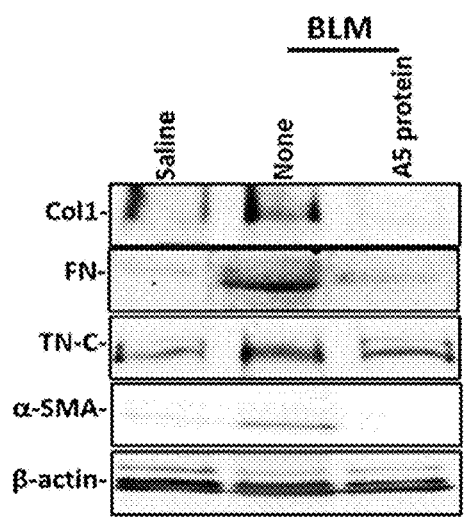
Figure 11J:
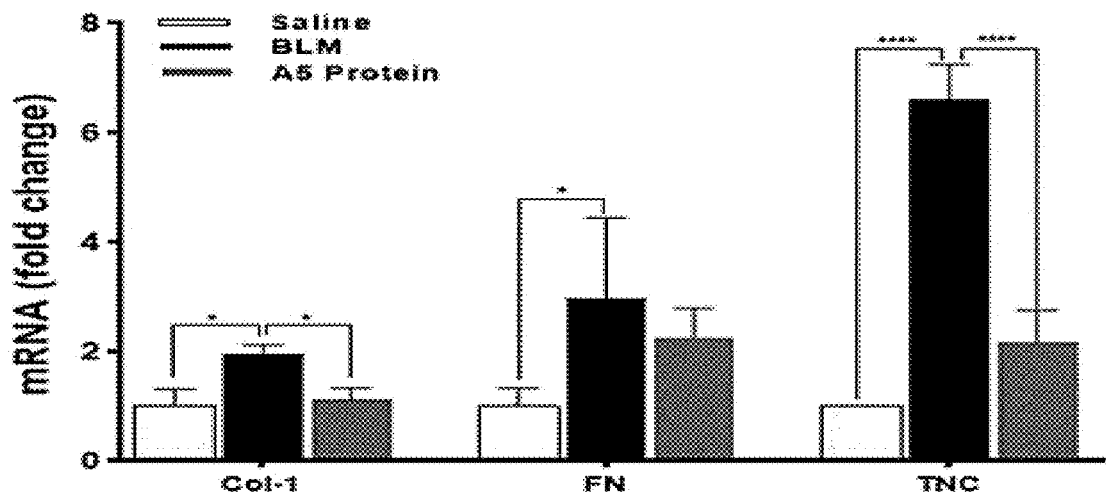
Figure 11K:
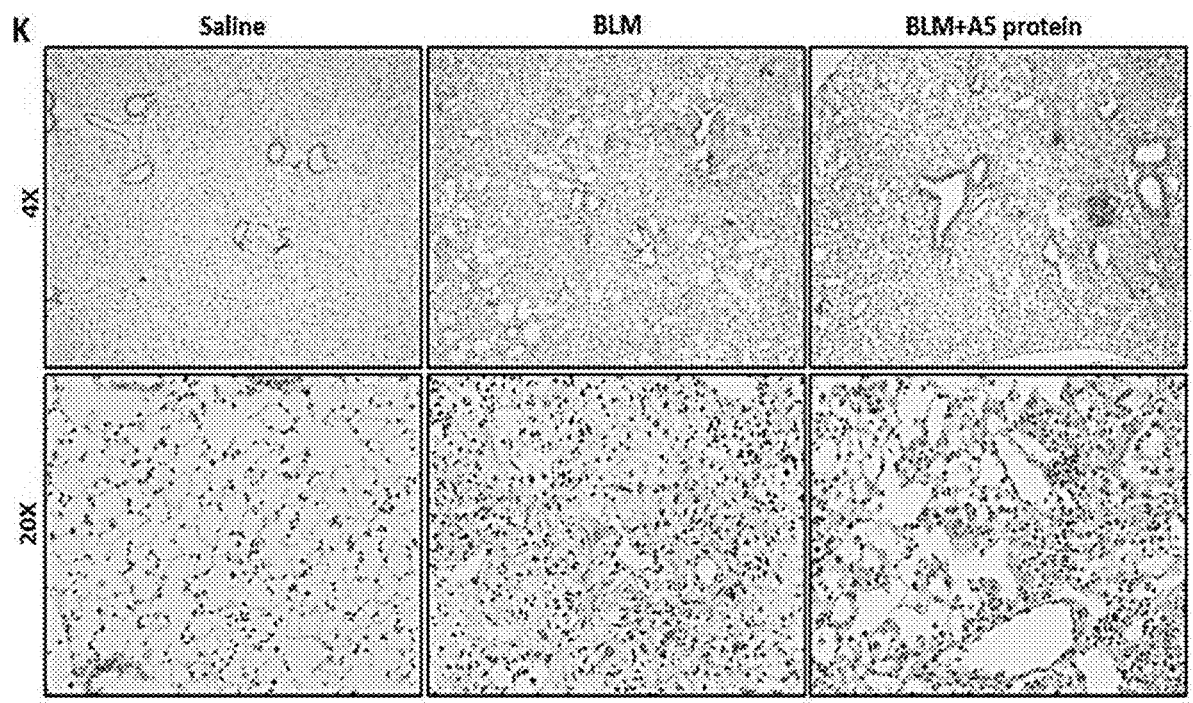
Figure 14A:
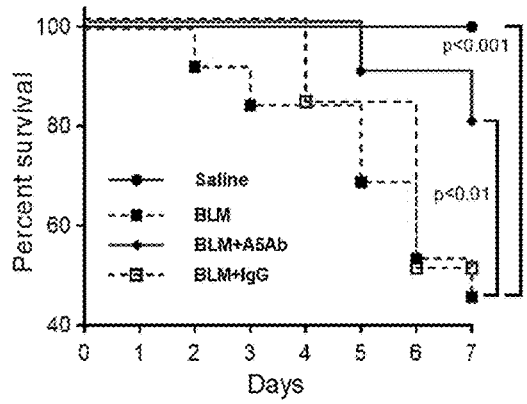
FIGS. 14A-14K. A polyclonal U5a antibody (U5a$^{pAb}$) mitigated BLM-induced pulmonary fibrosis. Mice exposed to saline or 1.0 U/kg BLM by intratracheal (IT) instillation received intraperitoneal (IP) injections with or without U5a$^{pAb}$ (2.5 mg/kg) daily for 7 days starting day 14 after BLM injury. Percent Survival (FIG. 14A) were shown. Total body weight (FIG. 14B), micro-CT images (FIG. 14C) and lung volumes (FIG. 14D) were measured by quantitative-CT renditions and lung compliance (FIG. 14E) and elastance (FIG. 14F) were measured using a flexiVent system on day 21 post-BLM. Lung weights (FIG. 14G) were measured on day 21 post-BLM. Lung homogenates were analyzed for total hydroxyproline (FIG. 14H), soluble collagen (FIG. 14I), pro-fibrogenic marker proteins (FIG. 14J) and their mRNAs (FIG. 14K).
Figure 14B:
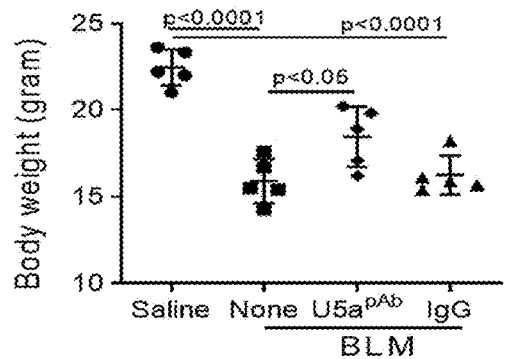
Figure 14C:
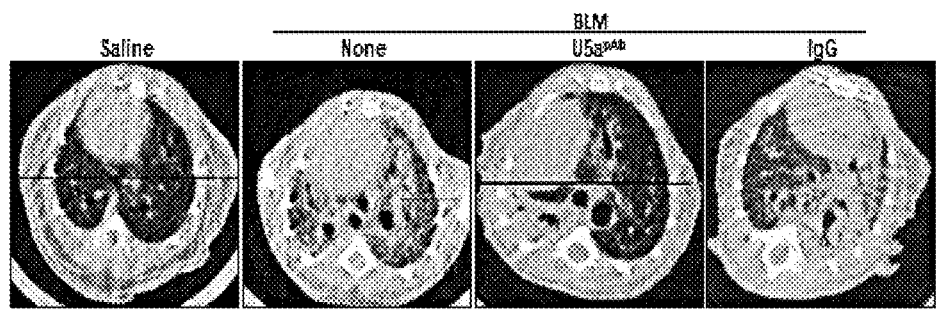
Figure 14D:
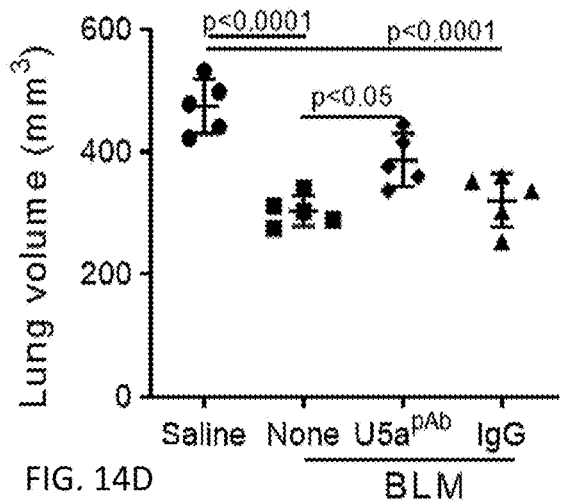
Figure 14E:
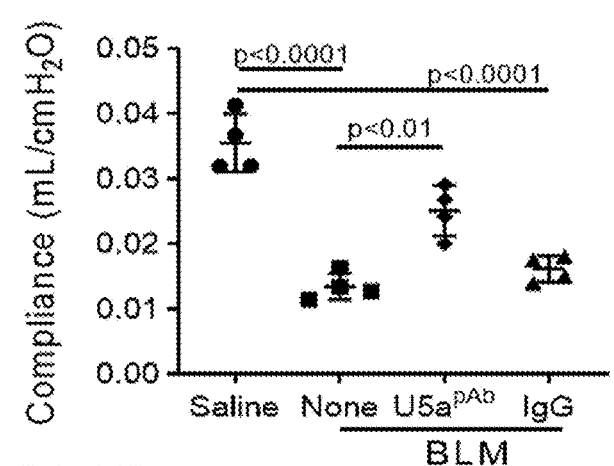
Figure 14F:
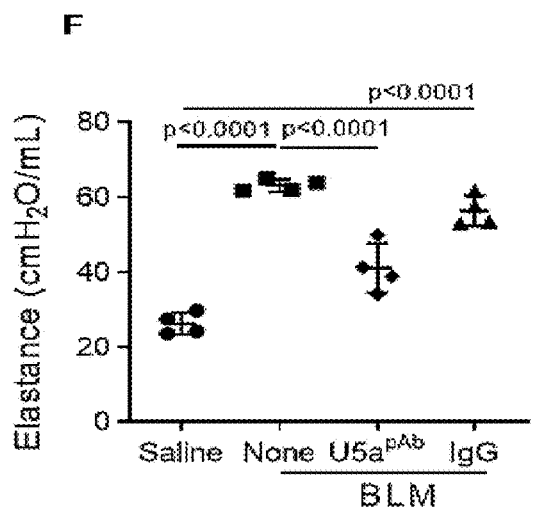
Figure 14G:
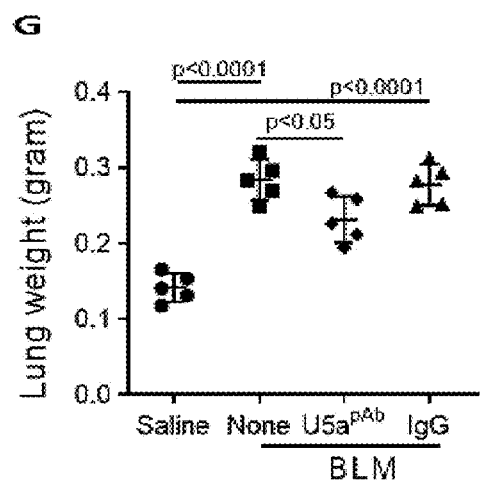
Figure 14H:
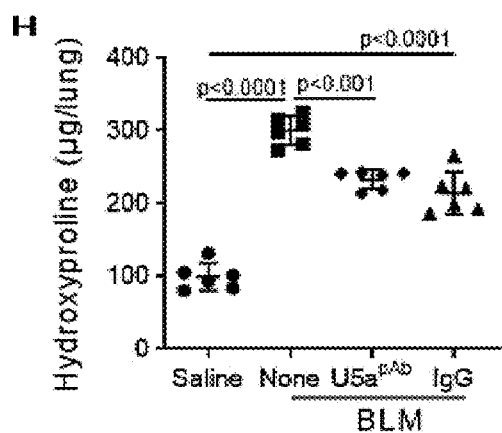
Figure 14I:
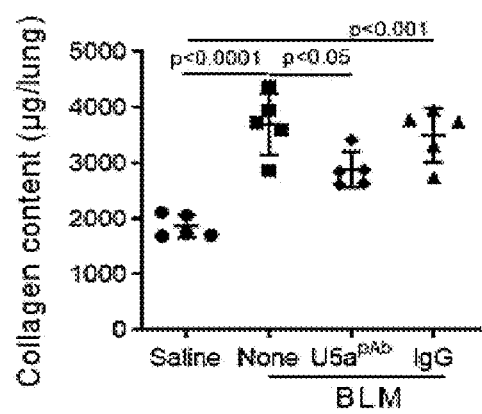
Figure 14J:
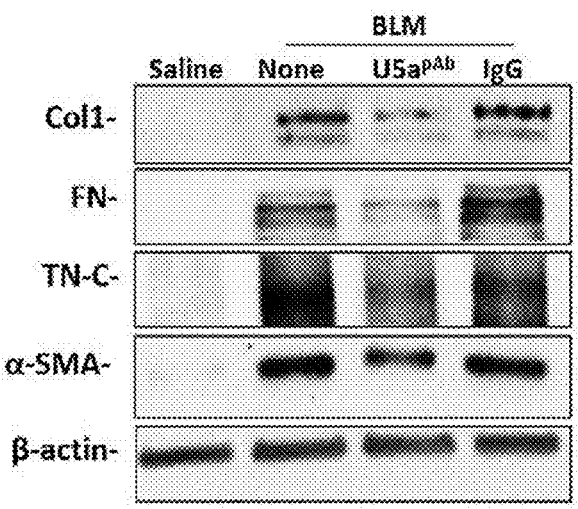
Figure 14K:
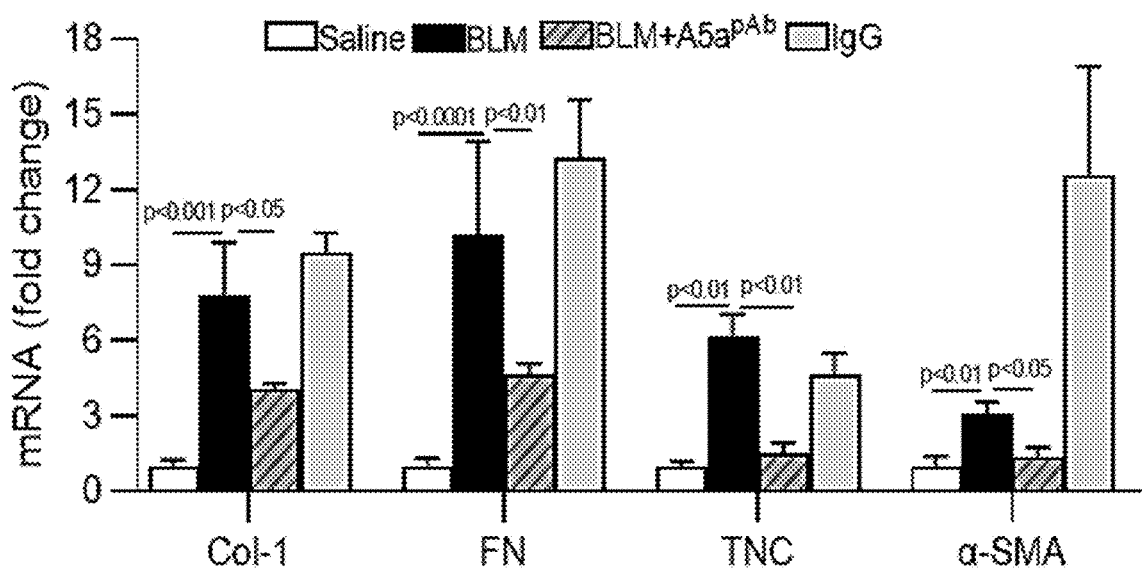
Figure 15A:
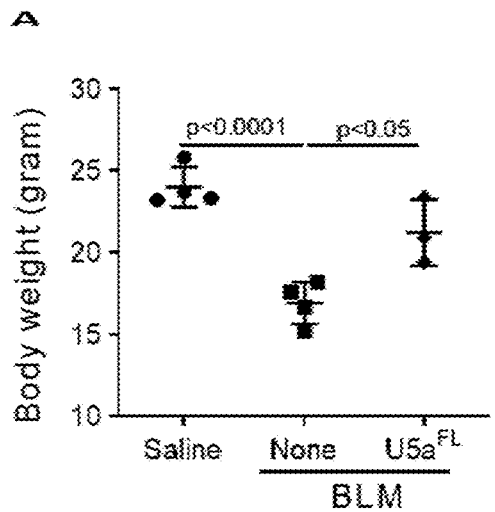
FIGS. 15A-15K. Recombinant full length U5a (U5a$^{FL}$) protein mitigated BLM-induced pulmonary fibrosis. Mice exposed to saline or 1.0 U/kg BLM by IT instillation were IP injected with or without U5a$^{FL}$ (7.5 mg/kg) daily for 7 days starting day 14 after BLM injury. Total body weight (FIG. 15A), micro-CT images (FIG. 15B) and lung volumes (FIG. 15C) were measured by quantitative-CT renditions and lung compliance (FIG. 15D) and elastance (FIG. 15E) were measured using a flexiVent system on day 21 post-BLM. Lung weights (FIG. 15F) were measured on day 21 post-BLM. Lung homogenates were analyzed for total hydroxyproline (FIG. 15G), soluble collagen (FIG. 15H), pro-fibrogenic marker proteins (FIG. 15I) and their mRNAs (J) day 21 after BLM. Lung sections were subjected H&E and Trichrome staining (FIG. 15K) to assess lung architectural distortion and collagen and other extracellular matrix deposition.
Figure 15C:
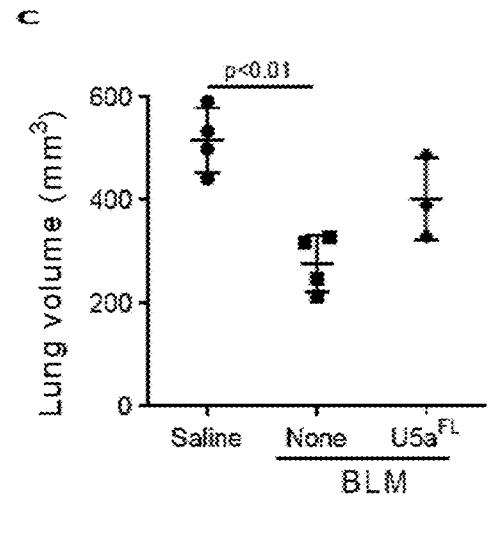
Figure 15B:
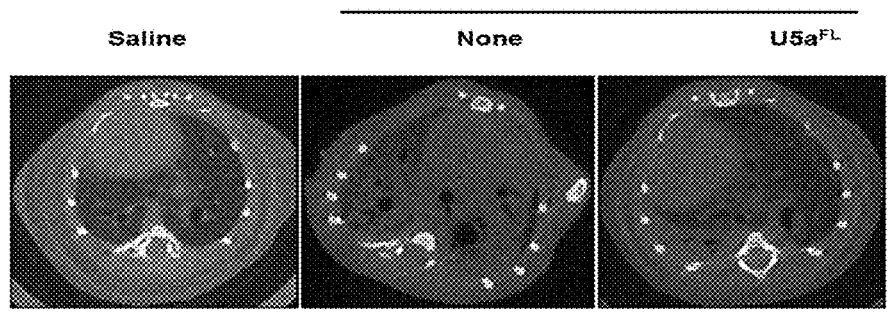
Figure 15D:
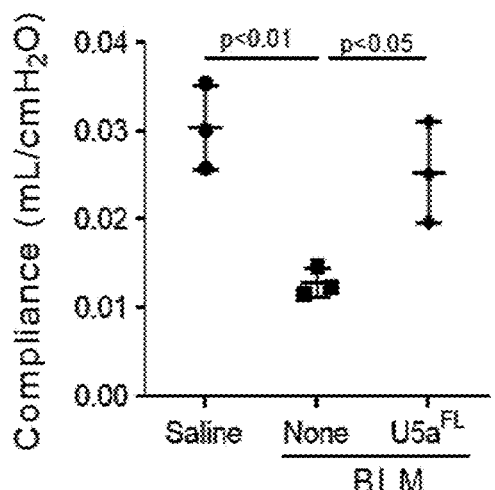
Figure 15E:
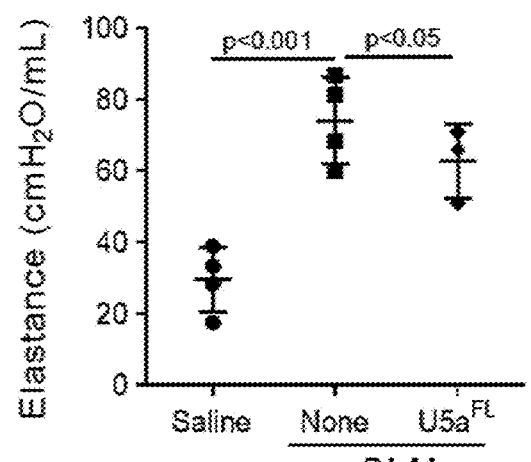
Figure 15F:
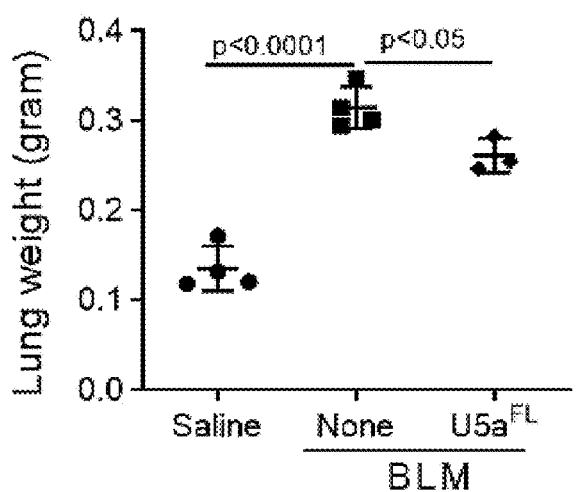
Figure 15G:
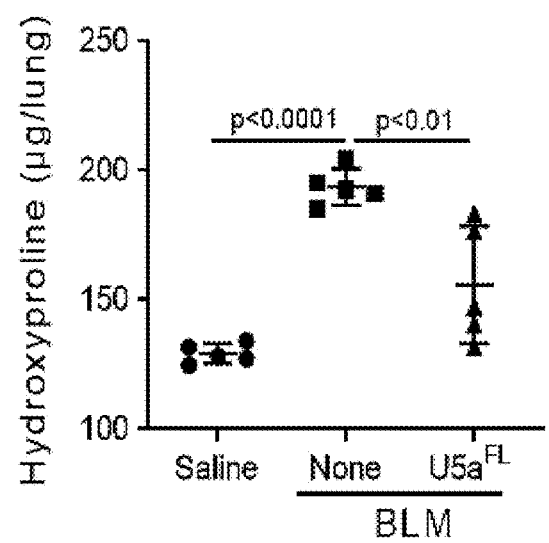
Figure 15H:
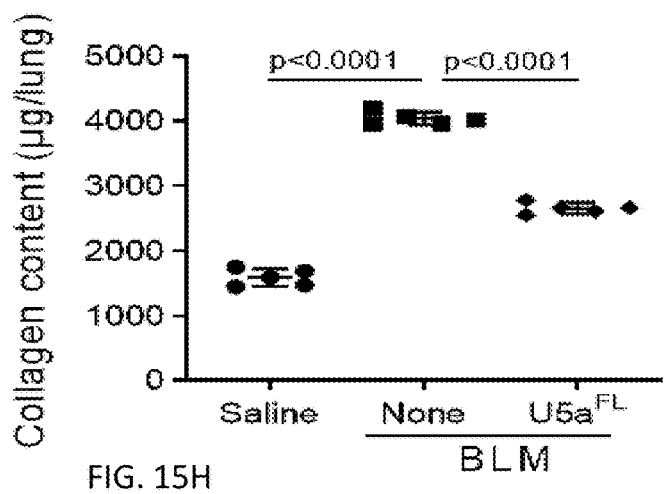
Figure 15I:
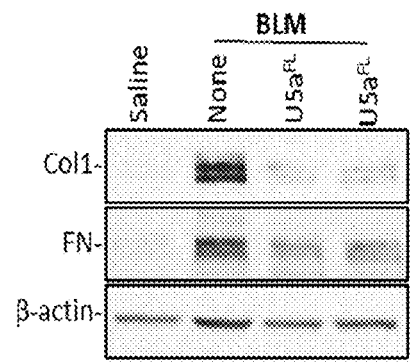
Figure 15J:
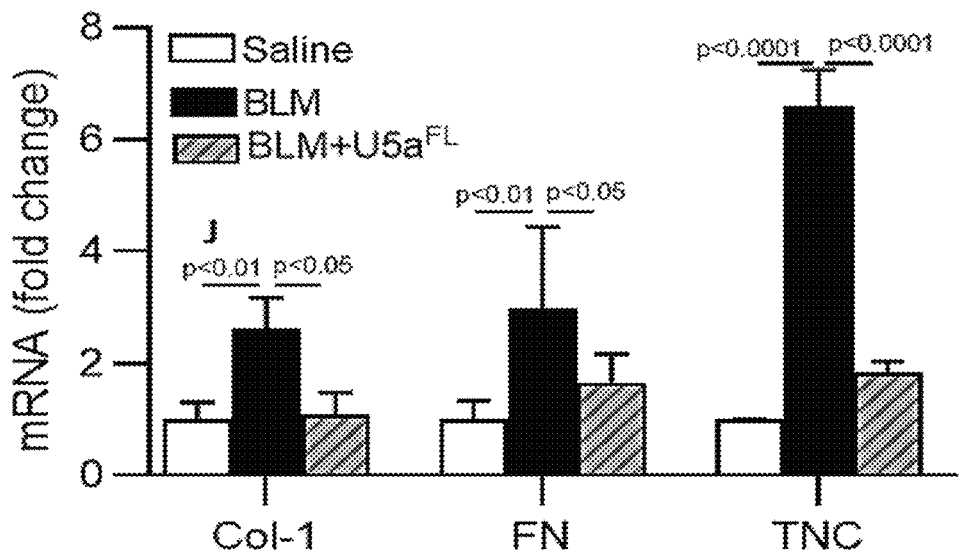
Figure 15K:
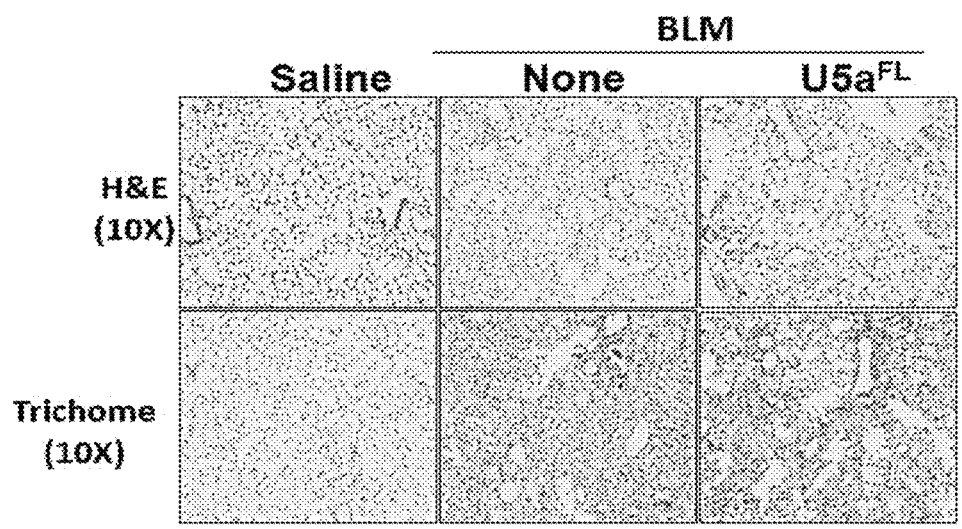
Figure 16A:
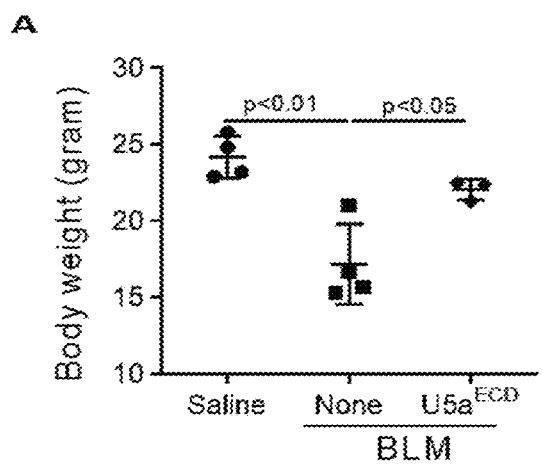
Figure 16C:
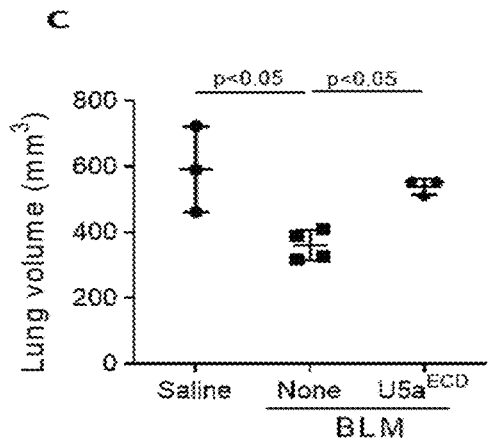
Figure 16B:
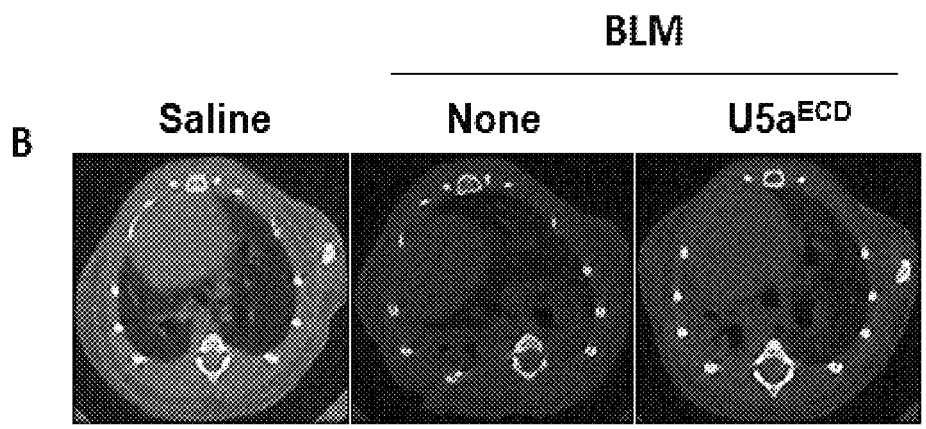
Figure 16D:
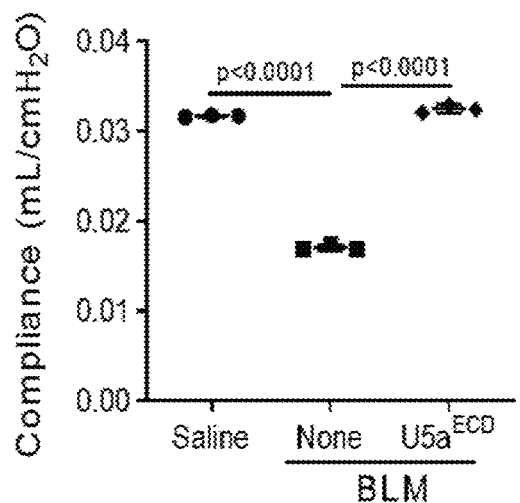
Figure 16E:
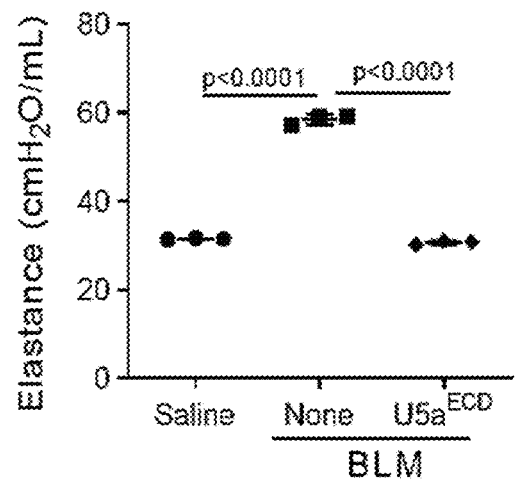

Treatment of mice with established PF for 7 days with recombinant A5 protein improved lung compliance and elastance indicating improvement in pulmonary function, which was otherwise compromised by existing pulmonary fibrosis (FIGS. 11A-11D). These changes were associated with parallel reduction in lung weight (FIG. 11E) and improvement in body weight (FIG. 11F), which was affected by bleomycin-induced lung fibrosis. This was further confirmed by reduction in whole lung total hydroxyproline (FIG. 11G) and soluble collagen (FIG. 11H) content reflecting inhibition of existing lung fibrosis after treatment with A5 protein for 7 days. These findings are consistent with inhibition of BLM-induced fibrogenic markers such as ColI, FN, TN-C and α-SMA proteins (FIG. 11I) and their transcripts (FIG. 11J) in whole lung homogenates of BLM-exposed mice treated with A5 protein. Trichrome staining of lungs sections after treatment with A5 showed reduction collagen and other extracellular matrix deposits, which were otherwise prevalent in fibrotic lung tissue, thereby demonstrating resolution of pulmonary fibrosis. Collectively, these findings indicate that recombinant A5 protein like specific antibody against A5 protein (FIGS. 4, 6 and 8A-8K) can mitigate lung fibrosis by competing with A5 protein both in injured type II alveolar epithelial (ATII) cell and fLfs in fibrotic lung tissues of BLM-induced PF (FIGS. 4 and 6) and presumably in IPF tissues. Therefore, the protein or peptide can be used directly as interventions like specific polyclonal or monoclonal antibodies against A5 protein for treatment of existing pulmonary fibrosis.

Therefore, in addition to (or in combination with) anti-A5 antibodies (polyclonal antibodies, monoclonal antibodies, or as otherwise defined here), A5 protein, and/or presumably, an active peptide fragment thereof, is useful for treating pulmonary fibrosis.

Example 12

IT Installation of rM9$^{ECD}$ Resolved 1x-BLM-Induced Existing PF.

This example demonstrates the effect of local delivery of M9$^{ECD}$ in the airway on a mouse PF model. Mice with BLM-induced PF were treated with M9$^{ECD}$ (rM9$^{ECD}$) (SEQ ID NO: 102) by IT instillation. The rM9$^{ECD}$ delivered by intratracheal (IT) instillation resolved existing PF and improved lung function (FIGS. 12A-12E). This indicates that rM9$^{ECD}$ can be delivered via airways to treat PF.

Example 13

M9$^{ECD}$-specific M9$^{mAb}$ resolved 1x-BLM-induced existing PF

This example demonstrates the effect of M9 monoclonal antibody specifically binding to the ECD of M9 on IPF fLFs and BLM-PF mice. The monoclonal antibody (M9$^{mAb}$) was developed using rM9$^{ECD}$ as an antigen. IPF fLFs were treated by the M9 monoclonal antibody in vitro and the protein and mRNA levels of pro-fibrogenic markers were measured. FIG. 13A shows that the M9 monoclonal antibody inhibited the protein and mRNA levels of pro-fibrogenic markers. In addition, the M9 monoclonal antibody was delivered by IP injection to BLM-PF mice and resolved 1x-BLM-induced existing PF in the mice (FIG. 13B), indicating that M9$^{mAb}$ can be used to treat PF.

Example 14

U5A Proteins and Anti-U5A Antibodies Mitigated BLM-Induced Pulmonary Fibrosis.

Figure 17A:
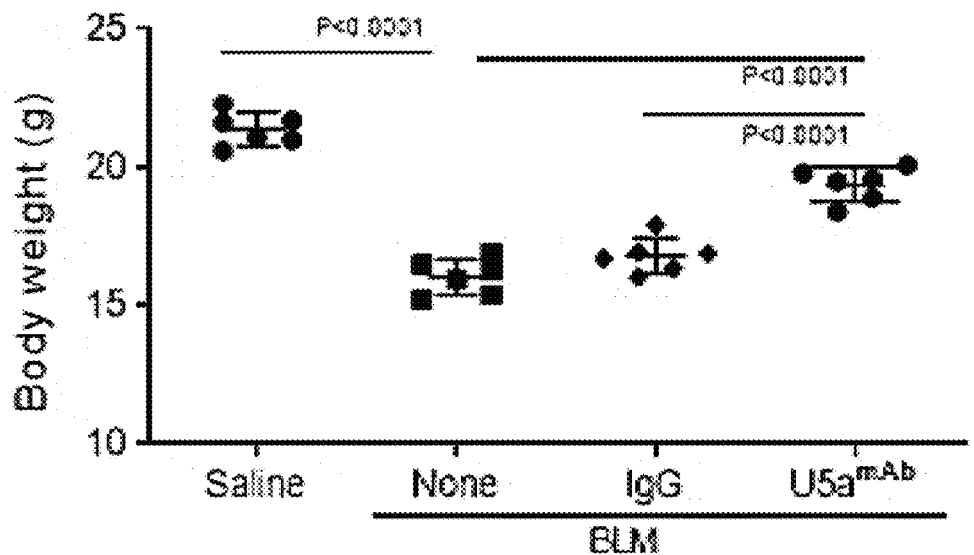
Figure 17B:
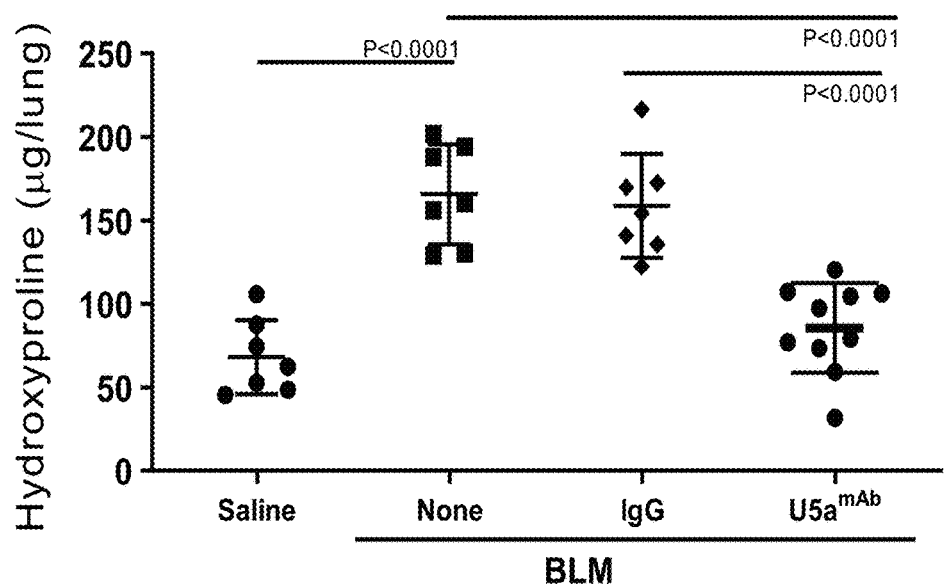
Figure 19D:
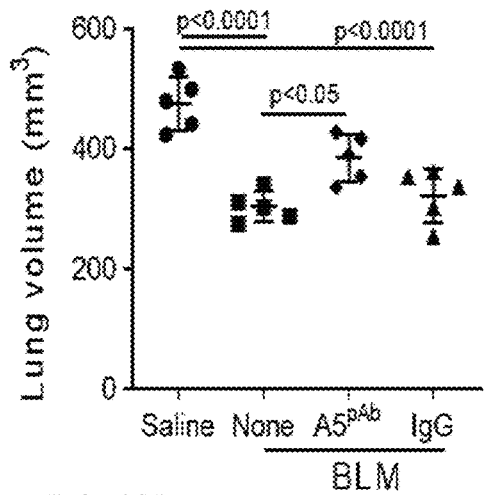
Figure 19E:
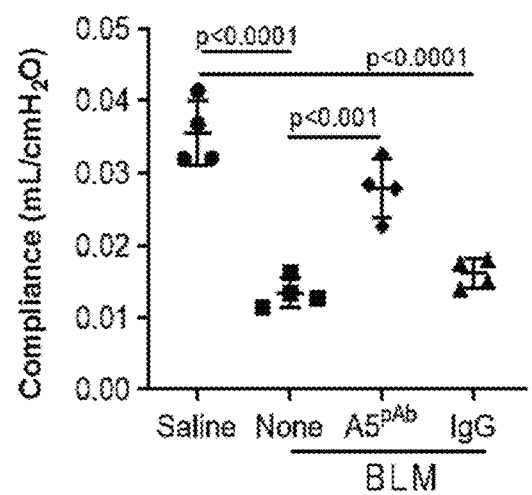
Figure 19F:
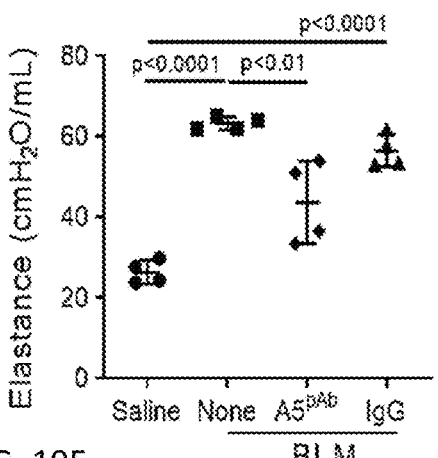
Figure 19G:
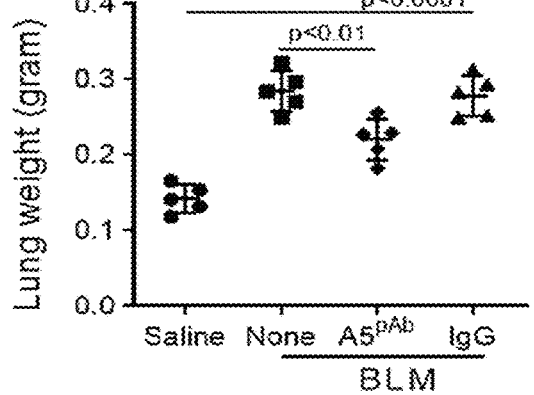
Figure 19H:
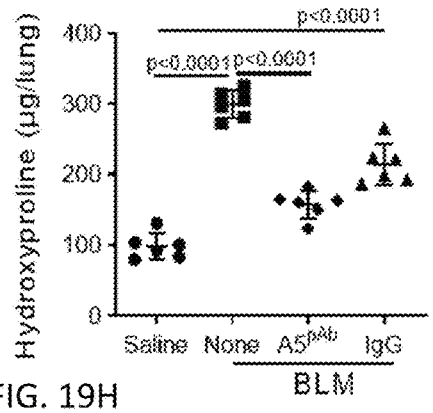
Figure 19I:
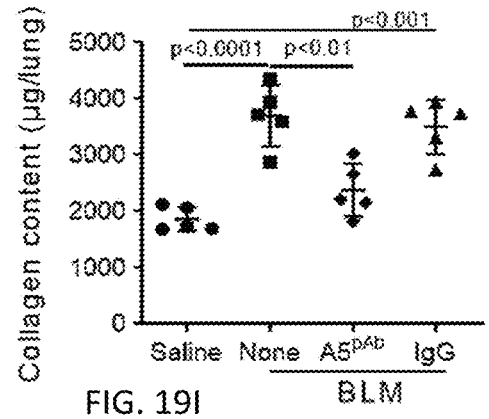
Figure 19J:
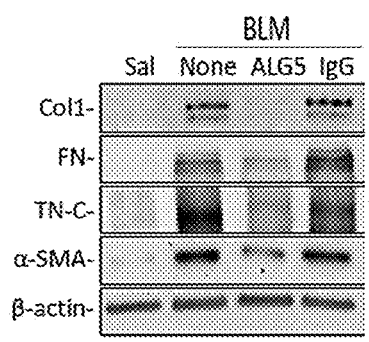
Figure 19K:
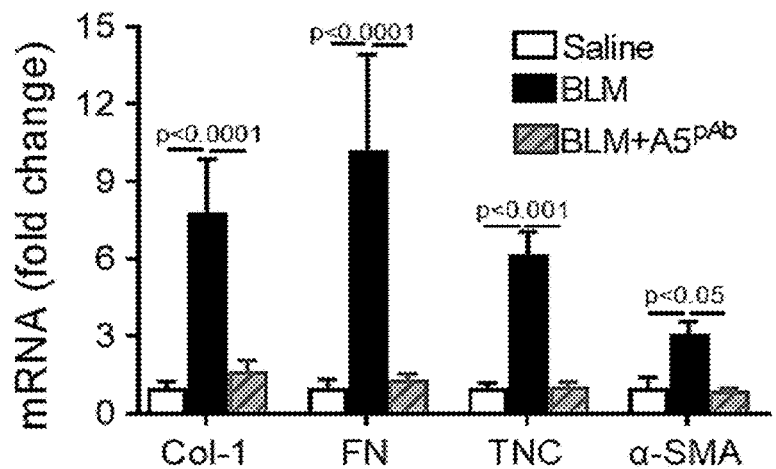
Figure 20A:
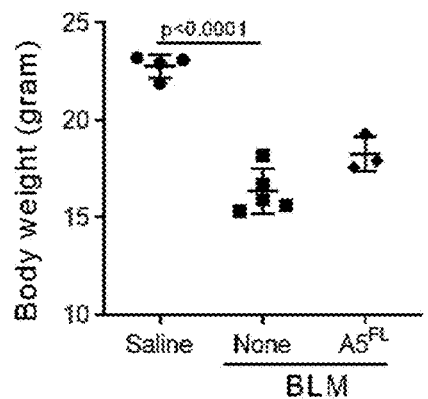
Figure 20C:
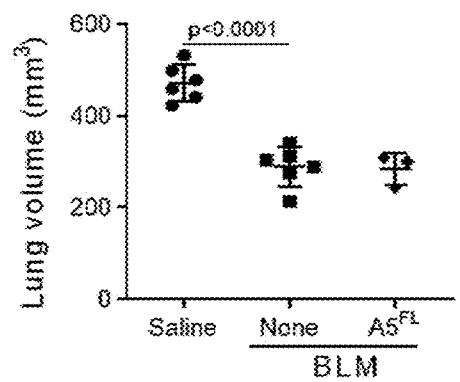
Figure 20B:
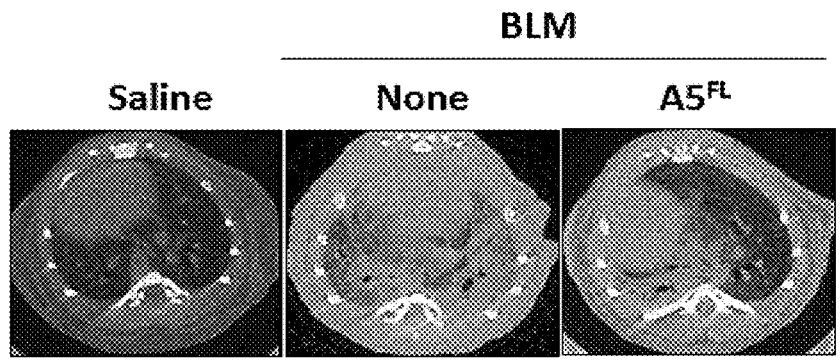
Figure 21B:
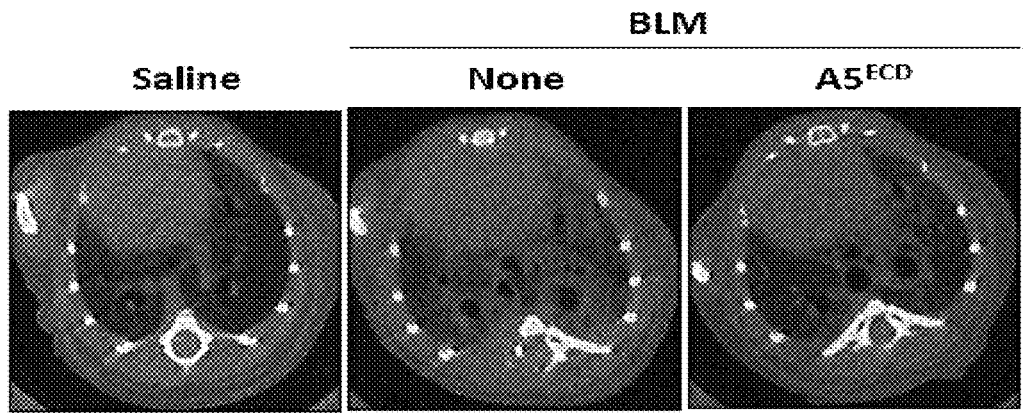
Figure 21D:
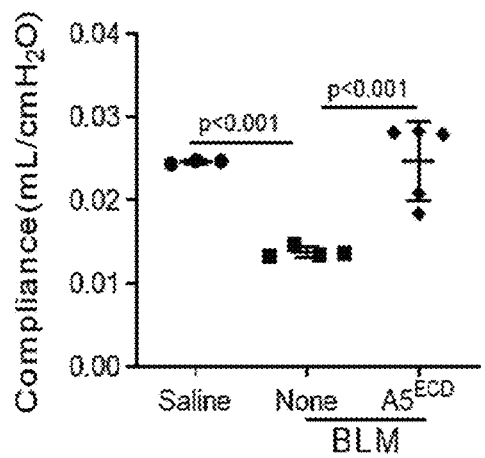
Figure 21E:
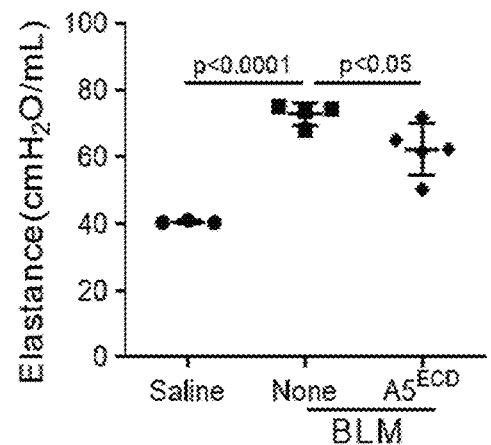
Figure 21F:
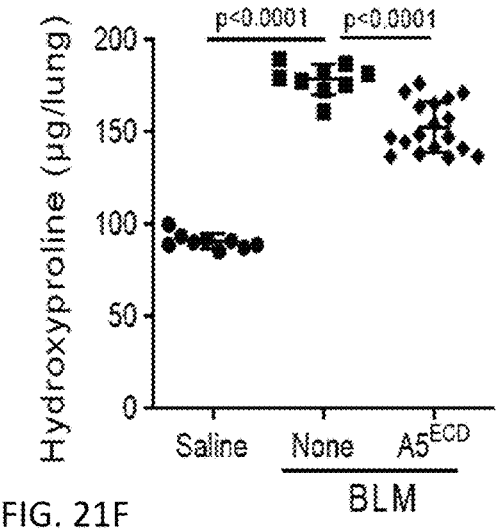
Figure 21G:
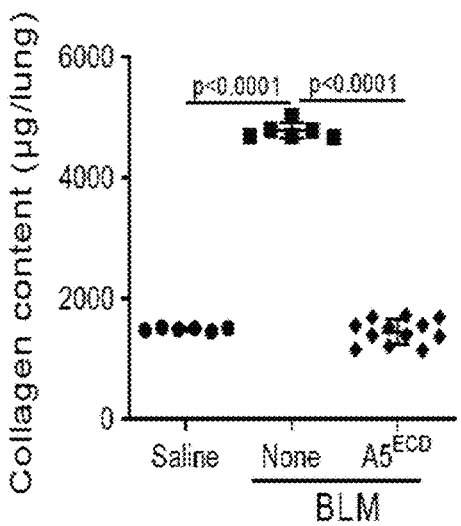
Figure 23B:
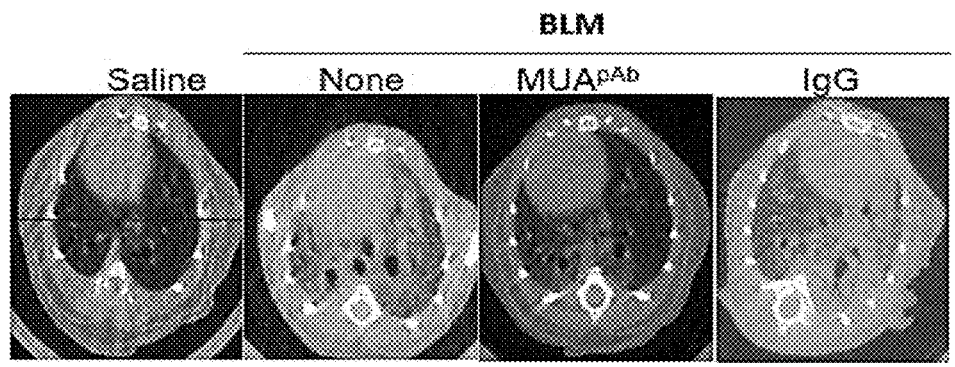
Figure 23D:
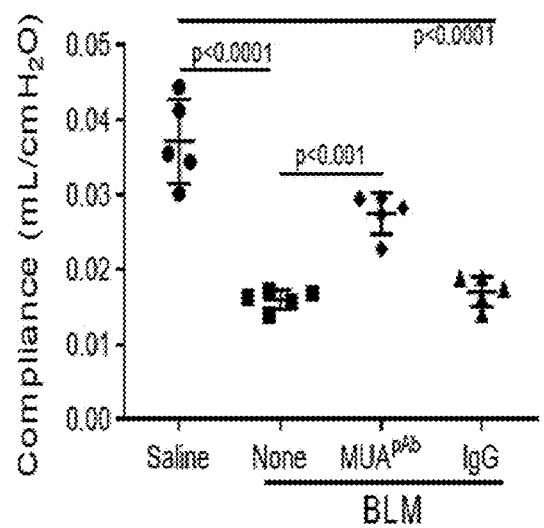
Figure 23E:
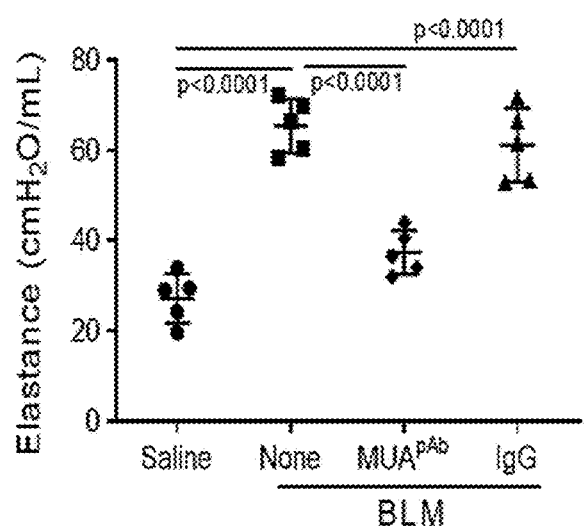
Figure 23F:
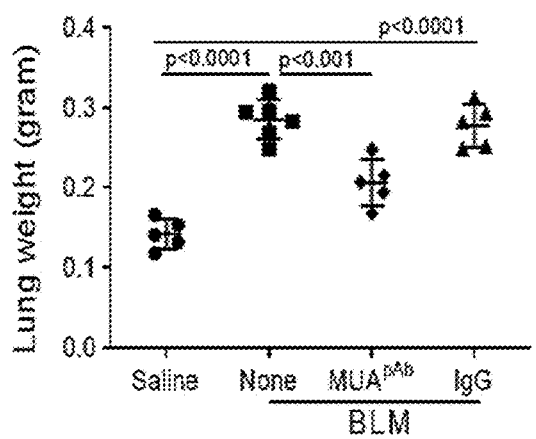
Figure 23G:
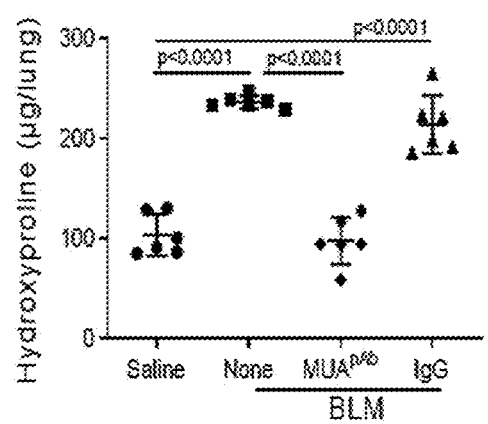
Figure 23H:
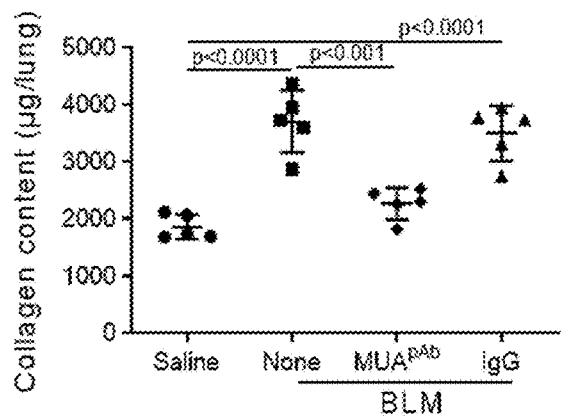
Figure 23I:
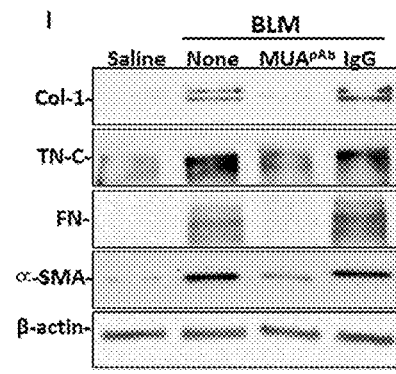
Figure 23J:
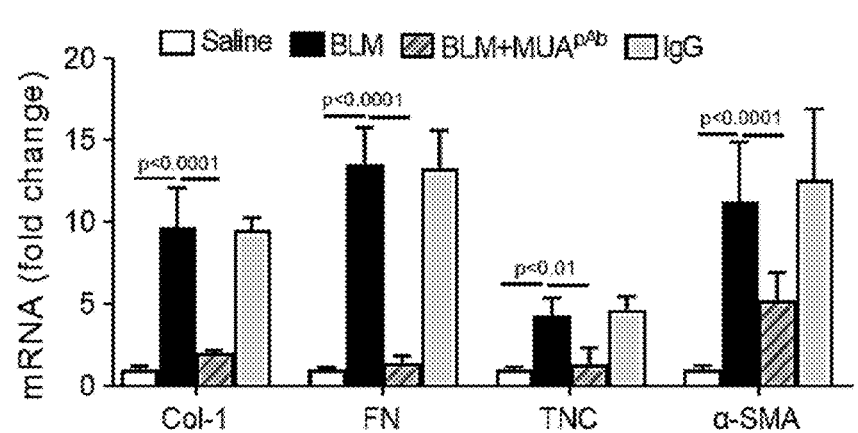
Figure 24A:
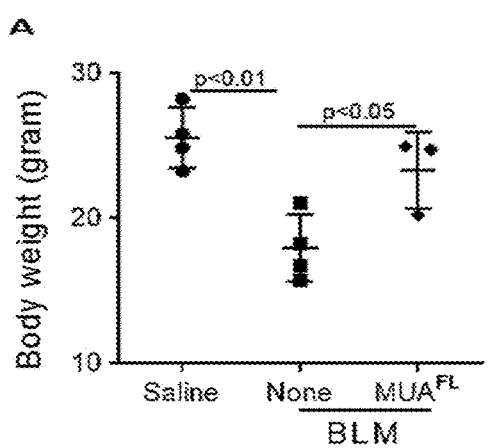
Figure 24C:
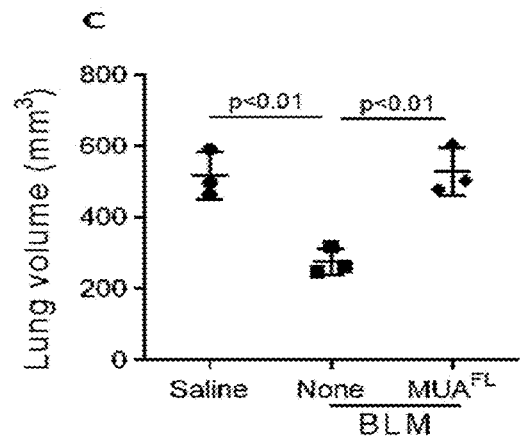
Figure 24B:
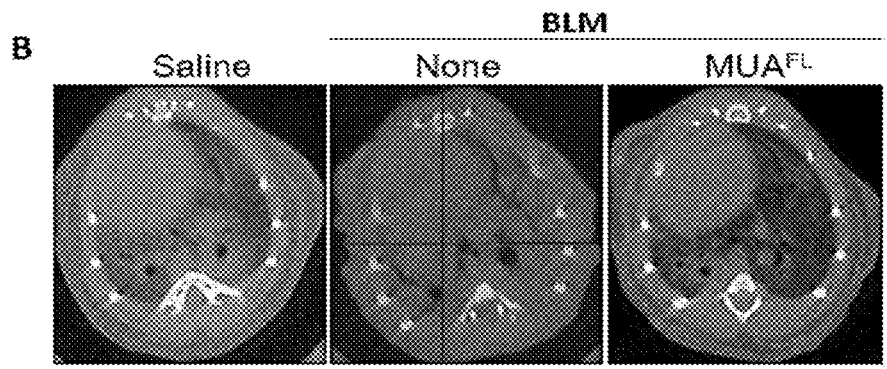
Figure 24D:
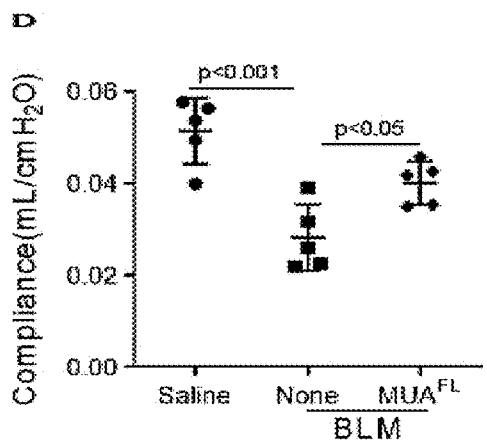
Figure 24E:
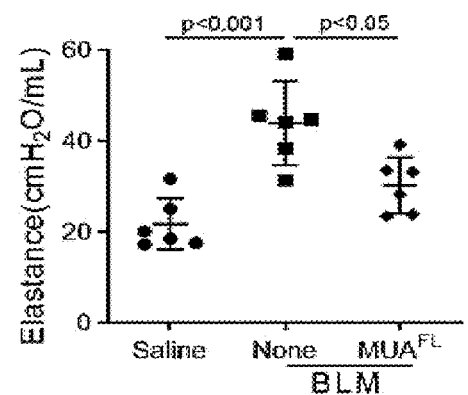
Figure 24F:
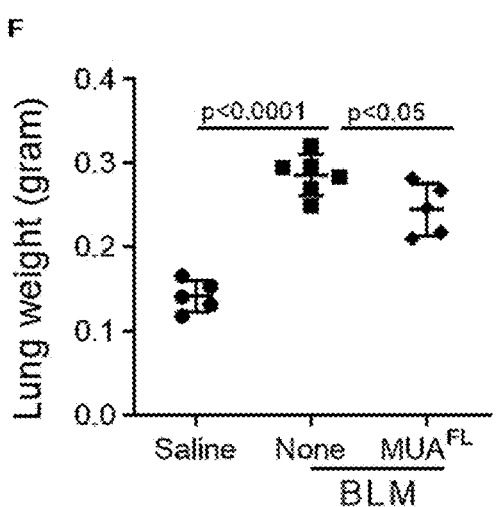
Figure 24G:
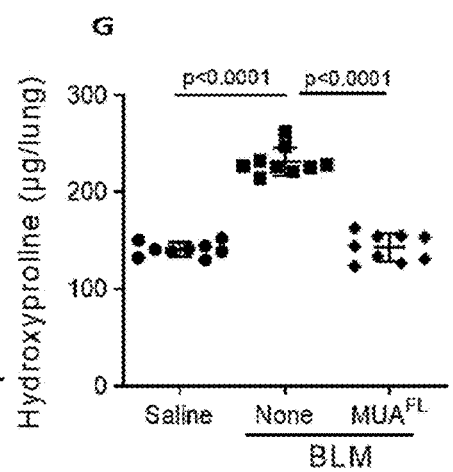
Figure 25B:
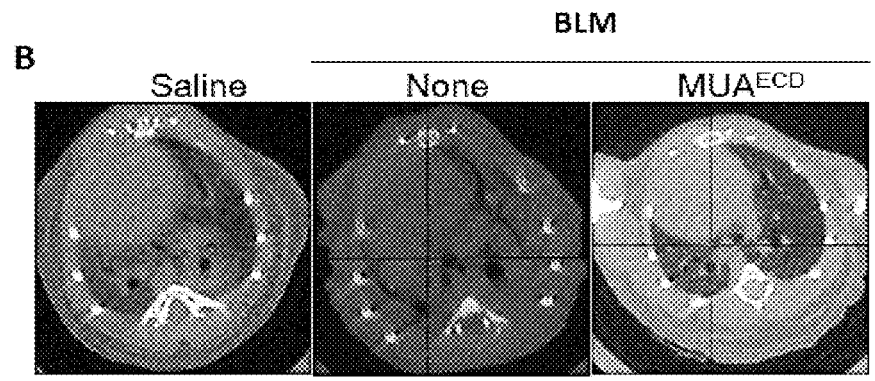
Figure 25D:
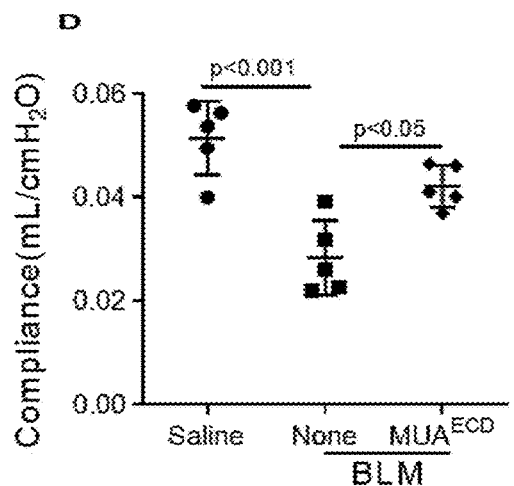
Figure 25E:
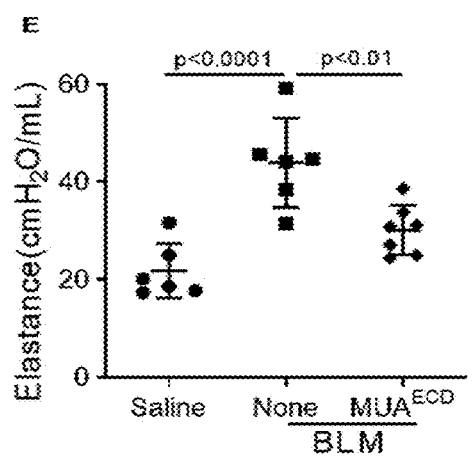
Figure 25F:
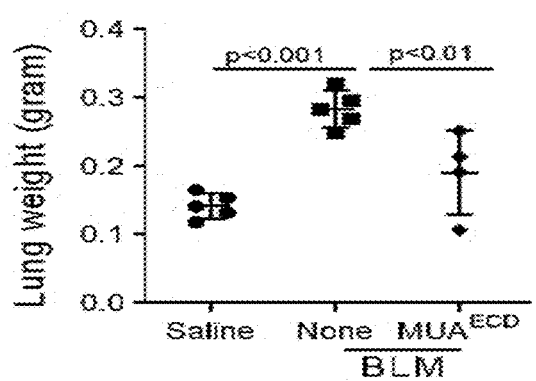
Figure 25G:
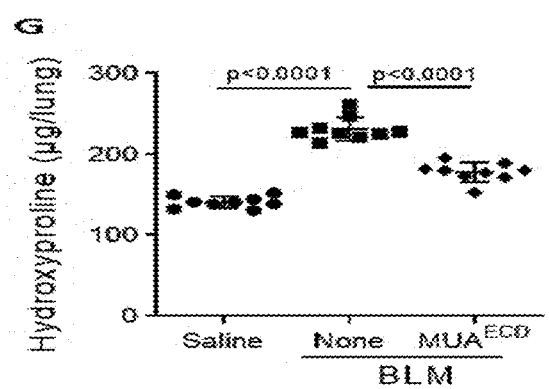

Wild type mice were exposed to saline or BLM by intranasal or IT instillation as described in Marudamuthu A S, et al., Caveolin-1-derived peptide limits development of pulmonary fibrosis. Sci Transl Med 11, eaat2848 (2019), and Nagaraja M R et al., p53 expression in lung fibroblasts is linked to mitigation of fibrotic lung remodeling. Am J Pathol 188: 2207-2222 (2018), which are incorporated herein by reference herein in their entireties. Fourteen days later, mice with BLM-induced PF were IP injected daily 200 μL of vehicle, a polyclonal anti-U5a antibody (ProteinTech, Catalog #22068-1-AP and Sigma, Catalog #SAB2108252) (FIGS. 14A-14K), recombinant full length U5a (SEQ ID NO: 5) (FIGS. 15A-15K), recombinant extracellular domain of U5a (SEQ ID NO: 103) (FIGS. 16A-16J), or a monoclonal anti-U5a antibody (FIGS. 17A-17C) as described in the legends to each figure for 7 days. Twenty-one days after BLM injury, mice were evaluated for changes in body weights, pulmonary function and lung tissues extracted these mice were tested for changes in total lung weights, soluble collagen, hydroxyproline and pro-fibrogenic proteins and their mRNAs to assess PF.

Based on the in vitro and in vivo results described herein, the full length or extracellular domain of U5a, as well as antibodies developed against U5a mitigated established PF by inhibiting both AEC apoptosis and fibrotic fibroblast (fLf) expansion.

Example 15

Differential Expression of ALG5 (A5) Protein in Human nLfs and fLfs

Normal lung fibroblasts (nLfs) were isolated from normal lung tissues from control subjects and fibrotic lung fibroblasts (fLfs) were isolated from fibrotic lung (fL) tissues from patients with IPF. Expression of A5 proteins were determined in the samples with Western blot. FIG. 18 shows that the expression levels of A5 protein are different between nLfs and fLfs.

Example 16

A5 Proteins and Anti-A5 Antibodies Mitigated BLM-Induced Pulmonary Fibrosis.

Wild type mice were exposed to saline or BLM by intranasal or IT instillation as described in Marudamuthu A S, et al., Caveolin-1-derived peptide limits development of pulmonary fibrosis. Sci Transl Med 11, eaat2848 (2019), and Nagaraja M R et al., p53 expression in lung fibroblasts is linked to mitigation of fibrotic lung remodeling. Am J Pathol 188: 2207-2222 (2018).

Fourteen days later, mice with BLM-induced PF were IP injected daily 200 µL of vehicle, a polyclonal anti-A5 antibody (Invitrogen, Catalog #PA5-52496) (FIGS. 19A-19K), recombinant full length A5 (SEQ ID NO: 9) (FIGS. 20A-20K), recombinant extracellular domain of A5 (FIGS. 21A-21I), or a monoclonal anti-A5 antibody (FIGS. 22A-22C) as described in the legends to each figure for 7 days. Twenty-one days after BLM injury, mice were evaluated for changes in body weights, pulmonary function and lung tissues extracted these mice were tested for changes in total lung weights, soluble collagen, hydroxyproline and pro-fibrogenic proteins and their mRNAs to assess PF.

Based on the in vitro and in vivo results described herein, the full length or extracellular domain of A5, as well as antibodies developed against A5 mitigated established PF by inhibiting both AEC apoptosis and fibrotic fibroblast (fLf) expansion.

Example 17

Combination of M9, U5a, and A5 Proteins, and Combination of Antibodies Against M9, U5a, and A5 Antibodies Mitigated BLM-Induced Pulmonary Fibrosis.

WT mice were exposed to saline or BLM by intranasal or IT instillation as we described in Marudamuthu A S, et al., Caveolin-1-derived peptide limits development of pulmonary fibrosis. Sci Transl Med 11, eaat2848 (2019), and Nagaraja M R et al., p53 expression in lung fibroblasts is linked to mitigation of fibrotic lung remodeling. Am J Pathol 188: 2207-2222 (2018).

Fourteen days later, mice with BLM-induced PF were IP injected daily 200 µL of vehicle, a combination of polyclonal anti-M9 antibody, anti-U5a antibody, and anti-A5 antibody (as described in Examples 4-6) (FIGS. 23A-23J), a combination of recombinant full length proteins of M9, U5, and A5 (FIGS. 24A-24J), a combination of recombinant extracellular domains of M9, U5a, and A5 (FIGS. 25A-25J) as described in the legends to each figure for 7 days. Twenty-one days after BLM injury, mice were evaluated for changes in body weights, pulmonary function and lung tissues extracted these mice were tested for changes in total lung weights, soluble collagen, hydroxyproline and pro-fibrogenic proteins and their mRNAs to assess PF.

Based on the in vitro and in vivo results described herein, the combination of full length proteins of M9, U5a, and A5, a combination of the ECDs of M9, U5a, and A5, as well as a combination of polyclonal anti-M9 antibody, anti-U5a antibody, and anti-A5 antibody mitigated established PF by inhibiting both AEC apoptosis and fibrotic fibroblast (fLf) expansion.

The present disclosure includes the following non-limiting list of numbered aspects:

1. A method of treating, reducing, ameliorating or inhibiting symptoms idiopathic pulmonary fibrosis (IPF) or interstitial pneumonia, comprising administering to a subject in need thereof an effective amount of
    a) multiple EGF-like-domains-9 (MEGF9) or a biologically active fragment thereof;
    b) uncoordinated receptor 5A (UNC5A) or a biologically active fragment thereof;
    c) dolichyl-phosphate beta-glucosyltransferase (ALG5) or a biologically active fragment thereof;
    d) a combination of two or three of a)-c);
    e) an antibody specifically binding to a);
    f) an antibody specifically binding to b);
    g) an antibody specifically binding to c);
    h) a combination of two or three of e)-g); or
    i) a combination of at least one of a)-c) and at least one of e)-g).

The method of numbered aspect 1, comprising administering MEGF9 or a biologically active fragment thereof; and UNC5A or a biologically active fragment thereof.

2. The method of any numbered aspect, comprising administering UNC5A or a biologically active fragment thereof; and ALG5 or a biologically active fragment thereof.

3. The method of any numbered aspect, comprising administering MEGF9 or a biologically active fragment thereof; and ALG5 or a biologically active fragment thereof.

4. The method of any numbered aspect, comprising administering MEGF9 or a biologically active fragment thereof; UNC5A or a biologically active fragment thereof; and ALG5 or a biologically active fragment thereof.

5. The method of any numbered aspect, wherein the MEGF9 comprises the sequence of SEQ ID NO: 1, or a sequence with at least 80%, at least 85%, at least 90%, or at least 95% sequence identity to SEQ ID NO: 1.

6. The method of any numbered aspect, wherein the UNC5A comprises the sequence of SEQ ID NO: 5, or a sequence with at least 80%, at least 85%, at least 90%, or at least 95% sequence identity to SEQ ID NO: 5.

7. The method of any numbered aspect 5, wherein the ALG5 comprises the sequence of SEQ ID NO: 9, or a sequence with at least 80%, at least 85%, at least 90%, or at least 95% sequence identity to SEQ ID NO: 9.

8. The method of any numbered aspect, wherein the biologically active fragment of the MEGF9 comprises the sequence of SEQ ID NO: 3, or a sequence with at least 80%, at least 85%, at least 90%, or at least 95% sequence identity to SEQ ID NO: 3.

9. The method of any numbered aspect, wherein the biologically active fragment of the MEGF9 consists of the sequence of SEQ ID NO: 3, or a sequence with at least 80%, at least 85%, at least 90%, or at least 95% sequence identity to SEQ ID NO: 3.

10. The method of any numbered aspect, wherein the biologically active fragment of the MEGF9 comprises the sequence of SEQ ID NO: 4, or a one-amino acid or two-amino acid modification thereof.

11. The method of any numbered aspect, wherein the biologically active fragment of the MEGF9 consists of the sequence of SEQ ID NO: 4, or a one-amino acid or two-amino acid modification thereof.

12. The method of any numbered aspect, wherein the biologically active fragment of the MEGF9 comprises the sequence of SEQ ID NO: 102, or a sequence with at least 80%, at least 85%, at least 90%, or at least 95% sequence identity to SEQ ID NO: 102.

13. The method of any numbered aspect, wherein the biologically active fragment of the MEGF9 consists of the sequence of SEQ ID NO: 102, or a sequence with at least 80%, at least 85%, at least 90%, or at least 95% sequence identity to SEQ ID NO: 102.

14. The method of any numbered aspect, wherein the biologically active fragment of the UNC5A comprises the sequence of SEQ ID NO: 7, or a sequence with at least 80%, at least 85%, at least 90%, or at least 95% sequence identity to SEQ ID NO: 7.

15. The method of any numbered aspect, wherein the biologically active fragment of the UNC5A consists of the sequence of SEQ ID NO: 7, or a sequence with at least 80%, at least 85%, at least 90%, or at least 95% sequence identity to SEQ ID NO: 7.
16. The method of any numbered aspect, wherein the biologically active fragment of the UNC5A comprises the sequence of SEQ ID NO: 8, or a sequence with at least 80%, at least 85%, at least 90%, or at least 95% sequence identity to SEQ ID NO: 8.
17. The method of any numbered aspect, wherein the biologically active fragment of the UNC5A consists of the sequence of SEQ ID NO: 8, or a sequence with at least 80%, at least 85%, at least 90%, or at least 95% sequence identity to SEQ ID NO: 8.
18. The method of any numbered aspect, wherein the biologically active fragment of the UNC5A comprises the sequence of SEQ ID NO: 103, or a sequence with at least 80%, at least 85%, at least 90%, or at least 95% sequence identity to SEQ ID NO: 103.
19. The method of any numbered aspect, wherein the biologically active fragment of the UNC5A consists of the sequence of SEQ ID NO: 103, or a sequence with at least 80%, at least 85%, at least 90%, or at least 95% sequence identity to SEQ ID NO: 103.
20. The method of any numbered aspect, wherein the biologically active fragment of the ALG5 comprises the sequence of SEQ ID NO: 104, or a sequence with at least 80%, at least 85%, at least 90%, or at least 95% sequence identity to SEQ ID NO: 104.
21. The method of any numbered aspect, wherein the biologically active fragment of the ALG5 consists of the sequence of SEQ ID NO: 104, or a sequence with at least 80%, at least 85%, at least 90%, or at least 95% sequence identity to SEQ ID NO: 104.
22. The method of any one or combination of any numbered aspect, further comprising administering a Cav1 scaffolding domain peptide (CSP).
23. The method of any numbered aspect, wherein the CSP comprises a sequence of SEQ ID NO: 11 or a one-amino acid modification thereof.
24. The method of any numbered aspect, further comprising administering a), b), c), d), e), f), g), h), or i) to the subject in the form of a pharmaceutical composition that further comprises a pharmaceutically acceptable carrier.
25. The method of any numbered aspect, further comprising administering the pharmaceutical composition via a route selected from the group consisting of intrapulmonary, intravenous, intramuscular, subcutaneous, oral, or in any combination thereof.
26. The method of any numbered aspect, wherein the route is intrapulmonary.
27. The method of any numbered aspect, wherein the intrapulmonary route is carried out by inhalation.
28. The method of any numbered aspect, wherein the route is intravenous.
29. The method of any numbered aspect, wherein the route is intratracheal.
30. The method of any numbered aspect, wherein the interstitial pneumonia is defined by radiographic and histologic presentation of lung scarring, extracellular matrix deposition, epithelial cell senescence and apoptosis, activation of myofibroblasts of fibrotic lung fibroblasts, M2 macrophage polarization and elaboration of profibrogenic cytokines, or a combination thereof.
31. The method of any numbered aspect 31, wherein the subject is a human.
32. The method of any numbered aspect, further comprising administering one or more additional therapeutic agents.
33. The method of any numbered aspect, wherein the one or more additional therapeutic agents comprises nintedanib, pirfenidone, or a combination thereof.
34. A vector comprising a nucleic acid molecule comprising one or more polynucleotides encoding:
a) MEGF9 or a biologically active fragment thereof;
b) UNC5A or a biologically active fragment thereof;
c) ALG5 or a biologically active fragment thereof;
d) a combination two or three of any of a-c;
e) an antibody specifically binding to a);
f) an antibody specifically binding to b);
g) an antibody specifically binding to c);
h) a combination of two or three of e)-g); or
i) a combination of at least one of a)-c) and at least one of e)-g).
35. A cell comprising the vector of numbered aspect 35.
36. A method of producing a therapeutic protein, comprising:
culturing the cell of numbered aspect 36 in a culture medium under a condition sufficient to produce a therapeutic protein comprising any one of a), b), c), d), e), f), g), h), or i); and
recovering the therapeutic protein from the cell or the culture medium.
37. The method of numbered aspect 37, further comprising isolating the therapeutic protein recovered from the cell or the culture medium.
38. The method of numbered aspect 37 or 38, further comprising formulating the therapeutic protein into a pharmaceutical composition.
39. A pharmaceutical composition comprising a pharmaceutically acceptable carrier and
a) MEGF9 or a biologically active fragment thereof;
b) UNC5A or a biologically active fragment thereof;
c) ALG5 or a biologically active fragment thereof;
d) a combination of two or three of a)-c);
e) an antibody specific for a);
f) an antibody specific for b);
g) an antibody specific for c);
h) a combination of two or three of e)-g); or
i) a combination of at least one of a)-c) and at least one of e)-g).
40. The pharmaceutical composition of numbered aspect 40, comprising MEGF9 or a biologically active fragment thereof; and UNC5A or a biologically active fragment thereof.
41. The pharmaceutical composition of numbered aspect 40, comprising UNC5A or a biologically active fragment thereof; and ALG5 or a biologically active fragment thereof.
42. The pharmaceutical composition of numbered aspect 40, comprising MEGF9 or a biologically active fragment thereof; and ALG5 or a biologically active fragment thereof.
43. The pharmaceutical composition of numbered aspect 40, comprising MEGF9 or a biologically active fragment thereof; UNC5A or a biologically active fragment thereof; and ALG5 or a biologically active fragment thereof.
44. The pharmaceutical composition of any one or combination of numbered aspects, wherein the MEGF9 comprises the sequence of SEQ ID NO: 1, or a sequence with at least 80%, at least 85%, at least 90%, or at least 95% sequence identity to SEQ ID NO: 1.

45. The pharmaceutical composition of any one or combination of numbered aspects, wherein the UNC5A comprises the sequence of SEQ ID NO: 5, or a sequence with at least 80%, at least 85%, at least 90%, or at least 95% sequence identity to SEQ ID NO: 5.

46. The pharmaceutical composition of any one or combination of numbered aspects, wherein the ALG5 comprises the sequence of SEQ ID NO: 9, or a sequence with at least 80%, at least 85%, at least 90%, or at least 95% sequence identity to SEQ ID NO: 9.

47. The pharmaceutical composition of any one or combination of numbered aspects, wherein the biologically active fragment of the MEGF9 comprises the sequence of SEQ ID NO: 3, or a sequence with at least 80%, at least 85%, at least 90%, or at least 95% sequence identity to SEQ ID NO: 3.

48. The pharmaceutical composition of any one or combination of numbered aspects, wherein the biologically active fragment of the MEGF9 consists of the sequence of SEQ ID NO: 3, or a sequence with at least 80%, at least 85%, at least 90%, or at least 95% sequence identity to SEQ ID NO: 3.

49. The pharmaceutical composition of any one or combination of numbered aspects, wherein the biologically active fragment of the MEGF9 comprises the sequence of SEQ ID NO: 4, or a one-amino acid or two-amino acid modification thereof.

50. The pharmaceutical composition of any one or combination of numbered aspects, wherein the biologically active fragment of the MEGF9 consists of the sequence of SEQ ID NO: 4, or a one-amino acid or two-amino acid modification thereof.

51. The pharmaceutical composition of any one or combination of numbered aspects, wherein the biologically active fragment of the MEGF9 comprises the sequence of SEQ ID NO: 102, or a sequence with at least 80%, at least 85%, at least 90%, or at least 95% sequence identity to SEQ ID NO: 102.

52. The pharmaceutical composition of any one or combination of numbered aspects, wherein the biologically active fragment of the MEGF9 consists of the sequence of SEQ ID NO: 102, or a sequence with at least 80%, at least 85%, at least 90%, or at least 95% sequence identity to SEQ ID NO: 102.

53. The pharmaceutical composition of any one or combination of numbered aspects, wherein the biologically active fragment of the UNC5A comprises the sequence of SEQ ID NO: 7, or a sequence with at least 80%, at least 85%, at least 90%, or at least 95% sequence identity to SEQ ID NO: 7.

54. The pharmaceutical composition of any one or combination of numbered aspects, wherein the biologically active fragment of the UNC5A consists of the sequence of SEQ ID NO: 7, or a sequence with at least 80%, at least 85%, at least 90%, or at least 95% sequence identity to SEQ ID NO: 7.

55. The pharmaceutical composition of any one or combination of numbered aspects, wherein the biologically active fragment of the UNC5A comprises the sequence of SEQ ID NO: 8, or a sequence with at least 80%, at least 85%, at least 90%, or at least 95% sequence identity to SEQ ID NO: 8.

56. The pharmaceutical composition of any one or combination of numbered aspects, wherein the biologically active fragment of the UNC5A consists of the sequence of SEQ ID NO: 8, or a sequence with at least 80%, at least 85%, at least 90%, or at least 95% sequence identity to SEQ ID NO: 8.

57. The pharmaceutical composition of any one or combination of numbered aspects, wherein the biologically active fragment of the UNC5A comprises the sequence of SEQ ID NO: 103, or a sequence with at least 80%, at least 85%, at least 90%, or at least 95% sequence identity to SEQ ID NO: 103.

58. The pharmaceutical composition of any one or combination of numbered aspects, wherein the biologically active fragment of the UNC5A consists of the sequence of SEQ ID NO: 103, or a sequence with at least 80%, at least 85%, at least 90%, or at least 95% sequence identity to SEQ ID NO: 103.

59. The pharmaceutical composition of any one or combination of numbered aspects, wherein the biologically active fragment of the ALG5 comprises the sequence of SEQ ID NO: 104, or a sequence with at least 80%, at least 85%, at least 90%, or at least 95% sequence identity to SEQ ID NO: 104.

60. The pharmaceutical composition of any one or combination of numbered aspects, wherein the biologically active fragment of the ALG5 consists of the sequence of SEQ ID NO: 104, or a sequence with at least 80%, at least 85%, at least 90%, or at least 95% sequence identity to SEQ ID NO: 104.

61. The pharmaceutical composition of any one or combination of the numbered aspects, further comprising administering a Cav1 scaffolding domain peptide (CSP).

62. The pharmaceutical composition of numbered aspect 62, wherein the CSP comprises a sequence of SEQ ID NO: 11 or a one-amino acid modification thereof.

63. Use of a pharmaceutical composition of any one or combination of numbered aspects, for the treatment of an idiopathic pulmonary fibrosis or interstitial pneumonia in a subject.

64. Use of a pharmaceutical composition of any one or combination of numbered aspects, for the manufacture of a medicament for treatment of an idiopathic pulmonary fibrosis or interstitial pneumonia in a subject.

65. The use of numbered aspect 65, wherein the interstitial pneumonia is defined by radiographic and histologic presentation of lung scarring, extracellular matrix deposition, epithelial cell senescence and apoptosis, activation of myofibroblasts of fibrotic lung fibroblasts, M2 macrophage polarization and elaboration of pro-fibrogenic cytokines, or a combination thereof.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

TABLE 2

Exemplary sequences

| SEQ ID NO | Notes | Sequences |
|---|---|---|
| 1 | Human MEGF9 full-length with signal peptide (amino acid 1-30) | MNGGAERAMR SLPSLGGLAL LCCAAAAAAA AVASAASAGN VTGGGGAAGQ VDASPGPGLR GEPSHPFPRA TAPTAQAPRT GPPRATVHRP LAATSPAQSP ETTPLWATAG PSSTTFQAPL GPSPTTPPAA ERTSTTSQAP TRPAPTTLST TTGPAPTTPV ATTVPAPTTP RTPTPDLPSS SNSSVLPTPP ATEAPSSPPP EYVCNCSVVG SLNVNRCNQT TGQCECRPGY QGLHCETCKE GFYLNYTSGL CQPCDCSPHG ALSIPCNSSG KCQCKVGVIG SICDRCQDGY YGFSKNGCLP CQCNNRSASC DALTGACLNC QENSKGNHCE ECKEGFYQSP DATKECLRCP CSAVTSTGSC SIKSSELEPE CDQCKDGYIG PNCNKCENGY YNFDSICRKC QCHGHVDPVK TPKICKPESG ECINCLHNTT GFWCENCLEG YVHDLEGNCI KKEVILPTPE GSTILVSNAS LTTSVPTPVI NSTFTPTTLQ TIFSVSTSEN STSALADVSW TQFNIIILTV IIIVVVLLMG FVGAVYMYRE YQNRKLNAPF WTIELKEDNI SFSSYHDSIP NADVSGLLED DGNEVAPNGQ LTLTTPIHNY KA |
| 2 | Mature human MEGF9 (amino acids 31-602 of SEQ ID NO: 1) | AVASAASAGN VTGGGGAAGQ VDASPGPGLR GEPSHPFPRA TAPTAQAPRT GPPRATVHRP LAATSPAQSP ETTPLWATAG PSSTTFQAPL GPSPTTPPAA ERTSTTSQAP TRPAPTTLST TTGPAPTTPV ATTVPAPTTP RTPTPDLPSS SNSSVLPTPP ATEAPSSPPP EYVCNCSVVG SLNVNRCNQT TGQCECRPGY QGLHCETCKE GFYLNYTSGL CQPCDCSPHG ALSIPCNSSG KCQCKVGVIG SICDRCQDGY YGFSKNGCLP CQCNNRSASC DALTGACLNC QENSKGNHCE ECKEGFYQSP DATKECLRCP CSAVTSTGSC SIKSSELEPE CDQCKDGYIG PNCNKCENGY YNFDSICRKC QCHGHVDPVK TPKICKPESG ECINCLHNTT GFWCENCLEG YVHDLEGNCI KKEVILPTPE GSTILVSNAS LTTSVPTPVI NSTFTPTTLQ TIFSVSTSEN STSALADVSW TQFNIIILTV IIIVVVLLMG FVGAVYMYRE YQNRKLNAPF WTIELKEDNI SFSSYHDSIP NADVSGLLED DGNEVAPNGQ LTLTTPIHNY KA |
| 3 | ECD of MEGF9 (amino acids 31-514 of SEQ ID NO: 1) | AVASAASAGN VTGGGGAAGQ VDASPGPGLR GEPSHPFPRA TAPTAQAPRT GPPRATVHRP LAATSPAQSP ETTPLWATAG PSSTTFQAPL GPSPTTPPAA ERTSTTSQAP TRPAPTTLST TTGPAPTTPV ATTVPAPTTP RTPTPDLPSS SNSSVLPTPP ATEAPSSPPP EYVCNCSVVG SLNVNRCNQT TGQCECRPGY QGLHCETCKE GFYLNYTSGL CQPCDCSPHG ALSIPCNSSG KCQCKVGVIG SICDRCQDGY YGFSKNGCLP CQCNNRSASC DALTGACLNC QENSKGNHCE ECKEGFYQSP DATKECLRCP CSAVTSTGSC SIKSSELEPE CDQCKDGYIG PNCNKCENGY YNFDSICRKC QCHGHVDPVK TPKICKPESG ECINCLHNTT GFWCENCLEG YVHDLEGNCI KKEVILPTPE GSTILVSNAS LTTSVPTPVI NSTFTPTTLQ TIFSVSTSEN STSALADVSW TQFN |
| 4 | A peptide in the ECD of MEGF9 (amino acids 403-413 of SEQ ID NO: 1) | HGHVDPVK TPKI |
| 5 | Human UNC5A full-length with signal peptide) (amino acid 1-30 | MAVRPGLWPA LLGIVLAAWL RGSGAQQSAT VANPVPGANP DLLPHFLVEP EDVYIVKNKP VLLVCKAVPA TQIFFKCNGE WVRQVHDVIE RSTDGSSGLP TMEVRINVSR QQVEKVFGLE EYWCQCVAWS SSGTTKSQKA YIRIAYLRKN FEQEPLAKEV SLEQGIVLPC RPPEGIPPAE VEWLRNEDLV DPSLDPNVYI TREHSLVVRQ ARLADTANYT CVAKNIVARR RSASAAVIVY VDGSWSPWSK WSACGLDCTH WRSRECSDPA PRNGGEECQG TDLDTRNCTS DLCVHTASGP EDVALYVGLI AVAVCLVLLL LVLILVYCRK KEGLDSDVAD SSILTSGFQP VSIKPSKADN PHLLTIQPDL STTTTYQGS LCPRQDGPSP KFQLTNGHLL SPLGGGRHTL HHSSPTSEAE EFVSRLSTQN YFRSLPRGTS NMTYGTFNFL GGRLMIPNTG ISLLIPPDAI PRGKIYEIYL TLHKPEDVRL PLAGCQTLLS PIVSCGPPGV LLTRPVILAM DHCGEPSPDS WSLRLKKQSC EGSWEDVLHL GEEAPSHLYY CQLEASACYV FTEQLGRFAL VGEALSVAAA KRLKLLLFAP VACTSLEYNI RVYCLHDTHD ALKEVVQLEK QLGGQLIQEP RVLHFKDSYH NLRLSIHDVP SSLWKSKLLV SYQEIPPYHI WNGTQRYLHC TFTLERVSPS TSDLACKLWV WQVEGDGQSF SINFNITKDT RFAELLALES EAGVPALVGP SAFKIPFLIR QKIISSLDPP CRRGADWRTL AQKLHLDSHL SFFASKPSPT AMILNLWEAR HFPNGNLSQL AAAVAGLGQP DAGLFTVSEA EC |
| 6 | Mature human UNC5A (amino acids 26-842 of SEQ ID NO: 5) | QQSAT VANPVPGANP DLLPHFLVEP EDVYIVKNKP VLLVCKAVPA TQIFFKCNGE WVRQVHDVIE RSTDGSSGLP TMEVRINVSR QQVEKVFGLE EYWCQCVAWS SSGTTKSQKA YIRIAYLRKN FEQEPLAKEV SLEQGIVLPC RPPEGIPPAE VEWLRNEDLV DPSLDPNVYI TREHSLVVRQ ARLADTANYT CVAKNIVARR RSASAAVIVY VDGSWSPWSK WSACGLDCTH WRSRECSDPA PRNGGEECQG TDLDTRNCTS DLCVHTASGP EDVALYVGLI AVAVCLVLLL LVLILVYCRK STTTTYQGS LCPRQDGPSP KFQLTNGHLL KEGLDSDVAD SSILTSGFQP VSIKPSKADN PHLLTIQPDL SPLGGGRHTL HHSSPTSEAE EFVSRLSTQN YFRSLPRGTS NMTYGTFNFL GGRLMIPNTG ISLLIPPDAI PRGKIYEIYL TLHKPEDVRL PLAGCQTLLS PIVSCGPPGV LLTRPVILAM DHCGEPSPDS WSLRLKKQSC EGSWEDVLHL GEEAPSHLYY CQLEASACYV FTEQLGRFAL VGEALSVAAA KRLKLLLFAP VACTSLEYNI RVYCLHDTHD ALKEVVQLEK QLGGQLIQEP RVLHFKDSYH NLRLSIHDVP SSLWKSKLLV SYQEIPPYHI WNGTQRYLHC TFTLERVSPS TSDLACKLWV WQVEGDGQSF SINFNITKDT RFAELLALES EAGVPALVGP SAFKIPFLIR QKIISSLDPP CRRGADWRTL AQKLHLDSHL SFFASKPSPT AMILNLWEAR HFPNGNLSQL AAAVAGLGQP DAGLFTVSEA EC |
| 7 | An exemplary biologically active fragment of UNC5A (amino acids 226-504 of SEQ ID NO: 5) | IVARRRSASA AVIVYVDGSW SPWSKWSACG LDCTHWRSRE CSDPAPRNGG EECQGTDLDT RNCTSDLCVH TASGPEDVAL YVGLIAVAVC LVLLLLVLIL VYCRKKEGLD SDVADSSILT SGFQPVSIKP SKADNPHLLT IQPDLSTTTT TYQGSLCPRQ DGPSPKFQLT NGHLLSPLGG GRHTLHHSSP TSEAEEFVSR LSTQNYFRSL PRGTSNMTYG TFNFLGGRLM IPNTGISLLI PPDAIPRGKI YEIYLTLHKP EDVRLPLAGC QTLLSPIVS |
| 8 | An exemplary biologically active fragment of UNC5A (amino acids 326-375 of SEQ ID NO: 5) | VYCRKKEGLD SDVADSSILT SGFQPVSIKP SKADNPHLLT IQPDLSTTTT |

TABLE 2-continued

Exemplary sequences

| SEQ ID NO | Notes | Sequences |
|---|---|---|
| 9 | Human ALG5 full-length | MAPLLLQLAV LGAALAAAAL VLISIVAFTT ATKMPALHRH EEEKFFLNAK GQKETLPSIW DSPTKQLSVV VPSYNEEKRL PVMMDEALSY LEKRQKRDPA FTYEVIVVDD GSKDQTSKVA FKYCQKYGSD KVRVITLVKN RGKGGAIRMG IFSSRGEKIL MADADGATKF PDVEKLEKGL NDLQPWPNQM AIACGSRAHL EKESIAQRSY FRTLLMYGFH FLVWFLCVKG IRDTQCGFKL FTREAASRTF SSLHVERWAF DVELLYIAQF FKIPIAEIAV NWTEIEGSKL VPFWSWLQMG KDLLFIRLRY LTGAWRLEQT RKMN |
| 10 | CSP | DGIWKASFTTFTVTKYWFYR |
| 11 | CSP7 | FTTFTVT |
| 102 | ECD of hMEGF9 (555 amino acid sequence) | MGWSCIILFLVATATGVHSAAVASAASAGNVT GGGGAAGQVDASPGPGLRGEPSHPFPRATAPT AQAPRTGPPRATVHRPLAATSPAQSPETTPLW ATAGPSSTTFQAPLGPSPTTPPAAERTSTTSQ APTRPAPTTLSTTTGPAPTTPVATTVPAPTTP RTPTPDLPSSSNSSVLPTPPATEAPSSPPPGH QWPVAKMPQKYLGKYACESNLKSKYLPLTQPV MNLRVSEAVKTEYVCNCSVVGSLNVNRCNQTT GQCECRPGYQGLHCETCKEGFYLNYTSGLCQP CDCSPHGALSIPCNSSGKCQCKVGVIGSICDR CQDGYYGFSKNGCLPCQCNNRSASCDALTGAC LNCQENSKGNHCEECKEGFYQSPDATKECLRC PCSAVTSTGSCSIKSSELEPECDQCKDGYIGP NCNKCENGYYNFDSICRKCQCHGHVDPVKTPK |
| | | ICKPESGECINCLHNTTGFWCENCLEGYVHDL EGNCIKKEVILPTPEGSTILVSNASLTTSVPT PVINSTFTPTTLQTIFSVSTSENSTSALADVS WTQFN |
| 103 | ECD of hUNC5a (312 amino acid sequence) | MAVRPGLWPALLGIVLAAWLRGSGAQQSATVA NPVPGANPDLLPHFLVEPEDVYIVKNKPVLLV CKAVPATQIFFKCNGEWVRQDVHVIERSTDGS SGLPTMEVRINVSRQQVEKVFGLEEYWCQCVA WSSSGTTKSQKAYIRIAYLRKNFEQEPLAKEV SLEQGIVLPCRPPEGIPPAEVEWLRNEDLVDP SLDPNVYITREHSLVVRQAALADTANYTCVAK NIVARRRSASAAVIVYVDGSWSPWSKWSACGL DCTHWRSRECSDPAPRNGGEECQGTDLDTRNC TSDLCVHTASGPEDVALY |
| 104 | ECD of hALG5 (303 amino acid sequence) | MTTATKMPALHRHEEEKFFLNAKGQKETLPSI WDSPTKQLSVVVPSYNEEKRLPVMMDEALSYL EKRQKADPAFTYEVIVVDDGSKDQTSKVAFKY CQKYGSDKVRVITLVKNRGKGGAIRMGIFSSR GEKILMADADGATKFPDVEKLEKGLNDLQPWP NQMAIACGSRAHLEKESIAQRSYFRTLLMYGF HFLVWFLCVKGIRDTQCGFKLFTREAASRTFS SLHVERWAFDVELLYIAQFFKIPIAEIAVNWT EIEGSKLVPFWSWLQMGKDLLFIRLRYLTGAW RLEQTRKMN |
| 105 | PP-2 | NYHYLESSMTALYTLGH |

---

The invention claimed is:

1. A pharmaceutical composition comprising a pharmaceutically acceptable carrier and a modified polypeptide, wherein the modified polypeptide is selected from the group consisting of:
   a polypeptide consisting of the sequence of SEQ ID NO: 3 having at least one amino acid substitution or deletion in SEQ ID NO: 3 and at least 95% sequence identity to the SEQ ID NO: 3,
   a polypeptide consisting of the sequence of SEQ ID NO: 4 in the form of a pharmaceutically acceptable salt, or a polypeptide consisting of the sequence of SEQ ID NO: 4 having a one amino acid or two-amino acid modification thereof, and
   a polypeptide consisting of the sequence of SEQ ID NO: 102 having at least one amino acid substitution or deletion in SEQ ID NO: 102 and at least 96% sequence identity to SEQ ID NO: 102.

2. The pharmaceutical composition of claim 1, wherein the modified polypeptide is the polypeptide consisting of the sequence of SEQ ID NO: 4 in the form of a pharmaceutically acceptable salt.

3. The pharmaceutical composition of claim 1, wherein the modified polypeptide is the polypeptide consisting of the sequence of SEQ ID NO: 4 having a one-amino acid or two-amino acid modification thereof.

4. The pharmaceutical composition of claim 1, wherein the modified polypeptide is the polypeptide consisting of the sequence of SEQ ID NO: 3 having at least one amino acid substitution or deletion in SEQ ID NO: 3 and at least 95% sequence identity to SEQ ID NO: 3.

5. The pharmaceutical composition of claim 1, wherein the modified polypeptide is the polypeptide consisting of the sequence of SEQ ID NO: 4 having a two-amino acid modification thereof.

6. The pharmaceutical composition of claim 1, wherein the modified polypeptide is the polypeptide consisting of the sequence of SEQ ID NO: 102 having at least one amino acid substitution or deletion in SEQ ID NO: 102 and at least 95% sequence identity to SEQ ID NO: 102.

7. The pharmaceutical composition of claim 1, wherein the modified polypeptide is the polypeptide consisting of the sequence of SEQ ID NO: 4 having a one-amino acid modification thereof.

8. The pharmaceutical composition of claim 1, wherein the modified polypeptide is the polypeptide consisting of the sequence of SEQ ID NO: 4 in the form of a pharmaceutically acceptable salt having a one-amino acid or two-amino acid modification thereof.

* * * * *

SEQUENCE LISTING

```
Sequence total quantity: 105
SEQ ID NO: 1                 moltype = AA  length = 602
FEATURE                      Location/Qualifiers
source                       1..602
                             mol_type = protein
                             organism = Homo sapiens
SEQUENCE: 1
MNGGAERAMR SLPSLGGLAL LCCAAAAAAA AVASAASAGN VTGGGGAAGQ VDASPGPGLR    60
GEPSHPFPRA TAPTAQAPRT GPPRATVHRP LAATSPAQSP ETTPLWATAG PSSTTFQAPL   120
GPSPTTPPAA ERTSTTSQAP TRPAPTTLST TTGPAPTTPV ATTVPAPTTP RTPTPDLPSS   180
SNSSVLPTPP ATEAPSSPPP EYVCNCSVVG SLNVNRCNQT TGQCECRPGY QGLHCETCKE   240
GFYLNYTSGL CQPCDCSPHG ALSIPCNSSG KCQCKVGVIG SICDRCQDGY YGFSKNGCLP   300
CQCNNRSASC DALTGACLNC QENSKGNHCE ECKEGFYQSP DATKECLRCP CSAVTSTGSC   360
SIKSSELEPE CDQCKDGYIG PNCNKCENGY YNFDSICRKC QCHGHVDPVK TPKICKPESG   420
ECINCLHNTT GFWCENCLEG YVHDLEGNCI KKEVILPTPE GSTILVSNAS LTTSVPTPVI   480
NSTFTPTTLQ TIFSVSTSEN STSALADVSW TQFNIIILTV IIIVVVLLMG FVGAVYMYRE   540
YQNRKLNAPF WTIELKEDNI SFSSYHDSIP NADVSGLLED DGNEVAPNGQ LTLTTPIHNY   600
KA                                                                 602

SEQ ID NO: 2                 moltype = AA  length = 572
FEATURE                      Location/Qualifiers
source                       1..572
                             mol_type = protein
                             organism = Homo sapiens
SEQUENCE: 2
AVASAASAGN VTGGGGAAGQ VDASPGPGLR GEPSHPFPRA TAPTAQAPRT GPPRATVHRP    60
LAATSPAQSP ETTPLWATAG PSSTTFQAPL GPSPTTPPAA ERTSTTSQAP TRPAPTTLST   120
TTGPAPTTPV ATTVPAPTTP RTPTPDLPSS SNSSVLPTPP ATEAPSSPPP EYVCNCSVVG   180
SLNVNRCNQT TGQCECRPGY QGLHCETCKE GFYLNYTSGL CQPCDCSPHG ALSIPCNSSG   240
KCQCKVGVIG SICDRCQDGY YGFSKNGCLP CQCNNRSASC DALTGACLNC QENSKGNHCE   300
ECKEGFYQSP DATKECLRCP CSAVTSTGSC SIKSSELEPE CDQCKDGYIG PNCNKCENGY   360
YNFDSICRKC QCHGHVDPVK TPKICKPESG ECINCLHNTT GFWCENCLEG YVHDLEGNCI   420
KKEVILPTPE GSTILVSNAS LTTSVPTPVI NSTFTPTTLQ TIFSVSTSEN STSALADVSW   480
TQFNIIILTV IIIVVVLLMG FVGAVYMYRE YQNRKLNAPF WTIELKEDNI SFSSYHDSIP   540
NADVSGLLED DGNEVAPNGQ LTLTTPIHNY KA                                 572
```

```
SEQ ID NO: 3              moltype = AA  length = 484
FEATURE                   Location/Qualifiers
source                    1..484
                          mol_type = protein
                          organism = Homo sapiens
SEQUENCE: 3
AVASAASAGN VTGGGGAAGQ VDASPGPGLR GEPSHPFPRA TAPTAQAPRT GPPRATVHRP    60
LAATSPAQSP ETTPLWATAG PSSTTFQAPL GPSPTTPPAA ERTSTTSQAP TRPAPTTLST   120
TTGPAPTTPV ATTVPAPTTP RTPTPDLPSS SNSSVLPTPP ATEAPSSPPP EYVCNCSVVG   180
SLNVNRCNQT TGQCECRPGY QGLHCETCKE GFYLNYTSGL CQPCDCSPHG ALSIPCNSSG   240
KCQCKVGVIG SICDRCQDGY YGFSKNGCLP CQCNNRSASC DALTGACLNC QENSKGNHCE   300
ECKEGFYQSP DATKECLRCP CSAVTSTGSC SIKSSELEPE CDQCKDGYIG PNCNKCENGY   360
YNFDSICRKC QCHGHVDPVK TPKICKPESG ECINCLHNTT GFWCENCLEG YVHDLEGNCI   420
KKEVILPTPE GSTILVSNAS LTTSVPTPVI NSTFTPTTLQ TIFSVSTSEN STSALADVSW   480
TQFN                                                                484

SEQ ID NO: 4              moltype = AA  length = 12
FEATURE                   Location/Qualifiers
source                    1..12
                          mol_type = protein
                          organism = Homo sapiens
SEQUENCE: 4
HGHVDPVKTP KI                                                        12

SEQ ID NO: 5              moltype = AA  length = 842
FEATURE                   Location/Qualifiers
source                    1..842
                          mol_type = protein
                          organism = Homo sapiens
SEQUENCE: 5
MAVRPGLWPA LLGIVLAAWL RGSGAQQSAT VANPVPGANP DLLPHFLVEP EDVYIVKNKP    60
VLLVCKAVPA TQIFFKCNGE WVRQVDHVIE RSTDGSSGLP TMEVRINVSR QQVEKVFGLE   120
EYWCQCVAWS SSGTTKSQKA YIRIAYLRKN FEQEPLAKEV SLEQGIVLPC RPPEGIPPAE   180
VEWLRNEDLV DPSLDPNVYI TREHSLVVRQ ARLADTANYT CVAKNIVARR RSASAAVIVY   240
VDGSWSPWSK WSACGLDCTH WRSRECSDPA PRNGGEECQG TDLDTRNCTS DLCVHTASGP   300
EDVALYVGLI AVAVCLVLLL LVLILVYCRK KEGLDSDVAD SSILTSGFQP VSIKPSKADN   360
PHLLTIQPDL STTTTTYQGS LCPRQDGPSP KFQLTNGHLL SPLGGGRHTL HHSSPTSEAE   420
EFVSRLSTQN YFRSLPRGTS NMTYGTFNFL GGRLMIPNTG ISLLIPPDAI PRGKIYEIYL   480
TLHKPEDVRL PLAGCQTLLS PIVSCGPPGV LLTRPVILAM DHCGEPSPDS WSLRLKKQSC   540
EGSWEDVLHL GEEAPSHLYY CQLEASACYV FTEQLGRFAL VGEALSVAAA KRLKLLLFAP   600
VACTSLEYNI RVYCLHDTHD ALKEVVQLEK QLGGQLIQEP RVLHFKDSYH NLRLSIHDVP   660
SSLWKSKLLV SYQEIPFYHI WNGTQRYLHC TFTLERVSPS TSDLACKLWV WQVEGDGQSF   720
SINFNITKDT RFAELLALES EAGVPALVGP SAFKIPFLIR QKIISSLDPP CRRGADWRTL   780
AQKLHLDSHL SFFASKPSPT AMILNLWEAR HFPNGNLSQL AAAVAGLGQP DAGLFTVSEA   840
EC                                                                  842

SEQ ID NO: 6              moltype = AA  length = 817
FEATURE                   Location/Qualifiers
source                    1..817
                          mol_type = protein
                          organism = Homo sapiens
SEQUENCE: 6
QQSATVANPV PGANPDLLPH FLVEPEDVYI VKNKPVLLVC KAVPATQIFF KCNGEWVRQV    60
DHVIERSTDG SSGLPTMEVR INVSRQQVEK VFGLEEYWCQ CVAWSSSGTT KSQKAYIRIA   120
YLRKNFEQEP LAKEVSLEQG IVLPCRPPEG IPPAEVEWLR NEDLVDPSLD PNVYITREHS   180
LVVRQARLAD TANYTCVAKN IVARRRSASA AVIVYVDGSW SPWSKWSACG LDCTHWRSRE   240
CSDPAPRNGG EECQGTDLDT RNCTSDLCVH TASGPEDVAL YVGLIAVAVC LVLLLLVLIL   300
VYCRKKEGLD SDVADSSILT SGFQPVSIKP SKADNPHLLT IQPDLSTTTT TYQGSLCPRQ   360
DGPSPKFQLT NGHLLSPLGG GRHTLHHSSP TSEAEEFVSR LSTQNYFRSL PRGTSNMTYG   420
TFNFLGGRLM IPNTGISLLI PPDAIPRGKI YEIYLTLHKP EDVRLPLAGC QTLLSPIVSC   480
GPPGVLLTRP VILAMDHCGE PSPDSWSLRL KKQSCEGSWE DVLHLGEEAP SHLYYCQLEA   540
SACYVFTEQL GRFALVGEAL SVAAAKRLKL LLFAPVACTS LEYNIRVYCL HDTHDALKEV   600
VQLEKQLGGQ LIQEPRVLHF KDSYHNLRLS IHDVPSSLWK SKLLVSYQEI PFYHIWNGTQ   660
RYLHCTFTLE RVSPSTSDLA CKLWVWQVEG DGQSFSINFN ITKDTRFAEL LALESEAGVP   720
ALVGPSAFKI PFLIRQKIIS SLDPPCRRGA DWRTLAQKLH LDSHLSFFAS KPSPTAMILN   780
LWEARHFPNG NLSQLAAAVA GLGQPDAGLF TVSEAEC                            817

SEQ ID NO: 7              moltype = AA  length = 279
FEATURE                   Location/Qualifiers
source                    1..279
                          mol_type = protein
                          organism = Homo sapiens
SEQUENCE: 7
IVARRRSASA AVIVYVDGSW SPWSKWSACG LDCTHWRSRE CSDPAPRNGG EECQGTDLDT    60
RNCTSDLCVH TASGPEDVAL YVGLIAVAVC LVLLLLVLIL VYCRKKEGLD SDVADSSILT   120
SGFQPVSIKP SKADNPHLLT IQPDLSTTTT TYQGSLCPRQ DGPSPKFQLT NGHLLSPLGG   180
GRHTLHHSSP TSEAEEFVSR LSTQNYFRSL PRGTSNMTYG TFNFLGGRLM IPNTGISLLI   240
PPDAIPRGKI YEIYLTLHKP EDVRLPLAGC QTLLSPIVS                          279
```

```
SEQ ID NO: 8            moltype = AA  length = 50
FEATURE                 Location/Qualifiers
source                  1..50
                        mol_type = protein
                        organism = Homo sapiens
SEQUENCE: 8
VYCRKKEGLD SDVADSSILT SGFQPVSIKP SKADNPHLLT IQPDLSTTTT            50

SEQ ID NO: 9            moltype = AA  length = 324
FEATURE                 Location/Qualifiers
source                  1..324
                        mol_type = protein
                        organism = Homo sapiens
SEQUENCE: 9
MAPLLLQLAV LGAALAAAAL VLISIVAFTT ATKMPALHRH EEEKFFLNAK GQKETLPSIW  60
DSPTKQLSVV VPSYNEEKRL PVMMDEALSY LEKRQKRDPA FTYEVIVVDD GSKDQTSKVA 120
FKYCQKYGSD KVRVITLVKN RGKGGAIRMG IFSSRGEKIL MADADGATKF PDVEKLEKGL 180
NDLQPWPNQM AIACGSRAHL EKESIAQRSY FRTLLMYGPH FLVWFLCVKG IRDTQCGFKL 240
FTREAASRTF SSLHVERWAF DVELLYIAQF FKIPIAEIAV NWTEIEGSKL VPFWSWLQMG 300
KDLLFIRLRY LTGAWRLEQT RKMN                                       324

SEQ ID NO: 10           moltype = AA  length = 20
FEATURE                 Location/Qualifiers
source                  1..20
                        mol_type = protein
                        organism = Homo sapiens
SEQUENCE: 10
DGIWKASFTT FTVTKYWFYR                                             20

SEQ ID NO: 11           moltype = AA  length = 7
FEATURE                 Location/Qualifiers
source                  1..7
                        mol_type = protein
                        organism = Homo sapiens
SEQUENCE: 11
FTTFTVT                                                            7

SEQ ID NO: 12           moltype = AA  length = 8
FEATURE                 Location/Qualifiers
source                  1..8
                        mol_type = protein
                        organism = Homo sapiens
SEQUENCE: 12
SFTTFTVT                                                           8

SEQ ID NO: 13           moltype = AA  length = 9
FEATURE                 Location/Qualifiers
source                  1..9
                        mol_type = protein
                        organism = Homo sapiens
SEQUENCE: 13
SFTTFTVTK                                                          9

SEQ ID NO: 14           moltype = AA  length = 10
FEATURE                 Location/Qualifiers
source                  1..10
                        mol_type = protein
                        organism = Homo sapiens
SEQUENCE: 14
FTTFTVTKYW                                                        10

SEQ ID NO: 15           moltype = AA  length = 10
FEATURE                 Location/Qualifiers
source                  1..10
                        mol_type = protein
                        organism = Homo sapiens
SEQUENCE: 15
ASFTTFTVTK                                                        10

SEQ ID NO: 16           moltype = AA  length = 11
FEATURE                 Location/Qualifiers
source                  1..11
                        mol_type = protein
                        organism = Homo sapiens
SEQUENCE: 16
FTTFTVTKYW F                                                      11
```

| | | |
|---|---|---|
| SEQ ID NO: 17<br>FEATURE<br>source<br><br>SEQUENCE: 17<br>ASFTTFTVTK Y | moltype = AA   length = 11<br>Location/Qualifiers<br>1..11<br>mol_type = protein<br>organism = Homo sapiens | <br><br><br><br><br>11 |
| SEQ ID NO: 18<br>FEATURE<br>source<br><br>SEQUENCE: 18<br>WKASFTTFTV T | moltype = AA   length = 11<br>Location/Qualifiers<br>1..11<br>mol_type = protein<br>organism = Homo sapiens | <br><br><br><br><br>11 |
| SEQ ID NO: 19<br>FEATURE<br>source<br><br>SEQUENCE: 19<br>SFTTFTVTKY WF | moltype = AA   length = 12<br>Location/Qualifiers<br>1..12<br>mol_type = protein<br>organism = Homo sapiens | <br><br><br><br><br>12 |
| SEQ ID NO: 20<br>FEATURE<br>source<br><br>SEQUENCE: 20<br>KASFTTFTVT KY | moltype = AA   length = 12<br>Location/Qualifiers<br>1..12<br>mol_type = protein<br>organism = Homo sapiens | <br><br><br><br><br>12 |
| SEQ ID NO: 21<br>FEATURE<br>source<br><br>SEQUENCE: 21<br>IWKASFTTFT VT | moltype = AA   length = 12<br>Location/Qualifiers<br>1..12<br>mol_type = protein<br>organism = Homo sapiens | <br><br><br><br><br>12 |
| SEQ ID NO: 22<br>FEATURE<br>source<br><br>SEQUENCE: 22<br>SFTTFTVTKY WFY | moltype = AA   length = 13<br>Location/Qualifiers<br>1..13<br>mol_type = protein<br>organism = Homo sapiens | <br><br><br><br><br>13 |
| SEQ ID NO: 23<br>FEATURE<br>source<br><br>SEQUENCE: 23<br>KASFTTFTVT KYW | moltype = AA   length = 13<br>Location/Qualifiers<br>1..13<br>mol_type = protein<br>organism = Homo sapiens | <br><br><br><br><br>13 |
| SEQ ID NO: 24<br>FEATURE<br>source<br><br>SEQUENCE: 24<br>IWKASFTTFT VTK | moltype = AA   length = 13<br>Location/Qualifiers<br>1..13<br>mol_type = protein<br>organism = Homo sapiens | <br><br><br><br><br>13 |
| SEQ ID NO: 25<br>FEATURE<br>source<br><br>SEQUENCE: 25<br>FTTFTVTKYW FYRL | moltype = AA   length = 14<br>Location/Qualifiers<br>1..14<br>mol_type = protein<br>organism = Homo sapiens | <br><br><br><br><br>14 |
| SEQ ID NO: 26<br>FEATURE<br>source | moltype = AA   length = 14<br>Location/Qualifiers<br>1..14<br>mol_type = protein<br>organism = Homo sapiens | |

```
SEQUENCE: 26
ASFTTFTVTK YWFY                                                      14

SEQ ID NO: 27        moltype = AA  length = 14
FEATURE              Location/Qualifiers
source               1..14
                     mol_type = protein
                     organism = Homo sapiens SEQUENCE: 27
WKASFTTFTV TKYW                                                      14

SEQ ID NO: 28        moltype = AA  length = 14
FEATURE              Location/Qualifiers
source               1..14
                     mol_type = protein
                     organism = Homo sapiens SEQUENCE: 28
GIWKASFTTF TVTK                                                      14

SEQ ID NO: 29        moltype = AA  length = 15
FEATURE              Location/Qualifiers
source               1..15
                     mol_type = protein
                     organism = Homo sapiens SEQUENCE: 29
FTTFTVTKYW FYRLL                                                     15

SEQ ID NO: 30        moltype = AA  length = 15
FEATURE              Location/Qualifiers
source               1..15
                     mol_type = protein
                     organism = Homo sapiens SEQUENCE: 30
ASFTTFTVTK YWFYR                                                     15

SEQ ID NO: 31        moltype = AA  length = 15
FEATURE              Location/Qualifiers
source               1..15
                     mol_type = protein
                     organism = Homo sapiens SEQUENCE: 31
WKASFTTFTV TKYWF                                                     15

SEQ ID NO: 32        moltype = AA  length = 15
FEATURE              Location/Qualifiers
source               1..15
                     mol_type = protein
                     organism = Homo sapiens SEQUENCE: 32
GIWKASFTTF TVTKY                                                     15

SEQ ID NO: 33        moltype = AA  length = 15
FEATURE              Location/Qualifiers
source               1..15
                     mol_type = protein
                     organism = Homo sapiens SEQUENCE: 33
FDGIWKASFT TFTVT                                                     15

SEQ ID NO: 34        moltype = AA  length = 16
FEATURE              Location/Qualifiers
source               1..16
                     mol_type = protein
                     organism = Homo sapiens SEQUENCE: 34
SFTTFTVTKY WFYRLL                                                    16

SEQ ID NO: 35        moltype = AA  length = 16
FEATURE              Location/Qualifiers
source               1..16
                     mol_type = protein
                     organism = Homo sapiens SEQUENCE: 35
KASFTTFTVT KYWFYR                                                    16

SEQ ID NO: 36        moltype = AA  length = 16
FEATURE              Location/Qualifiers
```

```
                               -continued source                  1..16
                        mol_type = protein
                        organism = Homo sapiens
SEQUENCE: 36
IWKASFTTFT VTKYWF                                                        16

SEQ ID NO: 37           moltype = AA   length = 16
FEATURE                 Location/Qualifiers
source                  1..16
                        mol_type = protein
                        organism = Homo sapiens
SEQUENCE: 37
DGIWKASFTT FTVTKY                                                        16

SEQ ID NO: 38           moltype = AA   length = 16
FEATURE                 Location/Qualifiers
source                  1..16
                        mol_type = protein
                        organism = Homo sapiens
SEQUENCE: 38
SFDGIWKASF TTFTVT                                                        16

SEQ ID NO: 39           moltype = AA   length = 17
FEATURE                 Location/Qualifiers
source                  1..17
                        mol_type = protein
                        organism = Homo sapiens
SEQUENCE: 39
SFTTFTVTKY WFYRLLS                                                       17

SEQ ID NO: 40           moltype = AA   length = 17
FEATURE                 Location/Qualifiers
source                  1..17
                        mol_type = protein
                        organism = Homo sapiens
SEQUENCE: 40
KASFTTFTVT KYWFYRL                                                       17

SEQ ID NO: 41           moltype = AA   length = 17
FEATURE                 Location/Qualifiers
source                  1..17
                        mol_type = protein
                        organism = Homo sapiens
SEQUENCE: 41
IWKASFTTFT VTKYWFY                                                       17

SEQ ID NO: 42           moltype = AA   length = 17
FEATURE                 Location/Qualifiers
source                  1..17
                        mol_type = protein
                        organism = Homo sapiens
SEQUENCE: 42
DGIWKASFTT FTVTKYW                                                       17

SEQ ID NO: 43           moltype = AA   length = 17
FEATURE                 Location/Qualifiers
source                  1..17
                        mol_type = protein
                        organism = Homo sapiens
SEQUENCE: 43
SFDGIWKASF TTFTVTK                                                       17

SEQ ID NO: 44           moltype = AA   length = 18
FEATURE                 Location/Qualifiers
source                  1..18
                        mol_type = protein
                        organism = Homo sapiens
SEQUENCE: 44
FTTFTVTKYW FYRLLSAL                                                      18

SEQ ID NO: 45           moltype = AA   length = 18
FEATURE                 Location/Qualifiers
source                  1..18
                        mol_type = protein
                        organism = Homo sapiens
SEQUENCE: 45
ASFTTFTVTK YWFYRLLS                                                      18
```

| | | |
|---|---|---|
| SEQ ID NO: 46<br>FEATURE<br>source | moltype = AA  length = 18<br>Location/Qualifiers<br>1..18<br>mol_type = protein<br>organism = Homo sapiens | |
| SEQUENCE: 46<br>WKASFTTFTV TKYWFYRL | | 18 |
| SEQ ID NO: 47<br>FEATURE<br>source | moltype = AA  length = 18<br>Location/Qualifiers<br>1..18<br>mol_type = protein<br>organism = Homo sapiens | |
| SEQUENCE: 47<br>GIWKASFTTF TVTKYWFY | | 18 |
| SEQ ID NO: 48<br>FEATURE<br>source | moltype = AA  length = 18<br>Location/Qualifiers<br>1..18<br>mol_type = protein<br>organism = Homo sapiens | |
| SEQUENCE: 48<br>FDGIWKASFT TFTVTKYW | | 18 |
| SEQ ID NO: 49<br>FEATURE<br>source | moltype = AA  length = 18<br>Location/Qualifiers<br>1..18<br>mol_type = protein<br>organism = Homo sapiens | |
| SEQUENCE: 49<br>HSFDGIWKAS FTTFTVTK | | 18 |
| SEQ ID NO: 50<br>FEATURE<br>source | moltype = AA  length = 19<br>Location/Qualifiers<br>1..19<br>mol_type = protein<br>organism = Homo sapiens | |
| SEQUENCE: 50<br>FTTFTVTKYW FYRLLSALF | | 19 |
| SEQ ID NO: 51<br>FEATURE<br>source | moltype = AA  length = 19<br>Location/Qualifiers<br>1..19<br>mol_type = protein<br>organism = Homo sapiens | |
| SEQUENCE: 51<br>ASFTTFTVTK YWFYRLLSA | | 19 |
| SEQ ID NO: 52<br>FEATURE<br>source | moltype = AA  length = 19<br>Location/Qualifiers<br>1..19<br>mol_type = protein<br>organism = Homo sapiens | |
| SEQUENCE: 52<br>WKASFTTFTV TKYWFYRLL | | 19 |
| SEQ ID NO: 53<br>FEATURE<br>source | moltype = AA  length = 19<br>Location/Qualifiers<br>1..19<br>mol_type = protein<br>organism = Homo sapiens | |
| SEQUENCE: 53<br>GIWKASFTTF TVTKYWFYR | | 19 |
| SEQ ID NO: 54<br>FEATURE<br>source | moltype = AA  length = 19<br>Location/Qualifiers<br>1..19<br>mol_type = protein<br>organism = Homo sapiens | |
| SEQUENCE: 54<br>FDGIWKASFT TFTVTKYWF | | 19 |
| SEQ ID NO: 55<br>FEATURE<br>source | moltype = AA  length = 19<br>Location/Qualifiers<br>1..19<br>mol_type = protein<br>organism = Homo sapiens | |

-continued

```
SEQUENCE: 55
HSFDGIWKAS FTTFTVTKY                                                        19

SEQ ID NO: 56           moltype = AA   length = 19
FEATURE                 Location/Qualifiers
source                  1..19
                        mol_type = protein
                        organism = Homo sapiens
SEQUENCE: 56
GTHSFDGIWK ASFTTFTVT                                                        19

SEQ ID NO: 57           moltype = AA   length = 8
FEATURE                 Location/Qualifiers
source                  1..8
                        mol_type = protein
                        organism = Homo sapiens
SEQUENCE: 57
FTTFTVTK                                                                    8

SEQ ID NO: 58           moltype = AA   length = 9
FEATURE                 Location/Qualifiers
source                  1..9
                        mol_type = protein
                        organism = Homo sapiens
SEQUENCE: 58
FTTFTVTKY                                                                   9

SEQ ID NO: 59           moltype = AA   length = 9
FEATURE                 Location/Qualifiers
source                  1..9
                        mol_type = protein
                        organism = Homo sapiens
SEQUENCE: 59
ASFTTFTVT                                                                   9

SEQ ID NO: 60           moltype = AA   length = 10
FEATURE                 Location/Qualifiers
source                  1..10
                        mol_type = protein
                        organism = Homo sapiens
SEQUENCE: 60
SFTTFTVTKY                                                                  10

SEQ ID NO: 61           moltype = AA   length = 10
FEATURE                 Location/Qualifiers
source                  1..10
                        mol_type = protein
                        organism = Homo sapiens
SEQUENCE: 61
KASFTTFTVT                                                                  10

SEQ ID NO: 62           moltype = AA   length = 11
FEATURE                 Location/Qualifiers
source                  1..11
                        mol_type = protein
                        organism = Homo sapiens
SEQUENCE: 62
SFTTFTVTKY W                                                                11

SEQ ID NO: 63           moltype = AA   length = 11
FEATURE                 Location/Qualifiers
source                  1..11
                        mol_type = protein
                        organism = Homo sapiens
SEQUENCE: 63
KASFTTFTVT K                                                                11

SEQ ID NO: 64           moltype = AA   length = 12
FEATURE                 Location/Qualifiers
source                  1..12
                        mol_type = protein
                        organism = Homo sapiens
SEQUENCE: 64
FTTFTVTKYW FY                                                               12

SEQ ID NO: 65           moltype = AA   length = 12
FEATURE                 Location/Qualifiers
```

```
source                    1..12
                          mol_type = protein
                          organism = Homo sapiens
SEQUENCE: 65
ASFTTFTVTK YW                                                              12

SEQ ID NO: 66             moltype = AA  length = 12
FEATURE                   Location/Qualifiers
source                    1..12
                          mol_type = protein
                          organism = Homo sapiens
SEQUENCE: 66
WKASFTTFTV TK                                                              12

SEQ ID NO: 67             moltype = AA  length = 13
FEATURE                   Location/Qualifiers
source                    1..13
                          mol_type = protein
                          organism = Homo sapiens
SEQUENCE: 67
FTTFTVTKYW FYR                                                             13

SEQ ID NO: 68             moltype = AA  length = 13
FEATURE                   Location/Qualifiers
source                    1..13
                          mol_type = protein
                          organism = Homo sapiens
SEQUENCE: 68
ASFTTFTVTK YWF                                                             13

SEQ ID NO: 69             moltype = AA  length = 13
FEATURE                   Location/Qualifiers
source                    1..13
                          mol_type = protein
                          organism = Homo sapiens
SEQUENCE: 69
WKASFTTFTV TKY                                                             13

SEQ ID NO: 70             moltype = AA  length = 13
FEATURE                   Location/Qualifiers
source                    1..13
                          mol_type = protein
                          organism = Homo sapiens
SEQUENCE: 70
GIWKASFTTF TVT                                                             13

SEQ ID NO: 71             moltype = AA  length = 14
FEATURE                   Location/Qualifiers
source                    1..14
                          mol_type = protein
                          organism = Homo sapiens
SEQUENCE: 71
SFTTFTVTKY WFYR                                                            14

SEQ ID NO: 72             moltype = AA  length = 14
FEATURE                   Location/Qualifiers
source                    1..14
                          mol_type = protein
                          organism = Homo sapiens
SEQUENCE: 72
KASFTTFTVT KYWF                                                            14

SEQ ID NO: 73             moltype = AA  length = 14
FEATURE                   Location/Qualifiers
source                    1..14
                          mol_type = protein
                          organism = Homo sapiens
SEQUENCE: 73
IWKASFTTFT VTKY                                                            14

SEQ ID NO: 74             moltype = AA  length = 14
FEATURE                   Location/Qualifiers
source                    1..14
                          mol_type = protein
                          organism = Homo sapiens
SEQUENCE: 74
DGIWKASFTT FTVT                                                            14

SEQ ID NO: 75             moltype = AA  length = 15
```

```
FEATURE                 Location/Qualifiers
source                  1..15
                        mol_type = protein
                        organism = Homo sapiens
SEQUENCE: 75
SFTTFTVTKY WFYRL                                                        15

SEQ ID NO: 76           moltype = AA  length = 15
FEATURE                 Location/Qualifiers
source                  1..15
                        mol_type = protein
                        organism = Homo sapiens
SEQUENCE: 76
KASFTTFTVT KYWFY                                                        15

SEQ ID NO: 77           moltype = AA  length = 15
FEATURE                 Location/Qualifiers
source                  1..15
                        mol_type = protein
                        organism = Homo sapiens
SEQUENCE: 77
IWKASFTTFT VTKYW                                                        15

SEQ ID NO: 78           moltype = AA  length = 15
FEATURE                 Location/Qualifiers
source                  1..15
                        mol_type = protein
                        organism = Homo sapiens
SEQUENCE: 78
DGIWKASFTT FTVTK                                                        15

SEQ ID NO: 79           moltype = AA  length = 16
FEATURE                 Location/Qualifiers
source                  1..16
                        mol_type = protein
                        organism = Homo sapiens
SEQUENCE: 79
FTTFTVTKYW FYRLLS                                                       16

SEQ ID NO: 80           moltype = AA  length = 16
FEATURE                 Location/Qualifiers
source                  1..16
                        mol_type = protein
                        organism = Homo sapiens
SEQUENCE: 80
ASFTTFTVTK YWFYRL                                                       16

SEQ ID NO: 81           moltype = AA  length = 16
FEATURE                 Location/Qualifiers
source                  1..16
                        mol_type = protein
                        organism = Homo sapiens
SEQUENCE: 81
WKASFTTFTV TKYWFY                                                       16

SEQ ID NO: 82           moltype = AA  length = 16
FEATURE                 Location/Qualifiers
source                  1..16
                        mol_type = protein
                        organism = Homo sapiens
SEQUENCE: 82
GIWKASFTTF TVTKYW                                                       16

SEQ ID NO: 83           moltype = AA  length = 16
FEATURE                 Location/Qualifiers
source                  1..16
                        mol_type = protein
                        organism = Homo sapiens
SEQUENCE: 83
FDGIWKASFT TFTVTK                                                       16

SEQ ID NO: 84           moltype = AA  length = 17
FEATURE                 Location/Qualifiers
source                  1..17
                        mol_type = protein
                        organism = Homo sapiens
SEQUENCE: 84
FTTFTVTKYW FYRLLSA                                                      17
```

-continued

| | | |
|---|---|---|
| SEQ ID NO: 85<br>FEATURE<br>source | moltype = AA   length = 17<br>Location/Qualifiers<br>1..17<br>mol_type = protein<br>organism = Homo sapiens | |
| SEQUENCE: 85<br>ASFTTFTVTK YWFYRLL | | 17 |
| SEQ ID NO: 86<br>FEATURE<br>source | moltype = AA   length = 17<br>Location/Qualifiers<br>1..17<br>mol_type = protein<br>organism = Homo sapiens | |
| SEQUENCE: 86<br>WKASFTTFTV TKYWFYR | | 17 |
| SEQ ID NO: 87<br>FEATURE<br>source | moltype = AA   length = 17<br>Location/Qualifiers<br>1..17<br>mol_type = protein<br>organism = Homo sapiens | |
| SEQUENCE: 87<br>GIWKASFTTF TVTKYWF | | 17 |
| SEQ ID NO: 88<br>FEATURE<br>source | moltype = AA   length = 17<br>Location/Qualifiers<br>1..17<br>mol_type = protein<br>organism = Homo sapiens | |
| SEQUENCE: 88<br>FDGIWKASFT TFTVTKY | | 17 |
| SEQ ID NO: 89<br>FEATURE<br>source | moltype = AA   length = 17<br>Location/Qualifiers<br>1..17<br>mol_type = protein<br>organism = Homo sapiens | |
| SEQUENCE: 89<br>HSFDGIWKAS FTTFTVT | | 17 |
| SEQ ID NO: 90<br>FEATURE<br>source | moltype = AA   length = 18<br>Location/Qualifiers<br>1..18<br>mol_type = protein<br>organism = Homo sapiens | |
| SEQUENCE: 90<br>SFTTFTVTKY WFYRLLSA | | 18 |
| SEQ ID NO: 91<br>FEATURE<br>source | moltype = AA   length = 18<br>Location/Qualifiers<br>1..18<br>mol_type = protein<br>organism = Homo sapiens | |
| SEQUENCE: 91<br>KASFTTFTVT KYWFYRLL | | 18 |
| SEQ ID NO: 92<br>FEATURE<br>source | moltype = AA   length = 18<br>Location/Qualifiers<br>1..18<br>mol_type = protein<br>organism = Homo sapiens | |
| SEQUENCE: 92<br>IWKASFTTFT VTKYWFYR | | 18 |
| SEQ ID NO: 93<br>FEATURE<br>source | moltype = AA   length = 18<br>Location/Qualifiers<br>1..18<br>mol_type = protein<br>organism = Homo sapiens | |
| SEQUENCE: 93<br>DGIWKASFTT FTVTKYWF | | 18 |
| SEQ ID NO: 94<br>FEATURE<br>source | moltype = AA   length = 18<br>Location/Qualifiers<br>1..18<br>mol_type = protein<br>organism = Homo sapiens | |
| SEQUENCE: 94<br>SFDGIWKASF TTFTVTKY | | 18 |

| | | |
|---|---|---|
| SEQ ID NO: 95 | moltype = AA length = 18 | |
| FEATURE | Location/Qualifiers | |
| source | 1..18 | |
| | mol_type = protein | |
| | organism = Homo sapiens | |
| SEQUENCE: 95 | | |
| THSFDGIWKA SFTTFTVT | | 18 |
| | | |
| SEQ ID NO: 96 | moltype = AA length = 19 | |
| FEATURE | Location/Qualifiers | |
| source | 1..19 | |
| | mol_type = protein | |
| | organism = Homo sapiens | |
| SEQUENCE: 96 | | |
| SFTTFTVTKY WFYRLLSAL | | 19 |
| | | |
| SEQ ID NO: 97 | moltype = AA length = 19 | |
| FEATURE | Location/Qualifiers | |
| source | 1..19 | |
| | mol_type = protein | |
| | organism = Homo sapiens | |
| SEQUENCE: 97 | | |
| KASFTTFTVT KYWFYRLLS | | 19 |
| | | |
| SEQ ID NO: 98 | moltype = AA length = 19 | |
| FEATURE | Location/Qualifiers | |
| source | 1..19 | |
| | mol_type = protein | |
| | organism = Homo sapiens | |
| SEQUENCE: 98 | | |
| IWKASFTTFT VTKYWFYRL | | 19 |
| | | |
| SEQ ID NO: 99 | moltype = AA length = 19 | |
| FEATURE | Location/Qualifiers | |
| source | 1..19 | |
| | mol_type = protein | |
| | organism = Homo sapiens | |
| SEQUENCE: 99 | | |
| DGIWKASFTT FTVTKYWFY | | 19 |
| | | |
| SEQ ID NO: 100 | moltype = AA length = 19 | |
| FEATURE | Location/Qualifiers | |
| source | 1..19 | |
| | mol_type = protein | |
| | organism = Homo sapiens | |
| SEQUENCE: 100 | | |
| SFDGIWKASF TTFTVTKYW | | 19 |
| | | |
| SEQ ID NO: 101 | moltype = AA length = 19 | |
| FEATURE | Location/Qualifiers | |
| source | 1..19 | |
| | mol_type = protein | |
| | organism = Homo sapiens | |
| SEQUENCE: 101 | | |
| THSFDGIWKA SFTTFTVTK | | 19 |
| | | |
| SEQ ID NO: 102 | moltype = AA length = 549 | |
| FEATURE | Location/Qualifiers | |
| source | 1..549 | |
| | mol_type = protein | |
| | organism = Homo sapiens | |
| SEQUENCE: 102 | | |

```
MGWSCIILFL VATATGVHSA AVASAASAGN VTGGGGAAGQ VDASPGPGLR GEPSHPFPRA    60
TAPTAQAPRT GPPRATVHRP LAATSPAQSP ETTPLWATAG PSSTTFQAPL GPSPTTPPAA   120
ERTSTTSQAP TRPAPTTLST TTGPAPTTPV ATTVPATTTP RTPTPDLPSS SNSSVLPTPP   180
ATEAPSSPPP GHQWPVAKMP QKYLGKYACE SNLKSKYLPL TQPVMNLRVS EAVKTEYVCN   240
CSVVGSLNVN RCNQTTGQCE CRPGYQGLHC ETCKEGFYLN YTSGLCQPCD CSPHGALSIP   300
CNSSGKCQCK VGVIGSICDR CQDGYYGFSK NGCLPCQCNN RSASCDALTG ACLNCQENSK   360
GNHCEECKEG FYQSPDATKE CLRCPCSAVT STGSCSIKSS ELEPECDQCK DGYIGPNCNK   420
CENGYYNFDS ICRKCQCHGH VDPVKTPKIC KPESGECINC LHNTTGFWCE NCLEGYVHDL   480
EGNCIKKEVI LPTPEGSTIL VSNASLTTSV PTPVINSTFT PTTLQTIFSV STSENSTSAL   540
ADVSWTQFN                                                          549
```

| | | |
|---|---|---|
| SEQ ID NO: 103 | moltype = AA length = 306 | |
| FEATURE | Location/Qualifiers | |
| source | 1..306 | |
| | mol_type = protein | |
| | organism = Homo sapiens | |

```
SEQUENCE: 103
MAVRPGLWPA LLGIVLAAWL RGSGAQQSAT VANPVPGANP DLLPHFLVEP EDVYIVKNKP    60
VLLVCKAVPA TQIFFKCNGE WVRQVDHVIE RSTDGSSGLP TMEVRINVSR QQVEKVFGLE   120
EYWCQCVAWS SSGTTKSQKA YIRIAYLRKN FEQEPLAKEV SLEQGIVLPC RPPEGIPPAE   180
VEWLRNEDLV DPSLDPNVYI TREHSLVVRQ AALADTANYT CVAKNIVARR RSASAAVIVY   240
VDGSWSPWSK WSACGLDCTH WRSRECSDPA PRNGGEECQG TDLDTRNCTS DLCVHTASGP   300
EDVALY                                                              306

SEQ ID NO: 104          moltype = AA  length = 297
FEATURE                 Location/Qualifiers
source                  1..297
                        mol_type = protein
                        organism = Homo sapiens
SEQUENCE: 104
MTTATKMPAL HRHEEEKFFL NAKGQKETLP SIWDSPTKQL SVVVPSYNEE KRLPVMMDEA    60
LSYLEKRQKA DPAFTYEVIV VDDGSKDQTS KVAFKYCQKY GSDKVRVITL VKNRGKGGAI   120
RMGIFSSRGE KILMADADGA TKFPDVEKLE KGLNDLQPWP NQMAIACGSR AHLEKESIAQ   180
RSYFRTLLMY GFHFLVWFLC VKGIRDTQCG FKLFTREAAS RTFSSLHVER WAFDVELLYI   240
AQFFKIPIAE IAVNWTEIEG SKLVPFWSWL QMGKDLLFIR LRYLTGAWRL EQTRKMN     297

SEQ ID NO: 105          moltype = AA  length = 17
FEATURE                 Location/Qualifiers
source                  1..17
                        mol_type = protein
                        organism = Homo sapiens
SEQUENCE: 105
NYHYLESSMT ALYTLGH                                                   17
```